(12) United States Patent
Chee et al.

(10) Patent No.: US 7,115,364 B1
(45) Date of Patent: Oct. 3, 2006

(54) ARRAYS OF NUCLEIC ACID PROBES ON BIOLOGICAL CHIPS

(75) Inventors: Mark Chee, Palo Alto, CA (US); Maureen T. Cronin, Los Altos, CA (US); Stephen P. A. Fodor, Palo Alto, CA (US); Thomas R. Gingeras, Santa Clara, CA (US); Xiaohua C. Huang, Mountain View, CA (US); Earl A. Hubbell, Mountain View, CA (US); Robert J. Lipshutz, Palo Alto, CA (US); Peter E. Lobban, Palo Alto, CA (US); Charles Garrett Miyada, Sunnyvale, CA (US); Macdonald S. Morris, San Jose, CA (US); Nila Shah, Saratoga, CA (US); Edward L. Sheldon, San Diego, CA (US)

(73) Assignee: Affymetrix, Inc., Santa Clara, CA (US)

( * ) Notice: Subject to any disclaimer, the term of this patent is extended or adjusted under 35 U.S.C. 154(b) by 32 days.

(21) Appl. No.: 08/510,521

(22) Filed: Aug. 2, 1995

Related U.S. Application Data

(63) Continuation-in-part of application No. PCT/US94/12305, filed on Oct. 26, 1994, and a continuation-in-part of application No. 08/284,064, filed on Aug. 2, 1994, now abandoned, which is a continuation-in-part of application No. 08/143,312, filed on Oct. 26, 1993, now abandoned.

(51) Int. Cl.
*C12Q 1/68* (2006.01)
*G01N 33/50* (2006.01)
*G01N 33/53* (2006.01)
*C07H 21/04* (2006.01)

(52) U.S. Cl. ................... 435/6; 422/50; 422/68.1; 536/24.3

(58) Field of Classification Search .................. 422/50, 422/68.1; 435/5, 6, 810, 91.2; 436/501; 536/23.1, 24.1, 24.3–24.33, 23.2, 25.3; 935/77, 935/78
See application file for complete search history.

(56) References Cited

U.S. PATENT DOCUMENTS

| | | | |
|---|---|---|---|
| 4,656,127 A | 4/1987 | Mundy | 435/6 |
| 4,683,195 A | 7/1987 | Mullis et al. | 435/6 |
| 5,002,867 A | 3/1991 | Macevicz | 435/6 |
| 5,143,854 A | 9/1992 | Pirrung et al. | 436/518 |
| 5,202,231 A | 4/1993 | Drmanac et al. | 435/6 |
| 5,273,632 A | 12/1993 | Stockham et al. | 204/108.1 |
| 5,472,842 A | 12/1995 | Stokke et al. | |
| 5,527,681 A | 6/1996 | Holmes | 435/6 |
| 5,620,848 A | 4/1997 | Levine et al. | |
| 5,670,314 A | 9/1997 | Christman et al. | |
| 5,690,894 A | 11/1997 | Pinkel et al. | |
| 5,700,637 A * | 12/1997 | Southern | 435/6 |
| 5,837,832 A * | 11/1998 | Chee et al. | 536/22.1 |
| 5,861,242 A * | 1/1999 | Chee et al. | 435/5 |
| 6,090,566 A | 7/2000 | Vogelstein et al. | |
| 6,309,823 B1 | 10/2001 | Cronin et al. | |
| 6,468,744 B1 | 10/2002 | Cronin et al. | |
| 2003/0165823 A1 | 9/2003 | Cronin et al. | |
| 2003/0165830 A1 | 9/2003 | Cronin et al. | |

FOREIGN PATENT DOCUMENTS

| | | |
|---|---|---|
| EP | 463 395 A1 | 1/1992 |
| EP | 512 342 A2 | 11/1992 |
| WO | WO 89/10977 | 11/1989 |
| WO | WO 89/11548 | 11/1989 |
| WO | WO 90/00626 | 1/1990 |
| WO | WO 90/03382 | 4/1990 |
| WO | WO 91/10745 A1 | 7/1991 |
| WO | WO 92/10092 | 6/1992 |
| WO | WO 92/10588 | 6/1992 |
| WO | WO 93/17126 | 9/1993 |
| WO | WO 94/03638 A1 | 2/1994 |
| WO | WO 95/00530 A1 | 1/1995 |
| WO | WO 95/11995 | 5/1995 |
| WO | WO 95/26973 | 10/1995 |

OTHER PUBLICATIONS

Chee et al., "Towards sequencing mitochondrial DNA polymorphisms by hybridization to a custom oligonucleotide probe array," poster, *American Society of Human Genetics, 43rd Annual Meeting*, Oct. 5-9, 1993, New Orleans, LA (abstract).

Chee et al., "Genetic analysis by hybridization to sequence-specific DNA arrays," poster, *American Society of Human Genetics, 43rd Annual Meeting*, Oct. 5-9, 1993, New Orleans, LA (abstract).

Chee et al., "Sequence analysis by hybridization: the human mitochondrial genome on a chip," poster and slide presentation, *Genome Sequencing and Analysis Conference V*, Sep. 17-21, 1994, Hilton Head, SC (abstract).

(Continued)

*Primary Examiner*—Marjorie A. Moran
*Assistant Examiner*—Marina Miller
(74) *Attorney, Agent, or Firm*—Townsend and Townsend and Crew LLP

(57) ABSTRACT

The invention provides chips of immobilized probes, and methods employing the chips, for comparing a reference polynucleotide sequence of known sequence with a target sequence showing substantial similarity with the reference sequence, but differing in the presence of e.g., mutations.

47 Claims, 64 Drawing Sheets

OTHER PUBLICATIONS

Chee et al., "Sequencing mitochondrial DNA polymorphisms by hybridization," slide presentation, *American Society of Human Genetics 44th Annual Meeting*, Oct. 18-22, 1994, Montreal, Quebec (abstract).

Chee, "Resequencing DNA by hybridization to oligonucleotide arrays," slide presentation, *Western Biotech Conference*, Oct. 18-21, 1995, San Diego, CA (abstract).

Cronin et al., "Hybridization to arrays of oligonucleotides," poster, *Nucleic Acids in Medical Applications Conference* sponsored by AACC, Jan., 1993, Cancun, Mexico (abstract).

Cronin et al., "Detection of cystic fibrosis gene mutations by hybridization to GeneChip™ probe arrays," poster, *Nucleic Acids in Medical Applications Conference* sponsored by AACC, Nov., 1993, Cancun, Mexico (abstract).

Cronin et al., "GeneChip™ screening assay for cystic fibrosis mutations," poster, *American Society of Human Genetics Meeting*, Oct., 1994, Montreal, Canada (abstract).

Cronin et al., "Detecting cystic fibrosis mutations by hybridization to DNA probe arrays," slide presentation, *UCSF School of Medicine Symposium: Molecular Approaches to Laboratory Diagnosis*, Feb., 1995 (abstract).

Elder, "Analysis of DNA oligonucleotide hybridization data by maximum entropy," *Maximum Entropy and Bayesian Methods*, pp. 1-10, Paris (1992).

Lipschutz, "Likelihood DNA sequencing by hybridization," *J. of Biomolecular Structure & Dynamics*, 11:637-653 (1993).

Lipshutz, "Oligonucleotide arrays for hybridization analysis," poster, *Genome Sequencing and Analysis Conference V*, Oct. 23-27, 1993, Hilton head, SC (abstract).

Lobban et al., "DNA chips for genetic analysis," poster, Genome Sequencing and Analysis Conference V, Oct. 23-27, 1993, Hilton Head, SC (abstract).

Lockhart et al., "DNA sequencing by hybridization on high density probe arrays: enzymatic enhancement and sequence reconstruction," poster, *American Society of Human Genetics 44th Annual Meeting*, Oct. 18-22, 1994, Montreal, Quebec (abstract).

Luo et al., "Cellular protein modulates effects of human immunodeficiency virus type 1 rev," *J. Virol.* 68:3850-3856 (1994).

Maxam et al., "A new method for sequencing DNA," *Proc. Natl. Acad. Sci. USA*, 74:560-564 (1977).

Maxam et al., "Sequencing end-labeled DNA with base-specific chemical cleavages," *Methods in Enzymology*, 65:499-560 (1980).

Miyada et al., "Detection of cystic fibrosis mutations in a GeneChip™ assay format," poster, *American Society of Human Genetics 44th Annual Meeting*, Oct., 1994, Montreal, Quebec (abstract).

Querat et al., "Nucleotide sequence analysis of SA-OMVV, a Visna-related ovine lentivirus: phylogenetic history of lentiviruses," *Virology*, 175:434-447 (1990).

Ratner et al., "Complete nucleotide sequence of the AIDS virus, HTLV-III," *Nature*, 313:277-284 (1985).

Sambrook et al., "Molecular cloning," Cold Spring Harbor Press, pp. 1145-1147 (1989).

Sanger et al., "DNA sequencing with chain-terminating inhibitors," *Proc. Natl. Acad. Sci. USA*, 74:5463-5467 (1977).

Southern et al., "Analyzing and comparing nucleic acid sequences by hybridization to arrays of oligonucleotides: evaluation using experimental models," *Geonimcs*, 13:1008-1017 (1992).

Stratagene 1988 Catalog, "Gene Characterization Kits," p. 39.

Wain-Hobson et al., "Nucleotide sequence of the AIDS virus, LAV," *Cell*, 40:9-17 (1985).

Chee et al., "Accessing Genetic Information with High Density DNA Arrays," *Science*, 274:610-614 (1996).

Chee et al., "A new method for rapid sequence analysis detection of HIV reverse transcriptase mutations," slide presentation, *HIV Drug Resistance Third International Workshop*, Aug. 2-5, 1994, Kauai, HI.

Cocco et al., "Lack of evidence for a role of the myelin basic protein gene in multiple sclerosis susceptibility in Sardinian patients," *J. Neurology*, 249(11):1552-1555 (2002).

Cronin et al., "Cystic fibrosis mutation detection by hybridization to light-generated DNA probe arrays," *Human Mutation*, 7(3):244-255 (1996).

Finch et al., "PCR/RFLP Assay for Copy Number of Mutant and Wild-Type Alleles," *BioTechniques*, 21:1055-1060 (1996).

Gonzales et al., "Pharmacogenetic Phenotyping and Genotyping, Present Status and Future Potential," *Clin. Pharmacokinet*, 26(1):59-70 (1994).

Hacia et al., "Detection of Heterozygous Mutations in BRCA 1 Using High Density Oligonucleotide Arrays and Two-Colour Fluorescence Analysis," *Nature Genetics*, 14:441-447 (1996).

Hagstrom et al., "Maximum likelihood genetic sequence reconstruction from oligo content," from *Argonne Nat'l Laboratory Preprint MCS-P309-0592* (1992).

Laan et al., "Solid-Phase Minisequencing Confirmed by FISH Analysis in Determination of Gene Copy Number," *Human Genetics*, 96:275-280 (1995).

Lipshutz et al., "Using Oligonucleotide Probe Arrays to Access Genetic Diversity," *Biotechniques*, 19(3):442-447 (1995).

Rudert et al., "Rapid Detection of Sequence Variations Using Polymers of Specific Oligonucleotides," *Nuc. Acids Res.*, 20(5):1146 (1992).

Stickland et al., "Quantification of Oncogene Dosage in Tumors by Simultaneous Dual Label Hybridization," *Oncogene*, 8:223-227 (1993).

Strachan et al., *Human Molecular Genetics*, pp. 466-471, Bios Scientific Publishers Limited, Oxford OX4 1RE, UK, (1996).

Takeda et al., "An increased *NM23H1* copy number may be a poor prognostic factor independent of LOH on lp in neuroblastomas," *Br. J. Cancer*, 74:1620-1626 (1996).

Tully et al., "Analysis of 6 VNTR Loci by Multiplex PCR and Automated Florescent Detection," *Human Genetics*, 92:554-562 (1993).

* cited by examiner $n_1n_2n_3n_4n_5$
A C T G T T A G C T A A T T G G ⟵ REF. SEQ.

A-LANE  TGAC  GAAA  ACAA  CAAT  AAAG
C-LANE  TGCC  GACA  ACCA  CACT  AACG
G-LANE  TGGC  GAGA  ACGA  CAGT  AAGG
T-LANE  TGTC  GATA  ACTA  CATT  AATG
         \      \     \     \     \
         $I_1$  $I_2$ $I_3$ $I_4$ $I_5$

WT. LANE  TGAC  GACA  ACAA  CAAT  AATG

FIG. 4

```
           m₁ m₂
ACTGTTAGCTAATTGG          CENTRAL
    5'TCG[A]TTA 3'        INTERROGATION
         I                POSITION

5'AATCG[A]T 3'         3'
          I               INTERROGATION
                          POSITION

5'T[T]AACC 3'       5'
          I               INTERROGATION
                          POSITION
```

*FIG. 4B*

```
GGGXCCCTTAF

CCC[A]GGG
CCC[C]GGG
CCC[G]GGG
CCC[T]GGG

[A]GGGAAT
    [C]GGGAAT
    [G]GGGAAT
    [T]GGGAAT
```

*FIG. 4C*

```
           n₁  n₂  n₃ ─── CORRESPONDING NUCLEOTIDES
A C T G T T A G C T A A T T G G ─── REF. SEQ.
      C [A] A [T] C [G] A ─── PROBE FROM FIRST SET
        i₁    i₂    i₃ ─── INTERROGATION POSITIONS

C [C] A T C G A  ⎫ CORRESPONDING PROBES
      C [G] A T C G A  ⎬ FROM SECOND, THIRD AND
      C [T] A T C G A  ⎭ FOURTH PROBE SETS
        i₁

C A A [A] C G A  ⎫ CORRESPONDING PROBES
      C A A [C] C G A  ⎬ FROM FIFTH, SIXTH AND
      C A A [G] C G A  ⎭ SEVENTH PROBE SETS
            i₂

C A A T C [A] A  ⎫ CORRESPONDING PROBES
      C A A T C [C] A  ⎬ FROM EIGHTH, NINTH AND
      C A A T C [T] A  ⎭ TENTH PROBE SETS
                i₃
```

*FIG. 7*

```
         n3  n4n1     n2
    A C T G T T A G C T A A T T G G ─── REF. SEQ.
          C A A T C A A T
          C A C T C C A T
          C A G T C G A T
          C A T T C T A T
              I1    I2 ─── INTERROGATION POSITIONS

T G A C T A T
    T G C C G A T
    T G G C C A T
    T G T C A A T
        I3  I4 ─── INTERROGATION POSITIONS
```

FIG. 8

```
                       n CORRESPONDING NUCLEOTIDE
    A T T C C C G G G A T C
          A G G G C C A T ─── PROBE FROM FIRST PROBE SET
          A G G C C C A T ┐
          A G G A C C A T ├ CORRESPONDING PROBES
          A G G T C C A T ┘ FROM SECOND, THIRD AND
                              FOURTH PROBE SETS
              I  ─── HELPER MUTATION
                  ─── INTERROGATION POSITION
```

```
5'Fluorescein-AAAGAAAAAAGACAGTACTAAATGGAGAAAAT  wildtype
PROBE 3'            tttttt•tgtcat                13mers
PROBE 3'           cttttttt•tgtcatg              15mers
PROBE 3'          tcttttttt•tgtcatga             17mers
PROBE 3'         ttctttttt•tgtcatgat             19mers
5'Fluorescein-AAAGAAAAAAAACAGTACTAAATGGAGAAAAT  mutant
```

FIG. 13

```
                        tcgagataat
                        81
ns093001wt3:            nngagatann  ⎫
ns093001cq2:            tcgagataat  ⎬ PRETREATMENT
ns093001cq3:            tcgagataat  ⎪
ns093001cq4:            tcgagataat  ⎭
ns093001cq5:            ncgggataat  ⎫
ns093002cq2:            tcgrgataat  ⎬ POSTTREATMENT
ns093002cq3:            tcgagataat  ⎪
ns093002cq4:            tcgagataat  ⎭
ns093002cq5:            tcgagataat
```

```
ns093001wt3:  ctatgtcctcgtctactatgtcataatctcttacttaaacgtcctttacctttggtttttactatcccttaacctccaaaatag
                91         101        111        121        126        136        146        156        166        176
ns093001cq2:  ntatgtcctcgtctactatgtcataatctcttacttaannnnnnnnnnnnaaacgtcctttnnnnnnnnnnnnnnnwncnacntaaacctccaaaatan
ns093001cq3:  ctatgtcctcgtctactatgtcataatctcttacttactnnnnnnnnactcttactaaacgtcctttactatcccttaacctccaaaatag
ns093001cq4:  ctatgtcctcgtctactatgtcataatctcttacttactaaacgtcctttactatatcccmcttaacctccaaaatag
ns093001cq5:  ctatgtcctcgtctactatgtcataatctcttacttactaaacgtcctttactatatcccmcttaacctccaaaatag
ns093002cq2:  ntatgtcctcgtctcyactatgtcataatctcannnnnnncnnncnnncaaacggtcctnnnnnnnncnncyahaaawcyaaccctccaaaatan
ns093002cq3:  ctatgtcctcgtctactatgtcataatctccnnncnnctcaaacgtcctycnnnnytggttnytactatcccctcaaaatag
ns093002cq4:  ctatgtcctcgtctactatgtcataatcchnctactcaaacgtcctctacctgttttactatatcccttaacctccaaaatag
ns093002cq5:  ctatgtcctcgtctactatgtcataatctctttacycaaacggtcctxctacccttggttttactatatcccmcttaacctccaaaatag
```

```
ns093001wt3:  tttcattctgtcatgctagtctatggacatcttagacacctgtatttcgatatccatgt
                186        196        206        216        226        236
ns093001cq2:  nnnnnntctnannnannnannnntctannngnacatannagtctatgngngnnntagacagnncnnnnntcgatatccatgt
ns093001cq3:  tttcattctgncatannagtctatgngngnnntagacagnncnnnnntcgatatccatgt
ns093001cq4:  tttcattctgtcatactagtctatgggtagcttagacamccgtatttcgatatccatgt
ns093001cq5:  tttcattctgtcatactagtctatgggtagcttagacacctgtatttcgatatccatgt
ns093002cq2:  nnnnnntctnnnnnannncnctnnnnnnnagngnnnagacacctgtatnnnntatncaygt
ns093002cq3:  tttcattctgncatacnnstctannxnnagxgttagacctttagacctgtatttcgatatccatgt
ns093002cq4:  tttcattctgtcatactagtctatgagtagcttagacgagcttagacctgtatttcgatatccatgt
ns093002cq5:  tttcattctgtcatactagtctatgagtagcttagacacctgtatttcgatatccatgt
```

WT "G" Substitution Target 12-mer
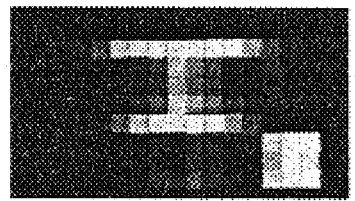
"T" Substitution Target 12-mer
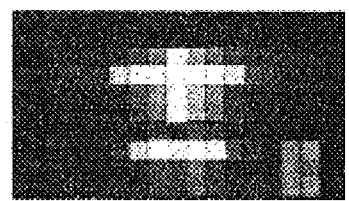
"C" Substitution Target 12-mer
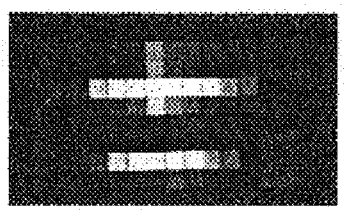
"A" Substitution Target 12-mer
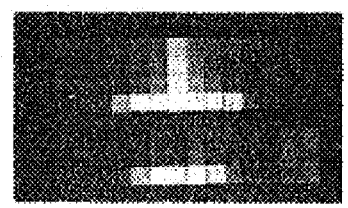
Fig. 29

Detection of 12-mer One-Base Substitution P53 Targets

4:1 Mixture of WT and "A" Substitution 12-mer Targets

FIG. 43

| Position: | 16519 | 152 | 263 | 344 | |
|---|---|---|---|---|---|
| Change: | T->C | T->C | A->G | T->C | |
| Result: |  |  |  |  | T<br>G<br>C<br>A |
Fig. 45

ARRAYS OF NUCLEIC ACID PROBES ON BIOLOGICAL CHIPS

CROSS-REFERENCE TO RELATED APPLICATION

This application is a continuation-in-part PCT/US94/12305, filed Oct. 26, 1994, which is a continuation-in-part of U.S. Ser. No. 08/284,064, filed Aug. 2, 1994 (now abandoned), which is a continuation-in-part of U.S. Ser. No. 08/143,312 (now abandoned), filed Oct. 26, 1993, each of which is incorporated by reference in its entirety for all purposes.

BACKGROUND OF THE INVENTION

1. Field of the Invention

The present invention provides arrays of oligonucleotide probes immobilized in microfabricated patterns on chips for analyzing molecular interactions of biological interest. The invention therefore relates to diverse fields impacted by the nature of molecular interaction, including chemistry, biology, medicine, and medical diagnostics.

2. Description of Related Art

Oligonucleotide probes have long been used to detect complementary nucleic acid sequences in a nucleic acid of interest (the "target" nucleic acid). In some assay formats, the oligonucleotide probe is tethered, i.e., by covalent attachment, to a solid support, and arrays of oligonucleotide probes immobilized on solid supports have been used to detect specific nucleic acid sequences in a target nucleic acid. See, e.g., PCT patent publication Nos. WO 89/10977 and 89/11548. Others have proposed the use of large numbers of oligonucleotide probes to provide the complete nucleic acid sequence of a target nucleic acid but failed to provide an enabling method for using arrays of immobilized probes for this purpose. See U.S. Pat. Nos. 5,202,231 and 5,002,867 and PCT patent publication No. WO 93/17126.

The development of VLSIPS™ technology has provided methods for making very large arrays of oligonucleotide probes in very small areas. See U.S. Pat. No. 5,143,854 and PCT patent publication Nos. WO 90/15070 and 92/10092, each of which is incorporated herein by reference. U.S. patent application Ser. No. 08/082,937, filed Jun. 25, 1993, describes methods for making arrays of oligonucleotide probes that can be used to provide the complete sequence of a target nucleic acid and to detect the presence of a nucleic acid containing a specific nucleotide sequence.

Microfabricated arrays of large numbers of oligonucleotide probes, called "DNA chips" offer great promise for a wide variety of applications. New methods and reagents are required to realize this promise, and the present invention helps meet that need.

SUMMARY OF THE INVENTION

The invention provides several strategies employing immobilized arrays of probes for comparing a reference sequence of known sequence with a target sequence showing substantial similarity with the reference sequence, but differing in the presence of, e.g., mutations. In a first embodiment, the invention provides a tiling strategy employing an array of immobilized oligonucleotide probes comprising at least two sets of probes. A first probe set comprises a plurality of probes, each probe comprising a segment of at least three nucleotides exactly complementary to a subsequence of the reference sequence, the segment including at least one interrogation position complementary to a corresponding nucleotide in the reference sequence. A second probe set comprises a corresponding probe for each probe in the first probe set, the corresponding probe in the second probe set being identical to a sequence comprising the corresponding probe from the first probe set or a subsequence of at least three nucleotides thereof that includes the at least one interrogation position, except that the at least one interrogation position is occupied by a different nucleotide in each of the two corresponding probes from the first and second probe sets. The probes in the first probe set have at least two interrogation positions corresponding to two contiguous nucleotides in the reference sequence. One interrogation position corresponds to one of the contiguous nucleotides, and the other interrogation position to the other.

In a second embodiment, the invention provides a tiling strategy employing an array comprising four probe sets. A first probe set comprises a plurality of probes, each probe comprising a segment of at least three nucleotides exactly complementary to a subsequence of the reference sequence, the segment including at least one interrogation position complementary to a corresponding nucleotide in the reference sequence. Second, third and fourth probe sets each comprise a corresponding probe for each probe in the first probe set. The probes in the second, third and fourth probe sets are identical to a sequence comprising the corresponding probe from the first probe set or a subsequence of at least three nucleotides thereof that includes the at least one interrogation position, except that the at least one interrogation position is occupied by a different nucleotide in each of the four corresponding probes from the four probe sets. The first probe set often has at least 100 interrogation positions corresponding to 100 contiguous nucleotides in the reference sequence. Sometimes the first probe set has an interrogation position corresponding to every nucleotide in the reference sequence. The segment of complementarity within the probe set is usually about 9–21 nucleotides. Although probes may contain leading or trailing sequences in addition to the 9–21 sequences, many probes consist exclusively of a 9–21 segment of complementarity.

In a third embodiment, the invention provides immobilized arrays of probes tiled for multiple reference sequences. One such array comprises at least one pair of first and second probe groups, each group comprising first and second sets of probes as defined in the first embodiment. Each probe in the first probe set from the first group is exactly complementary to a subsequence of a first reference sequence, and each probe in the first probe set from the second group is exactly complementary to a subsequence of a second reference sequence. Thus, the first group of probes are tiled with respect to a first reference sequence and the second group of probes with respect to a second reference sequence. Each group of probes can also include third and fourth sets of probes as defined in the second embodiment. In some arrays of this type, the second reference sequence is a mutated form of the first reference sequence.

In a fourth embodiment, the invention provides arrays for block tiling. Block tiling is a species of the basic tiling strategies described above. The usual unit of a block tiling array is a group of probes comprising a wildtype probe, a first set of three mutant probes and a second set of three mutant probes. The wildtype probe comprises a segment of at least three nucleotides exactly complementary to a subsequence of a reference sequence. The segment has at least first and second interrogation positions corresponding to first and second nucleotides in the reference sequence. The probes in the first set of three mutant probes are each identical to a sequence comprising the wildtype probe or a subsequence of at least three nucleotides thereof including the first and second interrogation positions, except in the first interrogation position, which is occupied by a different nucleotide in each of the three mutant probes and the wildtype probe. The probes in the second set of three mutant probes are each identical to a sequence comprising the wildtype probes or a subsequence of at least three nucleotides thereof including the first and second interrogation positions, except in the second interrogation position, which is occupied by a different nucleotide in each of the three mutant probes and the wildtype probe.

In a fifth embodiment, the invention provides methods of comparing a target sequence with a reference sequence using arrays of immobilized pooled probes. The arrays employed in these methods represent a further species of the basic tiling arrays noted above. In these methods, variants of a reference sequence differing from the reference sequence in at least one nucleotide are identified and each is assigned a designation. An array of pooled probes is provided, with each pool occupying a separate cell of the array. Each pool comprises a probe comprising a segment exactly complementary to each variant sequence assigned a particular designation. The array is then contacted with a target sequence comprising a variant of the reference sequence. The relative hybridization intensities of the pools in the array to the target sequence are determined. The identity of the target sequence is deduced from the pattern of hybridization intensities. Often, each variant is assigned a designation having at least one digit and at least one value for the digit. In this case, each pool comprises a probe comprising a segment exactly complementary to each variant sequence assigned a particular value in a particular digit. When variants are assigned successive numbers in a numbering system of base m having n digits, n×(m−1) pooled probes are used to assign each variant a designation.

In a sixth embodiment, the invention provides a pooled probe for trellis tiling, a further species of the basic tiling strategy. In trellis tiling, the identity of a nucleotide in a target sequence is determined from a comparison of hybridization intensities of three pooled trellis probes. A pooled trellis probe comprises a segment exactly complementary to a subsequence of a reference sequence except at a first interrogation position occupied by a pooled nucleotide N, a second interrogation position occupied by a pooled nucleotide selected from the group of three consisting of (1) M or K, (2) R or Y and (3) S or W, and a third interrogation position occupied by a second pooled nucleotide selected from the group. The pooled nucleotide occupying the second interrogation position comprises a nucleotide complementary to a corresponding nucleotide from the reference sequence when the second pooled probe and reference sequence are maximally aligned, and the pooled nucleotide occupying the third interrogation position comprises a nucleotide complementary to a corresponding nucleotide from the reference sequence when the third pooled probe and the reference sequence are maximally aligned. Standard IUPAC nomenclature is used for describing pooled nucleotides.

In trellis tiling, an array comprises at least first, second and third cells, respectively occupied by first, second and third pooled probes, each according to the generic description above. However, the segment of complementarity, location of interrogation positions, and selection of pooled nucleotide at each interrogation position may or may not differ between the three pooled probes subject to the following constraint. One of the three interrogation positions in each of the three pooled probes must align with the same corresponding nucleotide in the reference sequence. This interrogation position must be occupied by a N in one of the pooled probes, and a different pooled nucleotide in each of the other two pooled probes.

In a seventh embodiment, the invention provides arrays for bridge tiling. Bridge tiling is a species of the basic tiling strategies noted above, in which probes from the first probe set contain more than one segment of complementarity. In bridge tiling, a nucleotide in a reference sequence is usually determined from a comparison of four probes. A first probe comprises at least first and second segments, each of at least three nucleotides and each exactly complementary to first and second subsequences of a reference sequences. The segments including at least one interrogation position corresponding to a nucleotide in the reference sequence. Either (1) the first and second subsequences are noncontiguous in the reference sequence, or (2) the first and second subsequences are contiguous and the first and second segments are inverted relative to the first and second subsequences. The arrays further comprises second, third and fourth probes, which are identical to a sequence comprising the first probe or a subsequence thereof comprising at least three nucleotides from each of the first and second segments, except in the at least one interrogation position, which differs in each of the probes. In a species of bridge tiling, referred to as deletion tiling, the first and second subsequences are separated by one or two nucleotides in the reference sequence.

In an eighth embodiment, the invention provides arrays of probes for multiplex tiling. Multiplex tiling is a strategy, in which the identity of two nucleotides in a target sequence is determined from a comparison of the hybridization intensities of four probes, each having two interrogation positions. Each of the probes comprising a segment of at least 7 nucleotides that is exactly complementary to a subsequence from a reference sequence, except that the segment may or may not be exactly complementary at two interrogation positions. The nucleotides occupying the interrogation positions are selected by the following rules: (1) the first interrogation position is occupied by a different nucleotide in each of the four probes, (2) the second interrogation position is occupied by a different nucleotide in each of the four probes, (3) in first and second probes, the segment is exactly complementary to the subsequence, except at no more than one of the interrogation positions, (4) in third and fourth probes, the segment is exactly complementary to the subsequence, except at both of the interrogation positions.

In a ninth embodiment, the invention provides arrays of immobilized probes including helper mutations. Helper mutations are useful for, e.g., preventing self-annealing of probes having inverted repeats. In this strategy, the identity of a nucleotide in a target sequence is usually determined from a comparison of four probes. A first probe comprises a segment of at least 7 nucleotides exactly complementary to a subsequence of a reference sequence except at one or two positions, the segment including an interrogation position not at the one or two positions. The one or two positions are occupied by helper mutations. Second, third and fourth mutant probes are each identical to a sequence comprising the wildtype probe or a subsequence thereof including the interrogation position and the one or two positions, except in the interrogation position, which is occupied by a different nucleotide in each of the four probes.

In a tenth embodiment, the invention provides arrays of probes comprising at least two probe sets, but lacking a probe set comprising probes that are perfectly matched to a reference sequence. Such arrays are usually employed in methods in which both reference and target sequence are hybridized to the array. The first probe set comprising a plurality of probes, each probe comprising a segment exactly complementary to a subsequence of at least 3 nucleotides of a reference sequence except at an interrogation position. The second probe set comprises a corresponding probe for each probe in the first probe set, the corresponding probe in the second probe set being identical to a sequence comprising the corresponding probe from the first probe set or a subsequence of at least three nucleotides thereof that includes the interrogation position, except that the interrogation position is occupied by a different nucleotide in each of the two corresponding probes and the complement to the reference sequence.

In an eleventh embodiment, the invention provides methods of comparing a target sequence with a reference sequence comprising a predetermined sequence of nucleotides using any of the arrays described above. The methods comprise hybridizing the target nucleic acid to an array and determining which probes, relative to one another, in the array bind specifically to the target nucleic acid. The relative specific binding of the probes indicates whether the target sequence is the same or different from the reference sequence. In some such methods, the target sequence has a substituted nucleotide relative to the reference sequence in at least one undetermined position, and the relative specific binding of the probes indicates the location of the position and the nucleotide occupying the position in the target sequence. In some methods, a second target nucleic acid is also hybridized to the array. The relative specific binding of the probes then indicates both whether the target sequence is the same or different from the reference sequence, and whether the second target sequence is the same or different from the reference sequence. In some methods, when the array comprises two groups of probes tiled for first and second reference sequences, respectively, the relative specific binding of probes in the first group indicates whether the target sequence is the same or different from the first reference sequence. The relative specific binding of probes in the second group indicates whether the target sequence is the same or different from the second reference sequence. Such methods are particularly useful for analyzing heterologous alleles of a gene. Some methods entail hybridizing both a reference sequence and a target sequence to any of the arrays of probes described above. Comparison of the relative specific binding of the probes to the reference and target sequences indicates whether the target sequence is the same or different from the reference sequence.

In a twelfth embodiment, the invention provides arrays of immobilized probes in which the probes are designed to tile a reference sequence from a human immunodeficiency virus. Reference sequences from either the reverse transcriptase gene or protease gene of HIV are of particular interest. Some chips further comprise arrays of probes tiling a reference sequence from a 16S RNA or DNA encoding the 16S RNA from a pathogenic microorganism. The invention further provides methods of using such arrays in analyzing a HIV target sequence. The methods are particularly useful where the target sequence has a substituted nucleotide relative to the reference sequence in at least one position, the substitution conferring resistance to a drug used in treating a patient infected with a HIV virus. The methods reveal the existence of the substituted nucleotide. The methods are also particularly useful for analyzing a mixture of undetermined proportions of first and second target sequences from different HIV variants. The relative specific binding of probes indicates the proportions of the first and second target sequences.

The invention further provides a method of treating a patient infected with an HIV virus. A tissue sample from the patient containing a target nucleic acid is hybridized to an array of oligonucleotide probes immobilized on a solid support. The array comprises: (1) a first probe set comprising a plurality of probes, each probe comprising a segment of at least three nucleotides exactly complementary to a subsequence of a reference sequence comprising an HIV gene, the segment including at least one interrogation position complementary to a corresponding nucleotide in the reference sequence, and (2) a second probe set comprising a corresponding probe for each probe in the first probe set, the corresponding probe in the second probe set being identical to a sequence comprising the corresponding probe from the first probe set or a subsequence of at least three nucleotides thereof that includes the at least one interrogation position, except that the at least one interrogation position is occupied by a different nucleotide in each of the two corresponding probes from the first and second probe sets. The probes in the first probe set have at least three interrogation positions respectively corresponding to each of at least three nucleotides in the reference sequence. The method determines which probes in the first and second probe sets, relative to one another, in the array bind specifically to the target nucleic acid, the relative specific binding of the probes identifying a mutation in the target sequence relative to the reference sequence. The patient is then administered a drug effective against an HIV virus bearing the mutation.

In a thirteenth embodiment, the invention provides arrays of probes tiled based on reference sequence from a CFTR gene. A preferred array comprises at least a group of probes comprising a wildtype probe, and five sets of three mutant probes. The wildtype probe is exactly complementary to a subsequence of a reference sequence from the CFTR gene, the segment having at least five interrogation positions corresponding to five contiguous nucleotides in the reference sequence. The probes in the first set of three mutant probes are each identical to the wildtype probe, except in a first of the five interrogation positions, which is occupied by a different nucleotide in each of the three mutant probes and the wildtype probe. The probes in the second set of three mutant probes are each identical to the wildtype probe, except in a second of the five interrogation positions, which is occupied by a different nucleotide in each of the three mutant probes and the wildtype probe. The probes in the third set of three mutant probes are each identical to the wildtype probe, except in a third of the five interrogation positions, which is occupied by a different nucleotide in each of the three mutant probes and the wildtype probe. The probes in the fourth set of three mutant probes are each identical to the wildtype probe, except in a fourth of the five interrogation positions, which is occupied by a different nucleotide in each of the three mutant probes and the wildtype probe. The probes in the fifth set of three mutant probes are each identical to the wildtype probe, except in a fifth of the five interrogation positions, which is occupied by a different nucleotide in each of the three mutant probes and the wildtype probe. Preferably, a chip comprises two such groups of probes. The first group comprises a wildtype probe exactly complementary to a first reference sequence, and the second group comprises a wildtype probe exactly complementary to a second reference sequence that is a mutated form of the first reference sequence.

The invention further provides methods of using the arrays of the invention for analyzing target sequences from a CFTR gene. The methods are capable of simultaneously analyzing first and second target sequences representing heterozygous alleles of a CFTR gene.

In a fourteenth embodiment, the invention provides arrays of probes tiling a reference sequence from a p53 gene, an hMLH1 gene and/or an MSH2 gene. The invention further provides methods of using the arrays described above to analyze these genes. The method are useful, e.g., for diagnosing patients susceptible to developing cancer.

In a fifteenth embodiment, the invention provides arrays of probes tiling a reference sequence from a mitochondrial genome. The reference sequence may comprise part or all of the D-loop region, or all, or substantially all, of the mitochondrial genome. The invention further provides method of using the arrays described above to analyze target sequences from a mitochondrial genome. The methods are useful for identifying mutations associated with disease, and for forensic, epidemiological and evolutionary studies.

BRIEF DESCRIPTION OF THE FIGURES

FIG. 4: Exemplary arrangement of lanes on a chip. The chip shows four probe sets, each having five probes and each having a total of five interrogation positions (I1–I5), one per probe. The reference sequence is SEQ. ID. No. 478.

FIG. 4B: A tiling strategy for analyzing closing spaced mutations. The reference sequence is SEQ. ID. No. 478.

FIG. 4C: A tiling strategy for avoiding loss of signal due to probe self-annealing. The reference sequence is SEQ ID No. 493.

FIG. 7: Block tiling strategy. The perfectly matched probe has three interrogation positions. The probes from the other probe sets have only one of these interrogation positions. The reference sequence is SEQ. ID. No. 478.

FIG. 8: Multiplex tiling strategy. Each probe has two interrogation positions. The reference sequence is SEQ. ID. No. 478.

FIG. 9: Helper mutation strategy. The segment of complementarity differs from the complement of the reference sequence (SEQ Id. No. 500) at a helper mutation as well as the interrogation position.

FIG. 12 Sequence read from HV 407 chip hybridized to pPol19 and 4MUT18 (separate experiments). The reference sequence is designated "wildtype (SEQ. ID. No. 501)." Beneath the reference sequence are four rows of sequence (SEQ. ID. Nos. 502–505) read from the chip hybridized to the pPol19 target, the first row being read from 13 mers, the second row from 15 mers, the third row from 17 mers and the fourth row from 19 mers. Beneath these sequences, there are four further rows of sequence (SEQ. ID. Nos. 506–509) read from the chip hybridized to the HXB2 target. Successive rows are read from 13 mers, 15 mers, 17 mers and 19 mers. Each nucleotide in a row is called from the relative fluorescence intensities of probes in A-, C-, G- and T-lanes. Regions of ambiguous sequence read from the chip are highlighted. The strain differences between the HBX2 sequence and the reference sequence that were correctly detected are indicated (*), and those that could not be called are indicated (o). (The nucleotide at position 417 was read correctly in some experiments). The location of some mutations known to be associated with drug resistance that occur in readable regions of the chip are shown above (codon number) and below (mutant nucleotide) the sequence designated "wildtype." The locations of primer used to amplify the target sequence are indicated by arrows.

FIG. 13: Detection of mixed target sequences. The mutant target (SEQ. ID. No. 515) differs from the wildtype (SEQ. ID. No. 510) by a single mutation in codon 67 of the reverse transcriptase gene. Each different sized group of probes has a column of four probes for reading the nucleotide in which the mutation occurs (SEQ. ID. Nos. 511–514). The four probes occupying a column are represented by a single probe in the figure with the symbol (o) indicating the interrogation position, which is occupied by a different nucleotide in each probe.

FIG. 15: Sequence read from protease chip from four clinical samples before and after treatment with ddI. From top-bottom, the sequences are SEQ. ID. Nos. 516–524.

FIG. 27 shows the alignment of some of the probes (SEQ. ID. Nos. 544–556) on a p53 DNA chip with a 12-mer model target nucleic acid (SEQ. ID. No. 543).

FIG. 28 shows a set of 10-mer probes (SEQ. ID. Nos. 557–568) for a p53 exon 6 DNA chip and a 12-mer model target nucleic acid (SEQ. Id. No. 543).

FIG. 29 shows that very distinct patterns are observed after hybridization of p53 DNA chips with targets having different 1 base substitutions. In the first image in FIG. 29, the 12-mer probes that form perfect matches with the wild-type target are in the first row (top). The 12-mer probes with single base mismatches are located in the second, third, and fourth rows and have much lower signals.

FIG. 43 provides a 5' to 3' sequence listing of one target corresponding to the probes on the chip (SEQ. ID. No. 570). X is a control probe. Positions that differ in the target (i.e., are mismatched with the probe at the designated site) are in bold.

FIG. 45 illustrates the detection of 4 transitions in the target sequence relative to the wild-type probes on the chip in FIG. 44.

DETAILED DESCRIPTION OF THE INVENTION

Figure 1:
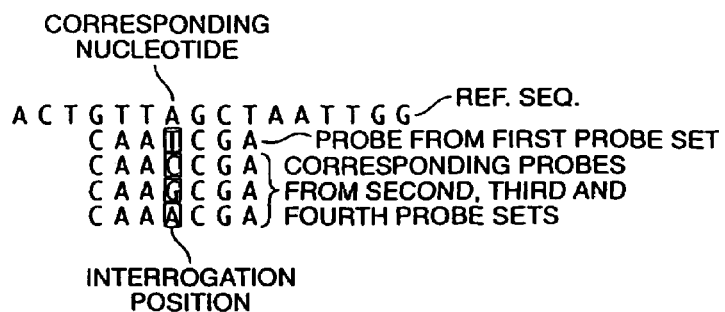
FIG. 1: Basic tiling strategy. The figure illustrates the relationship between an interrogation position (I) and a corresponding nucleotide (n) in the reference sequence (SEQ. ID. No. 478), and between a probe from the first probe set and corresponding probes from second, third and fourth probe sets.

The invention provides a number of strategies for comparing a polynucleotide of known sequence (a reference sequence) with variants of that sequence (target sequences). The comparison can be performed at the level of entire genomes, chromosomes, genes, exons or introns, or can focus on individual mutant sites and immediately adjacent bases. The strategies allow detection of variations, such as mutations or polymorphisms, in the target sequence irrespective whether a particular variant has previously been characterized. The strategies both define the nature of a variant and identify its location in a target sequence.

The strategies employ arrays of oligonucleotide probes immobilized to a solid support. Target sequences are analyzed by determining the extent of hybridization at particular probes in the array. The strategy in selection of probes facilitates distinction between perfectly matched probes and probes showing single-base or other degrees of mismatches. The strategy usually entails sampling each nucleotide of interest in a target sequence several times, thereby achieving a high degree of confidence in its identity. This level of confidence is further increased by sampling of adjacent nucleotides in the target sequence to nucleotides of interest. The present tiling strategies result in sequencing and comparison methods suitable for routine large-scale practice with a high degree of confidence in the sequence output.

I. General Tiling Strategies

A. Selection of Reference Sequence

The chips are designed to contain probes exhibiting complementarity to one or more selected reference sequence whose sequence is known. The chips are used to read a target sequence comprising either the reference sequence itself or variants of that sequence. Target sequences may differ from the reference sequence at one or more positions but show a high overall degree of sequence identity with the reference sequence (e.g., at least 75, 90, 95, 99, 99.9 or 99.99%). Any polynucleotide of known sequence can be selected as a reference sequence. Reference sequences of interest include sequences known to include mutations or polymorphisms associated with phenotypic changes having clinical significance in human patients. For example, the CFTR gene and P53 gene in humans have been identified as the location of several mutations resulting in cystic fibrosis or cancer respectively. Other reference sequences of interest include those that serve to identify pathogenic microorganisms and/or are the site of mutations by which such microorganisms acquire drug resistance (e.g., the HIV reverse transcriptase gene). Other reference sequences of interest include regions where polymorphic variations are known to occur (e.g., the D-loop region of mitochondrial DNA). These reference sequences have utility for, e.g., forensic or epidemiological studies. Other reference sequences of interest include p34 (related to p53), p65 (implicated in breast, prostate and liver cancer), and DNA segments encoding cytochromes P450 and other biotransformation genes (see Meyer et al., *Pharmac. Ther.* 46, 349–355 (1990)). Other reference sequences of interest include those from the genome of pathogenic viruses (e.g., hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus. Other reference sequences of interest are from genomes or episomes of pathogenic bacteria, particularly regions that confer drug resistance or allow phylogenic characterization of the host (e.g., 16S rRNA or corresponding DNA). For example, such bacteria include chlamydia, rickettsial bacteria, mycobacteria, staphylococci, treptocci, pneumonococci, meningococci and conococci, *klebsiella, proteus, serratia*, pseudomonas, *legionella*, diphtheria, *salmonella*, bacilli, cholera, tetanus, botulism, anthrax, plague, leptospirosis, and Lymes disease bacteria. Other reference sequences of interest include those in which mutations result in the following autosomal recessive disorders: sickle cell anemia, β-thalassemia, phenylketonuria, galactosemia, Wilson's disease, hemochromatosis, severe combined immunodeficiency, alpha-1-antitrypsin deficiency, albinism, alkaptonuria, lysosomal storage diseases and Ehlers-Danlos syndrome. Other reference sequences of interest include those in which mutations result in X-linked recessive disorders: hemophilia, glucose-6-phosphate dehydrogenase, agammaglobulimenia, diabetes insipidus, Lesch-Nyhan syndrome, muscular dystrophy, Wiskott-Aldrich syndrome, Fabry's disease and fragile X-syndrome. Other reference sequences of interest includes those in which mutations result in the following autosomal dominant disorders: familial hypercholesterolemia, polycystic kidney disease, Huntingdon's disease, hereditary spherocytosis, Marfan's syndrome, von Willebrand's disease, neurofibromatosis, tuberous sclerosis, hereditary hemorrhagic telangiectasia, familial colonic polyposis, Ehlers-Danlos syndrome, myotonic dystrophy, muscular dystrophy, osteogenesis imperfecta, acute intermittent porphyria, and von Hippel-Lindau disease.

The length of a reference sequence can vary widely from a full-length genome, to an individual chromosome, episome, gene, component of a gene, such as an exon, intron or regulatory sequences, to a few nucleotides. A reference sequence of between about 2, 5, 10, 20, 50, 100, 5000, 1000, 5,000 or 10,000, 20,000 or 100,000 nucleotides is common. Sometimes only particular regions of a sequence (e.g., exons of a gene) are of interest. In such situations, the particular regions can be considered as separate reference sequences or can be considered as components of a single reference sequence, as matter of arbitrary choice.

A reference sequence can be any naturally occurring, mutant, consensus or purely hypothetical sequence of nucleotides, RNA or DNA. For example, sequences can be obtained from computer data bases, publications or can be determined or conceived de novo. Usually, a reference sequence is selected to show a high degree of sequence identity to envisaged target sequences. Often, particularly, where a significant degree of divergence is anticipated between target sequences, more than one reference sequence is selected. Combinations of wildtype and mutant reference sequences are employed in several applications of the tiling strategy.

B. Chip Design

1. Basic Tiling Strategy

The basic tiling strategy provides an array of immobilized probes for analysis of target sequences showing a high degree of sequence identity to one or more selected reference sequences. The strategy is first illustrated for an array that is subdivided into four probe sets, although it will be apparent that in some situations, satisfactory results are obtained from only two probe sets. A first probe set comprises a plurality of probes exhibiting perfect complementarity with a selected reference sequence. The perfect complementarity usually exists throughout the length of the probe. However, probes having a segment or segments of perfect complementarity that is/are flanked by leading or trailing sequences lacking complementarity to the reference sequence can also be used. Within a segment of complementarity, each probe in the first probe set has at least one interrogation position that corresponds to a nucleotide in the reference sequence. That is, the interrogation position is aligned with the corresponding nucleotide in the reference sequence, when the probe and reference sequence are aligned to maximize complementarity between the two. If a probe has more than one interrogation position, each corresponds with a respective nucleotide in the reference sequence. The identity of an interrogation position and corresponding nucleotide in a particular probe in the first probe set cannot be determined simply by inspection of the probe in the first set. As will become apparent, an interrogation position and corresponding nucleotide is defined by the comparative structures of probes in the first probe set and corresponding probes from additional probe sets.

In principle, a probe could have an interrogation position at each position in the segment complementary to the reference sequence. Sometimes, interrogation positions provide more accurate data when located away from the ends of a segment of complementarity. Thus, typically a probe having a segment of complementarity of length x does not contain more than x-2 interrogation positions. Since probes are typically 9–21 nucleotides, and usually all of a probe is complementary, a probe typically has 1–19 interrogation positions. Often the probes contain a single interrogation position, at or near the center of probe.

Figure 2:
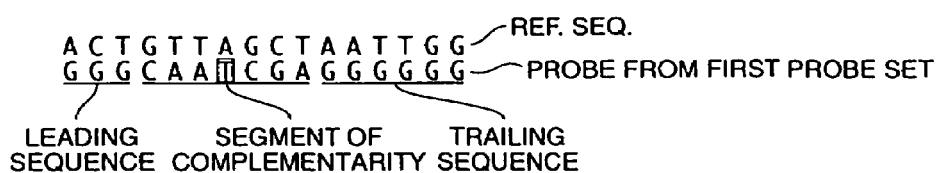
FIG. 2: Segment of complementarity in a probe from the first probe set (SEQ. ID. No. 479).

For each probe in the first set, there are, for purposes of the present illustration, up to three corresponding probes from three additional probe sets. See FIG. 1. Thus, there are four probes corresponding to each nucleotide of interest in the reference sequence. Each of the four corresponding probes has an interrogation position aligned with that nucleotide of interest. Usually, the probes from the three additional probe sets are identical to the corresponding probe from the first probe set with one exception. The exception is that at least one (and often only one) interrogation position, which occurs in the same position in each of the four corresponding probes from the four probe sets, is occupied by a different nucleotide in the four probe sets. For example, for an A nucleotide in the reference sequence, the corresponding probe from the first probe set has its interrogation position occupied by a T, and the corresponding probes from the additional three probe sets have their respective interrogation positions occupied by A, C, or G, a different nucleotide in each probe. Of course, if a probe from the first probe set comprises trailing or flanking sequences lacking complementarity to the reference sequences (see FIG. 2), these sequences need not be present in corresponding probes from the three additional sets. Likewise corresponding probes from the three additional sets can contain leading or trailing sequences outside the segment of complementarity that are not present in the corresponding probe from the first probe set. Occasionally, the probes from the additional three probe set are identical (with the exception of interrogation position(s)) to a contiguous subsequence of the full complementary segment of the corresponding probe from the first probe set. In this case, the subsequence includes the interrogation position and usually differs from the full-length probe only in the omission of one or both terminal nucleotides from the termini of a segment of complementarity. That is, if a probe from the first probe set has a segment of complementarity of length n, corresponding probes from the other sets will usually include a subsequence of the segment of at least length n−2. Thus, the subsequence is usually at least 3, 4, 7, 9, 15, 21, or 25 nucleotides long, most typically, in the range of 9–21 nucleotides. The subsequence should be sufficiently long to allow a probe to hybridize detectably more strongly to a variant of the reference sequence mutated at the interrogation position than to the reference sequence.

The probes can be oligodeoxyribonucleotides or oligoribonucleotides, or any modified forms of these polymers that are capable of hybridizing with a target nucleic sequence by complementary base-pairing. Complementary base pairing means sequence-specific base pairing which includes e.g., Watson-Crick base pairing as well as other forms of base pairing such as Hoogsteen base pairing. Modified forms include 2'-O-methyl oligoribonucleotides and so-called PNAs, in which oligodeoxyribonucleotides are linked via peptide bonds rather than phophodiester bonds. The probes can be attached by any linkage to a support (e.g., 3', 5' or via the base). 3' attachment is more usual as this orientation is compatible with the preferred chemistry for solid phase synthesis of oligonucleotides.

The number of probes in the first probe set (and as a consequence the number of probes in additional probe sets) depends on the length of the reference sequence, the number of nucleotides of interest in the reference sequence and the number of interrogation positions per probe. In general, each nucleotide of interest in the reference sequence requires the same interrogation position in the four sets of probes. Consider, as an example, a reference sequence of 100 nucleotides, 50 of which are of interest, and probes each having a single interrogation position. In this situation, the first probe set requires fifty probes, each having one interrogation position corresponding to a nucleotide of interest in the reference sequence. The second, third and fourth probe sets each have a corresponding probe for each probe in the first probe set, and so each also contains a total of fifty probes. The identity of each nucleotide of interest in the reference sequence is determined by comparing the relative hybridization signals at four probes having interrogation positions corresponding to that nucleotide from the four probe sets.

In some reference sequences, every nucleotide is of interest. In other reference sequences, only certain portions in which variants (e.g., mutations or polymorphisms) are concentrated are of interest. In other reference sequences, only particular mutations or polymorphisms and immediately adjacent nucleotides are of interest. Usually, the first probe set has interrogation positions selected to correspond to at least a nucleotide (e.g., representing a point mutation) and one immediately adjacent nucleotide. Usually, the probes in the first set have interrogation positions corresponding to at least 3, 10, 50, 100, 1000, or 20,000 contiguous nucleotides. The probes usually have interrogation positions corresponding to at least 5, 10, 30, 50, 75, 90, 99 or sometimes 100% of the nucleotides in a reference sequence. Frequently, the probes in the first probe set completely span the reference sequence and overlap with one another relative to the reference sequence. For example, in one common arrangement each probe in the first probe set differs from another probe in that set by the omission of a 3' base complementary to the reference sequence and the acquisition of a 5' base complementary to the reference sequence. See FIG. 3.

The number of probes on the chip can be quite large (e.g., $10^5$–$10^6$). However, often only a relatively small proportion (i.e., less than about 50%, 25%, 10%, 5% or 1%) of the total number of probes of a given length are selected to pursue a particular tiling strategy. For example, a complete set of octomer probes comprises 65,536 probes; thus, an array of the invention typically has fewer than 32,768 octomer probes. A complete array of decamer probes comprises 1,048,576 probes; thus, an array of the invention typically has fewer than about 500,000 decamer probes. Often arrays have a lower limit of 25, 50 or 100 probes and an upper limit of 1,000,000, 100,000, 10,000 or 1000 probes. The arrays can have other components besides the probes such as linkers attaching the probes to a support.

Some advantages of the use of only a proportion of all possible probes of a given length include: (i) each position in the array is highly informative, whether or not hybridization occurs; (ii) nonspecific hybridization is minimized; (iii) it is straightforward to correlate hybridization differences with sequence differences, particularly with reference to the hybridization pattern of a known standard; and (iv) the ability to address each probe independently during synthesis, using high resolution photolithography, allows the array to be designed and optimized for any sequence. For example the length of any probe can be varied independently of the others.

Figure 3:
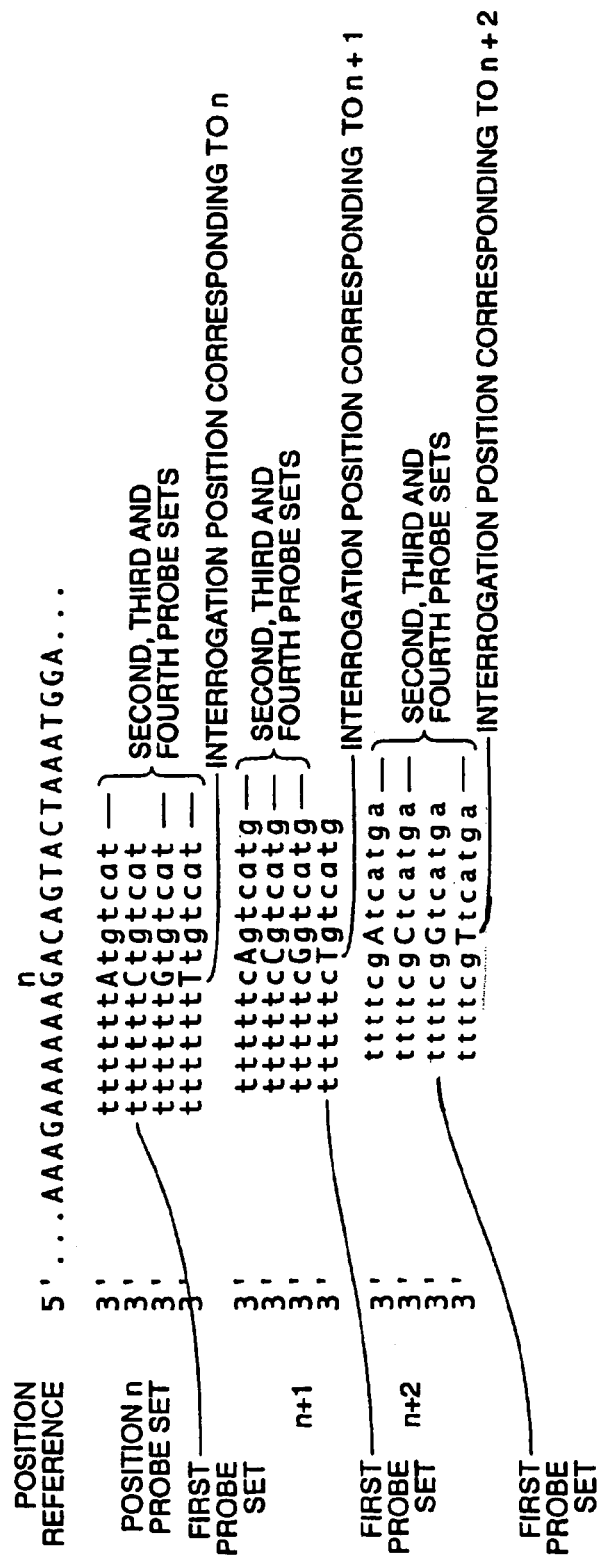
FIG. 3: Incremental succession of probes in a basic tiling strategy. The figure shows four probe sets, each having three probes (SEQ. ID. Nos. 481–492). Note that each probe differs from its predecessor in the same set by the acquisition of a 5' nucleotide and the loss of a 3' nucleotide, as well as in the nucleotide occupying the interrogation position. The reference sequence is SEQ. ID. No. 480.

For conceptual simplicity, the probes in a set are usually arranged in order of the sequence in a lane across the chip. A lane contains a series of overlapping probes, which represent or tile across, the selected reference sequence (see FIG. 3). The components of the four sets of probes are usually laid down in four parallel lanes, collectively constituting a row in the horizontal direction and a series of 4-member columns in the vertical direction. Corresponding probes from the four probe sets (i.e., complementary to the same subsequence of the reference sequence) occupy a column. Each probe in a lane usually differs from its predecessor in the lane by the omission of a base at one end and the inclusion of additional base at the other end as shown in FIG. 3. However, this orderly progression of probes can be interrupted by the inclusion of control probes or omission of probes in certain columns of the array. Such columns serve as controls to orient the chip, or gauge the background, which can include target sequence nonspecifically bound to the chip.

The probes sets are usually laid down in lanes such that all probes having an interrogation position occupied by an A form an A-lane, all probes having an interrogation position occupied by a C form a C-lane, all probes having an interrogation position occupied by a G form a G-lane, and all probes having an interrogation position occupied by a T (or U) form a T lane (or a U lane). Note that in this arrangement there is not a unique correspondence between probe sets and lanes. Thus, the probe from the first probe set is laid down in the A-lane, C-lane, A-lane, A-lane and T-lane for the five columns in FIG. 4. The interrogation position on a column of probes corresponds to the position in the target sequence whose identity is determined from analysis of hybridization to the probes in that column. Thus, $I_1$–$I_5$ respectively correspond to $N_1$–$N_5$ in FIG. 4. The interrogation position can be anywhere in a probe but is usually at or near the central position of the probe to maximize differential hybridization signals between a perfect match and a single-base mismatch. For example, for an 11 mer probe, the central position is the sixth nucleotide.

Although the array of probes is usually laid down in rows and columns as described above, such a physical arrangement of probes on the chip is not essential. Provided that the spatial location of each probe in an array is known, the data from the probes can be collected and processed to yield the sequence of a target irrespective of the physical arrangement of the probes on a chip. In processing the data, the hybridization signals from the respective probes can be reasserted into any conceptual array desired for subsequent data reduction whatever the physical arrangement of probes on the chip.

A range of lengths of probes can be employed in the chips. As noted above, a probe may consist exclusively of a complementary segments, or may have one or more complementary segments juxtaposed by flanking, trailing and/or intervening segments. In the latter situation, the total length of complementary segment(s) is more important that the length of the probe. In functional terms, the complementary segment(s) of the first probe sets should be sufficiently long to allow the probe to hybridize detectably more strongly to a reference sequence compared with a variant of the reference including a single base mutation at the nucleotide corresponding to the interrogation position of the probe. Similarly, the complementary segment(s) in corresponding probes from additional probe sets should be sufficiently long to allow a probe to hybridize detectably more strongly to a variant of the reference sequence having a single nucleotide substitution at the interrogation position relative to the reference sequence. A probe usually has a single complementary segment having a length of at least 3 nucleotides, and more usually at least 5, 6, 7, 8, 9, 10, 11, 12, 13, 14, 15, 16, 17, 18, 19, 20, 21, 22, 23, 24, 25 or 30 bases exhibiting perfect complementarity (other than possibly at the interrogation position(s) depending on the probe set) to the reference sequence. In bridging strategies, where more than one segment of complementarity is present, each segment provides at least three complementary nucleotides to the reference sequence and the combined segments provide at least two segments of three or a total of six complementary nucleotides. As in the other strategies, the combined length of complementary segments is typically from 6–30 nucleotides, and preferably from about 9–21 nucleotides. The two segments are often approximately the same length. Often, the probes (or segment of complementarity within probes) have an odd number of bases, so that an interrogation position can occur in the exact center of the probe.

In some chips, all probes are the same length. Other chips employ different groups of probe sets, in which case the probes are of the same size within a group, but differ between different groups. For example, some chips have one group comprising four sets of probes as described above in which all the probes are 11 mers, together with a second group comprising four sets of probes in which all of the probes are 13 mers. Of course, additional groups of probes can be added. Thus, some chips contain, e.g., four groups of probes having sizes of 11 mers, 13 mers, 15 mers and 17 mers. Other chips have different size probes within the same group of four probe sets. In these chips, the probes in the first set can vary in length independently of each other. Probes in the other sets are usually the same length as the probe occupying the same column from the first set. However, occasionally different lengths of probes can be included at the same column position in the four lanes. The different length probes are included to equalize hybridization signals from probes irrespective of whether A-T or C-G bonds are formed at the interrogation position.

The length of probe can be important in distinguishing between a perfectly matched probe and probes showing a single-base mismatch with the target sequence. The discrimination is usually greater for short probes. Shorter probes are usually also less susceptible to formation of secondary structures. However, the absolute amount of target sequence bound, and hence the signal, is greater for larger probes. The probe length representing the optimum compromise between these competing considerations may vary depending on inter alia the GC content of a particular region of the target DNA sequence, secondary structure, synthesis efficiency and cross-hybridization. In some regions of the target, depending on hybridization conditions, short probes (e.g., 11 mers) may provide information that is inaccessible from longer probes (e.g., 19 mers) and vice versa. Maximum sequence information can be read by including several groups of different sized probes on the chip as noted above. However, for many regions of the target sequence, such a strategy provides redundant information in that the same sequence is read multiple times from the different groups of probes. Equivalent information can be obtained from a single group of different sized probes in which the sizes are selected to maximize readable sequence at particular regions of the target sequence. The appropriate size of probes at different regions of the target sequence can be determined from, e.g., FIG. 12, which compares the readability of different sized probes in different regions of a target. The strategy of customizing probe length within a single group of probe sets minimizes the total number of probes required to read a particular target sequence. This leaves ample capacity for the chip to include probes to other reference sequences.

The invention provides an optimization block which allows systematic variation of probe length and interrogation position to optimize the selection of probes for analyzing a particular nucleotide in a reference sequence. The block comprises alternating columns of probes complementary to the wildtype target and probes complementary to a specific mutation. The interrogation position is varied between columns and probe length is varied down a column. Hybridization of the chip to the reference sequence or the mutant form of the reference sequence identifies the probe length and interrogation position providing the greatest differential hybridization signal.

Variation of interrogation position in probes for analyzing different regions of a target sequence offers a number of advantages. If a segment of a target sequence contains two closely spaced mutations, m1, and m2, and probes for analyzing that segment have an interrogation position at or near the middle, then no probe has an interrogation position aligned with one of the mutations without overlapping the other mutation (see first probe in FIG. 4B). Thus, the presence of a mutation would have to be detected by comparing the hybridization signal of a single-mismatched probe with a double-mismatched probe. By contrast, if the interrogation position is near the 3' end of the probes, probes can have their interrogation position aligned with m1 without overlapping m2 (second probe in FIG. 4B). Thus, the mutation can be detected by a comparison of a perfectly matched probe with single based mismatched probes. Similarly, if the interrogation position is near the 5' end of the probes, probes can have their interrogation position aligned with m2 without overlapping m1 (third probe in FIG. 4B).

Variation of the interrogation position also offers the advantage of reducing loss of signal due to self-annealing of certain probes. FIG. 4C shows a target sequence having a nucleotide X, which can be read either from the relative signals of the four probes having a central interrogation position (shown at the left of the figure) or from the four probes having the interrogation position near the three prime end (shown at the right of the figure). Only the probes having the central interrogation position are capable of self-annealing. Thus, a higher signal is obtained from the probes having the interrogation position near the terminus.

The probes are designed to be complementary to either strand of the reference sequence (e.g., coding or noncoding). Some chips contain separate groups of probes, one complementary to the coding strand, the other complementary to the noncoding strand. Independent analysis of coding and noncoding strands provides largely redundant information. However, the regions of ambiguity in reading the coding strand are not always the same as those in reading the noncoding strand. Thus, combination of the information from coding and noncoding strands increases the overall accuracy of sequencing.

Some chips contain additional probes or groups of probes designed to be complementary to a second reference sequence. The second reference sequence is often a subsequence of the first reference sequence bearing one or more commonly occurring mutations or interstrain variations. The second group of probes is designed by the same principles as described above except that the probes exhibit complementarity to the second reference sequence. The inclusion of a second group is particular useful for analyzing short subsequences of the primary reference sequence in which multiple mutations are expected to occur within a short distance commensurate with the length of the probes (i.e., two or more mutations within 9 to 21 bases). Of course, the same principle can be extended to provide chips containing groups of probes for any number of reference sequences. Alternatively, the chips may contain additional probe(s) that do not form part of a tiled array as noted above, but rather serves as probe(s) for a conventional reverse dot blot. For example, the presence of mutation can be detected from binding of a target sequence to a single oligomeric probe harboring the mutation. Preferably, an additional probe containing the equivalent region of the wildtype sequence is included as a control.

Although only a subset of probes is required to analyze a particular target sequence, it is quite possible that other probes superfluous to the contemplated analysis are also included on the chip. In the extreme case, the chip could can a complete set of all probes of a given length notwithstanding that only a small subset is required to analyze the particular reference sequence of interest. Although such a situation might appear wasteful of resources, a chip including a complete set of probes offers the advantage of including the appropriate subset of probes for analyzing any reference sequence. Such a chip also allows simultaneous analysis of a reference sequence from different subsets of probes (e.g., subsets having the interrogation site at different positions in the probe).

In its simplest terms, the analysis of a chip reveals whether the target sequence is the same or different from the reference sequence. If the two are the same, all probes in the first probe set show a stronger hybridization signal than corresponding probes from other probe sets. If the two are different, most probes from the first probe set still show a stronger hybridization signal than corresponding probes from the other probe sets, but some probes from the first probe set do not. Thus, when a probe from another probe sets light up more strongly than the corresponding probe from the first probe set, this provides a simple visual indication that the target sequence and reference sequence differ.

Figure 6:
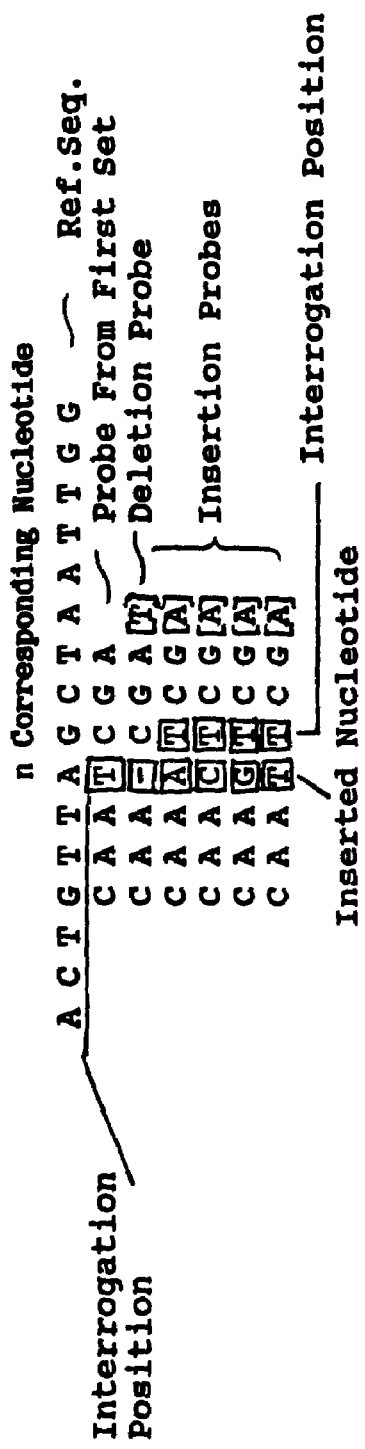
FIG. 6: Strategies for detecting deletion and insertion mutations. Bases in brackets may or may not be present. The reference sequence is SEQ. ID. No. 478.

The chips also reveal the nature and position of differences between the target and reference sequence. The chips are read by comparing the intensities of labelled target bound to the probes in an array. Specifically, for each nucleotide of interest in the target sequence, a comparison is performed between probes having an interrogation position aligned with that position. These probes form a column (actual or conceptual) on the chip. For example, a column often contains one probe from each of A, C, G and T lanes. The nucleotide in the target sequence is identified as the complement of the nucleotide occupying the interrogation position in the probe showing the highest hybridization signal from a column. FIG. 6 shows the hybridization pattern of a chip hybridized to its reference sequence. The dark square in each column represents the probe from the column having the highest hybridization signal. The sequence can be read by following the pattern of dark squares from left to right across the chip. The first dark square is in the A lane indicating that the nucleotide occupying the interrogation position of the probe represented by this square is an A. The first nucleotide in the reference sequence is the complement of nucleotide occupying the interrogation position of this probe (i.e., a T). Similarly, the second dark square is in the T-lane, from which it can be deduced that the second nucleotide in the reference sequence is an A. Likewise the third dark square is in the T-lane, from which it can be deduced that the third nucleotide in the reference sequence is also an A, and so forth. By including probes in the first probe set (and by implication in the other probe sets) with interrogation positions corresponding to every nucleotide in a reference sequence, it is possible to read substantially every nucleotide in a target sequence, thereby revealing the complete or nearly complete sequence of the target.

Of the four probes in a column, only one can exhibit a perfect match to the target sequence whereas the others usually exhibit at least a one base pair mismatch. The probe exhibiting a perfect match usually produces a substantially greater hybridization signal than the other three probes in the column and is thereby easily identified. However, in some regions of the target sequence, the distinction between a perfect match and a one-base mismatch is less clear. Thus, a call ratio is established to define the ratio of signal from the best hybridizing probes to the second best hybridizing probe that must be exceeded for a particular target position to be read from the probes. A high call ratio ensures that few if any errors are made in calling target nucleotides, but can result in some nucleotides being scored as ambiguous, which could in fact be accurately read. A lower call ratio results in fewer ambiguous calls, but can result in more erroneous calls. It has been found that at a call ratio of 1.2 virtually all calls are accurate. However, a small but significant number of bases (e.g., up to about 10%) may have to be scored as ambiguous.

Although small regions of the target sequence can sometimes be ambiguous, these regions usually occur at the same or similar segments in different target sequences. Thus, for precharacterized mutations, it is known in advance whether that mutation is likely to occur within a region of unambiguously determinable sequence.

An array of probes is most useful for analyzing the reference sequence from which the probes were designed and variants of that sequence exhibiting substantial sequence similarity with the reference sequence (e.g., several single-base mutants spaced over the reference sequence). When an array is used to analyze the exact reference sequence from which it was designed, one probe exhibits a perfect match to the reference sequence, and the other three probes in the same column exhibits single-base mismatches. Thus, discrimination between hybridization signals is usually high and accurate sequence is obtained. High accuracy is also obtained when an array is used for analyzing a target sequence comprising a variant of the reference sequence that has a single mutation relative to the reference sequence, or several widely spaced mutations relative to the reference sequence. At different mutant loci, one probe exhibits a perfect match to the target, and the other three probes occupying the same column exhibit single-base mismatches, the difference (with respect to analysis of the reference sequence) being the lane in which the perfect match occurs.

For target sequences showing a high degree of divergence from the reference strain or incorporating several closely spaced mutations from the reference strain, a single group of probes (i.e., designed with respect to a single reference sequence) will not always provide accurate sequence for the highly variant region of this sequence. At some particular columnar positions, it may be that no single probe exhibits perfect complementarity to the target and that any comparison must be based on different degrees of mismatch between the four probes. Such a comparison does not always allow the target nucleotide corresponding to that columnar position to be called. Deletions in target sequences can be detected by loss of signal from probes having interrogation positions encompassed by the deletion. However, signal may also be lost from probes having interrogation positions closely proximal to the deletion resulting in some regions of the target sequence that cannot be read. Target sequence bearing insertions will also exhibit short regions including and proximal to the insertion that usually cannot be read.

The presence of short regions of difficult-to-read target because of closely spaced mutations, insertions or deletions, does not prevent determination of the remaining sequence of the target as different regions of a target sequence are determined independently. Moreover, such ambiguities as might result from analysis of diverse variants with a single group of probes can be avoided by including multiple groups of probe sets on a chip. For example, one group of probes can be designed based on a full-length reference sequence, and the other groups on subsequences of the reference sequence incorporating frequently occurring mutations or strain variations.

A particular advantage of the present sequencing strategy over conventional sequencing methods is the capacity simultaneously to detect and quantify proportions of multiple target sequences. Such capacity is valuable, e.g., for diagnosis of patients who are heterozygous with respect to a gene or who are infected with a virus, such as HIV, which is usually present in several polymorphic forms. Such capacity is also useful in analyzing targets from biopsies of tumor cells and surrounding tissues. The presence of multiple target sequences is detected from the relative signals of the four probes at the array columns corresponding to the target nucleotides at which diversity occurs. The relative signals of the four probes for the mixture under test are compared with the corresponding signals from a homogeneous reference sequence. An increase in a signal from a probe that is mismatched with respect to the reference sequence, and a corresponding decrease in the signal from the probe which is matched with the reference sequence, signal the presence of a mutant strain in the mixture. The extent in shift in hybridization signals of the probes is related to the proportion of a target sequence in the mixture. Shifts in relative hybridization signals can be quantitatively related to proportions of reference and mutant sequence by prior calibration of the chip with seeded mixtures of the mutant and reference sequences. By this means, a chip can be used to detect variant or mutant strains constituting as little as 1, 5, 20, or 25% of a mixture of stains.

Similar principles allow the simultaneous analysis of multiple target sequences even when none is identical to the reference sequence. For example, with a mixture of two target sequences bearing first and second mutations, there would be a variation in the hybridization patterns of probes having interrogation positions corresponding to the first and second mutations relative to the hybridization pattern with the reference sequence. At each position, one of the probes having a mismatched interrogation position relative to the reference sequence would show an increase in hybridization signal, and the probe having a matched interrogation position relative to the reference sequence would show a decrease in hybridization signal. Analysis of the hybridization pattern of the mixture of mutant target sequences, preferably in comparison with the hybridization pattern of the reference sequence, indicates the presence of two mutant target sequences, the position and nature of the mutation in each strain, and the relative proportions of each strain.

In a variation of the above method, several target sequences target sequences are differentially labelled before being simultaneously applied to the array. For example, each different target sequence can be labelled with a fluorescent labels emitting at different wavelength. After applying a mixtures of target sequence to the arrays, the individual target sequences can be distinguished and independently analyzed by virture of the differential labels. For example, the methods target sequences obtained from a patient at different stages of a disease can be differently labelled and analyzed simultaneously, facilitating identification of new mutations.

2. Omission of Probes

The basic strategy outlined above employs four probes to read each nucleotide of interest in a target sequence. One probe (from the first probe set) shows a perfect match to the reference sequence and the other three probes (from the second, third and fourth probe sets) exhibit a mismatch with the reference sequence and a perfect match with a target sequence bearing a mutation at the nucleotide of interest. The provision of three probes from the second, third and fourth probe sets allows detection of each of the three possible nucleotide substitutions of any nucleotide of interest. However, in some reference sequences or regions of reference sequences, it is known in advance that only certain mutations are likely to occur. Thus, for example, at one site it might be known that an A nucleotide in the reference sequence may exist as a T mutant in some target sequences but is unlikely to exist as a C or G mutant. Accordingly, for analysis of this region of the reference sequence, one might include only the first and second probe sets, the first probe set exhibiting perfect complementarity to the reference sequence, and the second probe set having an interrogation position occupied by an invariant A residue (for detecting the T mutant). In other situations, one might include the first, second and third probes sets (but not the fourth) for detection of a wildtype nucleotide in the reference sequence and two mutant variants thereof in target sequences. In some chips, probes that would detect silent mutations (i.e., not affecting amino acid sequence) are omitted.

Figure 3B:
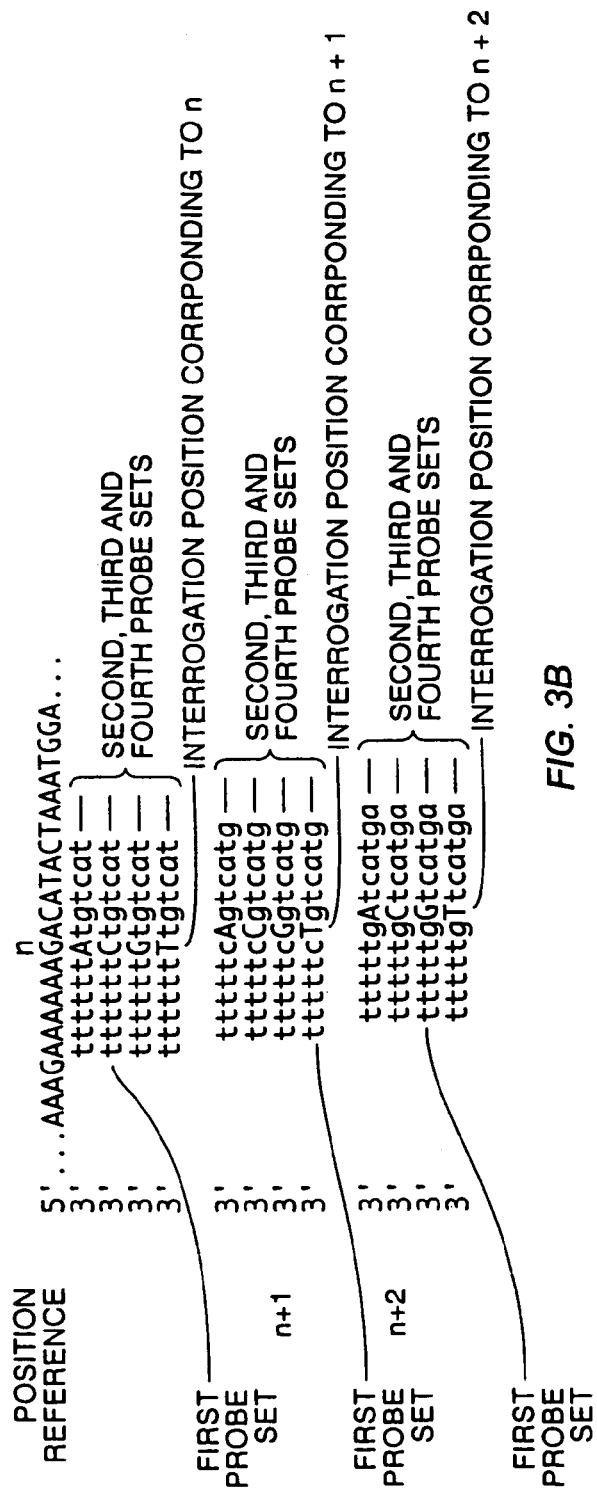
FIG. 3B: Arrangement of probe sets (SEQ ID NOS: 481–488, and 582–585) in tiling arrays lacking a perfectly matched probe set vs. a reference sequence (SEQ ID NO:581).
Figure 5:
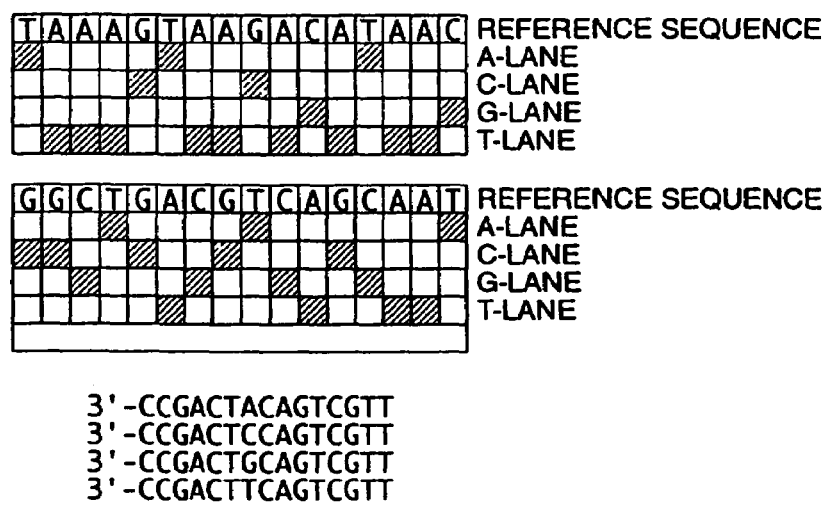
FIG. 5: Hybridization pattern of chip having probes laid down in lanes. Dark patches indicate hybridization. The probes in the lower part of the figure (SEQ. ID. Nos. 496–499) occur at the column of the array indicated by the arrow when the probes length is 15 and the interrogation position 7. The reference sequences are SEQ. ID. Nos. 494 and 495.

Some chips effectively contain the second, third and optionally, the fourth probes sets described in the basic tiling strategy (i.e., the mismatched probe sets) but omit some or all of the probes from the first probe set (i.e., perfectly matched probes). Therefore, such chips comprise at least two probe sets, which will arbitrarily be referred to as probe sets A and B (to avoid confusion with the nomenclature used to describe the four probe sets in the basic tiling strategy). Probe set A has a plurality of probes. Each probe comprises a segment exactly complementary to a subsequence of a reference sequence except in at least one interrogation position. The interrogation position corresponds to a nucleotide in the reference sequence juxtaposed with the interrogation position when the reference sequence and probe are maximally aligned. Probe set B has a corresponding probe for each probe in the first probe set. The corresponding probe in probe set B is identical to a sequence comprising the corresponding probe from the first probe set or a subsequence thereof that includes the at least one (and usually only one) interrogation position except that the at least one interrogation position is occupied by a different nucleotide in each of the two corresponding probes from the probe sets A and B. An additional probe set C, if present, also comprises a corresponding probe for each probe in the probe set A except in the at least one interrogation position, which differs in the corresponding probes from probe sets A, B and C. The arrangement of probe sets A, B and C is shown in FIG. 3B. FIG. 3B is the same as FIG. 3 except that the first probe set has been omitted and the second, third and fourth probe sets in FIG. 3 have been relabelled as probe sets A, B and C in FIG. 3B.

Chips lacking perfectly matched probes are preferably analyzed by hybridization to both target and reference sequences. The hybridizations can be performed sequentially, or, if the target and reference are differentially labelled, concurrently. The hybridization data are then analyzed in two ways. First, considering only the hybridization signals of the probes to the target sequence, one compares the signals of corresponding probes for each position of interest in the target sequence. For a position of mismatch with the reference sequence, one of the probes having an interrogation position aligned with that position in the target sequence shows a substantially higher signal than other corresponding probes. The nucleotide occupying the position of mismatch in the target sequence is the complement of the nucleotide occupying the interrogation position of the corresponding probe showing the highest signal. For a position where target and reference sequence are the same, none of the corresponding probes having an interrogation position aligned with that position in the target sequence is matched, and corresponding probes generally show weak signals, which may vary somewhat from each other.

In a second level of analysis, the ratio of hybridization signals to the target and reference sequences is determined for each probe in the array. For most probes in the array the ratio of hybridization signals is about the same. For such a probe, it can be deduced that the interrogation position of the probe corresponds to a nucleotide that is the same in target and reference sequences. A few probes show a much higher ratio of target hybridization to reference hybridization than the majority of probes. For such a probe, it can be deduced that the interrogation position of the probe corresponds to a nucleotide that differs between target and reference sequences, and that in the target, this nucleotide is the complement of the nucleotide occupying the interrogation position of the probe. The second level of analysis serves as a control to confirm the identification of differences between target and reference sequence from the first level of analysis.

3. Wildtype Probe Lane

When the chips comprise four probe sets, as discussed supra, and the probe sets are laid down in four lanes, an A lane, a C-lane, a G lane and a T or U lane, the probe having a segment exhibiting perfect complementarity to a reference sequence varies between the four lanes from one column to another. This does not present any significant difficulty in computer analysis of the data from the chip. However, visual inspection of the hybridization pattern of the chip is sometimes facilitated by provision of an extra lane of probes, in which each probe has a segment exhibiting perfect complementarity to the reference sequence. See FIG. 4. This extra lane of probes is called the wildtype lane and contains only probes from the first probe set. Each wildtype lane probe has a segment that is identical to a segment from one of the probes in the other four lanes (which lane depending on the column position). The wildtype lane hybridizes to a target sequence at all nucleotide positions except those in which deviations from the reference sequence occurs. The hybridization pattern of the wildtype lane thereby provides a simple visual indication of mutations.

4. Deletion, Insertion and Multiple-Mutation Probes

Some chips provide an additional probe set specifically designed for analyzing deletion mutations. The additional probe set comprises a probe corresponding to each probe in the first probe set as described above. However, a probe from the additional probe set differs from the corresponding probe in the first probe set in that the nucleotide occupying the interrogation position is deleted in the probe from the additional probe set. See FIG. 6. Optionally, the probe from the additional probe set bears an additional nucleotide at one of its termini relative to the corresponding probe from the first probe set (shown in brackets in FIG. 6). The probe from the additional probe set will hybridize more strongly than the corresponding probe from the first probe set to a target sequence having a single base deletion at the nucleotide corresponding to the interrogation position. Additional probe sets are provided in which not only the interrogation position, but also an adjacent nucleotide is deleted.

Similarly, other chips provide additional probe sets for analyzing insertions. For example, one additional probe set has a probe corresponding to each probe in the first probe set as described above. However, the probe in the additional probe set has an extra T nucleotide inserted adjacent to the interrogation position. See FIG. 6 (the extra T is shown in a square box). Optionally, the probe has one fewer nucleotide at one of its termini relative to the corresponding probe from the first probe set (shown in brackets). The probe from the additional probe set hybridizes more strongly than the corresponding probe from the first probe set to a target sequence having an A insertion to the left of nucleotide "n" the reference sequence in FIG. 6. Similar additional probe sets can be constructed having C, G or A nucleotides inserted adjacent to the interrogation position.

Usually, four such additional probe sets, one for each nucleotide, are used in combination. Comparison of the hybridization signal of the probes from the additional probe sets with the corresponding probe from the first probe set indicates whether the target sequence contains and insertion. For example, if a probe from one of the additional probe sets shows a higher hybridization signal than a corresponding probe from the first probe set, it is deduced that the target sequence contains an insertion adjacent to the corresponding nucleotide (n) in the target sequence. The inserted base in the target is the complement of the inserted base in the probe from the additional probe set showing the highest hybridization signal. If the corresponding probe from the first probe set shows a higher hybridization signal than the corresponding probes from the additional probe sets, then the target sequence does not contain an insertion to the left of corresponding position (("n" in FIG. 6)) in the target sequence.

Other chips provide additional probes (multiple-mutation probes) for analyzing target sequences having multiple closely spaced mutations. A multiple-mutation probe is usually identical to a corresponding probe from the first set as described above, except in the base occupying the interrogation position, and except at one or more additional positions, corresponding to nucleotides in which substitution may occur in the reference sequence. The one or more additional positions in the multiple mutation probe are occupied by nucleotides complementary to the nucleotides occupying corresponding positions in the reference sequence when the possible substitutions have occurred.

5. Block Tiling

In block tiling, a perfectly matched or wildtype probe is compared with multiple sets of mismatched or mutant probes. The perfectly matched probe and the multiple sets of mismatched probes with which it is compared collectively form a group or block of probes on the chip. Each set comprises at least one, and usually, three mismatched probes. FIG. 7 shows a perfectly matched probe (CAATCGA) having three interrogation positions ($I_1$, $I_2$ and $I_3$). The perfectly matched probe is compared with three sets of probes (arbitrarily designated A, B and C), each having three mutant probes. In set A, the three mutant probes are identical to a sequence comprising the wildtype probe or a subsequence thereof including the interrogation positions, except at the first interrogation position. That is, the mutant probes in the set A differ from the wildtype probe set at the first interrogation position. Thus, the relative hybridization signals of the wildtype probe and the mutant probes in the set A indicates the identity of the nucleotide in a target sequence corresponding to the first interrogation position. This nucleotide is the complement of the nucleotide occupying the interrogation position of the probe showing the highest signal. Similarly, set B comprises three mutant probes, that differ from the wildtype probe at the second interrogation position. The relative hybridization intensities of the wildtype probe and the three mutant probes of set B reveal the identity of the nucleotide in the target sequence corresponding to the second interrogation position (i.e., n2 in FIG. 7). Similarly, the three mutant probes in set C in FIG. 7 differ from the wildtype probe at the third interrogation position. Comparison of the hybridization intensities of the wildtype probe and the probes in the set C reveals the identity of the nucleotide in the target sequence corresponding to the third interrogation position (n3).

As noted above, a wildtype probe may have seven or more interrogation positions. If there are seven interrogation positions, there are seven sets of three mutant probe, each set serving to identify the nucleotide corresponding to one of the seven interrogation positions. Similarly, if there are 20 interrogation positions in the wildtype probe, then 20 sets of three mutant probes are employed. As in other tiling strategies, selected probes can be omitted if it is known in advance that only certain types of mutations are likely to arise.

Each block of probes allows short regions of a target sequence to be read. For example, for a block of probes having seven interrogation positions, seven nucleotides in the target sequence can be read. Of course, a chip can contain any number of blocks depending on how many nucleotides of the target are of interest. The hybridization signals for each block can be analyzed independently of any other block. The block tiling strategy can also be combined with other tiling strategies, with different parts of the same reference sequence being tiled by different strategies.

The block tiling strategy is a species of the basic tiling strategy discussed above, in which the probe from the first probe set has more than one interrogation position. The wildtype probe in the block tiling strategy is equivalent to a probe from the first probe set in the basic tiling strategy. The three mutant probes in set A in block tiling are equivalent to probes from the second, third and fourth probe sets in the basic tiling strategy. The three mutant probes in set B of block tiling are equivalent to probes from additional probe sets in basic tiling arbitrarily designated the fifth, sixth and seventh probe sets. The three mutant probes in set C of blocking tiling are equivalent to probes from three further probe sets in basic tiling arbitrarily designated the eighth, ninth and tenth probe sets.

The block tiling strategy offers two advantages over a basic strategy in which each probe in the first set has a single interrogation position. One advantage is that the same sequence information can be obtained from fewer probes. A second advantage is that each of the probes constituting a block (i.e., a probe from the first probe set and a corresponding probe from each of the other probe sets) can have identical 3' and 5' sequences, with the variation confined to a central segment containing the interrogation positions. The identity of 3' sequence between different probes simplifies the strategy for solid phase synthesis of the probes on the chip and results in more uniform deposition of the different probes on the chip, thereby in turn increasing the uniformity of signal to noise ratio for different regions of the chip.

6. Multiplex Tiling

In the block tiling strategy discussed above, the identity of a nucleotide in a target or reference sequence is determined by comparison of hybridization patterns of one probe having a segment showing a perfect match with that of other probes (usually three other probes) showing a single base mismatch. In multiplex tiling, the identity of at least two nucleotides in a reference or target sequence is determined by comparison of hybridization signal intensities of four probes, two of which have a segment showing perfect complementarity or a single base mismatch to the reference sequence, and two of which have a segment showing perfect complementarity or a double-base mismatch to a segment. The four probes whose hybridization patterns are to be compared each have a segment that is exactly complementary to a reference sequence except at two interrogation positions, in which the segment may or may not be complementary to the reference sequence. The interrogation positions correspond to the nucleotides in a reference or target sequence which are determined by the comparison of intensities. The nucleotides occupying the interrogation positions in the four probes are selected according to the following rule. The first interrogation position is occupied by a different nucleotide in each of the four probes. The second interrogation position is also occupied by a different nucleotide in each of the four probes. In two of the four probes, designated the first and second probes, the segment is exactly complementary to the reference sequence except at not more than one of the two interrogation positions. In other words, one of the interrogation positions is occupied by a nucleotide that is complementary to the corresponding nucleotide from the reference sequence and the other interrogation position may or may not be so occupied. In the other two of the four probes, designated the third and fourth probes, the segment is exactly complementary to the reference sequence except that both interrogation positions are occupied by nucleotides which are noncomplementary to the respective corresponding nucleotides in the reference sequence.

There are number of ways of satisfying these conditions depending on whether the two nucleotides in the reference sequence corresponding to the two interrogation positions are the same or different. If these two nucleotides are different in the reference sequence (probability ¾), the conditions are satisfied by each of the two interrogation positions being occupied by the same nucleotide in any given probe. For example, in the first probe, the two interrogation positions would both be A, in the second probe, both would be C, in the third probe, each would be G, and in the fourth probe each would be T or U. If the two nucleotides in the reference sequence corresponding to the two interrogation positions are different, the conditions noted above are satisfied by each of the interrogation positions in any one of the four probes being occupied by complementary nucleotides. For example, in the first probe, the interrogation positions could be occupied by A and T, in the second probe by C and G, in the third probe by G and C, and in the four probe, by T and A. See (FIG. 8).

When the four probes are hybridized to a target that is the same as the reference sequence or differs from the reference sequence at one (but not both) of the interrogation positions, two of the four probes show a double-mismatch with the target and two probes show a single mismatch. The identity of probes showing these different degrees of mismatch can be determined from the different hybridization signals. From the identity of the probes showing the different degrees of mismatch, the nucleotides occupying both of the interrogation positions in the target sequence can be deduced.

For ease of illustration, the multiplex strategy has been initially described for the situation where there are two nucleotides of interest in a reference sequence and only four probes in an array. Of course, the strategy can be extended to analyze any number of nucleotides in a target sequence by using additional probes. In one variation, each pair of interrogation positions is read from a unique group of four probes. In a block variation, different groups of four probes exhibit the same segment of complementarity with the reference sequence, but the interrogation positions move within a block. The block and standard multiplex tiling variants can of course be used in combination for different regions of a reference sequence. Either or both variants can also be used in combination with any of the other tiling strategies described.

7. Helper Mutations

Occasionally, small regions of a reference sequence give a low hybridization signal as a result of annealing of probes. The self-annealing reduces the amount of probe effectively available for hybridizing to the target. Although such regions of the target are generally small and the reduction of hybridization signal is usually not so substantial as to obscure the sequence of this region, this concern can be avoided by the use of probes incorporating helper mutations. A helper mutation refers to a position of mismatch in a probe other than at an interrogation position. The helper mutation(s) serve to break-up regions of internal complementarity within a probe and thereby prevent annealing. Usually, one or two helper mutations are quite sufficient for this purpose. The inclusion of helper mutations can be beneficial in any of the tiling strategies noted above. In general each probe having a particular interrogation position has the same helper mutation(s). Thus, such probes have a segment in common which shows perfect complementarity with a reference sequence, except that the segment contains at least one helper mutation (the same in each of the probes) and at least one interrogation position (different in all of the probes). For example, in the basic tiling strategy, a probe from the first probe set comprises a segment containing an interrogation position and showing perfect complementarity with a reference sequence except for one or two helper mutations. The corresponding probes from the second, third and fourth probe sets usually comprise the same segment (or sometimes a subsequence thereof including the helper mutation(s) and interrogation position), except that the base occupying the interrogation position varies in each probe. See FIG. 9.

Usually, the helper mutation tiling strategy is used in conjunction with one of the tiling strategies described above. The probes containing helper mutations are used to tile regions of a reference sequence otherwise giving low hybridization signal (e.g., because of self-complementarity), and the alternative tiling strategy is used to tile intervening regions.

8. Pooling Strategies

Pooling strategies also employ arrays of immobilized probes. Probes are immobilized in cells of an array, and the hybridization signal of each cell can be determined independently of any other cell. A particular cell may be occupied by pooled mixture of probes. Although the identity of each probe in the mixture is known, the individual probes in the pool are not separately addressable. Thus, the hybridization signal from a cell is the aggregate of that of the different probes occupying the cell. In general, a cell is scored as hybridizing to a target sequence if at least one probe occupying the cell comprises a segment exhibiting perfect complementarity to the target sequence.

A simple strategy to show the increased power of pooled strategies over a standard tiling is to create three cells each containing a pooled probe having a single pooled position, the pooled position being the same in each of the pooled probes. At the pooled position, there are two possible nucleotide, allowing the pooled probe to hybridize to two target sequences. In tiling terminology, the pooled position of each probe is an interrogation position. As will become apparent, comparison of the hybridization intensities of the pooled probes from the three cells reveals the identity of the nucleotide in the target sequence corresponding to the interrogation position (i.e., that is matched with the interrogation position when the target sequence and pooled probes are maximally aligned for complementarity).

The three cells are assigned probe pools that are perfectly complementary to the target except at the pooled position, which is occupied by a different pooled nucleotide in each probe as follows:

[AC]=M, [GT]=K, [AG]=R as substitutions in the probe

IUPAC standard ambiguity notation)
   X—interrogation position

Target (SEQ. ID. No.:1): TAACCACTCACGGGAGCA

| Pool 1: | (SEQ. ID. Nos. 2–4) | |
|---|---|---|
| | ATTGGMGAGTGCCC = | |
| | ATTGGaGAGTGCCC + | (complement to mutant 't') |
| | ATTGGcGAGTGCCC | (complement to mutant 'g') |
| Pool 2: | (SEQ. ID. Nos. 5–7) | |
| | ATTGGKGAGTGCCC = | |
| | ATTGGgGAGTGCCC + | (complement to mutant 'C') |
| | ATTGGtGAGTGCCC | (complement to wild type 'a') |
| Pool 3: | (SEQ. ID. Nos. 8, 3, and 6, respectively) | |
| | ATTGGRGAGTGCCC = | |
| | ATTGGaGAGTGCCC + | (complement to mutant 't') |
| | ATTGGgGAGTGCCC | (complement to mutant 'c') |

With 3 pooled probes, all 4 possible single base pair states (wild and 3 mutants) are detected. A pool hybridizes with a target if some probe contained within that pool is complementary to that target.

| | | Hybridization? | | |
|---|---|---|---|---|
| | | 1 | 2 | 3 |
| Pool: | | | | |
| Target | (SEQ. ID. No. 1): TAACCACTCACGGGAGCA | n | y | n |
| Mutant | (SEQ. ID. Nos. 9–11): TAACCcCTCACGGGAGCA | n | y | y |
| Mutant: | TAACCgCTCACGGGAGCA | y | n | n |
| Mutant: | TAACCtCTCACGGGAGCA | y | n | y |

A cell containing a pair (or more) of oligonucleotides lights up when a target complementary to any of the oligonucleotide in the cell is present. Using the simple strategy, each of the four possible targets (wild and three mutants) yields a unique hybridization pattern among the three cells.

Since a different pattern of hybridizing pools is obtained for each possible nucleotide in the target sequence corresponding to the pooled interrogation position in the probes, the identity of the nucleotide can be determined from the hybridization pattern of the pools. Whereas, a standard tiling requires four cells to detect and identify the possible single-base substitutions at one location, this simple pooled strategy only requires three cells.

A more efficient pooling strategy for sequence analysis is the 'Trellis' strategy. In this strategy, each pooled probe has a segment of perfect complementarity to a reference sequence except at three pooled positions. One pooled position is an N pool (IUPAC standard ambiguity code). The three pooled positions may or may not be contiguous in a probe. The other two pooled positions are selected from the group of three pools consisting of (1) M or K, (2) R or Y and (3) W or S, where the single letters are IUPAC standard ambiguity codes. The sequence of a pooled probe is thus, of the form XXXN[(M/K) or (R/Y) or (W/S)][(M/K) or (R/Y) or (W/S)]XXXXX, where XXX represents bases complementary to the reference sequence. The three pooled positions may be in any order, and may be contiguous or separated by intervening nucleotides. For, the two positions occupied by [(M/K) or (R/Y) or (W/S)], two choices must be made. First, one must select one of the following three pairs of pooled nucleotides (1) M/K, (2) R/Y and (3) W/S. The one of three pooled nucleotides selected may be the same or different at the two pooled positions. Second, supposing, for example, one selects M/K at one position, one must then choose between M or K. This choice should result in selection of a pooled nucleotide comprising a nucleotide that complements the corresponding nucleotide in a reference sequence, when the probe and reference sequence are maximally aligned. The same principle governs the selection between R and Y, and between W and S. A trellis pool probe has one pooled position with four possibilities, and two pooled positions, each with two possibilities. Thus, a trellis pool probe comprises a mixture of 16 (4×2×2) probes. Since each pooled position includes one nucleotide that complements the corresponding nucleotide from the reference sequence, one of these 16 probes has a segment that is the exact complement of the reference sequence. A target sequence that is the same as the reference sequence (i.e., a wildtype target) gives a hybridization signal to each probe cell. Here, as in other tiling methods, the segment of complementarity should be sufficiently long to permit specific hybridization of a pooled probe to a reference sequence be detected relative to a variant of that reference sequence. Typically, the segment of complementarity is about 9–21 nucleotides.

A target sequence is analyzed by comparing hybridization intensities at three pooled probes, each having the structure described above. The segments complementary to the reference sequence present in the three pooled probes show some overlap. Sometimes the segments are identical (other than at the interrogation positions). However, this need not be the case. For example, the segments can tile across a reference sequence in increments of one nucleotide (i.e., one pooled probe differs from the next by the acquisition of one nucleotide at the 5' end and loss of a nucleotide at the 3' end). The three interrogation positions may or may not occur at the same relative positions within each pooled probe (i.e., spacing from a probe terminus). All that is required is that one of the three interrogation positions from each of the three pooled probes aligns with the same nucleotide in the reference sequence, and that this interrogation position is occupied by a different pooled nucleotide in each of the three probes. In one of the three probes, the interrogation position is occupied by an N. In the other two pooled probes the interrogation position is occupied by one of (M/K) or (R/Y) or (W/S).

In the simplest form of the trellis strategy, three pooled probes are used to analyze a single nucleotide in the reference sequence. Much greater economy of probes is achieved when more pooled probes are included in an array. For example, consider an array of five pooled probes each having the general structure outlined above. Three of these pooled probes have an interrogation position that aligns with the same nucleotide in the reference sequence and are used to read that nucleotide. A different combination of three probes have an interrogation position that aligns with a different nucleotide in the reference sequence. Comparison of these three probe intensities allows analysis of this second nucleotide. Still another combination of three pooled probes from the set of five have an interrogation position that aligns with a third nucleotide in the reference sequence and these probes are used to analyze that nucleotide. Thus, three nucleotides in the reference sequence are fully analyzed from only five pooled probes. By comparison, the basic tiling strategy would require 12 probes for a similar analysis.

As an example, a pooled probe for analysis of a target sequence by the trellis strategy is shown below:

Target (SEQ. ID. No. 12): ATTAACCACTCACGG-GAGCTCT

Pool (SEQ. ID. No. 13): TGGTGNKYGCCCT

The pooled probe actually comprises 16 individual probes (SEQ. ID. Nos. 14–29):

TGGTGAGcGCCCT
+TGGTGcGcGCCCT
+TGGTGgGcGCCCT
+TGGTGtGcGCCCT
+TGGTGAtcGCCCT
+TGGTGctcGCCCT
+TGGTGgtcGCCCT
+TGGTGttcGCCCT
+TGGTGAGTGCCCT
+TGGTGcGTGCCCT
+TGGTGgGTGCCCT
+TGGTGtGTGCCCT
+TGGTGAtTGCCCT
+TGGTGctTGCCCT
+TGGTGgtTGCCCT
+TGGTGttTGCCCT The trellis strategy employs an array of probes having at least three cells, each of which is occupied by a pooled probe as described above.

Consider the use of three such pooled probes for analyzing a target sequence, of which one position may contain any single base substitution to the reference sequence (i.e, there are four possible target sequences to be distinguished). Three cells are occupied by pooled probes having a pooled interrogation position corresponding to the position of possible substitution in the target sequence, one cell with an 'N', one cell with one of 'M' or 'K', and one cell with 'R' or 'Y'. An interrogation position corresponds to a nucleotide in the target sequence if it aligns adjacent with that nucleotide when the probe and target sequence are aligned to maximize complementarity. Note that although each of the pooled probes has two other pooled positions, these positions are not relevant for the present illustration. The positions are only relevant when more than one position in the target sequence is to be read, a circumstance that will be considered later. For present purposes, the cell with the 'N' in the interrogation position lights up for the wildtype sequence and any of the three single base substitutions of the target sequence. The cell with M/K in the interrogation position lights up for the wildtype sequence and one of the single-base substitutions. The cell with R/Y in the interrogation position lights up for the wildtype sequence and a second of the single-base substitutions. Thus, the four possible target sequences hybridize to the three pools of probes in four distinct patterns, and the four possible target sequences can be distinguished.

To illustrate further, consider four possible target sequences (differing at a single position) and a pooled probe having three pooled positions, N, K and Y with the Y position as the interrogation position (i.e., aligned with the variable position in the target sequence):

Target

Wild (SEQ. ID. No. 12): ATTAACCACTCACGGGAGCTCT (w)

Mutants (SEQ. ID. No. 30): ATTAACCACTCcCGGGAGCTCT (c)

Mutants (SEQ. ID. No. 31): ATTAACCACTCgCGGGAGCTCT (g)

Mutants (SEQ. ID. No. 32): ATTAACCACTCtCGGGAGCTCT (t)

TGGTGNKYGCCCT (pooled probe) (SEQ. ID. No.:13).

The sixteen individual component probes (SEQ. ID. Nos. 14–23, 571, and 25–29, respectively) of the pooled probe hybridize to the four possible target sequences as follows:

|  | TARGET | | | |
| --- | --- | --- | --- | --- |
|  | w | c | g | t |
| TGGTGAGcGCCCT | n | n | y | n |
| TGGTGcGcGCCCT | n | n | n | n |
| TGGTGgGcGCCCT | n | n | n | n |
| TGGTGtGcGCCCT | n | n | n | n |
| TGGTGAtcGCCCT | n | n | n | n |
| TGGTGctcGCCCT | n | n | n | n |
| TGGTGgtcGCCCT | n | n | n | n |
| TGGTGttcGCCCT | n | n | n | n |
| TGGTGAGTGCCCT | y | n | n | n |
| TGGTGcGTGCCCT | n | n | n | n |
| TGGTGgGTGCCCT | n | n | n | n |
| TGGTGtGTGCCCT | n | n | n | n |
| TGGTGAtTGCCCT | n | n | n | n |
| TGGTGctTGCCCT | n | n | n | n |
| TGGTGgtTGCCCT | n | n | n | n |
| TGGTGttTGCCCT | n | n | n | n |

The pooled probe hybridizes according to the aggregate of its components:

Pool (SEQ. ID. No. 13): TGGTGNKYGCCCT y n y n

Thus, as stated above, it can be seen that a pooled probe having a y at the interrogation position hybridizes to the wildtype target and one of the mutants. Similar tables can be drawn to illustrate the hybridization patterns of probe pools having other pooled nucleotides at the interrogation position.

The above strategy of using pooled probes to analyze a single base in a target sequence can readily be extended to analyze any number of bases. At this point, the purpose of including three pooled positions within each probe will become apparent. In the example that follows, ten pools of probes, each containing three pooled probe positions, can be used to analyze a each of a contiguous sequence of eight nucleotides in a target sequence.

ATTAACCACTCACGGGAGCTCT Reference sequence (SEQ. ID. No.:12)

--------Readable nucleotides

Pools (SEQ. ID. Nos. 33–36, 13, and 37–41):

| 4 | TAATTNKYGAGTG |
| --- | --- |
| 5 | AATTGNKRAGTGC |
| 6 | ATTGGNKRGTGCC |
| 7 | TTGGTNMRTGCCC |
| 8 | TGGTGNKYGCCCT |
| 9 | GGTGANKRCCCTC |
| 10 | GTGAGNKYCCTCG |
| 11 | TGAGTNMYCTCGA |
| 12 | GAGTGNMYTCGAG |
| 13 | AGTGCNMYCGAGA |

In this example, the different pooled probes tile across the reference sequence, each pooled probe differing from the next by increments of one nucleotide. For each of the readable nucleotides in the reference sequence, there are three probe pools having a pooled interrogation position aligned with the readable nucleotide. For example, the 12th nucleotide from the left in the reference sequence is aligned with pooled interrogation positions in pooled probes 8, 9, and 10. Comparison of the hybridization intensities of these pooled probes reveals the identity of the nucleotide occupying position 12 in a target sequence.

|  |  | Pools | | |
| --- | --- | --- | --- | --- |
| Targets |  | 8 | 9 | 10 |
| Wild | (SEQ. ID. No. 12): ATTAACCACTCACGGGAGCTCT | Y | Y | Y |
| Mutants | (SEQ. ID. No. 30) ATTAACCACTCcCGGGAGCTCT | N | Y | Y |
| Mutants | (SEQ. ID. No. 31): ATTAACCACTCgCGGGAGCTCT | Y | N | Y |
| Mutants | (SEQ. ID. No. 32): ATTAACCACTCtCGGGAGCTCT | N | N | Y |

Example Intensities:

| = lit cell | Wild |
| --- | --- |
| = blank cell | 'C' |
|  | 'G' |
|  | 'T' |
|  | None |

Thus, for example, if pools 8, 9 and 10 all light up, one knows the target sequence is wildtype, If pools, 9 and 10 light up, the target sequence has a C mutant at position 12. If pools 8 and 10 light up, the target sequence has a G mutant at position 12. If only pool 10 lights up, the target sequence has a t mutant at position 12.

The identity of other nucleotides in the target sequence is determined by a comparison of other sets of three pooled probes. For example, the identity of the 13th nucleotide in the target sequence is determined by comparing the hybridization patterns of the probe pools designated 9, 10 and 11.

Similarly, the identity of the 14th nucleotide in the target sequence is determined by comparing the hybridization patterns of the probe pools designated 10, 11, and 12.

In the above example, successive probes tile across the reference sequence in increments of one nucleotide, and each probe has three interrogation positions occupying the same positions in each probe relative to the terminus of the probe (i.e., the 7, 8 and 9th positions relative to the 3' terminus). However, the trellis strategy does not require that probes tile in increments of one or that the interrogation position positions occur in the same position in each probe. In a variant of trellis tiling referred to as "loop" tiling, a nucleotide of interest in a target sequence is read by comparison of pooled probes, which each have a pooled interrogation position corresponding to the nucleotide of interest, but in which the spacing of the interrogation position in the probe differs from probe to probe. Analogously to the block tiling approach, this allows several nucleotides to be read from a target sequence from a collection of probes that are identical except at the interrogation position. The identity in sequence of probes, particularly at their 3' termini, simplifies synthesis of the array and result in more uniform probe density per cell.

To illustrate the loop strategy, consider a reference sequence of which the 4, 5, 6, 7 and 8th nucleotides (from the 3' termini are to be read. All of the four possible nucleotides at each of these positions can be read from comparison of hybridization intensities of five pooled probes. Note that the pooled positions in the probes are different (for example in probe 55, the pooled positions are 4, 5 and 6 and in probe 56, 5, 6 and 7).

TAACCACTCACGGGAGCA Reference sequence (SEQ ID No. 1)

(SEQ. ID. Nos. 42–46)

55 ATTNKYGAGTGCC

56 ATTGNKRAGTGCC

57 ATTGGNKRGTGCC

58 ATTRGTNMGTGCC

59 ATTKRTGNGTGCC

Each position of interest in the reference sequence is read by comparing hybridization intensities for the three probe pools that have an interrogation position aligned with the nucleotide of interest in the reference sequence. For example, to read the fourth nucleotide in the reference sequence, probes 55, 58 and 59 provide pools at the fourth position. Similarly, to read the fifth nucleotide in the reference sequence, probes 55, 56 and 59 provide pools at the fifth position. As in the previous trellis strategy, one of the three probes being compared has an N at the pooled position and the other two have M or K, and (2) R or Y and (3) W or S.

The hybridization pattern of the five pooled probes to target sequences representing each possible nucleotide substitution at five positions in the reference sequence is shown below. Each possible substitution results in a unique hybridization pattern at three pooled probes, and the identity of the nucleotide at that position can be deduced from the hybridization pattern.

| Targets | | | Pools | | | | |
|---|---|---|---|---|---|---|---|
| | | | 55 | 56 | 57 | 58 | 59 |
| Wild | (SEQ. ID. No. 1): TAACCACTCACGGGAGCA | | Y | Y | Y | Y | Y |
| Mutant | (SEQ. ID. No. 47): TAAgCACTCACGGGAGCA | | Y | N | N | N | N |
| Mutant | (SEQ. ID. No. 48): TAAtCACTCACGGGAGCA | | Y | N | N | Y | N |
| Mutant | (SEQ. ID. No. 49) TAAaCACTCACGGGAGCA | | Y | N | N | N | Y |
| Mutant | (SEQ. ID. No. 50): TAACgACTCACGGGAGCA | | N | Y | N | N | N |
| Mutant | (SEQ. ID. No. 51) TAACtACTCACGGGAGCA | | N | Y | N | N | Y |
| Mutant | (SEQ. ID. No. 52): TAACaACTCACGGGAGCA | | Y | Y | N | N | N |
| Mutant | (SEQ. ID. No. 9): TAACCcCTCACGGGAGCA | | N | Y | Y | N | N |
| Mutant | (SEQ. ID. No. 10) TAACCgCTCACGGGAGCA | | Y | N | Y | N | N |
| Mutant | (SEQ. ID. No. 11) TAACCtCTCACGGGAGCA | | N | N | Y | N | N |
| Mutant | (SEQ. ID. No. 53) TAACCAgTCACGGGAGCA | | N | N | N | Y | N |
| Mutant | (SEQ. ID. No. 54) TAACCAtTCACGGGAGCA | | N | Y | N | Y | N |
| Mutant | (SEQ. ID. No. 55) TAACCAaTCACGGGAGCA | | N | N | Y | Y | N |
| Mutant | (SEQ. ID. No. 56) TAACCACaCACGGGAGCA | | N | N | N | N | Y |
| Mutant | (SEQ. ID. No. 57) TAACCACcCACGGGAGCA | | N | N | Y | N | Y |
| Mutant | (SEQ. ID. No. 58) TAACCACgCACGGGAGCA | | N | N | N | Y | Y |

Many variations on the loop and trellis tilings can be created. All that is required is that each position in sequence must have a probe with a 'N', a probe containing one of R/Y, M/K or W/S, and a probe containing a different pool from that set, complementary to the wild type target at that position, and at least one probe with no pool at all at that position. This combination allows all mutations at that position to be uniquely detected and identified.

A further class of strategies involving pooled probes are termed coding strategies. These strategies assign code words from some set of numbers to variants of a reference sequence. Any number of variants can be coded. The variants can include multiple closely spaced substitutions, deletions or insertions. The designation letters or other symbols assigned to each variant may be any arbitrary set of numbers, in any order. For example, a binary code is often used, but codes to other bases are entirely feasible. The numbers are often assigned such that each variant has a designation having at least one digit and at least one nonzero value for that digit. For example, in a binary system, a variant assigned the number 101, has a designation of three digits, with one possible nonzero value for each digit.

The designation of the variants are coded into an array of pooled probes comprising a pooled probe for each nonzero value of each digit in the numbers assigned to the variants. For example, if the variants are assigned successive number in a numbering system of base m, and the highest number assigned to a variant has n digits, the array would have about n×(m−1) pooled probes. In general, $\log_m (3N+1)$ probes are required to analyze all variants of N locations in a reference sequence, each having three possible mutant substitutions. For example, 10 base pairs of sequence may be analyzed with only 5 pooled probes using a binary coding system.

Each pooled probe has a segment exactly complementary to the reference sequence except that certain positions are pooled. The segment should be sufficiently long to allow specific hybridization of the pooled probe to the reference sequence relative to a mutated form of the reference sequence. As in other tiling strategies, segments lengths of 9–21 nucleotides are typical. Often the probe has no nucleotides other than the 9–21 nucleotide segment. The pooled positions comprise nucleotides that allow the pooled probe to hybridize to every variant assigned a particular nonzero value in a particular digit. Usually, the pooled positions further comprises a nucleotide that allows the pooled probe to hybridize to the reference sequence. Thus, a wildtype target (or reference sequence) is immediately recognizable from all the pooled probes being lit.

When a target is hybridized to the pools, only those pools comprising a component probe having a segment that is exactly complementary to the target light up. The identity of the target is then decoded from the pattern of hybridizing pools. Each pool that lights up is correlated with a particular value in a particular digit. Thus, the aggregate hybridization patterns of each lighting pool reveal the value of each digit in the code defining the identity of the target hybridized to the array.

As an example, consider a reference sequence having four positions, each of which can be occupied by three possible mutations. Thus, in total there are 4×3 possible variant forms of the reference sequence. Each variant is assigned a binary number 0001-1100 and the wildtype reference sequence is assigned the binary number 1111.

| X | X | X | X - 4 Positions |
|---|---|---|---|
| Target: TAACCACGGGAGCA (SEQ. ID. No. 59) ||||
| C=1111 | A=1111 | C=1111 | T=1111 |
| G=0001 | C=0010 | G=0011 | A=0100 |
| T=0101 | G=0110 | T=0111 | C=1000 |
| A=1001 | T=1010 | A=1011 | G=1100 |

A first pooled probe is designed by including probes that complement exactly each variant having a 1 in the first digit.

```
target     TAAC  C  A  C  T CACGGGAGCA
(1111):                       (SEQ. ID. No. 1)
Mutant     TAAC  g  A  C  T CACGGGAGCA
(0001):                       (SEQ. ID. No. 50)
Mutant     TAAC  t  A  C  T CACGGGAGCA
(0101):                       (SEQ. ID. No. 51)
Mutant     TAAC  a  A  C  T CACGGGAGCA
(1001):                       (SEQ. ID. No. 52)
Mutant     TAAC  C  A  g  T CACGGGAGCA
(0011):                       (SEQ. ID. No. 53)
Mutant     TAAC  C  A  t  T CACGGGAGCA
(0111):                       (SEQ. ID. No. 54)
Mutant     TAAC  C  A  a  T CACGGGAGCA
(1101):                       (SEQ. ID. No. 55)
First pooled probe
      = ATTG [GCAT] T  [GCAT] A GTGCCC
      = ATTG   N    T    N    A GTGCCC
```

Second, third and fourth pooled probes are then designed respectively including component probes that hybridize to each variant having a 1 in the second, third and fourth digit.

| XXXX - 4 positions examined |||
|---|---|---|
| Target: TAACCACTCACGGGAGCA (SEQ. ID. No. 1) |||
| Pool 1(1) | (SEQ. ID. No. 60):  ATTGnTnAGTGCCC = 16 probes | (4x1x4x1) |
| Pool 2(2) | (SEQ. ID. No. 572): ATTGGnnAGTGCCC = 16 probes | (1x4x4x1) |
| Pool 3(4) | (SEQ. ID. No. 573): ATTGyrydGTGCCC = 24 probes | (2x2x2x3) |
| Pool 4(8) | (SEQ. ID. No. 574): ATTGmwmbGTGCCC = 24 probes | (2x2x2x3) |

The pooled probes hybridize to variant targets as follows: Hybridization pattern:

| | | Pools ||||
|---|---|---|---|---|---|
| | | 1 | 2 | 3 | 4 |
| Targets ||||||
| Wild(1111) | (SEQ. ID. No. 1): TAACCACTCACGGGAGCA | Y | Y | Y | Y |
| Mutant(0001) | (SEQ. ID. No. 50): TAACgACTCACGGGAGCA | Y | N | N | N |
| Mutant(0101) | (SEQ. ID. No. 51): TAACtACTCACGGGAGCA | Y | N | Y | N |
| Mutant(1001) | (SEQ. ID. No. 52): TAACaACTCACGGGAGCA | Y | N | N | Y |
| Mutant(0010) | (SEQ. ID. No. 9): TAACCcCTCACGGGAGCA | N | Y | N | N |
| Mutant(0110) | (SEQ. ID. No. 10): TAACCgCTCACGGGAGCA | N | Y | Y | N |
| Mutant(1010) | (SEQ. ID. No. 11): TAACCtCTCACGGGAGCA | N | Y | N | Y |
| Mutant(0011) | (SEQ. ID. No. 53): TAACCAgTCACGGGAGCA | Y | Y | N | N |
| Mutant(0111) | (SEQ. ID. No. 54): TAACCAtTCACGGGAGCA | Y | Y | Y | N |
| Mutant(1101) | (SEQ. ID. No. 55): TAACCAaTCACGGGAGCA | Y | N | Y | Y |
| Mutant(0100) | (SEQ. ID. No. 56): TAACCACaCACGGGAGCA | N | N | Y | N |
| Mutant(1000) | (SEQ. ID. No. 57): TAACCACcCACGGGAGCA | N | N | N | Y |
| Mutant(1100) | (SEQ. ID. No. 58): TAACCACgCACGGGAGCA | N | N | Y | Y |

The identity of a variant (i.e., mutant) target is read directly from the hybridization pattern of the pooled probes. For example the mutant assigned the number 0001 gives a hybridization pattern of NNNY with respect to probes 4, 3, 2 and 1 respectively.

In the above example, variants are assigned successive numbers in a numbering system. In other embodiments, sets of numbers can be chosen for their properties. If the codewords are chosen from an error-control code, the properties of that code carry over to sequence analysis. An error code is a numbering system in which some designations are assigned to variants and other designations serve to indicate errors that may have occurred in the hybridization process. For example, if all codewords have an odd number of nonzero digits ('binary coding+error detection'), any single error in hybridization will be detected by having an even number of pools lit.

Wild

Target: TAACCACTCACGGGAGCA (SEQ. ID. No. 1)

| Pool 1(1) | (SEQ. ID. No. 61): ATTGnAnAGTGCCC = | 16 Probes | (4x1x4x1) |
| Pool 2(2) | (SEQ. ID. No. 575): ATTGGnnAGTGCCC = | 16 Probes | (1X4X4X1) |
| Pool 3(4) | (SEQ. ID. No. 62): ATTGryrhGTGCCC = | 24 Probes | (2X2X2X3) |
| Pool 4(8) | (SEQ. ID. No. 63): ATTGkwkvGTGCCC = | 24 Probes | (2X2X2X3) |

A fifth probe can be added to make the number of pools that hybridize to any single mutation odd.

Pool 5(c) (SEQ. ID. No. 64):

| ATTGdhsmGTGCCC = | 36 probes | (2x2x3x3) |

Hybridization of pooled probes to targets

| | | Pool | | | | |
| Target | | 1 | 2 | 3 | 4 | 5 |
| --- | --- | --- | --- | --- | --- | --- |
| Target(11111) | (SEQ. ID. No. 1): TAACCACTCACGGGAGCA | Y | Y | Y | Y | Y |
| Mutant(00001) | (SEQ. ID. No. 50): TAACgACTCACGGGAGCA | Y | N | N | N | N |
| Mutant(10101) | (SEQ. ID. No. 51): TAACtACTCACGGGAGCA | Y | N | N | N | N |
| Mutant(11001) | (SEQ. ID. No. 52): TAACaACTCACGGGAGCA | Y | N | N | Y | Y |
| Mutant(00010) | (SEQ. ID. No. 9): TAACCcCTCACGGGAGCA | N | Y | N | N | N |
| Mutant(10110) | (SEQ. ID. No. 10): TAACCgCTCACGGGAGCA | N | Y | N | N | Y |
| Mutant(11010) | (SEQ. ID. No. 11): TAACCtCTCACGGGAGCA | N | Y | N | Y | Y |
| Mutant(10011) | (SEQ. ID. No. 53): TAACCAgTCACGGGAGCA | Y | Y | N | N | Y |
| Mutant(00111) | (SEQ. ID. No. 576): TAACAtTCACGGGAGCA | Y | Y | Y | N | N |
| Mutant(01101) | (SEQ. ID. No. 55): TAACCAaTCACGGGAGCA | Y | N | Y | Y | N |
| Mutant(00100) | (SEQ. ID. No. 56): TAACCACaCACGGGAGCA | N | N | Y | N | N |
| Mutant(01000) | (SEQ. ID. No. 57): TAACCAcCACGGGAGCA | N | N | N | Y | N |
| Mutant(11100) | (SEQ. ID. No. 58): TAACCACgCACGGGAGCA | N | N | Y | Y | Y |

9. Bridging Strategy

Probes that contain partial matches to two separate (i.e., non contiguous) subsequences of a target sequence sometimes hybridize strongly to the target sequence. In certain instances, such probes have generated stronger signals than probes of the same length which are perfect matches to the target sequence. It is believed (but not necessary to the invention) that this observation results from interactions of a single target sequence with two or more probes simultaneously. This invention exploits this observation to provide arrays of probes having at least first and second segments, which are respectively complementary to first and second subsequences of a reference sequence. Optionally, the probes may have a third or more complementary segments. These probes can be employed in any of the strategies noted above. The two segments of such a probe can be complementary to disjoint subsequences of the reference sequences or contiguous subsequences. If the latter, the two segments in the probe are inverted relative to the order of the complement of the reference sequence. The two subsequences of the reference sequence each typically comprises about 3 to 30 contiguous nucleotides. The subsequences of the reference sequence are sometimes separated by 0, 1, 2 or 3 bases. Often the sequences, are adjacent and nonoverlapping.

For example, a wild-type probe is created by complementing two sections of a reference sequence (indicated by subscript and superscript) and reversing their order. The interrogation position is designated (*) and is apparent from comparison of the structure of the wildtype probe with the three mutant probes. The corresponding nucleotide in the reference sequence is the "a" in the superscripted segment.

Reference (SEQ. ID. No. 65): 5'$T_{GGCTA}{}^{CGAGG}$AATCATCT-GTTA
*

Probes (SEQ. ID. Nos. 66–69):

```
3' GCTCC CCGAT    (Probe from first probe set)

3' GCACC CCGAT

3' GCCCC CCGAT

3' GCGCC CCGAT
```

The expected hybridizations are:

```
                                          (SEQ. ID. No. 66)
Match:     GCTCCCCGAT
                                          (SEQ. ID. No. 65)
           . . . TGGCTACGAGGAATCATCTGTTA
                                          (SEQ. ID. No. 66)
                  GCTCCCCGAT
                                          (SEQ. ID. No. 66)
Mismatch:  GCTCCCCGAT
                                          (SEQ. ID. No. 65)
           . . . TGGCTACGAGGAATCATCTGTTA
                                          (SEQ. ID. No. 69)
                  GCGCCCCGAT
```

Bridge tilings are specified using a notation which gives the length of the two constituent segments and the relative position of the interrogation position. The designation n/m indicates a segment complementary to a region of the reference sequence which extends for n bases and is located such that the interrogation position is in the mth base from the 5' end. If m is larger than n, this indicates that the entire segment is to the 5' side of the interrogation position. If m is negative, it indicates that the interrogation position is the absolute value of m bases 5' of the first base of the segment (m cannot be zero). Probes comprising multiple segments, such as n/m+a/b+ . . . have a first segment at the 3' end of the probe and additional segments added 5' with respect to the first segment. For example, a 4/8 tiling consists of (from the 3' end of the probe) a 4 base complementary segment, starting 7 bases 5' of the interrogation position, followed by a 6 base region in which the interrogation position is located at the third base. Between these two segments, one base from the reference sequence is omitted. By this notation, the set shown above is a 5/3+5/8 tiling. Many different tilings are possible with this method, since the lengths of both segments can be varied, as well as their relative position (they may be in either order and there may be a gap between them) and their location relative to the interrogation position.

As an example, a 16 mer oligo target was hybridized to a chip containing all $4^{10}$ probes of length 10. The chip includes short tilings of both standard and bridging types. The data from a standard 10/5 tiling was compared to data from a 5/3+5/8 bridge tiling (see Table 1). Probe intensities (mean count/pixel) are displayed along with discrimination ratios (correct probe intensity/highest incorrect probe intensity). Missing intensity values are less than 50 counts. Note that for each base displayed the bridge tiling has a higher discrimination value.

TABLE 1

Comparison of Standard and Bridge Tilings

| TILING | PROBE BASE: | CORRECT PROBE BASE | | | |
|---|---|---|---|---|---|
| | | C | A | C | C |
| STANDARD | A | 92 | 496 | 294 | 299 |
| (10/5) | C | 536 | 148 | 532 | 534 |
| | G | 69 | 167 | 72 | 52 |
| | T | 146 | 95 | 212 | 126 |
| DISCRIMINATION: | | 3.7 | 3.0 | 1.8 | 1.8 |
| BRIDGING | A | — | 404 | — | 156 |
| 5/3 + 5/8 | C | 276 | — | 345 | 379 |
| | G | — | 80 | — | — |
| | T | — | — | — | 58 |
| DISCRIMINATION: | | >5.5 | 5.1 | 2.4 | 1.26 |

The bridging strategy offers the following advantages:

(1) Higher discrimination between matched and mismatched probes, (2) The possibility of using longer probes in a bridging tiling, thereby increasing the specificity of the hybridization, without sacrificing discrimination, (3) The use of probes in which an interrogation position is located very off-center relative to the regions of target complementarity. This may be of particular advantage when, for example, when a probe centered about one region of the target gives low hybridization signal. The low signal is overcome by using a probe centered about an adjoining region giving a higher hybridization signal.

(4) Disruption of secondary structure that might result in annealing of certain probes (see previous discussion of helper mutations).

10. Deletion Tiling

Deletion tiling is related to both the bridging and helper mutant strategies described above. In the deletion strategy, comparisons are performed between probes sharing a common deletion but differing from each other at an interrogation position located outside the deletion. For example, a first probe comprises first and second segments, each exactly complementary to respective first and second subsequences of a reference sequence, wherein the first and second subsequences of the reference sequence are separated by a short distance (e.g., 1 or 2 nucleotides). The order of the first and second segments in the probe is usually the same as that of the complement to the first and second subsequences in the reference sequence. The interrogation position is usually separated from The comparison is performed with three other probes, which are identical to the first probe except at an interrogation position, which is different in each probe.

Reference(SEQ. ID. No. 70): . . . AGTACCAGATCT CTAA . . .

Probe set(SEQ. ID. No. 71): CATGGNC AGAGA (N=interrogation position).

Such tilings sometimes offer superior discrimination in hybridization intensities between the probe having an interrogation position complementary to the target and other probes. Thermodynamically, the difference between the hybridizations to matched and mismatched targets for the probe set shown above is the difference between a single-base bulge, and a large asymmetric loop (e.g., two bases of target, one of probe). This often results in a larger difference in stability than the comparison of a perfectly matched probe with a probe showing a single base mismatch in the basic tiling strategy.

The superior discrimination offered by deletion tiling is illustrated by Table 2, which compares hybridization data from a standard 10/5 tiling with a (4/8+6/3) deletion tiling of the reference sequence. (The numerators indicate the length of the segments and the denominators, the spacing of the deletion from the far termini of the segments.) Probe intensities (mean count/pixel) are displayed along with discrimination ratios (correct probe intensity/highest incorrect probe intensity). Note that for each base displayed the deletion tiling has a higher discrimination value than either standard tiling shown.

TABLE 2

Comparison of Standard and Deletion Tilings

| TILING | PROBE BASE: | CORRECT PROBE BASE | | | |
|---|---|---|---|---|---|
| | | C | A | C | C |
| STANDARD | A | 92 | 496 | 294 | 299 |
| (10/5) | C | 536 | 148 | 532 | 534 |
| | G | 69 | 167 | 72 | 52 |
| | T | 146 | 95 | 212 | 126 |
| DISCRIMINATION: | | 3.7 | 3.0 | 1.8 | 1.8 |
| | A | 6 | 412 | 29 | 48 |
| DELETION | C | 297 | 32 | 465 | 160 |
| 4/8 + 6/3 | G | 8 | 77 | 10 | 4 |
| | T | 8 | 26 | 31 | 5 |
| DISCRIMINATION: | | 37.1 | 5.4 | 15 | 3.3 |
| STANDARD | A | 347 | 533 | 228 | 277 |
| (10/7) | C | 729 | 194 | 536 | 496 |
| | G | 232 | 231 | 102 | 89 |
| | T | 344 | 133 | 163 | 150 |
| DISCRIMINATION: | | 2.1 | 2.3 | 2.3 | 1.8 |

The use of deletion or bridging probes is quite general. These probes can be used in any of the tiling strategies of the invention. As well as offering superior discrimination, the use of deletion or bridging strategies is advantageous for certain probes to avoid self-hybridization (either within a probe or between two probes of the same sequence)

11. Nucleotide Repeats

Recently a new form of human mutation, expansion of trinucleotide repeats, has been found to cause the diseases of fragile X-syndrome, spinal and bulbar atrophy, myotonic dystrophy and Huntington's disease. See Ross et al., TINS 16, 254–259 (1993). Long lengths of trinucleotide repeats are associated with the mutant form of a gene. The longer the length, the more severe the consequences of the mutation and the earlier the age of onset. The invention provides arrays and methods for analyzing the length of such repeats.

The different probes in such an array comprise different numbers of repeats of the complement of the trinucleotide repeat of interest. For example, one probe might be a trimer, having one copy of the repeat, a second probe might be a sixmer, having two copies of the repeat, and a third probe might be a ninmer having three copies, and so forth. The largest probes can have up to about sixty bases or 20 trinucleotide repeats.

The hybridization signal of such probes to a target of trinucleotide repeats is related to the length of the target. It has been found that on increasing the target size up to about the length of the probe, the hybridization signal shows a relatively large increase for each complete trinucleotide repeat unit in the target, and a small increase for each additional base in the target that does not complete a trinucleotide repeat. Thus, for example, the hybridization signals for different target sizes to a 20 mer probe show small increases as the target size is increased from 6–8 nucleotides and a larger increase as the target size is increased to 9 nucleotides.

Arrays of probes having different numbers of repeats are usually calibrated using known amounts of target of different length. For each target of known length, the hybridization intensity is recorded for each probe. Thus, each target size is defined by the relative hybridization signals of a series of probes of different lengths. The array is then hybridized to an unknown target sequence and the relative hybridization signals of the different sized probes are determined. Comparison of the relative hybridization intensity profile for different probes with comparable data for targets of known size allows interpolation of the size of the unknown target. Optionally, hybridization of the unknown target is performed simultaneously with hybridization of a target of known size labelled with a different color.

C. Preparation of Target Samples

The target polynucleotide, whose sequence is to be determined, is usually isolated from a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it is usually reverse transcribed to DNA. DNA samples or cDNA resulting from reverse transcription are usually amplified, e.g., by PCR. Depending on the selection of primers and amplifying enzyme(s), the amplification product can be RNA or DNA. Paired primers are selected to flank the borders of a target polynucleotide of interest. More than one target can be simultaneously amplified by multiplex PCR in which multiple paired primers are employed. The target can be labelled at one or more nucleotides during or after amplification. For some target polynucleotides (depending on size of sample), e.g., episomal DNA, sufficient DNA is present in the tissue sample to dispense with the amplification step.

When the target strand is prepared in single-stranded form as in preparation of target RNA, the sense of the strand should of course be complementary to that of the probes on the chip. This is achieved by appropriate selection of primers. The target is preferably fragmented before application to the chip to reduce or eliminate the formation of secondary structures in the target. The average size of targets segments following hybridization is usually larger than the size of probe on the chip.

II. Illustrative Chips

A. HIV Chip

HIV has infected a large and expanding number of people, resulting in massive health care expenditures. HIV can rapidly become resistant to drugs used to treat the infection, primarily due to the action of the heterodimeric protein (51 kDa and 66 kDa) HIV reverse transcriptase (RT) both subunits of which are encoded by the 1.7 kb pol gene. The high error rate (5–10 per round) of the RT protein is believed to account for the hypermutability of HIV. The nucleoside analogues, i.e., AZT, ddI, ddC, and d4T, commonly used to treat HIV infection are converted to nucleotide analogues by sequential phosphorylation in the cytoplasm of infected cells, where incorporation of the analogue into the viral DNA results in termination of viral replication, because the 5'->3' phosphodiester linkage cannot be completed. However, after about 6 months to 1 year of treatment or less, HIV typically mutates the RT gene so as to become incapable of incorporating the analogue and so resistant to treatment. Several mutations known to be associated with drug resistance are shown in the table below. After a virus having drug resistance via a mutation becomes predominant, the patient suffers dramatically increased viral load, worsening symptoms (typically more frequent and difficult-to-treat infections), and ultimately death. Switching to a different treatment regimen as soon as a resistant mutant virus takes hold may be an important step in patient management which prolongs patient life and reduces morbidity during life.

TABLE 3

SOME RT MUTATIONS ASSOCIATED WITH DRUG RESISTANCE

| ANTIVIRAL | CODON | aa CHANGE | nt CHANGE |
|---|---|---|---|
| AZT | 67 | Asp -> Asn | GAC -> AAC |
| AZT | 70 | Lys -> Arg | AAA -> AGA |
| AZT | 215 | Thr -> Phe or Tyr | ACC -> TTC or TAC |
| AZT | 219 | Lys -> Gln or Glu | AAA -> CAA or GAA |
| AZT | 41 | Met -> Leu | ATG -> TTG or CTG |
| ddI and ddC | 184 | Met -> Val | ATG -> GTG |
| ddI and ddC | 74 | Leu -> Val | |
| TIBO 82150 | 100 | Leu -> Ile | |
| ddC | 65 | Lys -> Asn | AAA -> AGA |
| ddC | 69 | Thr -> Asp | ACT -> GAT |
| 3TC | 184 | Met -> Val | ATG -> GTG or GTA |
| 3TC | 184 | Met -> Ile | ATG -> ATA |
| AZT + ddI | 62 | Ala -> Val | GCC -> GTC |
| AZT + ddI | 75 | Val -> Ile | GTA -> ATA |
| AZT + ddI | 77 | Phe -> Leu | TTC -> TTA |
| AZT + ddI | 116 | Phe -> Tyn | TTT -> TAT |
| AZT + ddI | 151 | Gln -> Met | CAG -> ATG |
| Nevaripine | 103 | Lys -> Asn | AAA -> AAT |
| | 106 | Val -> Ala | GTA -> GCA |
| | 108 | | |
| | 181 | Tyr -> Cys | TAT -> TGT |
| | 188 | Tyr -> His | TAT -> CAT |
| | 190 | Gly -> Ala | GGA -> GCA |

N.B. Other mutations confer resistance to other drugs.

A second important therapeutic target for anti-HIV drugs is the aspartyl protease enzyme encoded by the HIV genome, whose function is required for the formation of infectious progeny. See Robbins & Plattner, *J. Acquired Immune Deficiency Syndromes* 6, 162–170 (1993); Kozal et al., *Curr. Op. Infect. Dis.* 7:72–81 (1994). The protease function in processing of viral precursor polypeptides to their active forms. Drugs targeted against this enzyme do not impair endogenous human proteases, thereby achieving a high degree of selective toxicity. Moreover, the protease is expressed later in the life-cycle than reverse transcriptase, thereby offering the possibility of a combined attack on HIV at two different times in its life-cycle. As for drugs targeted against the reverse transcriptase, administration of drugs to the protease can result in acquisition of drug resistance through mutation of the protease. By monitoring the protease gene from patients, it is possible to detect the occurrence of mutations, and thereby make appropriate adjustments in the drug(s) being administered.

In addition to being infected with HIV, AIDS patients are often also infected with a wide variety of other infectious agents giving rise to a complex series of symptoms. Often diagnosis and treatment is difficult because many different pathogens (some life-threatening, others routine) cause similar symptoms. Some of these infections, so-called opportunistic infections, are caused by bacterial, fungal, protozoan or viral pathogens which are normally present in small quantity in the body, but are held in check by the immune system. When the immune system in AIDS patients fails, these normally latent pathogens can grow and generate rampant infection. In treating such patients, it would be desirable simultaneously to diagnose the presence or absence of a variety of the most lethal common infections, determine the most effective therapeutic regime against the HIV virus, and monitor the overall status of the patient's infection.

The present invention provides DNA chips for detecting the multiple mutations in HIV genes associated with resistance to different therapeutics. These DNA chips allow physicians to monitor mutations over time and to change therapeutics if resistance develops. Some chips also provide probes for diagnosis of pathogenic microorganisms that typically occur in AIDS patients.

The sequence selected as a reference sequence can be from anywhere in the HIV genome, but should preferably cover a region of the HIV genome in which mutations associated with drug resistance are known to occur. A reference sequence is usually between about 5, 10, 20, 50, 100, 5000, 1000, 5,000 or 10,000 bases in length, and preferably is about 100–1700 bases in length. Some reference sequences encompass at least part of the reverse transcriptase sequence encoded by the pol gene. Preferably, the reference sequence encompasses all, or substantially all (i.e, about 75 or 90%) of the reverse transcriptase gene. Reverse transcriptase is the target of several drugs and as noted, above, the coding sequence is the site of many mutations associated with drug resistance. In some chips, the reference sequence contains the entire region coding reverse transcriptase (850 bp), and in other chips, subfragments thereof. In some chips, the reference sequence includes other subfragments of the pol gene encoding HIV protease or endonuclease, instead of, or as well as the segment encoding reverse transcriptase. In some chips, the reference sequence also includes other HIV genes such as env or gag as well as or instead of the reverse transcriptase gene. Certain regions of the gag and env genes are relatively well conserved, and their detection provides a means for identifying and quantifying the amount of HIV virus infecting a patient. In some chips, the reference sequence comprises an entire HIV genome.

It is not critical from which strain of HIV the reference sequence is obtained. HIV strains are classified as HIV-I, HIV-II or HIV-III, and within these generic groupings there are several strains and polymorphic variants of each of these. BRU, SF2, HXB2, HXB2R are examples of HIV-1 strains, the sequences of which are available from GenBank. The reverse transcriptase genes of the BRU and SF2 strains differ at 23 nucleotides. The HXB2 and HXB2R strains have the same reverse transcriptase gene sequence, which differs from that of the BRU strain at four nucleotides, and that of SF2 by 27 nucleotides. In some chips, the reference sequence corresponds exactly to the reverse transcriptase sequence in the wildtype version of a strain. In other chips, the reference sequence corresponds to a consensus sequence of several HIV strains. In some chips, the reference sequence corresponds to a mutant form of a HIV strain.

Chips are designed in accordance with the tiling strategies noted above. The probes are designed to be complementary to either the coding or noncoding strand of the HIV reference sequence. If only one strand is to be read, it is preferable to read the coding strand. The greater percentage of A residues in this strand relative to the noncoding strand generally result in fewer regions of ambiguous sequence.

Some chips contain additional probes or groups of probes designed to be complementary to a second reference sequence. The second reference sequence is often a subsequence of the first reference sequence bearing one or more commonly occurring HIV mutations or interstrain variations (e.g., within codons 67, 70, 215 or 219 of the reverse transcriptase gene). The inclusion of a second group is particularly useful for analyzing short subsequences of the primary reference sequence in which multiple mutations are expected to occur within a short distance commensurate with the length of the probes (i.e., two or more mutations within 9 to 21 bases).

The total number of probes on the chips depends on the tiling strategy, the length of the reference sequence and the options selected with respect to inclusion of multiple probe lengths and secondary groups of probes to provide confirmation of the existence of common mutations. To read much or all of the HIV reverse transcriptase gene (857 b for the BRU strain), chips tiled by the basic strategy typically contain at least 857×4=3428 probes.

The target HIV polynucleotide, whose sequence is to be determined, is usually isolated from blood samples (peripheral blood lymphocytes or PBMC) in the form of RNA. The RNA is reverse transcribed to DNA, and the DNA product is then amplified. Depending on the selection of primers and amplifying enzyme, the amplification product can be RNA or DNA. Suitable primers for amplification of target are shown in the table below.

TABLE 4

AMPLIFICATION OF TARGET

| TARGET SIZE | FORWARD PRIMER | REVERSE PRIMER |
| --- | --- | --- |
| 1,742 bp | GTAGAATTCTGTTGACTCAGATTGG (SEQ. ID. No. 72) | GATAAGCTTGGGCCTTATCTATTCCAT (SEQ. ID. No. 74) |
| 535 bp | AAATCCATACAATACTCCAGTATTTGC (SEQ. ID. No. 73) | ACCCATCCAAAGGAATGGAGGTTCTTTC (SEQ. ID. No. 75) |
| 323 bp | Genbank # K02013 1889–1908 AATTAACCCTCACTAAAGGGAga ggaagaatctgttgactcagattggt (RT#1-T3) (SEQ. ID. No. 76) AATTAACCCTCACTAAAGGGAga agtatactgcattaccatacctagta (RT#3-T3) | bases 2211–2192 AATTTAATACGACTCACTATAGGGAttttccccac taacttctgtatgtcattgaca-3' (89-391 T7) (SEQ. ID. No. 77) |

TABLE 4-continued

AMPLIFICATION OF TARGET

| TARGET SIZE | FORWARD PRIMER | REVERSE PRIMER |
|---|---|---|
| | (SEQ. ID. No. 78) TAATACGACTCACTATAGGGAGA tcgacgcaggactcggcttgctgaa (HV1-T2) (SEQ. ID. No. 79) AATTAACCCTCACTAAAGGGAGA ccttgtaagtcattggtcttaaaggta (HV2-T3) (SEQ. ID. No. 80) | |

In another aspect of the invention, chips are provided for simultaneous detection of HIV and microorganisms that commonly parasitize AIDS patients (e.g., cytomegalovirus (CMV), *Pneumocystis carini* (PCP), fungi (*candida albicans*), mycobacteria). Non-HIV viral pathogens are detected and their drug resistance determined using a similar strategy as for HIV. That is groups of probes are designed to show complementarity to a target sequence from a region of the genome of a nonviral pathogen known to be associated with acquisition of drug resistance. For example, CMV and HSV viruses, which frequently co-parasitize AIDS patients, undergo mutations to acquire resistance to acyclovir.

For detection of non-viral pathogens, the chips include an array of probes which allow full-sequence determination of 16S ribosomal RNA or corresponding genomic DNA of the pathogens. The additional probes are designed by the same principles as described above except that the target sequence is a variable region from a 16S RNA (or corresponding DNA) of a pathogenic microorganism. Alternatively, the target sequence can be a consensus sequences of variable 16S rRNA regions from multiple organisms. 16S ribosomal DNA and RNA is present in all organisms (except viruses) and the sequence of the DNA or RNA is closely related to the evolutionary genetic distance between any two species. Hence, organisms which are quite close in type (e.g., all mycobacteria) share a common region of 16S rDNA, and differ in other regions (variable regions) of the 16S rRNA. These differences can be exploited to allow identification of the different subtype strains. The full sequence of 16S ribosomal RNA or DNA read from the chip is compared against a database of the sequence of thousands of known pathogens to type unambiguously most nonviral pathogens infecting AIDS patients.

In a further embodiment, the invention provides chips which also contain probes for detection of bacterial genes conferring antibiotic resistance. An antibiotic resistance gene can be detected by hybridization to a single probe employed in a reverse dot blot format. Alternatively, a group of probes can be designed according to the same principles discussed above to read all or part the DNA sequence encoding an antibiotic resistance gene. Analogous probes groups are designed for reading other antibiotic resistance gene sequences. Antibiotic resistance frequently resides in one of the following genes in microorganisms coparasitizing AIDS patients: rpoB (encoding RNA polymerase), katG (encoding catalase peroxidase, and DNA gyrase A and B genes.

The inclusion of probes for combinations of tests on a single chip simulates the clinical diagnosis tree that a physician would follow based on the presentation of a given syndrome which could be caused by any number of possible pathogens. Such chips allow identification of the presence and titer of HIV in a patient, identification of the HIV strain type and drug resistance, identification of opportunistic pathogens, and identification of the drug resistance of such pathogens. Thus, the physician is simultaneously apprised of the full spectrum of pathogens infecting the patient and the most effective treatments therefor.

Exemplary HIV Chips (a) HV 273

The HV 273 chip contains an array of oligonucleotide probes for analysis of an 857 base HIV amplicon between nucleotides 2090 and 2946 (HIVBRU strain numbering). The chip contains four groups of probes: 11 mers, 13 mers, 15 mers and 17 mers. From top to bottom, the HV 273 chip is occupied by rows of 11 mers, followed by rows of 13 mers, followed by rows of 15 mers followed by rows of 17 mers. The interrogation position is nucleotide 6, 7, 8 and 9 respectively in the different sized chips. This arrangement of the different sized probes is referred to as being "in series." Within each size group, there are four probe sets laid down in an A-lane, a C-lane a G-lane and a T-lane respectively. Each lane contains an overlapping series of probes with one probe for each nucleotide in the 2090–2946 HIV reverse transcriptase reference sequence. (i.e., 857 probes per lane). The lanes also include a few column positions which are empty or occupied by control probes. These positions serve to orient the chip, determine background fluorescence and punctuate different subsequences within the target. The chip has an area of 1.28×1.28 cm, within which the probes form a 130×135 matrix (17,550 cells total). The area occupied by each probe (i.e., a probe cell) is about 98×95 microns.

The chip was tested for its capacity to sequence a reverse transcriptase fragment from the HIV strain SF2. An 831 bp RNA fragment (designated pPol19) spanning most of the HIV reverse transcriptase coding sequence was amplified by PCR, using primers tagged with T3 and T7 promoter sequences. The primers, designated RT#1-T3 and 89-391 T7 are shown in Table 4; see also Gingeras et al., *J. Inf. Dis.* 164, 1066–1074 (1991) (incorporated by reference in its entirety for all purposes). RNA was labelled by incorporation of fluorescent nucleotides. The RNA was fragmented by heating and hybridized to the chip for 40 min at 30 degrees. Hybridization signals were quantified by fluorescence imaging.

Taking the best data from the four probes sets at each position in the target sequence, 715 out of 821 bases were read correctly (87%). (Comparisons are based on the sequence of pPol19 determined by the conventional dideoxy method to be identical to SF2). In general, the longer sized probes yielded more sequence than the shorter probes. Of the 21 positions at which the SF2 and BRU strains diverged within the target, 19 were read correctly.

Many of the short ambiguous regions in the target arise in segments of the target flanking the points at which the SF2 and BRU sequences diverge. These ambiguities arise because in these regions the comparison of hybridization signals is not drawn between perfectly matched and single base mismatch probes but between a single-mismatched probe and three probes having two mismatches. These ambiguities in reading an SF2 sequence would not detract from the chip's ability to read a BRU sequence either alone or in a mixture with an SF2 target sequence.

In a variation of the above procedure, the chip was treated with RNase after hybridization of the pPol19 target to the probes. Addition of RNase digests mismatched target and thereby increases the signal to noise ratio. RNase treatment increased the number of correctly read bases to 743/821 or 90% (combining the data from the four groups of probes).

In a further variation, the RNA target was replaced with a DNA target containing the same segment of the HIV genome. The DNA probe was prepared by linear amplification using Taq polymerase, RT#1-T3 primer, and fluorescein d-UTP label. The DNA probe was fragmented with uracil DNA glycosylase and heat treatment. The hybridization pattern across the array and percentage of readable sequence were similar to those obtained using an RNA target. However, there were a few regions of sequence that could be read from the RNA target that could not be read from the DNA target and vice versa.

(b) HV 407 Chip

Figure 10A:
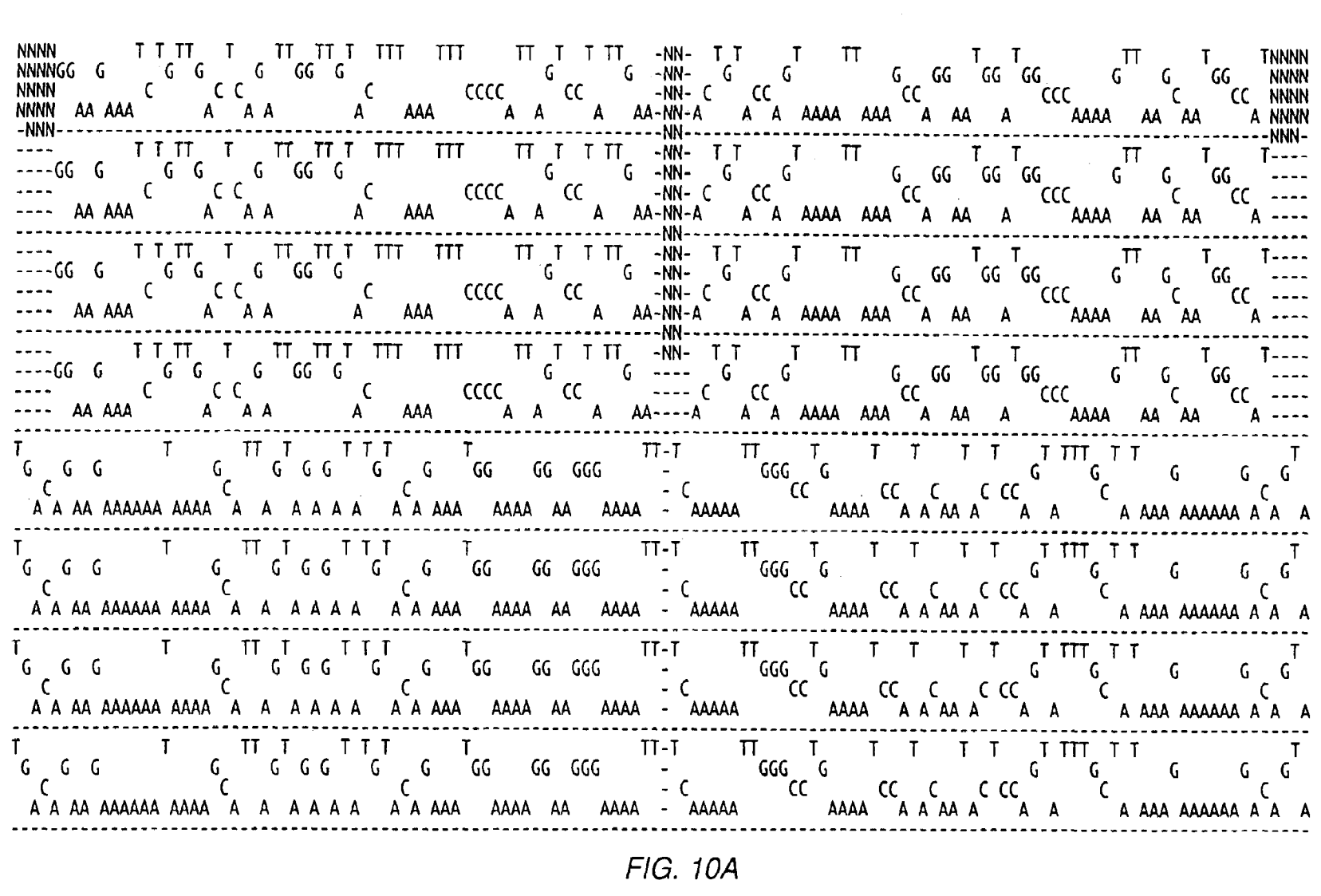
Figure 10B:
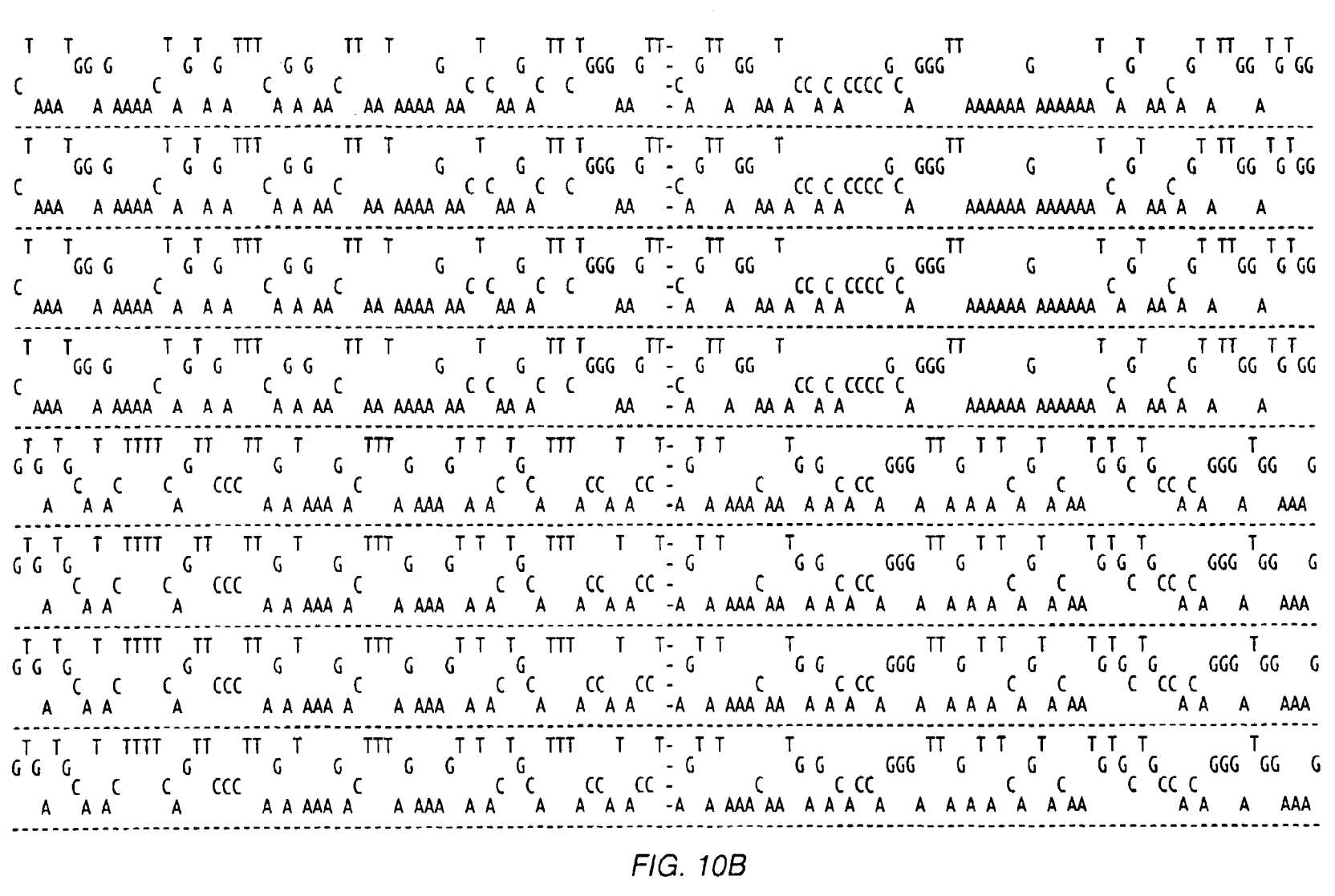
Figure 10C:
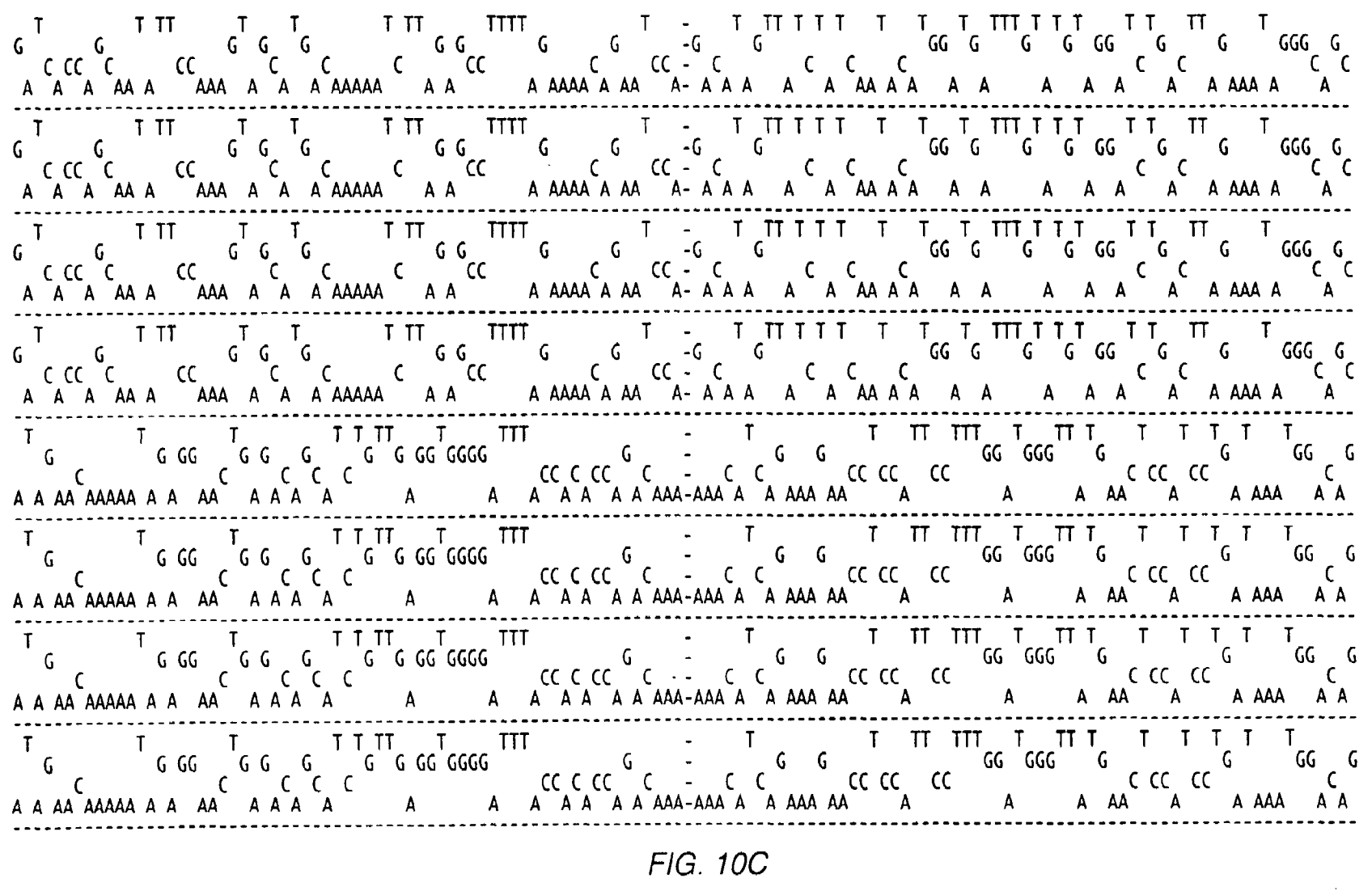
Figure 10D:
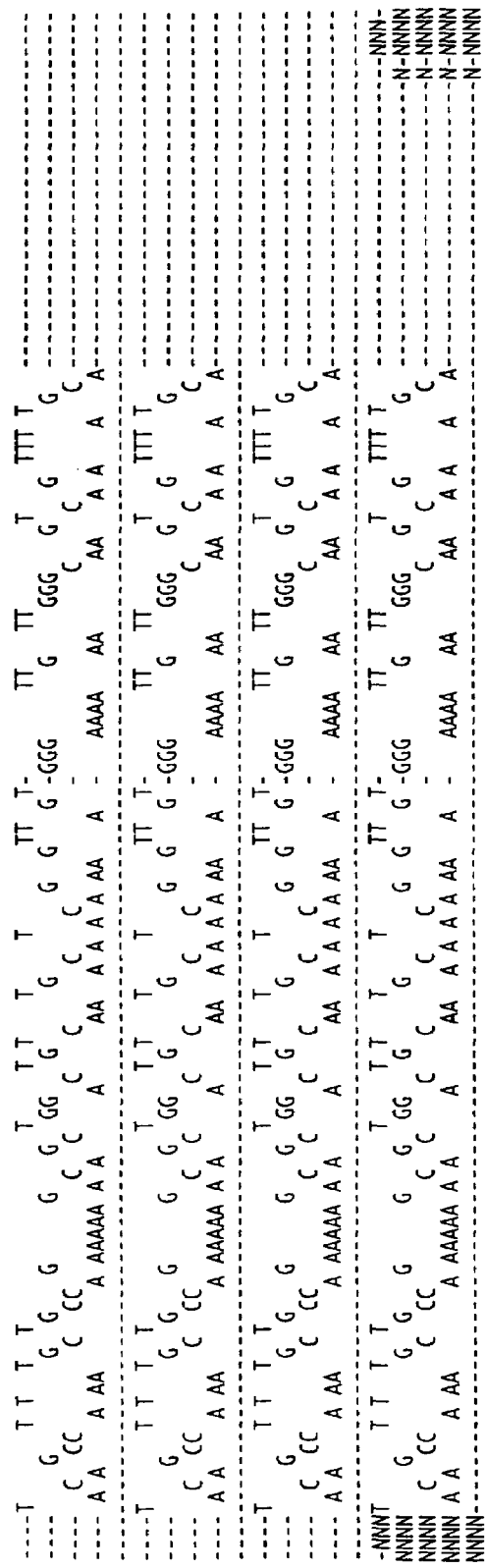
FIG. 10: Layout of probes on the HV 407 chip. The figure shows successive rows of sequence each of which is subdivided into four lanes. The four lanes correspond to the A-, C-, G- and T-lanes on the chip. Each probe is represented by the nucleotide occupying its interrogation position. The letter "N" indicates a control probe or empty column. The different sized-probes are laid out in parallel. That is, from top-to-bottom, a row of 13 mers is followed by a row of 15 mers, which is followed by a row of 17 mers, which is followed by a row of 19 mers.

The 407 chip was designed according to the same principles as the HV 273 chip, but differs in several respects. First, the oligonucleotide probes on this chip are designed to exhibit perfect sequence identity (with the exception of the interrogation position on each probe) to the HIV strain SF2 (rather than the BRU strain as was the case for the HV 273 chip). Second, the 407 chip contains 13 mers, 15 mers, 17 mers and 19 mers (with interrogation positions at nucleotide 7, 8, 9 and 10 respectively), rather than the 11 mers, 13 mers, 15 mers and 17 mers on the HV 273 chip. Third, the different sized groups of oligomers are arranged in parallel in place of the in-series arrangement on the HV 273 chip. In the parallel arrangement, the chip contains from top to bottom a row of 13 mers, a row of 15 mers, a row of 17 mers, a row of 19 mers, followed by a further row of 13 mers, a row of 15 mers, a row of 17 mers, a row of 19 mers, followed by a row of 13 mers, and so forth. Each row contains 4 lanes of probes, an A lane, a C lane, a G lane and a T lane, as described above. The probes in each lane tile across the reference sequence. The layout of probes on the HV 407 chip is shown in FIG. 10.

Figure 11:
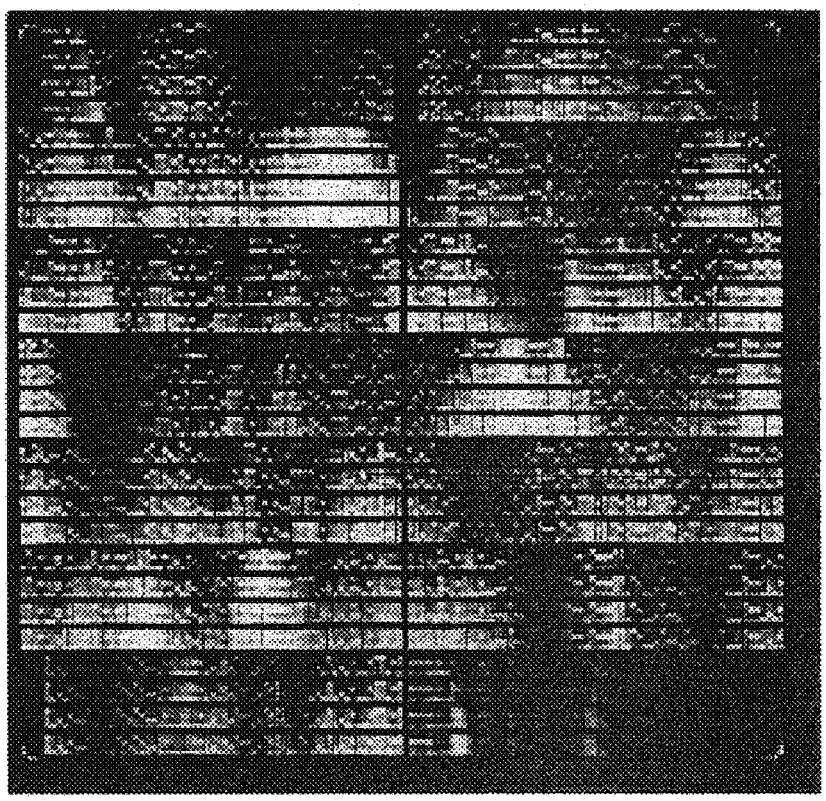
FIG. 11 Fluorescence pattern of HV 407 hybridized to a target sequence (pPol19) identical to the chips reference sequence.

The 407 chip was separately tested for its ability to sequence two targets, pPol19 RNA and 4MUT18 RNA. pPol19 contains an 831 bp fragment from the SF2 reverse transcriptase gene which exhibits perfect complementarity to the probes on the 407 chip (except of course for the interrogation positions in three of the probes in each column). 4MUT18 differs from the reference sequence at thirty-one positions within the target, including five positions in codons 67, 70, 215 and 219 associated with acquisition of drug resistance. Target RNA was prepared, labelled and fragmented as described above and hybridized to the HV 407 chip. The hybridization pattern for the pPol19 target is shown in FIG. 11.

Figure 12A:
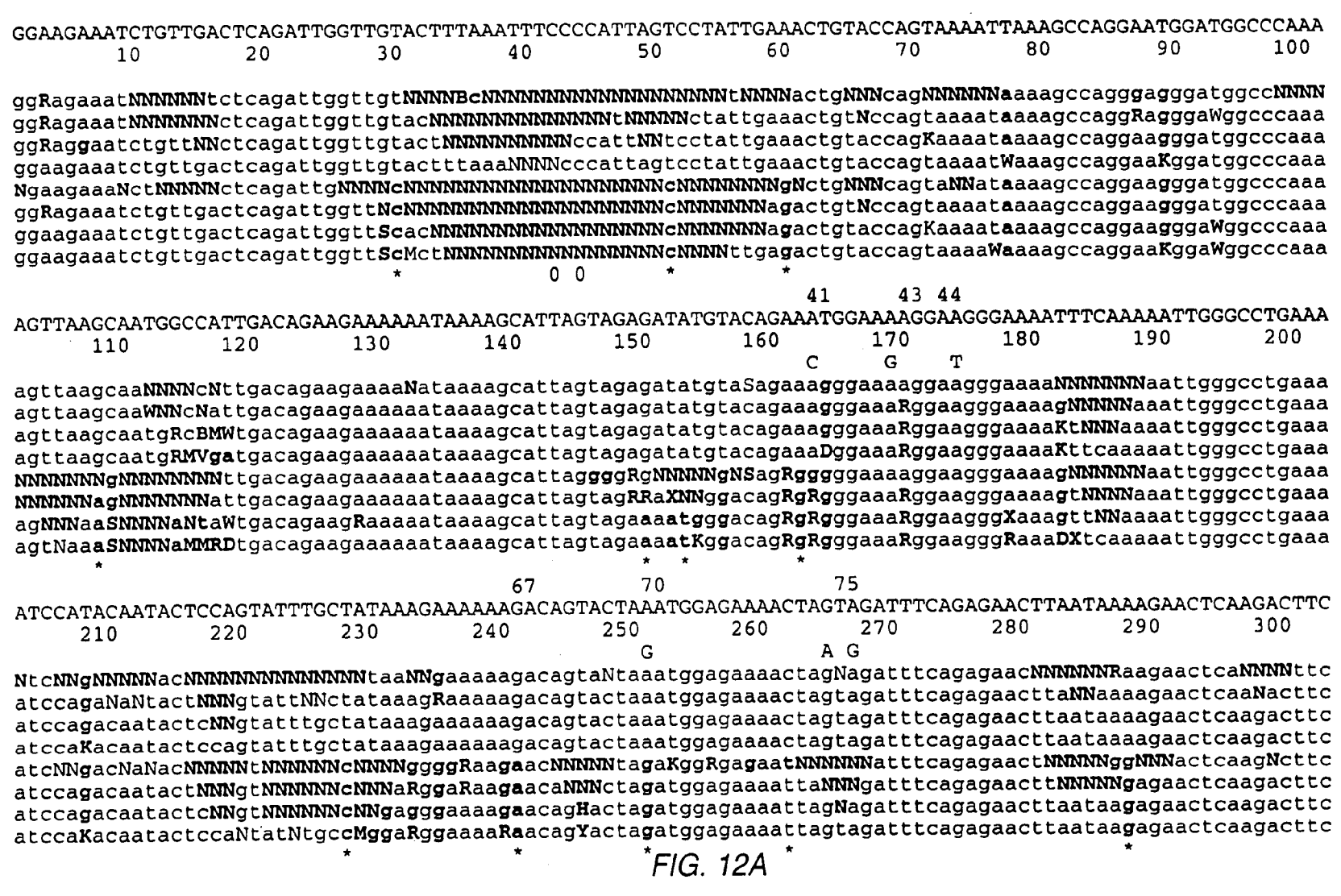
Figure 12B:
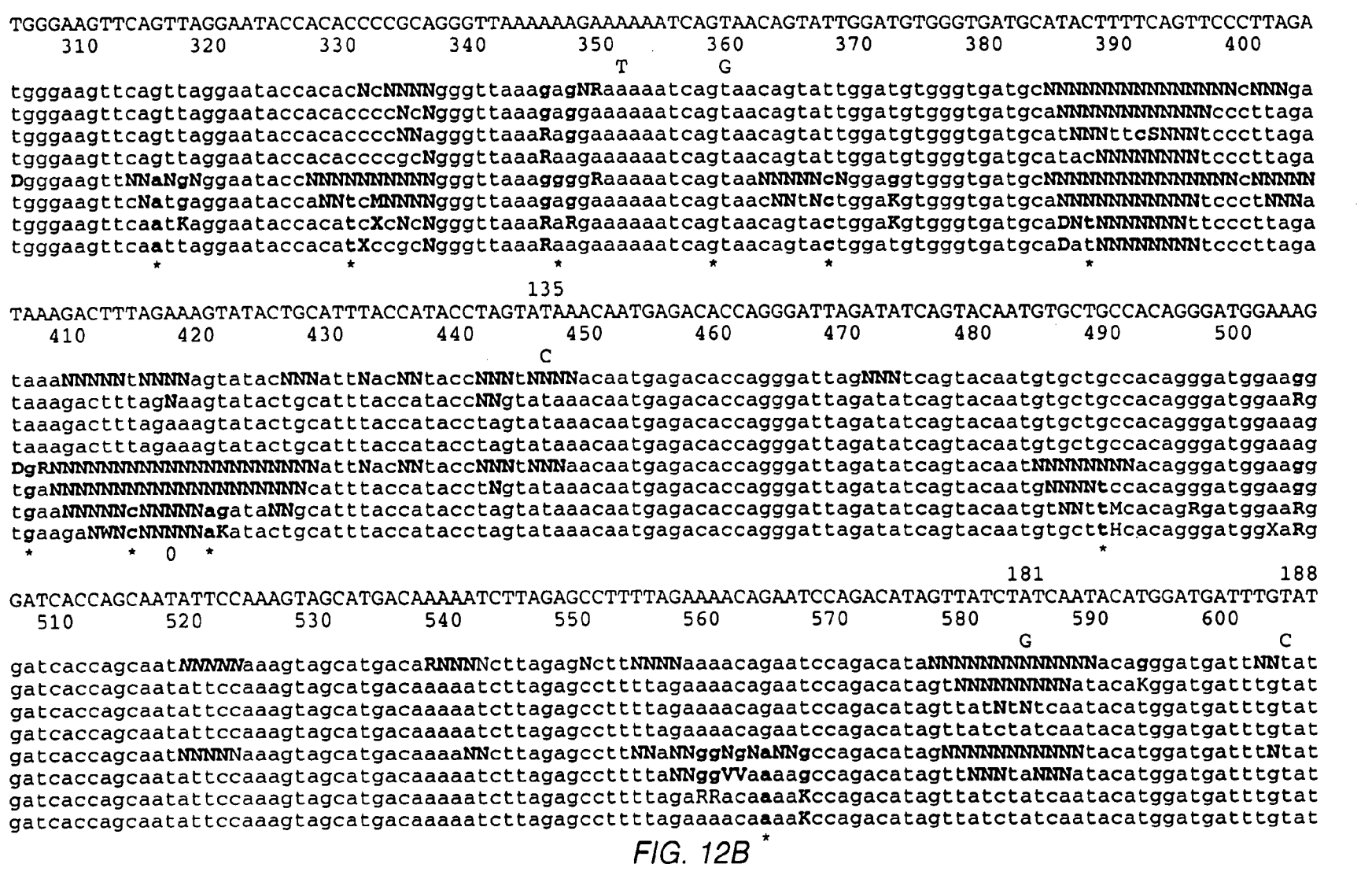

The sequences read off the chip for the pPol19 and 4MUT18 targets are both shown in FIG. 12 (although the two sequences were determined in different experiments). The sequence labelled wildtype in the Figure is the reference sequence. The four lanes of sequence immediately below the reference sequence are the respective sequences read from the four-sized groups of probes for the pPol19 target (from top-to-bottom, 13 mers, 15 mers, 17 mers and 19 mers). The next four lanes of sequence are the sequences read from the four-sized groups of probes for the 4MUT18 target (from top-to-bottom in the same order). The regions of sequences shown in normal type are those that could be read unambiguously from the chip. Regions where sequence could not be accurately read are shown highlighted. Some regions of sequence that could not be read from one sized set of probes could be read from another.

Taking the best result from the four sized groups of probes at each column position, about 97% of bases in the pPol19 sequence and about 90% of bases in the 4MUT18 sequence were read accurately. Of the 31 nucleotide differences between 4MUT18 and the reference sequence, twenty-seven were read correctly including three of the nucleotide changes associated with acquisition of drug resistance. Of the ambiguous regions in the 4MUT18 sequence determination, most occurred in the 4MUT18 segments flanking points of divergence between the 4MUT18 and reference sequences. Notably, most of the common mutations in HIV reverse transcriptase associated with drug resistance (see Table 3) occur at sequence positions that can be read from the chip. Thus, most of the commonly occurring mutations can be detected by a chip containing an array of probes based on a single reference sequence.

Comparison of the sequence read of the probes of different sizes is useful in determining the optimum size probe to use for different regions of the target. The strategy of customizing probe length within a single group of probe sets minimizes the total number of probes required to read a particular target sequence. This leaves ample capacity for the chip to include probes to other reference sequences (e.g., 16S RNA for pathogenic microorganisms) as discussed below.

Figure 14:
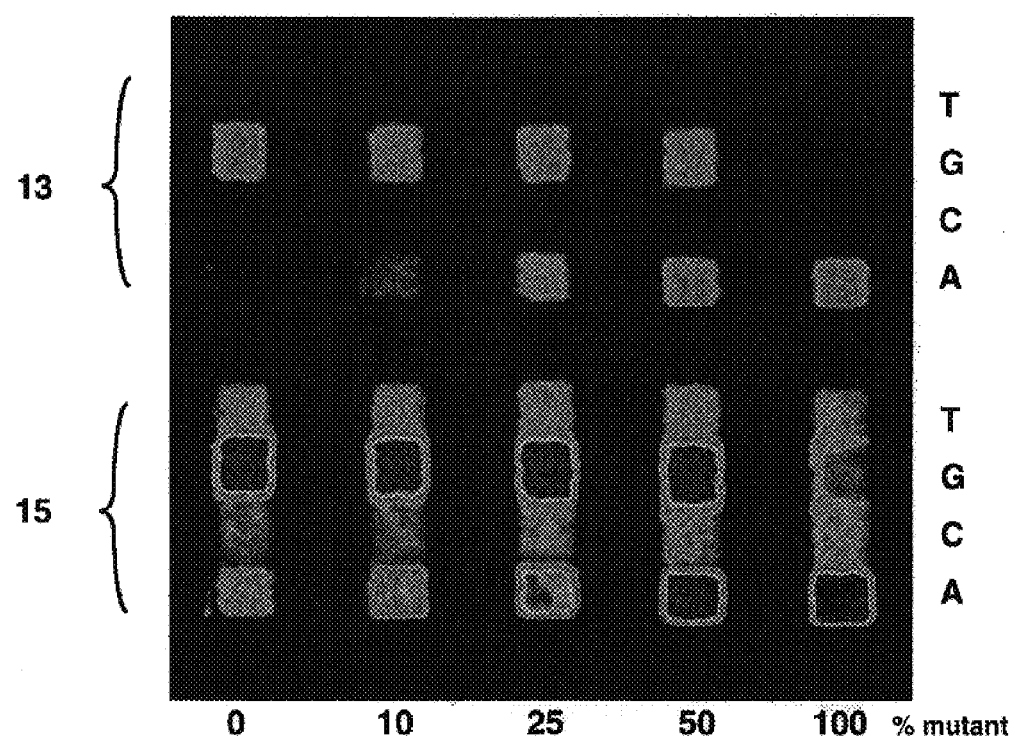
FIG. 14: Fluorescence intensities of target bound to 13 mers and 15 mers for different proportions of mutant and wildtype target. The fluorescence intensities are from probes having interrogation positions for reading the nucleotide at which the mutant and wildtype targets diverge.

The HV 407 chip has also been tested for its capacity to detect mixtures of different HIV strains. The mixture comprises varying proportions of two target sequences; one a segment of a reverse transcriptase gene from a wildtype SF2 strain, the other a corresponding segment from an SF2 strain bearing a codon 67 mutation. See FIG. 13. The Figure also represents the probes on the chip having an interrogation position for reading the nucleotide in which the mutation occurs. A single probe in the Figure represents four probes on the chip with the symbol (o) indicating the interrogation position, which differs in each of the four probes. FIG. 14 shows the fluorescence intensity for the four 13 mers and the four 15 mers having an interrogation position for reading the nucleotide in the target sequence in which the mutation occurs. As the percentage of mutant target is increase, the fluorescence intensity of the probe exhibiting perfect complementarity to the wildtype target decreases, and the intensity of the probe exhibiting perfect complementarity to the mutant sequence increases. The intensities of the other two probes do not change appreciably. It is concluded that the chip can be used to analyze simultaneously a mixture of strains, and that a strain comprising as little as ten percent of a mixture can be easily detected.

c. Protease Chip

A protease chip was constructed using the basic tiling strategy. The chip comprises four probes tiling across a 382 nucleotide span including 297 nucleotides from the protease coding sequence. The reference sequence was a consensus Clay-B HIV protease sequence. Different probes lengths were employed for tiling different regions of the reference sequence. Probe lengths were 11, 14, 17 and 20 nucleotides with interrogation positions at or adjacent to the center of each probe. Lengths were optimized from prior hybridization data employing a chip having multiple tilings, each with a different probe length.

The chip was hybridized to four different single-stranded DNA protease target sequences (HXB2, SF2, NY5, pPol4mut18). Both sense and antisense strands were sequenced. Data from the chip was compared with that from an ABI sequencer. The overall accuracy from sequencing the four targets is illustrated in the Table 5 below.

TABLE 5

|  | ABI | | Protease Chip | |
| --- | --- | --- | --- | --- |
|  | Sense | Antisense | Sense | Antisense |
| No call | 0 | 4 | 9 | 4 |
| Ambiguous | 6 | 14 | 17 | 8 |
| Wrong call | 2 | 3 | 3 | 1 |
| TOTAL | 8 | 21 | 29 | 13 |

ABI (sense) - 99.5%
Chip (sense) - 98.1%
ABI (antisense) - 98.6%
Chip (antisense) - 99.1%

Combining the data from sense and antisense strands, both the chip and the ABI sequencer provided 100% accurate data for all of the sequence from all four clones.

In a further test, the chip was hybridized to protease target sequences from viral isolates obtained from four patients before and after ddI treatment. The sequence read from the chip is shown in FIG. 15. Several mutations (indicated by arrows) have arisen in the samples obtained posttreatment. Particularly noteworthy was the chip's capacity to read a g/a mutation at nucleotide 207, notwithstanding the presence of two additional mutations (gt) at adjacent positions.

B. Cystic Fibrosis Chips

A number of years ago, cystic fibrosis, the most common severe autosomal recessive disorder in humans, was shown to be associated with mutations in a gene thereafter named the Cystic Fibrosis Transmembrane Conductance Regulator (CFTR) gene. The CFTR gene is about 250 kb in size and has 27 exons. Wildtype genomic sequence is available for all exonic regions and exons/intron boundaries (Zielenski et al., *Genomics* 10, 214–228 (1991). The full-length wildtype cDNA sequence has also been described (see Riordan et al., *Science* 245, 1059–1065 (1989). Over 400 mutations have been mapped (see Tsui et al, *Hu. Mutat.* 1, 197–203 (1992). Many of the more common mutations are shown in Table 6. The most common cystic fibrosis mutation is a three-base deletion resulting in the omission of amino acid #508 from the CFTR protein. The frequency of mutations varies widely in populations of different geographic or ethnic origin (see column 4 of Table 6). About 90% of all mutations having phenotypic effects occur in coding regions.

Detection of CFTR mutations is useful in a number of respects. For example, screening of populations can identify asymptomatic heterozygous individuals. Such individuals are at risk of giving rise to affected offspring suffering from CF if they reproduce with other such individuals. In utero screening of fetuses is also useful in identifying fetuses bearing 2 CFTR mutations. Identification of such mutations offers the possibility of abortion, or gene therapy. For couples known to be at risk of giving rise to affected progeny, diagnosis can be combined with in vitro reproduction procedures to identify an embryo having at least one wildtype CF allele before implantation. Screening children shortly after birth is also of value in identifying those having 2 copies of the defective gene. Early detection allows administration of appropriate treatment (e.g., Pulmozyme Antibiotics, Pertussive Therapy) thereby improving the quality of life and perhaps prolonging the life expectancy of an individual.

The source of target DNA for detecting of CFTR mutations is usually genomic. In adults, samples can conveniently be obtained from blood or mouthwash epithelial cells. In fetuses, samples can be obtained by several conventional techniques such as amniocentesis, chorionic villus sampling or fetal blood sampling. At birth, blood from the amniotic chord is a useful tissue source.

The target DNA is usually amplified by PCR. Some appropriate pairs of primers for amplifying segments of DNA including the sites of known mutations are listed in Tables 5 and 6.

TABLE 7

| OLIGO NUMBER | SEQUENCE | SEQ. ID. No. |
| --- | --- | --- |
| 787 | TCTCCTTGGATATACTTGTGTGAATCAA | 81 |
| 788 | TCACCAGATTTCGTAGTCTTTTCATA | 82 |
| 851 | GTCTTGTGTTGAAATTCTCAGGGTAT | 83 |
| 769 | CTTGTACCAGCTCACTACCTAAT | 84 |
| 887 | ACCTGAGAAGATAGTAAGCTAGATGAA | 85 |
| 888 | AACTCCGCCTTTCCAGTTGTAT | 86 |
| 934 | TTAGTTTCTAGGGGTGGAAGATACA | 87 |
| 935 | TTAATGACACTGAAGATCACTGTTCTAT | 88 |
| 789 | CCATTCCAAGATCCCTGATATTTGAA | 577 |
| 790 | GCACATTTTTGCAAAGTTCATTAGA | 89 |
| 891 | TCATGGGCCATGTGCTTTTCAA | 90 |
| 892 | ACCTTCCAGCACTACAAACTAGAA | 91 |
| 760 | CAAGTGAATCCTGAGCGTGATTT | 92 |
| 850 | GGTAGTGTGAAGGGTTCATATGCATA | 93 |
| 762 | GATTACATTAGAAGGAAGATGTGCCTTT | 94 |
| 763 | ACATGAATGACATTTACAGCAAATGCTT | 95 |
| 931 | GTGACCATATTGTAATGCATGTAGTGA | 96 |
| 932 | ATGGTGAACATATTTCTCAAGAGGTAA | 97 |
| 955 | TGT CTC TGT AAA CTG ATG GCT AAC A | 98 |
| 884 | TCGTATAGAGTTGATTGGATTGAGAA | 99 |
| 885 | CCATTAACTTAATGTGGTCTCATCACAA | 100 |
| 886 | CTACCATAATGCTTGGGAGAAATGAA | 101 |
| 782 | TCAAAGAATGGCACCAGTGTGAAA | 102 |
| 901 | TGCTTAGCTAAAGTTAATGAGTTCAT | 103 |
| 784 | AATTGTGAAATTGTCTGCCATTCTTAA | 104 |
| 785 | GATTCACTTACTGAACACAGTCTAACAA | 105 |
| 791 | AGGCTTCTCAGTGATCTGTTG | 106 |
| 792 | GAATCATTCAGTGGGTATAAGCA | 107 |
| 1013 | GCCATGGTACCTATATGTCACAGAA | 108 |
| 1012 | TGCAGAGTAATATGAATTTCTTGAGTACA | 109 |
| 766 | GGGACTCCAAATATTGCTGTAGTAT | 110 |
| 1065 | GTACCTGTTGCTCCAGGTATGTT | 111 |

Other primers can be readily devised from the known genomic and cDNA sequences of CFTR. The selection of primers, of course, depends on the areas of the target sequence that are to be screened. The choice of primers also depends on the strand to be amplified. For some regions of the CFTR gene, it makes little difference to the hybridization signal whether the coding or noncoding strand is used. In other regions, one strand may give better discrimination in hybridization signals between matched and mismatched probes than the other. The upper limit in the length of a segment that can be amplified from one pair of PCR primers is about 50 kb. Thus, for analysis of mutants through all or much of the CFTR gene, it is often desirable to amplify several segments from several paired primers. The different segments may be amplified sequentially or simultaneously by multiplex PCR. Frequently, fifteen or more segments of the CFTR gene are simultaneously amplified by PCR. The primers and amplifications conditions are preferably selected to generate DNA targets. An asymmetric labelling strategy incorporating fluorescently labelled dNTPs for random labelling and dUTP for target fragmentation to an average length of less than 60 bases is preferred. The use of dUTP and fragmentation with uracil N-glycosylase has the added advantage of eliminating carry over between samples.

Mutations in the CFTR gene can be detected by any of the tiling strategies noted above. The block tiling strategy is one particularly useful approach. In this strategy, a group (or block) of probes is used to analyze a short segment of contiguous nucleotides (e.g., 3, 5, 7 or 9) from a CFTR gene centered around the site of a mutation. The probes in a group are sometimes referred to as constituting a block because all probes in the group are usually identical except at their interrogation positions. As noted above, the probes may also differ in the presence of leading or trailing sequences flanking regions of complementary. However, for ease of illustration, it will be assumed that such sequences are not present. As an example, to analyze a segment of five contiguous nucleotides from the CFTR gene, including the site of a mutation (such as one of the mutations in Table 6), a block of probes usually contains at least one wildtype probe and five sets of mutant probes, each having three probes. The wildtype probe has five interrogation positions corresponding to the five nucleotides being analyzed from the reference sequence. However, the identity of the interrogation positions is only apparent when the structure of the wildtype probe is compared with that of the probes in the five mutant probe sets. The first mutant probe set comprises three probes, each being identical to the wildtype probe, except in the first interrogation position, which differs in each of the three mutant probes and the wildtype probe. The second through fifth mutant probe sets are similarly composed except that the differences from the wildtype probe occur in the second through fifth interrogation position respectively. Note that in practice, each set of mutant probes is sometimes laid down on the chip juxtaposed with an associated wildtype probe. In this situation, a block would comprise five wildtype probes, each effectively providing the same information. However, visual inspection and confidence analysis of the chip is facilitated by the largely redundant information provided by five wildtype probes.

After hybridization to labelled target, the relative hybridization signals are read from the probes. Comparison of the intensities of the three probes in the first mutant probe set with that of the wildtype probe indicates the identity of the nucleotide in the target sequence corresponding to the first interrogation position. Comparison of the intensities of the three probes in the second mutant probe set with that of the wildtype probe indicates the identity of the nucleotide in the target sequence corresponding to the second interrogation position, and so forth. Collectively, the relative hybridization intensities indicate the identity of each of the five contiguous nucleotides in the reference sequence.

In a preferred embodiment, a first group (or block) of probes is tiled based on a wildtype reference sequence and a second group is tiled based a mutant version of the wildtype reference sequence. The mutation can be a point mutation, insertion or deletion or any combination of these. The combination of first and second groups of probes facilitates analysis when multiple target sequences are simultaneously applied to the chip, as is the case when a patient being diagnosed is heterozygous for the CFTR allele.

Figure 16:
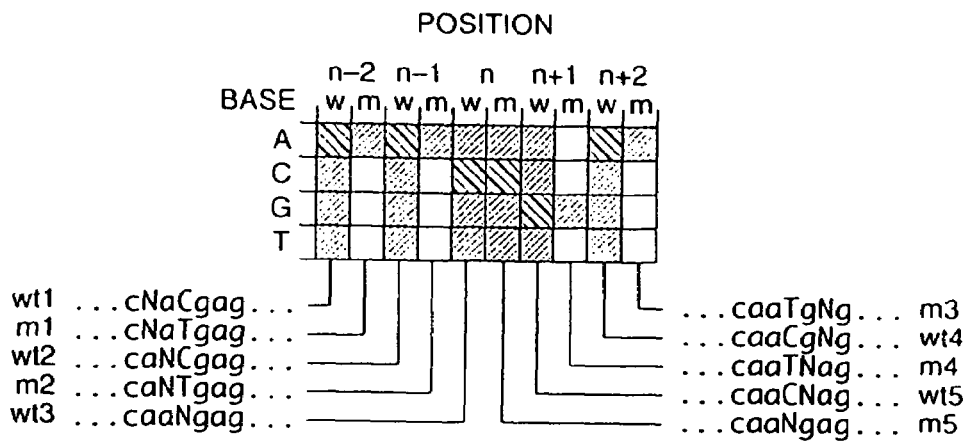
FIG. 16: Block tiling array of probes for analyzing a CFTR point mutation. Each probe shown actually represents four probes, with one probe having each of A, C, G or T at the interrogation position N. In the order shown, the first probe shown on the left is tiled from the wildtype reference sequence (SEQ. ID. No. 525), the second probe from the mutant sequence (SEQ. ID. No. 526), and so on in alternating fashion. Note that all of the probes are identical except at the interrogation position, which shifts one position between successive probes tiled from the same reference sequence (e.g., the first, third and fifth probes in the left hand column.) The grid shows the hybridization intensities when the array is hybridized to the reference sequence.

The above strategy is illustrated in FIG. 16, which shows two groups of probes tiled for a wildtype reference sequence and a point mutation thereof. The five mutant probe sets for the wildtype reference sequence are designated wt1–5, and the five mutant probe sets for the mutant reference sequence are designated m1–5. The letter N indicates the interrogation position, which shifts by one position in successive probe sets from the same group. The figure illustrates the hybridization pattern obtained when the chip is hybridized with a homozygous wildtype target sequence comprising nucleotides n–2 to n+2, where n is the site of a mutation. For the group of probes tiled based on the reference sequence, four probes are compared at each interrogation position. At each position, one of the four probes exhibits a perfect match with the target, and the other three exhibit a single-base mismatch. For the group of probes tiled based on the mutant reference sequence, again four probes are compared at each interrogation position. At position, n, one probe exhibits a perfect match, and three probes exhibit a single base mismatch. Hybridization to a homozygous mutant yields an analogous pattern, except that the respective hybridization patterns of probes tiled on the wildtype and mutant reference sequences are reversed.

Figure 17:
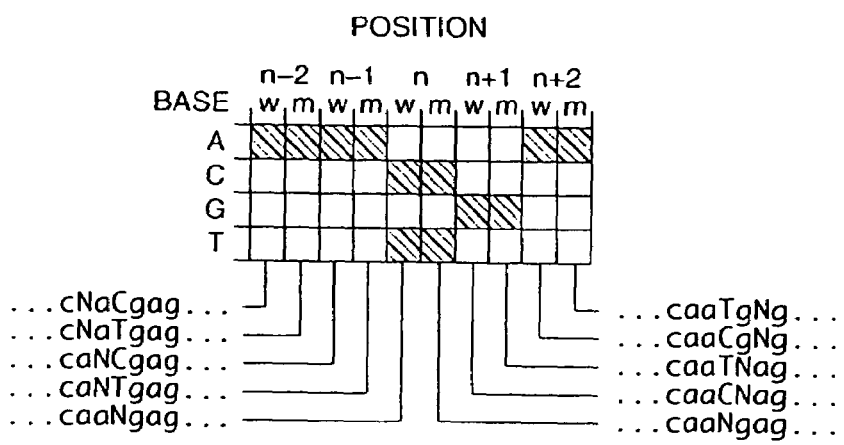
FIG. 17: Hybridization pattern for heterozygous target. The figure shows the hybridization pattern when the array of the previous figure is hybridized to a mixture of mutant and wildtype reference sequences.

The hybridization pattern is very different when the chip is hybridized with a sample from a patient who is heterozygous for the mutant allele (see FIG. 17). For the group of probes tiled based on the wildtype sequence, at all positions but n, one probe exhibits a perfect match at each interrogation position, and the other three probes exhibit a one base mismatch. At position n, two probes exhibit a perfect match (one for each allele), and the other probes exhibit single-base mismatches. For the group of probes tiled on the mutant sequence, the same result is obtained. Thus, the heterozygote point mutant is easily distinguished from both the homozygous wildtype and mutant forms by the identity of hybridization patterns from the two groups of probes.

Typically, a chip comprises several paired groups of probes, each pair for detecting a particular mutation. For example, some chips contain 5, 10, 20, 40 or 100 paired groups of probes for detecting the corresponding numbers of mutations. Some chips are customized to include paired groups of probes for detecting all mutations common in particular populations (see Table 6). Chips usually also contain control probes for verifying that correct amplification has occurred and that the target is properly labelled.

The goal of the tiling strategy described above is to focus on short regions of the CTFR region flanking the sites of known mutation. Other tiling strategies analyze much larger regions of the CFTR gene, and are appropriate for locating and identifying hitherto uncharacterized mutations. For example, the entire genomic CFTR gene (250 kb) can be tiled by the basic tiling strategy from an array of about one million probes. Synthesis and scanning of such an array of probes is entirely feasible. Other tiling strategies, such as the block tiling, multiplex tiling or pooling can cover the entire gene with fewer probes. Some tiling strategies analyze some or all of components of the CFTR gene, such as the cDNA coding sequence or individual exons. Analysis of exons 10 and 11 is particularly informative because these are location of many common mutations including the ΔF508 mutation.

Exemplary CFTR Chips

One illustrative chip bears an array of 1296 probes covering the full length of exon 10 of the CFTR gene arranged in a 36×36 array of 356 μm elements. The probes in the array can have any length, preferably in the range of from 10 to 18 residues and can be used to detect and sequence any single-base substitution and any deletion within the 192-base exon, including the three-base deletion known as ΔF508. As described in detail below, hybridization of nanomolar concentrations of wild-type and ΔF508 oligonucleotide target nucleic acids labeled with fluorescein to these arrays produces highly specific signals (detected with confocal scanning fluorescence microscopy) that permit discrimination between mutant and wild-type target sequences in both homozygous and heterozygous cases.

Sets of probes of a selected length in the range of from 10 to 18 bases and complementary to subsequences of the known wild-type CFTR sequence are synthesized starting at a position a few bases into the intron on the 5'-side of exon 10 and ending a few bases into the intron on the 3'-side. There is a probe for each possible subsequence of the given segment of the gene, and the probes are organized into a "lane" in such a way that traversing the lane from the upper left-hand corner of the chip to the lower righthand corner corresponded to traversing the gene segment base-by-base from the 5'-end. The lane containing that set of probes is, as noted above, called the "wild-type lane."

Relative to the wild-type lane, a "substitution" lane, called the "A-lane", was synthesized on the chip. The A-lane probes were identical in sequence to an adjacent (immediately below the corresponding) wild-type probe but contained, regardless of the sequence of the wild-type probe, a dA residue at position 7 (counting from the 3'-end). In similar fashion, substitution lanes with replacement bases dC, dG, and dT were placed onto the chip in a "C-lane," a "G-lane," and a "T-lane," respectively. A sixth lane on the chip consisted of probes identical to those in the wild-type lane but for the deletion of the base in position 7 and restoration of the original probe length by addition to the 5'-end the base complementary to the gene at that position.

The four substitution lanes enable one to deduce the sequence of a target exon 10 nucleic acid from the relative intensities with which the target hybridizes to the probes in the various lanes. Various versions of such exon 10 DNA chips were made as described above with probes 15 bases long, as well as chips with probes 10, 14, and 18 bases long. For the results described below, the probes were 15 bases long, and the position of substitution was 7 from the 3'-end.

The sequences of several important probes are shown below. In each case, the letter "X" stands for the interrogation position in a given column set, so each of the sequences actually represents four probes, with A, C, G, and T, respectively, taking the place of the "X." Sets of shorter probes derived from the sets shown below by removing up to five bases from the 5'-end of each probe and sets of longer probes made from this set by adding up to three bases from the exon 10 sequence to the 5'-end of each probe, are also useful and provided by the invention (SEQ. ID. Nos. 112–120).

```
3'- TTTATAXTAGAAACC
3'-  TTATAGXAGAAACCA
3'-   TATAGTXGAAACCAC
3'-    ATAGTAXAAACCACA
3'-     TAGTAGXAACCACAA
3'-      AGTAGAXACCACAAA
3'-       GTAGAAXCCACAAAG
3'-        TAGAAAXCACAAAGG
3'-         AGAAACXACAAAGGA
```

To demonstrate the ability of the chip to distinguish the ΔF508 mutation from the wild-type, two synthetic target nucleic acids were made. The first, a 39-mer complementary to a subsequence of exon 10 of the CFTR gene having the three bases involved in the ΔF508 mutation near its center, is called the "wild-type" or wt508 target, corresponds to positions 111–149 of the exon, and has the sequence shown below (SEQ. ID. No. 121):

5'-CATTAAAGAAAATATCATCTTTGGT-GTTTCCTATGATGA.

The second, a 36-mer probe derived from the wild-type target by removing those same three bases, is called the "mutant" target or mu508 target and has the sequence shown below, first with dashes to indicate the deleted bases, and then without dashes but with one base underlined (to indicate the base detected by the T-lane probe, as discussed below)

(SEQ. ID. No. 122):

5'-CATTAAAGAAAATATCAT---TGGTGTTTCCTAT-GATGA;

5'-CATTAAAGAAAATATC<u>A</u>TTGGTGTTTCCTATGATGA.

Both targets were labeled with fluorescein at the 5'-end.

In three separate experiments, the wild-type target, the mutant target, and an equimolar mixture of both targets was exposed (0.1 nM wt508, 0.1 nM mu508, and 0.1 nM wt508 plus 0.1 nM mu508, respectively, in a solution compatible with nucleic acid hybridization) to a CF chip. The hybridization mixture was incubated overnight at room temperature, and then the chip was scanned on a reader (a confocal fluorescence microscope in photon-counting mode); images of the chip were constructed from the photon counts) at several successively higher temperatures while still in contact with the target solution. After each temperature change, the chip was allowed to equilibrate for approximately one-half hour before being scanned. After each set of scans, the chip was exposed to denaturing solvent and conditions to wash, i.e., remove target that had bound, the chip so that the next experiment could be done with a clean chip.

Figure 18:
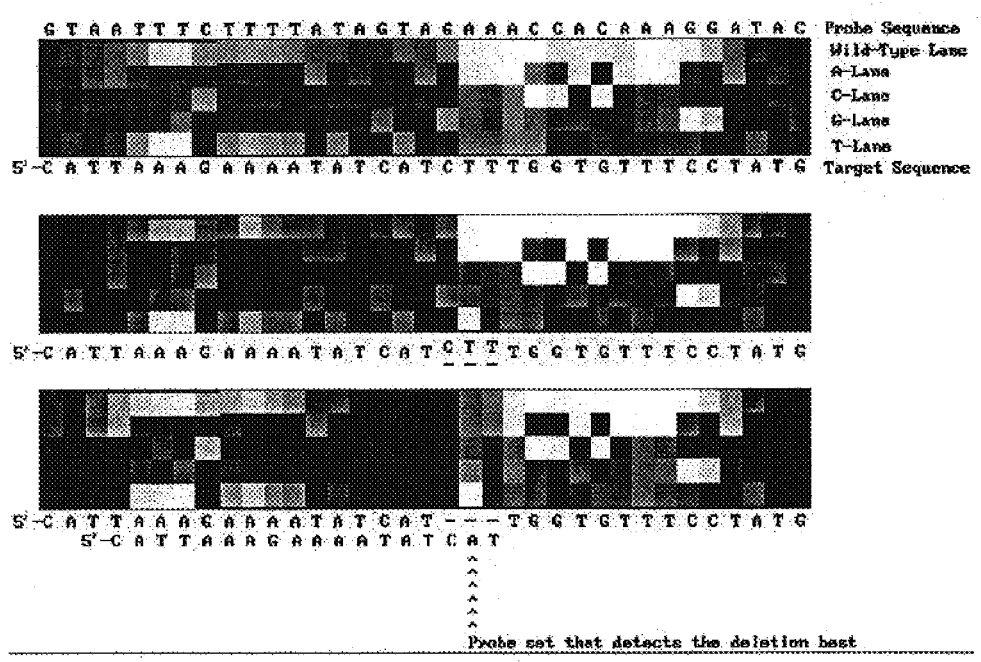
FIG. 18, in panels A, B, and C, shows an image made from the region of a DNA chip containing CFTR exon 10 probes; in panel A, the chip was hybridized to a wild-type target; in panel C, the chip was hybridized to a mutant ΔF508 target; and in panel B, the chip was hybridized to a mixture of the wild-type and mutant targets. The probe sequence and the three target sequences in A, B and C are SEQ. ID. Nos. 527–530.
Figure 19A:
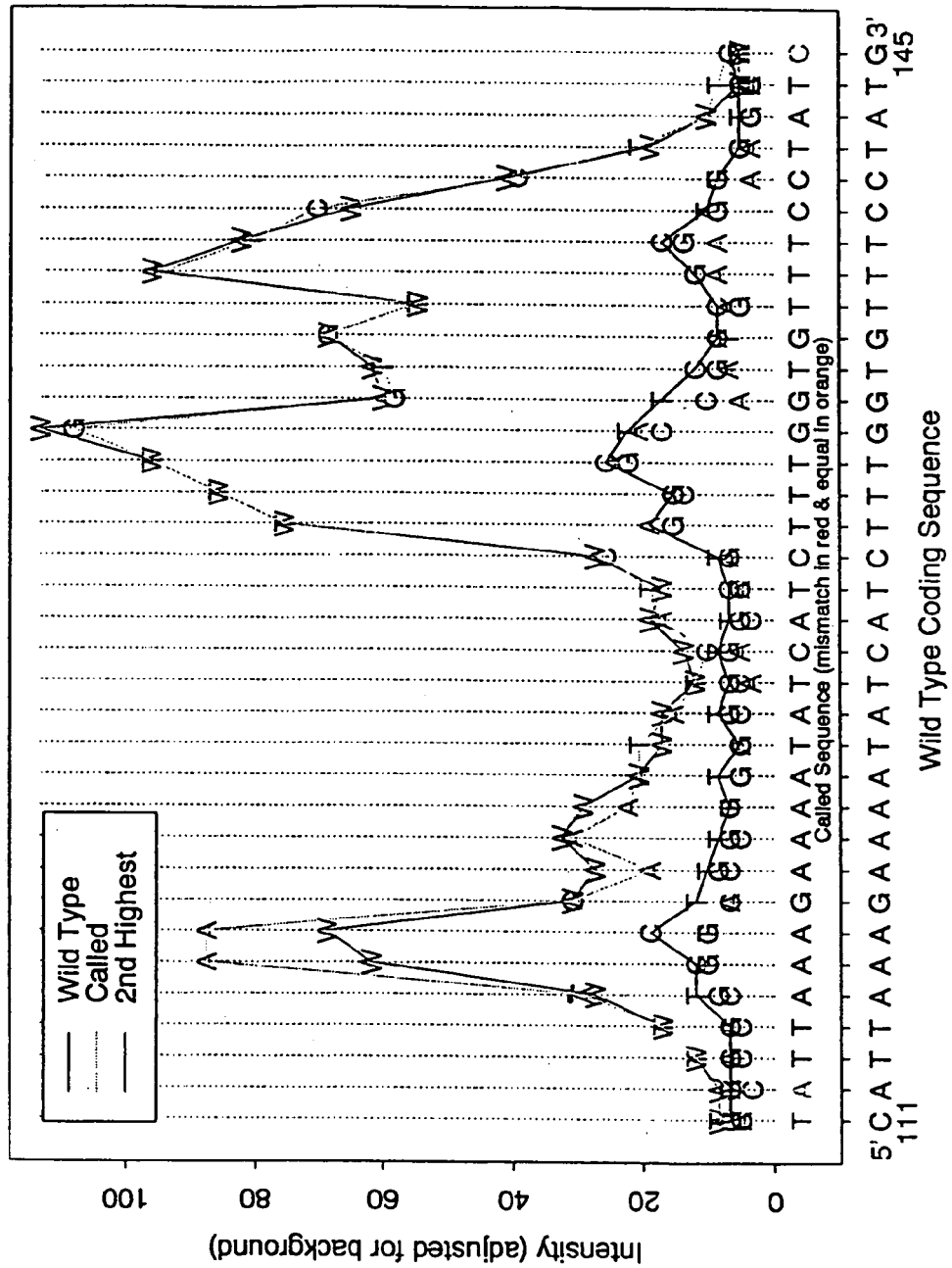
FIG. 19, in sheets 1–3, corresponding to panels A, B, and C of FIG. 18, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest"). The called sequences in A, B and C are SEQ. ID. Nos. 531–533, respectively.
Figure 19B:
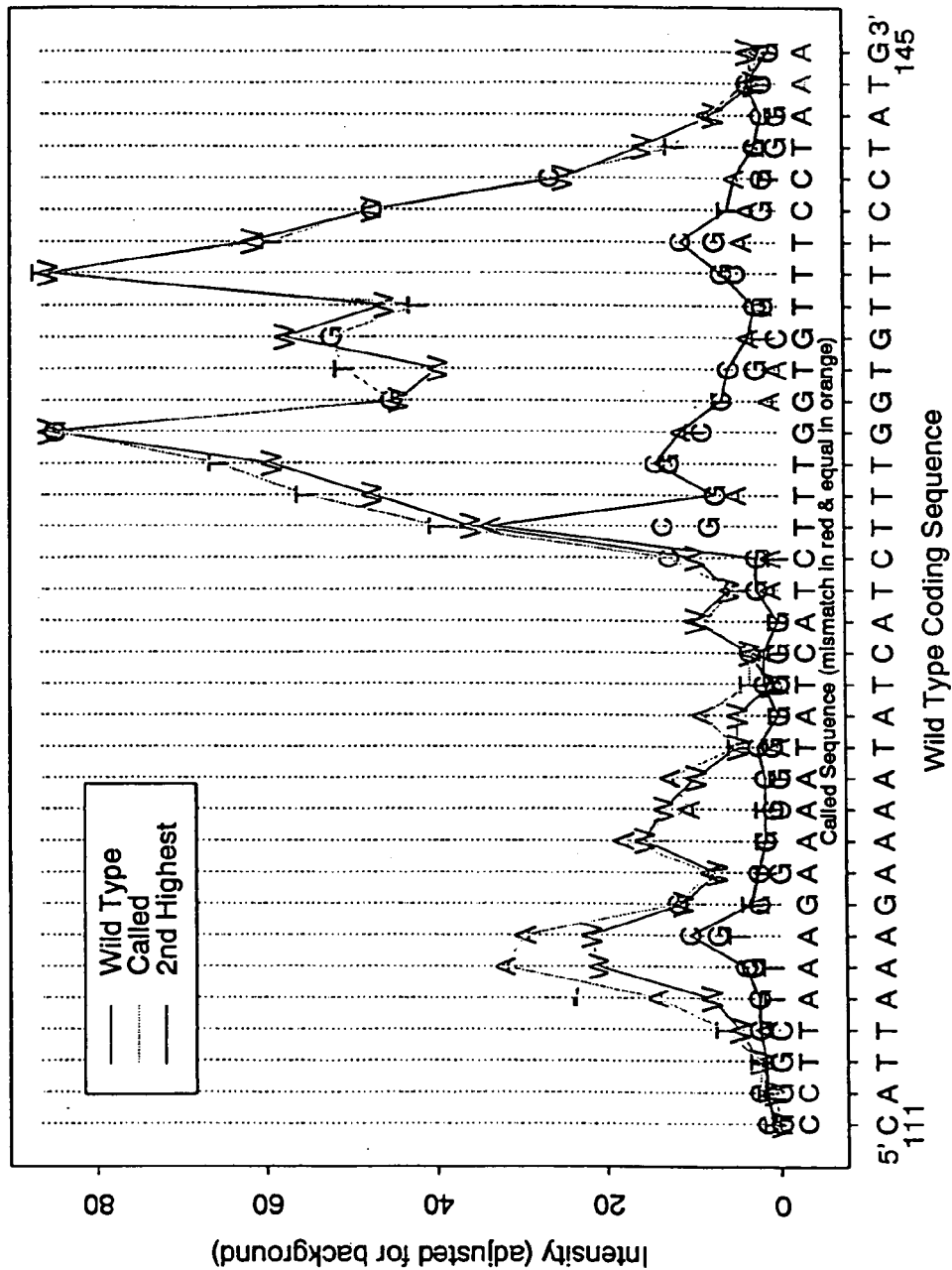
Figure 19C:
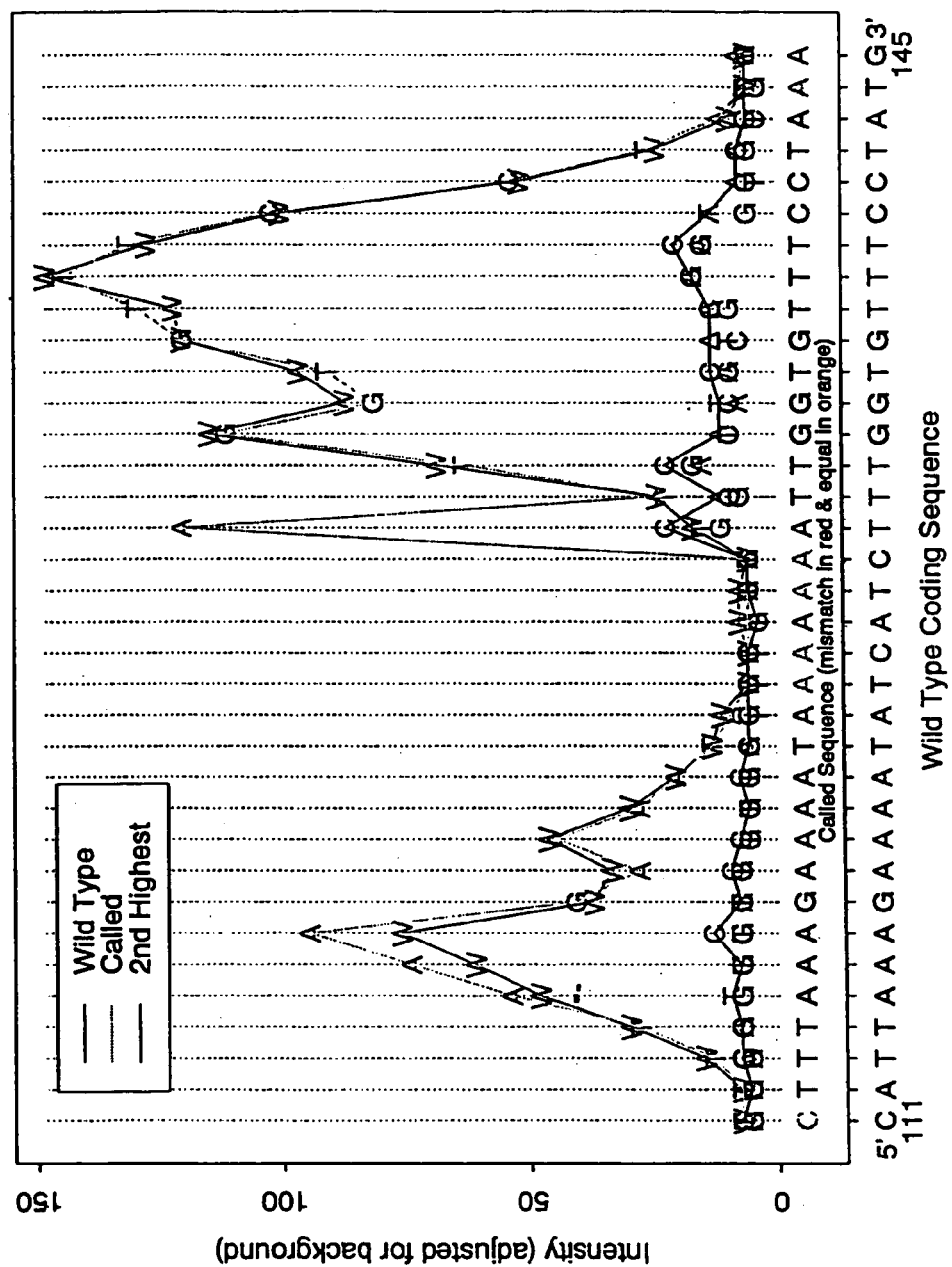

The results of the experiments are shown in FIGS. 18, 19, 20, and 21. FIG. 18, in panels A, B, and C, shows an image made from the region of a DNA chip containing CFTR exon 10 probes; in panel A, the chip was hybridized to a wild-type target; in panel C, the chip was hybridized to a mutant ΔF508 target; and in panel B, the chip was hybridized to a mixture of the wild-type and mutant targets. FIG. 19, in sheets 1–3, corresponding to panels A, B, and C of FIG. 18, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").

These figures show that, for the wild-type target and the equimolar mixture of targets, the substitution probe with a nucleotide sequence identical to the corresponding wild-type probe bound the most target, allowing for an unambiguous assignment of target sequence as shown by letters near the points on the curve. The target wt508 thus hybridized to the probes in the wild-type lane of the chip, although the strength of the hybridization varied from probe-to-probe, probably due to differences in melting temperature. The sequence of most of the target can thus be read directly from the chip, by inference from the pattern of hybridization in the lanes of substitution probes (if the target hybridizes most intensely to the probe in the A-lane, then one infers that the target has a T in the position of substitution, and so on).

For the mutant target, the sequence could similarly be called on the 3'-side of the deletion. However, the intensity of binding declined precipitously as the point of substitution approached the site of the deletion from the 3'-end of the target, so that the binding intensity on the wild-type probe whose point of substitution corresponds to the T at the 3'-end of the deletion was very close to background. Following that pattern, the wild-type probe whose point of substitution corresponds to the middle base (also a T) of the deletion bound still less target. However, the probe in the T-lane of that column set bound the target very well. Examination of the sequences of the two targets reveals that the deletion places an A at that position when the sequences are aligned at their 3'-ends and that the T-lane probe is complementary to the mutant target with but two mismatches near an end (shown below in lower-case letters, with the position of substitution underlined):

Target(SEQ. ID. No. 121):
 5'-CATTAAAGAAAATATCATTGGTGTTTCCTATG-ATGA

Probe (SEQ. ID. No.123): 3'-TagTAGTAACCACAA

Thus the T-lane probe in that column set calls the correct base from the mutant sequence. Note that, in the graph for the equimolar mixture of the two targets, that T-lane probe binds almost as much target as does the A-lane probe in the same column set, whereas in the other column sets, the probes that do not have wild-type sequence do not bind target at all as well. Thus, that one column set, and in particular the T-lane probe within that set, detects the ΔF508 mutation under conditions that simulate the homozygous case and also conditions that simulate the heterozygous case.

Although in this example the sequence could not be reliably deduced near the ends of the target, where there is not enough overlap between target and probe to allow effective hybridization, and around the center of the target, where hybridization was weak for some other reason, perhaps high AT-content, the results show the method and the probes of the invention can be used to detect the mutation of interest. The mutant target gave a pattern of hybridization that was very similar to that of the wt508 target at the ends, where the two share a common sequence, and very different in the middle, where the deletion is located. As one scans the image from right to left, the intensity of hybridization of the target to the probes in the wild-type lane drops off much more rapidly near the center of the image for mu508 than for wt508; in addition, there is one probe in the T-lane that hybridizes intensely with mu508 and hardly at all with wt508. The results from the equimolar mixture of the two targets, which represents the case one would encounter in testing a heterozygous individual for the mutation, are a blend of the results for the separate targets, showing the power of the invention to distinguish a wild-type target sequence from one containing the ΔF508 mutation and to detect a mixture of the two sequences.

The results above clearly demonstrate how the DNA chips of the invention can be used to detect a deletion mutation, ΔF508; another model system was used to show that the chips can also be used to detect a point mutation as well. One mutation in the CFTR gene is G480C, which involves the replacement of the G in position 46 of exon 10 by a T, resulting in the substitution of a cysteine for the glycine normally in position #480 of the CFTR protein. The model target sequences included the 21-mer probe wt480 to represent the wild-type sequence at positions 37–55 of exon 10 (SEQ. ID. No. 124): 5'-CCTTCAGAGGGTAAAATTAAG and the 21-mer probe mu480 to represent the mutant sequence (SEQ. ID. No. 125):
 5'-CCTTCAGAGTGTAAAATTAAG.

Figure 20:
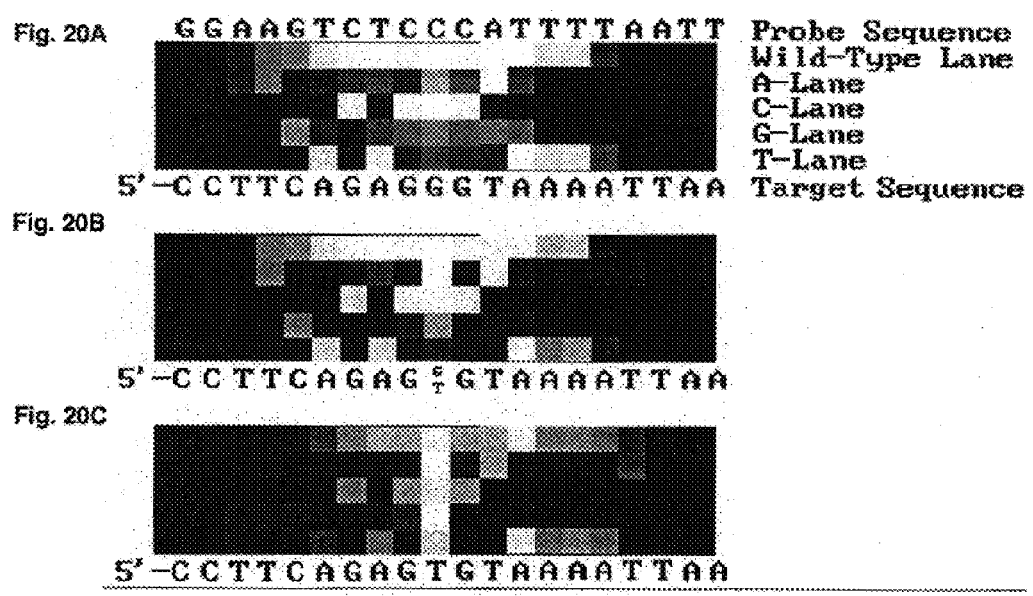
FIG. 20, in panels A (SEQ. ID. Nos. 534, 535), B (SEQ. ID. No. 536), and C (SEQ. ID. No. 537), shows an image made from a region of a DNA chip containing CFTR exon 10 probes; in panel A, the chip was hybridized to the wt480 target; in panel C, the chip was hybridized to the mu480 target; and in panel B, the chip was hybridized to a mixture of the wild-type and mutant targets.
Figure 21A:
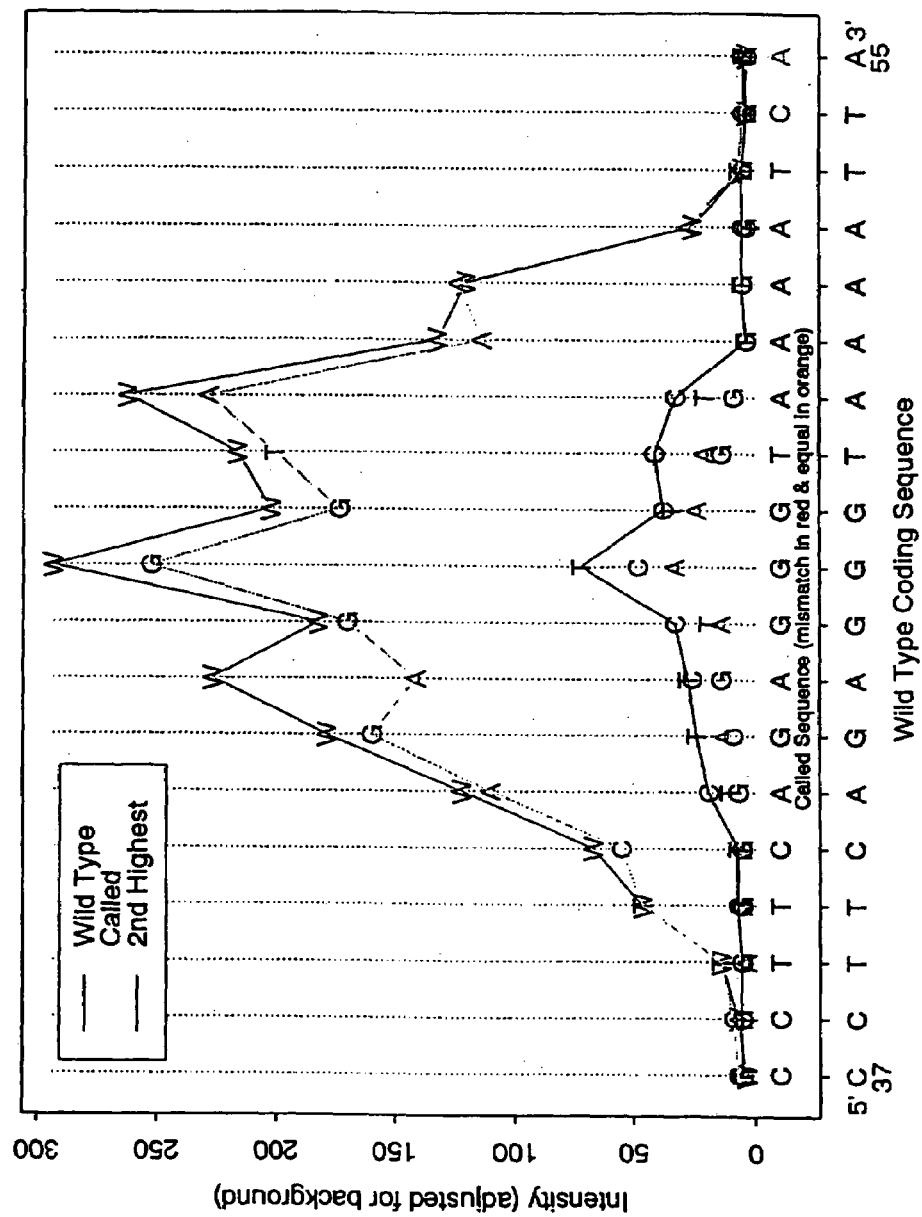
FIG. 21, in sheets 1–3, corresponding to panels A, B, and C of FIG. 20, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest"). Called sequences in sheets 1–3 are SEQ. ID. Nos. 538–540.
Figure 21B:
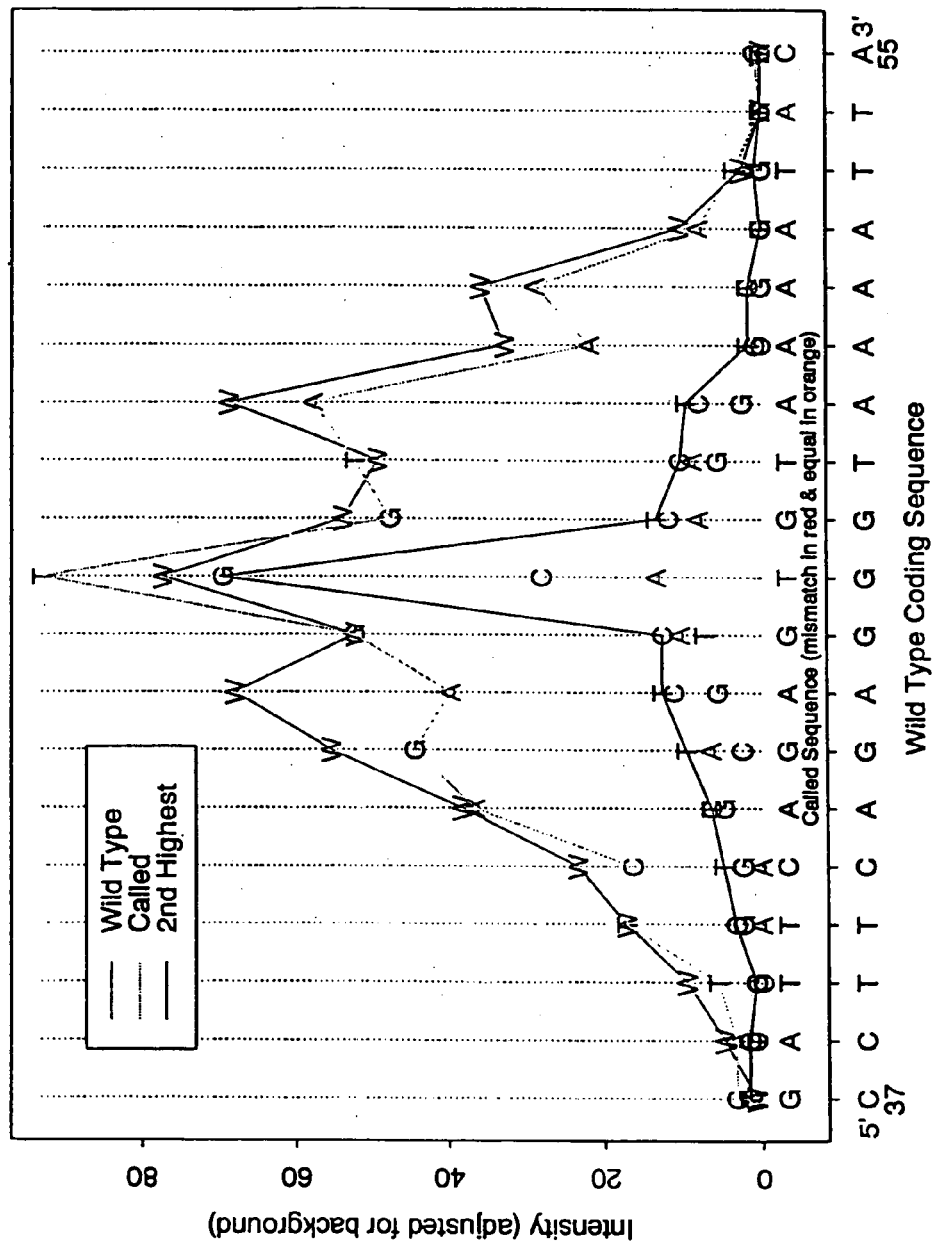
Figure 21C:
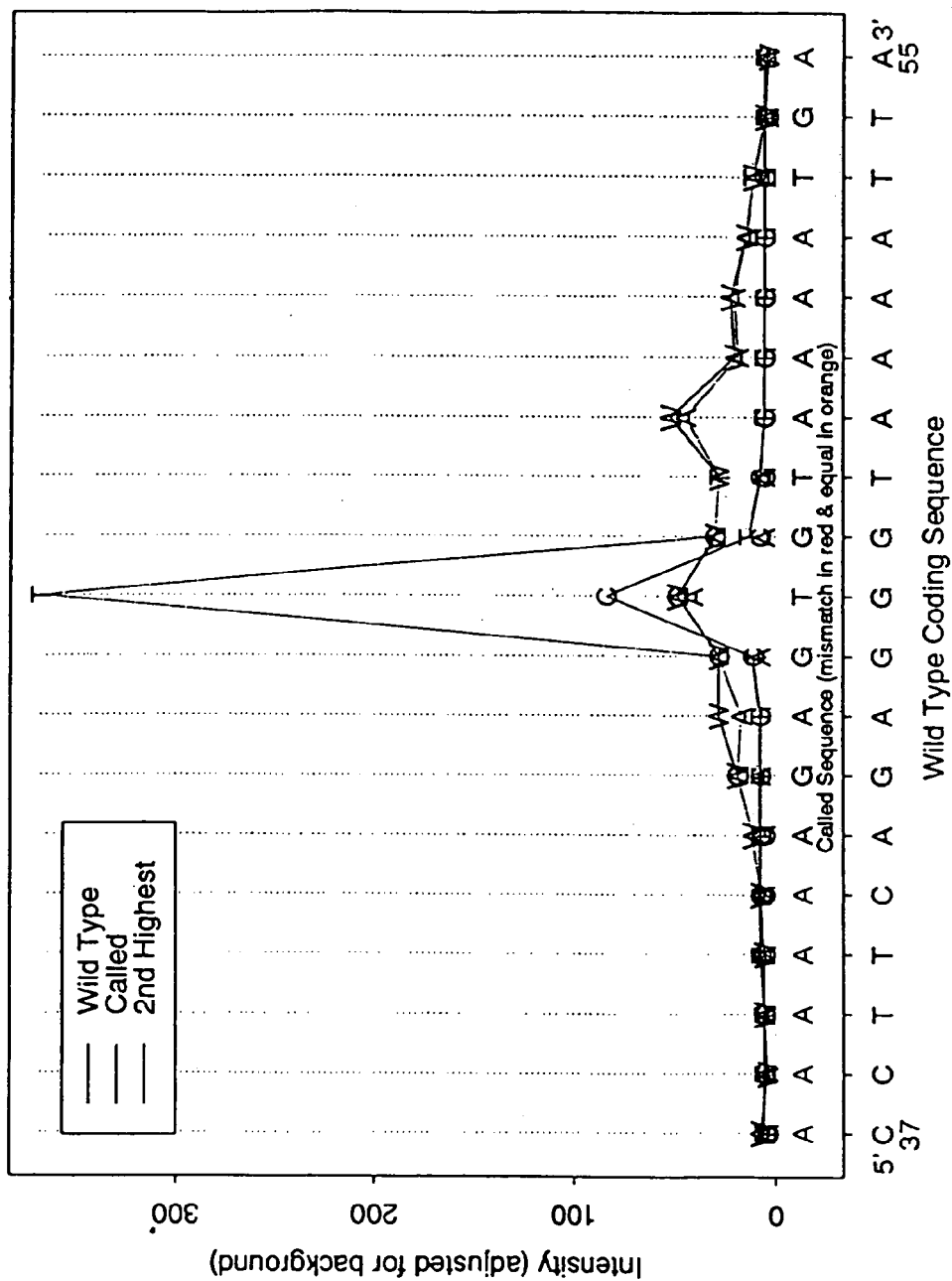

In separate experiments, a DNA chip was hybridized to each of the targets wt480 and mu480, respectively, and then scanned with a confocal microscope. FIG. 20, in panels A, B, and C, shows an image made from the region of a DNA chip containing CFTR exon 10 probes; in panel A, the chip was hybridized to the wt480 target; in panel C, the chip was hybridized to the mu480 target; and in panel B, the chip was hybridized to a mixture of the wild-type and mutant targets. FIG. 21, in sheets 1–3, corresponding to panels A, B, and C of FIG. 20, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").

These figures show that the chip could be used to sequence a 16-base stretch from the center of the target wt480 and that discrimination against mismatches is quite good throughout the sequenced region. When the DNA chip was exposed to the target mu480, only one probe in the portion of the chip shown bound the target well: the probe in the set of probes devoted to identifying the base at position 46 in exon 10 and that has an A in the position of substitution and so is fully complementary to the central portion of the mutant target. All other probes in that region of the chip have at least one mismatch with the mutant target and therefore bind much less of it. In spite of that fact, the sequence of mu480 for several positions to both sides of the mutation can be read from the chip, albeit with much-reduced intensities from those observed with the wild-type target.

The results also show that, when the two targets were mixed together and exposed to the chip, the hybridization pattern observed was a combination of the other two patterns. The wild-type sequence could easily be read from the chip, but the probe that bound the mu480 target so well when only the mu480 target was present also bound it well when both the mutant and wild-type targets were present in a mixture, making the hybridization pattern easily distinguishable from that of the wild-type target alone. The results again show the power of the DNA chips of the invention to detect point mutations in both homo- and heterozygous individuals.

To demonstrate clinical application of the DNA chips of the invention, the chips were used to study and detect mutations in nucleic acids from genomic samples. Genomic samples from a individual carrying only the wild-type gene and an individual heterozygous for ΔF508 were amplified by PCR using exon 10 primers containing the promoter for T7 RNA polymerase. Illustrative primers of the invention are shown below.

Exon Name Sequence ((SEQ. ID. Nos. 126–131)

10 CFi9-T7

TAATACGACTCACTATAGGGAGatgacctaataatga-tgggttt

10 CFi10c-T7
TAATACGACTCACTATAGGGAGtagtgt-
gaagggttcatatgc
10 CFi10c-T3
CTCGGAATTAACCCTCACTAAAGGtagt-
gtgaagggttcatatgc
11 CFi10-T7

TAATACGACTCACTATAGGGAGagcatactaaaagtgactctc
11 CFi11c-T7
TAATACGACTCACTATAGGGAGacat-
gaatgacatttacagcaa
11 CFi11c-T3
CGGAATTAACCCTCACTAAAGGacat-
gaatgacatttacagcaa These primers can be used to amplify exon 10 or exon 11 sequences; in another embodiment, multiplex PCR is employed, using two or more pairs of primers to amplify more than one exon at a time.

Figure 22:
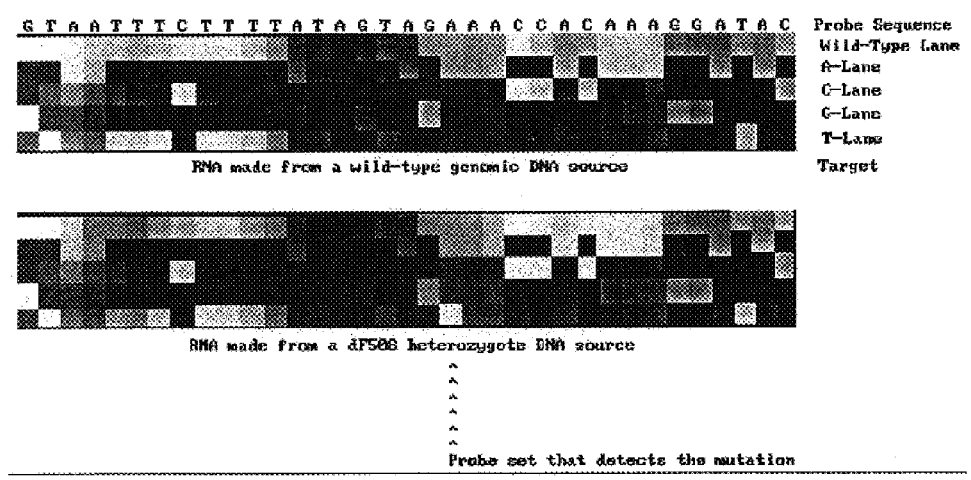
FIG. 22, in panels A and B, shows an image made from a region of a DNA chip containing CFTR exon 10 probes; in panel A, the chip was hybridized to nucleic acid derived from the genomic DNA of an individual with wild-type ΔF508 sequences (SEQ. ID. No. 541); in panel B, the target nucleic acid originated from a heterozygous (with respect to the ΔF508 mutation) individual.
Figure 23A:
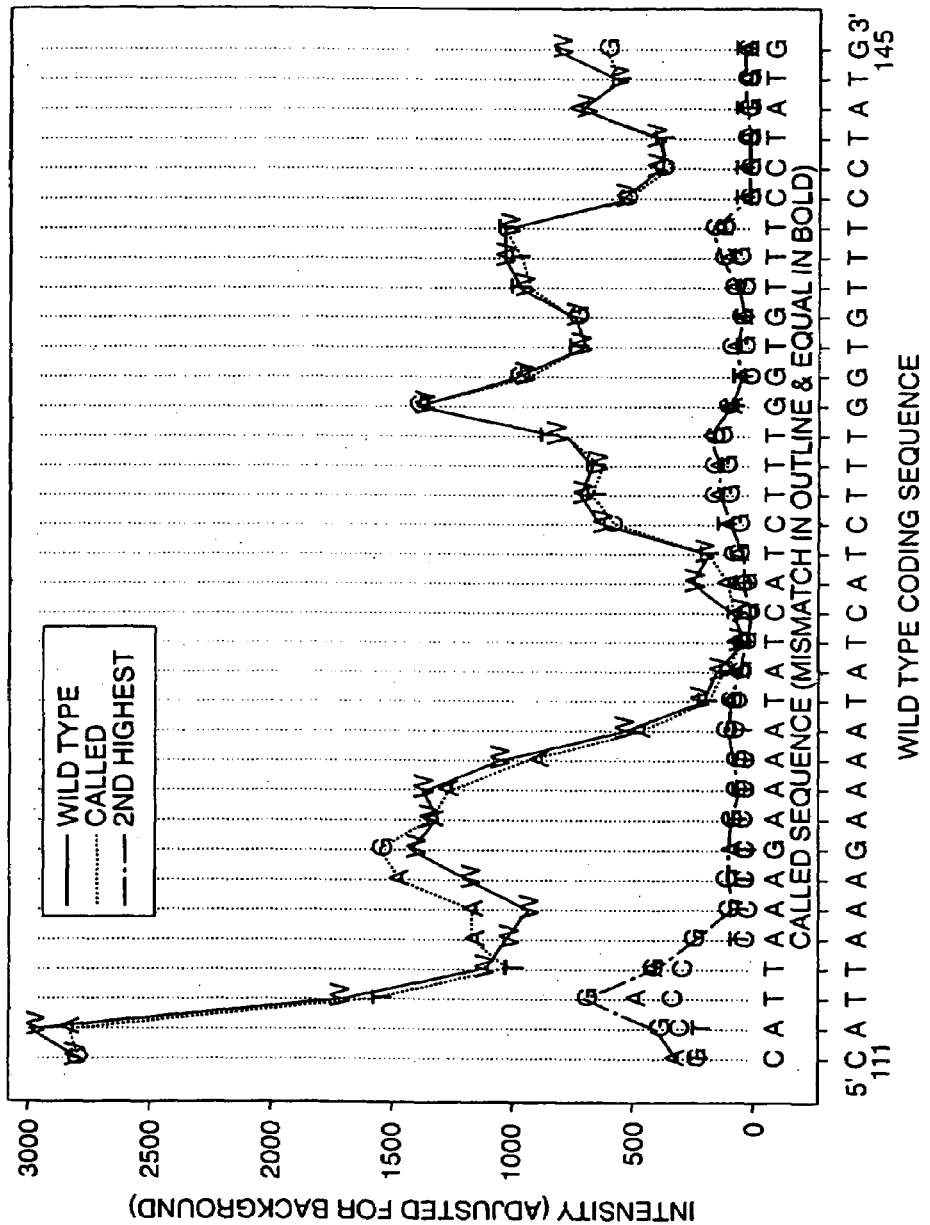
FIG. 23, in sheets 1 and 2 (SEQ. ID. No. 542), corresponding to panels A and B of FIG. 22, shows graphs of fluorescence intensity versus tiling position. The labels on the horizontal axis show the bases in the wild-type sequence corresponding to the position of substitution in the respective probes. Plotted are the intensities observed from the features (or synthesis sites) containing wild-type probes, the features containing the substitution probes that bound the most target ("called"), and the feature containing the substitution probes that bound the target with the second highest intensity of all the substitution probes ("2nd Highest").
Figure 23B:
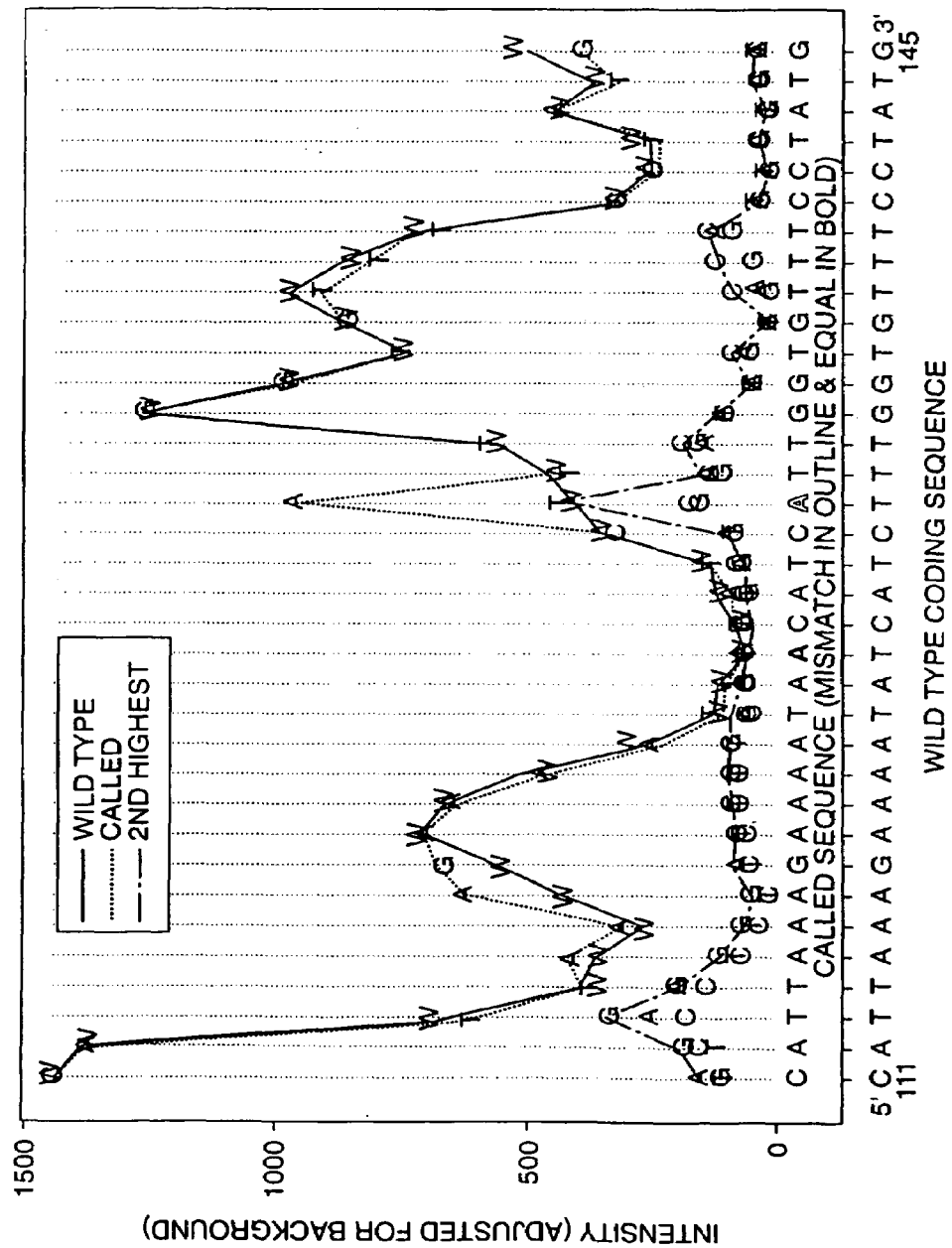

The product of amplification was then used as a template for the RNA polymerase, with fluoresceinated UTP present to label the RNA product. After sufficient RNA was made, it was fragmented and applied to an exon 10 DNA chip for 15 minutes, after which the chip was washed with hybridization buffer and scanned with the fluorescence microscope. A useful positive control included on many CF exon 10 chips is the 8-mer 3'-CGCCGCCG-5'. FIG. 22, in panels A and B, shows an image made from a region of a DNA chip containing CFTR exon 10 probes; in panel A, the chip was hybridized to nucleic acid derived from the genomic DNA of an individual with wild-type ΔF508 sequences; in panel B, the target nucleic acid originated from a heterozygous (with respect to the ΔF508 mutation) individual. FIG. 23, in sheets 1 and 2, corresponding to panels A and B of FIG. 22, shows graphs of fluorescence intensity versus tiling position.

These figures show that the sequence of the wild-type RNA can be called for most of the bases near the mutation. In the case of the ΔF508 heterozygous carrier, one particular probe, the same one that distinguished so clearly between the wild-type and mutant oligonucleotide targets in the model system described above, in the T-lane binds a large amount of RNA, while the same probe binds little RNA from the wild-type individual. These results show that the DNA chips of the invention are capable of detecting the ΔF508 mutation in a heterozygous carrier.

Further chips were constructed using the block tiling strategy to provide an array of probes for analyzing a CFTR mutation. The array comprised 93 mm×96 μm features arranged into eleven columns and four rows (44 total probes). Probes in five of these columns were from four probe sets tiled based on the wildtype CFTR sequence and having interrogation positions corresponding to the site of a mutation and two bases on either side. Five of the remaining columns contained four sets of probes tiled based on the mutant version of the CFTR sequence. These probe sets also had interrogation positions corresponding to the site of mutation and two nucleotides on either side. The eleventh column contained four cells for control probes.

Fluorescently labeled hybridization targets were prepared by PCR amplification. 100 μg of genomic DNA, 0.4 μM of each primer, 50 μM each dATP, dCTP, dCTP and dUTP (Pharmacia) n 10 mM Tris-Cl, pH 8.3, 50 mM KCl, 2.5 mM MgCl$_2$ and 2 U Taq polymerase (Perkin-Elmer) were cycled 36 times using a Perkin-Elmer 9600 thermocycler and the following times and temperatures: 95° C., 10 sec., 55° C., 10 sec., 72° C., 30 sec. 10 μl of this reaction product was used as a template in a second, asymmetric PCR reaction. Conditions included 1 μM asymmetric PCR primer, 50 μM each dATP, dCTP, TTP, 25 μM fluorescein-dGTP (DuPont), 10 mM Tris-Cl, pH 9.1, 75 mM KCl, 3.5 mM MgCl$_2$. The reaction was cycled 5× with the following conditions: 95° C., 10 sec, 60° C., 10 sec, 55° C., 1 min. and 72° C., 1.5 min. This was immediately followed with another 20 cycles using the following conditions: 95° C., 10 sec, 60° C., 10 sec., 72° C., 1.5 min.

Amplification products were fragmented by treating with 2 U of Uracil-N-glycosylase (Gibco) at 30° C. for 30 min. followed by heat denaturation at 95° C. for 5 min. Finally, the labeled, fragmented PCR product was diluted into hybridization buffer made up of 5×SSPE and 1 mM Cetyl-trimethylammonium Bromide (CTAB). The dilution factor ranged from 10× to 25× with 40 μl of sample being diluted into 0.4 ml to 1 ml of hybridization solution.

Target hybridization was generally carried out with the chip shaking in a small dish containing 500 μl to 1 ml total volume of hybridization solution. All hybridizations were done at 30° C. constant temperature. Alternatively, some hybridizations were carried out with chips enclosed in a plastic package with the 1 cm×1 cm chip glued facing a 250 μl fluid chamber. 250–350 μl of hybridization solution was introduced and mixed using a syringe pump. Temperature was controlled by interfacing the back surface of the package with a Peltier heating/cooling device. Following hybridization chips were washed with 5×SSPE, 0.1% Triton X-100 at 25° C.–30° C. prior to fluorescent image generation.

Hybridized, washed DNA chips were scanned for fluorescence using a stage-scanning confocal epifluorescent microscope and 488 nm argon ion laser excitation. Emitted light was collected through a band pass filter centered at 530 nM. The resulting fluorescence image was spatially reconstructed and intensity data were then analyzed. Features with the peak fluorescence intensity in each column were identified and compared with any signal intensity at the remaining single base mismatch probe sites in the same column. The sequences of the highest intensity features were then compared across all ten columns of each sub-array to determine whether peak intensity scores for the wild type sequence and the mutant sequence were similar or significantly different. These results were used to generate the genotype call of wild type (high intensity signals only in wild type probe columns), mutant (high intensity signals only in the mutant probe columns) or heterozygous (high intensity signals in both the wild type and mutant probe columns).

Figures 24A, 24B:
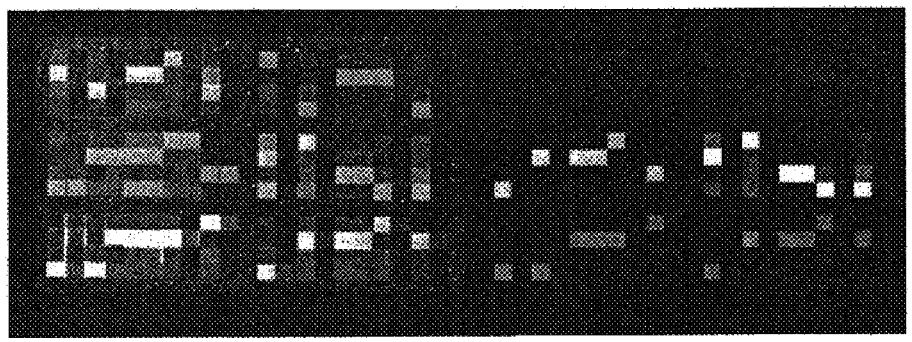
FIG. 24: Hybridization of homozygous wildtype (A) and heterozygous (B) target sequences from exon 11 of the CFTR gene to a block tiling array designed to detect G551D and Q552X mutations in CFTR gene.

FIG. 24 (panel A) shows an image of the fluorescence signals in arrays designed to detect the G551D(G>A) and Q552X(C>T) CFTR mutations. The hybridization target is an exon 11 amplicon generated from wild type genomic DNA. Wild type hybridization patterns are evident at both locations. No significant fluorescence signal resulted at any of the features with probes complementary to mutant or mismatched sequences. Relative fluorescence intensities were six fold brighter for the perfect matched wildtype features compared with the background signal intensity at mutant and mismatch features. In addition, the sequence at these loci can be confirmed as AGGTC and GTCAA, respectively, where the bold type face indicates the mutation sites. FIG. 24 (panel B) shows the same probe array features after hybridization with a fluorescent target generated from DNA heterozygous for the G551D mutation. Both the wild type and mutant probe columns have features with significant fluorescence intensity, indicating the hybridization of both wild type and mutant CFTR alleles at this site. Only wildtype probes hybridized with any significant fluorescence signal in the Q552X subarray indicating a wild type target sequence. However, an additional feature that did not hybridize in the first experiment shows significant fluorescence intensity in this experiment. Because the G551D and Q552X mutations are only two bases apart, the a probe sequence in the additional feature has a perfectly matched 12-mer overlap with the mutant G551D target.

Figure 25A:
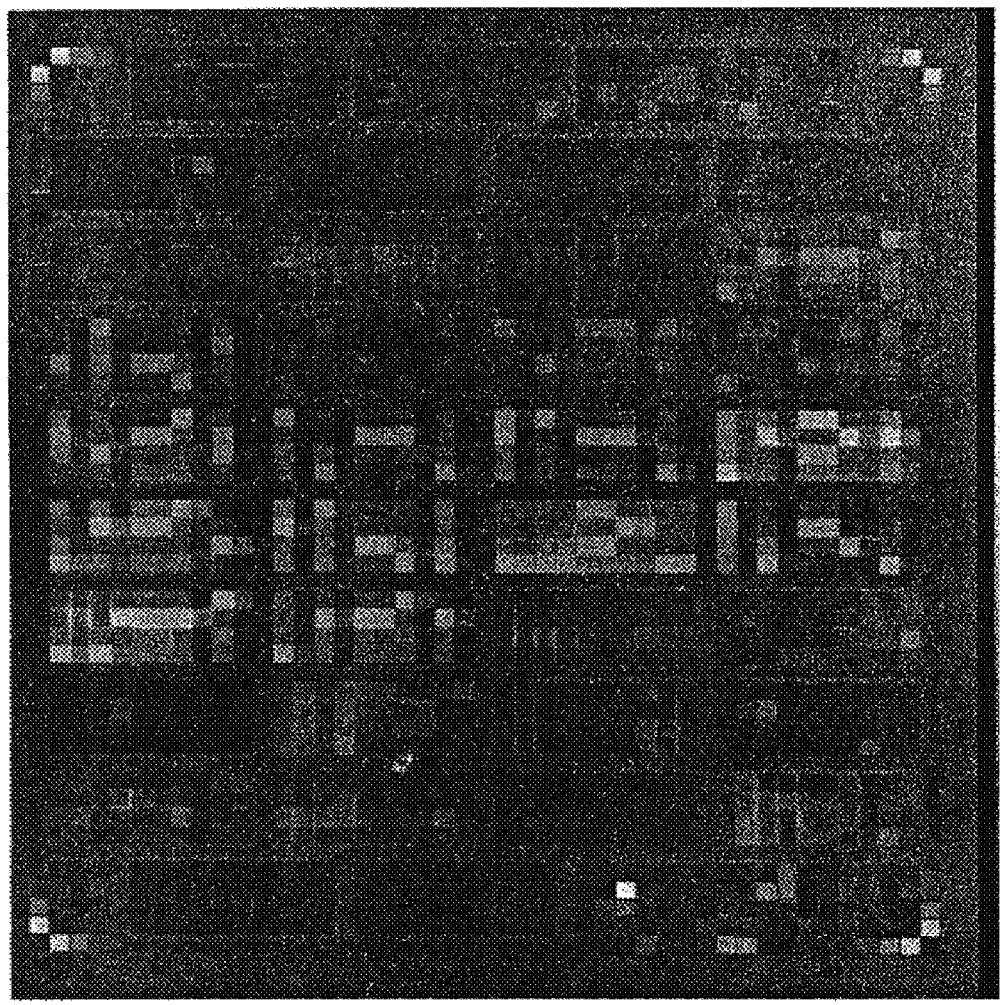
FIG. 25: Hybridization of homozygous wildtype (A) and ΔF508 mutant (B) target sequences from exon 10 of the CFTR gene to a block tiling array designed to detect mutations, ΔF508, ΔI507 and F508C.
Figure 25B:
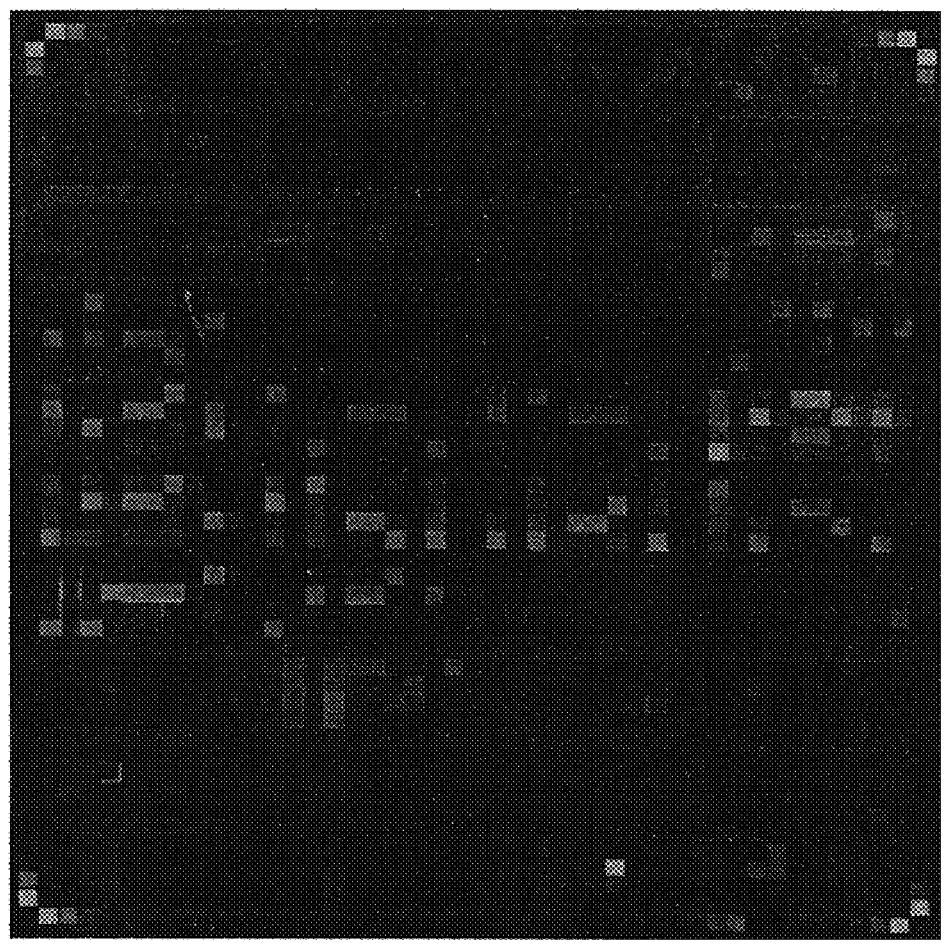

FIG. 25 (panels A and B) illustrates mutation analysis for ΔF508, a three base pair deletion in Exon 10 of the CFTR gene. In contrast to the hybridization pattern seen in base change mutations, in mutations where bases are inserted or deleted, probe arrays show a different hybridization pattern. Identical probes are synthesized in the two central columns of base substitution arrays. As a result, either mutant or wild type target hybridizations always result in two side-by-side features (a doublet) with high fluorescence intensity at the center of the array. In a heterozygote hybridization, two sets of doublets, one matched to the wild type sequence and one to the mutant sequence occur (FIG. 24, panel B). In contrast, wild type and mutant probe column sequences are offset from each other for deletion or insertion mutations and hybridization doublets are not seen. Instead of the six high intensity signals with one doublet, five independent features in alternating columns characterize a homozygote and ten features, one in each column will be positive with heterozygote targets. This is evident from the ΔF508 hybridization pattern in FIG. 25, panel A. Although a wildtype target has been hybridized and the highest intensity features confirm the wild type sequence (ATCTT), there is an additional hybridization in the first mutant column. Analysis of that probe sequence shows a 10 base perfect match with the mutant sequence.

The image in FIG. 25, panel B resulted from hybridizing a DNA chip with a target homozygous for ΔF508. In this image five features, all with probe sequences complementary to the mutant show significant signal. The mutation sequence bridging the deletion site, ATTGG, is confirmed. Similar to what was seen in the example of the G551D mutation, there is added information in neighboring subarrays designed to detect the _I507 and F508C mutations. This is expected since they are in such close proximity to ΔF508 that their probe sets significantly overlap the ΔF508 probes. The ΔF508 homozygous target has no perfect matches with wild type or mutant probes in the _I507 and F508C subarrays. However, there are some low intensity signals within these two blocks of probes. The F508C array has a doublet that matches 11 bases of the mutant ΔF508 target. Similarly, the hybridization in the eighth column of the _I507 array has a probe that matches 13/14 bases with the target.

Figure 26:
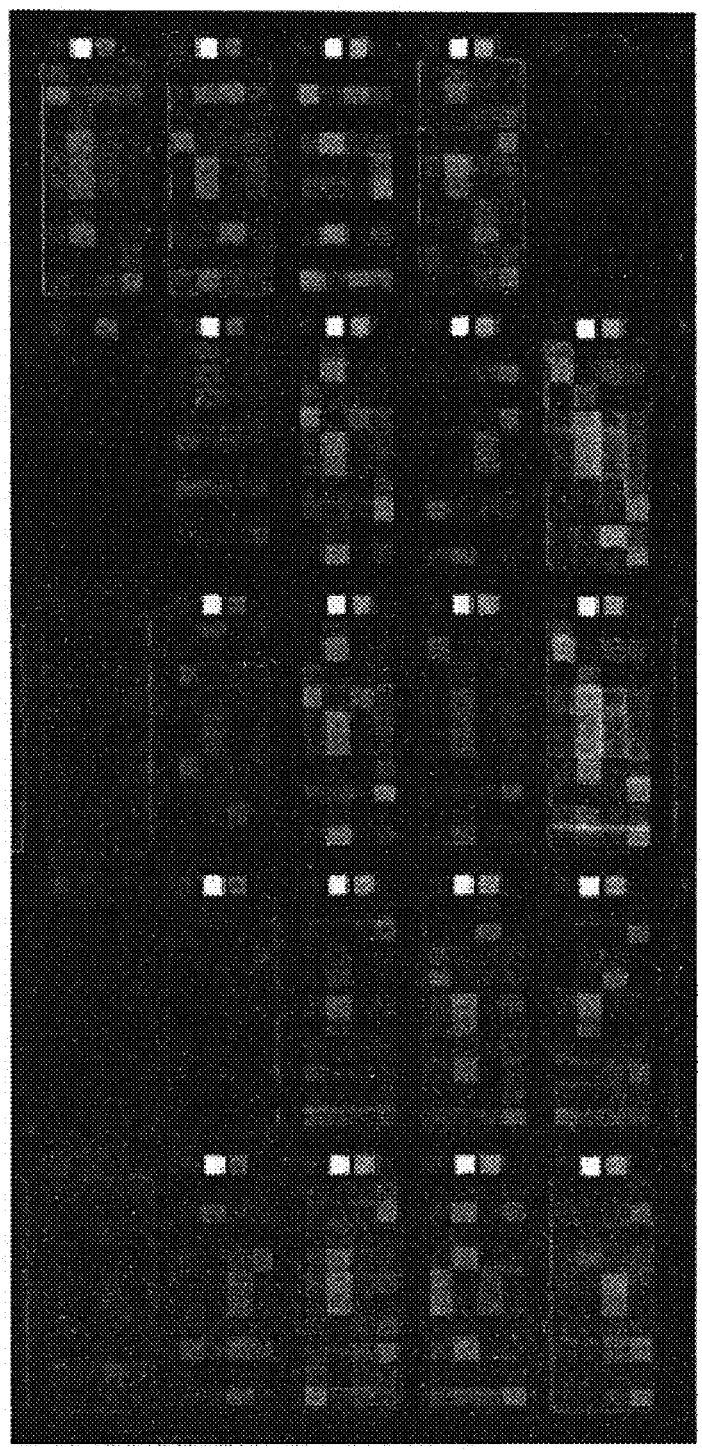
FIG. 26: Hybridization of heterozygous mutant target sequences, ΔF508/F508C, to the array of FIG. 25.
Figure 30A:
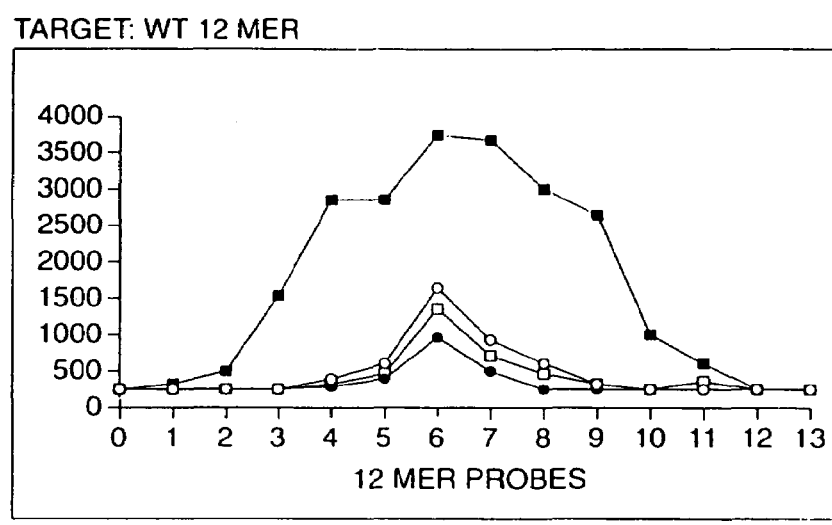
FIG. 30, in graphs 2, 3, and 4, graphically depicts the data in FIG. 29. On each graph, the X ordinate is the position of the probe in its row on the chip, and the Y ordinate is the signal at that probe site after hybridization.
Figure 30B:
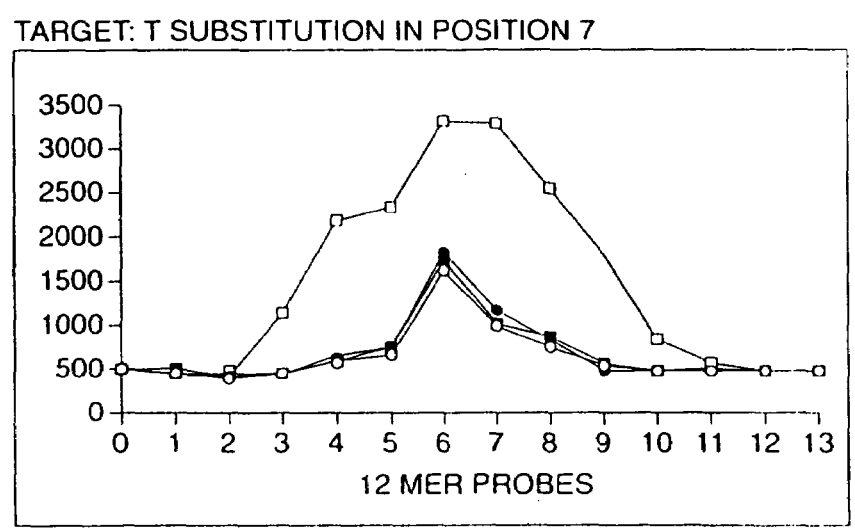
Figure 30C:
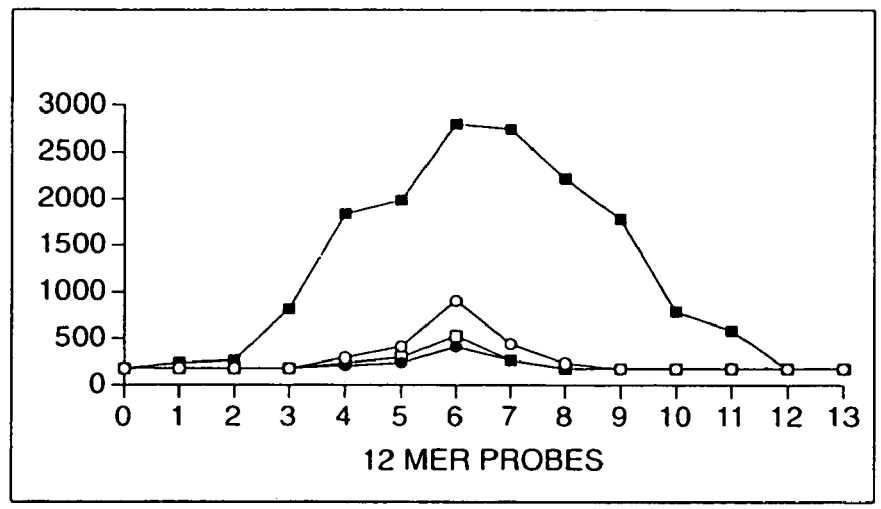
Figure 30D:
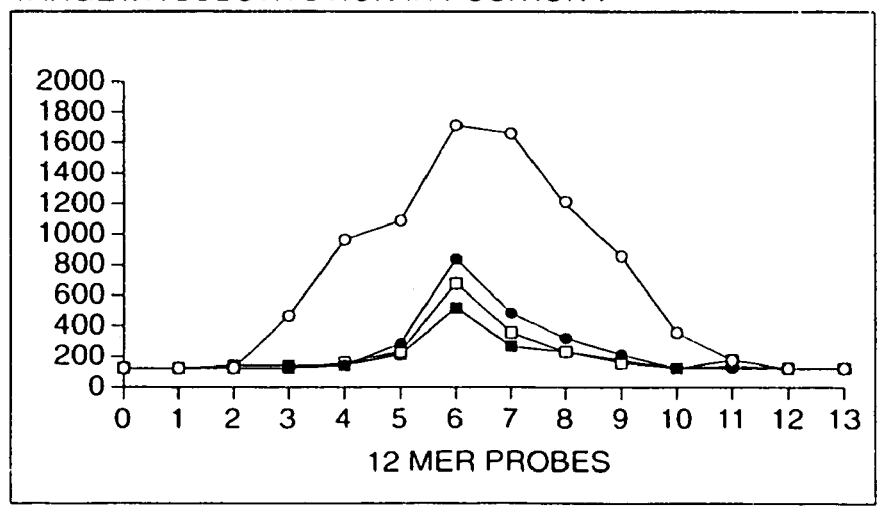

FIG. 26 shows hybridization of a heterozygous double mutant ΔF508/F508C to the same array as described above. Conventional reverse dot blot would score this sample as a homozygous ΔF508 mutant. In the present assays, the ΔF508 and F508C alleles are separately detected by the respective subarrays designed to detect these mutations.

C. Chips for Cancer Diagnosis

There are at least two types of genes which are often altered in cancerous cells. The first type of gene is an oncogene, and the second type of gene is a tumor suppressor gene such as a transcription factor. Examples of oncogenes genes include hMSH2 (Fishel et al., *Cell* 75, 1027–1038 (1993)) and hMLH1 (Papadopoulos et al., *Science* 263, 1625–1628 (1994)), which function in mismatch repair. Other examples of oncogenes altered in tumors include K-Ras, H-Ras, N-Ras, cyclins, neu/Her/2, myc, L-myc, N-myc, bc12 and met. See Marx, *Science* 260, 751–752 (1993); Cotran et al., *Robbins Pathologic Basis of Disease* (4th ed. 1989). The most well-known example of a tumor suppressor gene is the p53 protein gene (Buchman et al., *Gene* 70, 245–252 (1988)). Other tumor suppressor genes include APC, DCC, Rb, WT1, and NF1 (Marks, supra; Marshall, *Cell* 64, 313–326 (1991)). Variant forms (i.e., mutants) of oncogenes and tumor suppressor genes are associated with the development of the cancerous state. By monitoring the state of both oncogenes and tumor suppressor genes (individually and in combination) in a patient, it is possible to determine individual susceptibility to a cancer, a patient's prognosis upon cancer diagnosis, and to target therapy more efficiently.

The p53 gene spans 20 kbp in humans and has 11 exons, 10 of which are protein coding (see Tominaga et al., 1992, *Critical Reviews in Oncogenesis* 3:257–282, incorporated herein by reference). The gene produces a 53 kilodalton phosphoprotein that regulates DNA replication. The protein acts to halt replication at the G1/S boundary in the cell cycle and is believed to act as a "molecular policeman," shutting down replication when the DNA is damaged or blocking the reproduction of DNA viruses (see Lane, 1992, *Nature* 358: 15–16, incorporated herein by reference). The p53 transcription factor is part of a fundamental pathway which controls cell growth. Wild-type p53 can halt cell growth, or in some cases bring about programmed cell death (apoptosis). Such tumor-suppressive effects are absent in a variety of known p53 gene mutations. Moreover, p53 mutants not only deprive a cell of wild-type p53 tumor suppression, they also may spur abnormal cell growth.

In tumor cells, p53 is the most commonly mutated gene discovered to date (see Levine et al., 1991, *Nature* 351: 453–456, and Hollstein et al., 1991, *Science* 253:49–53, each of which is incorporated herein by reference). Over half of the 6.5 million patients diagnosed with cancer annually possess p53 mutations in their tumor cells. Among common tumors, about 70% of colorectal cancers, 50% of lung cancers and 40% of breast cancers contain p53 mutations. In all, over 51 types of human tumors have been documented to possess p53 mutations, including bladder, brain, breast, cervix, colon, esophagus, larynx, liver, lung, ovary, pancreas, prostate, skin, stomach, and thyroid tumors (Culotta & Koshland, *Science* 262, 1958–1961 (1993); Rodrigues et al., 1990, *PNAS* 87:7555–7559, incorporated herein by reference). According to data presented by David Sidransky (1992 San Diego Conference), over 400 mutations in p53 are known. The presence of a p53 mutation in a tumor has also been correlated with a patient's prognosis. Patients who possess p53 mutations have a lower 5-year survival rate.

Proper diagnosis of the form of p53 in tumor cells is critical to clinicians to prescribe appropriate therapeutic regimens. For instance, patients with breast cancer who show no invasion of nearby lymph nodes generally do not relapse after standard surgical treatment and chemotherapy. Of the 25% who do relapse after surgery and chemotherapy, additional chemotherapy is appropriate. At present, there is no clear way to determine which patients will benefit from such additional chemotherapy prior to relapse. However, correlating p53 mutations to tumorigenicity and metastasis provides clinicians with a means to determine whether such additional treatments are warranted.

In addition to facilitating conventional chemotherapy, appropriate diagnosis of p53 mutations provides clinicians with the ability to identify individuals who will benefit the most from gene therapy techniques, in which appropriately operative p53 copies are restored to a tumor site. Clinical p53 gene therapy trials are presently underway (Culotta & Koshland, supra).

The analysis of p53 mutations can also be used to identify which carcinogens lead to particular tumors (Harris, *Science* 262, 1980–1981 (1993)). For instance, dietary aflatoxin $B_1$ exposure is associated with G:C to T:A transversions at residue 249 of p53 in hepatocellular carcinomas (Hsu et al., *Nature* 350, 427 (1991); Bressac et al., *Nature* 350, 429 (1991); Harris, supra).

While most described p53 mutations are somatic in origin, some types of cancer are associated with germline p53 mutation. For instance, Li-Fraumeni syndrome is a hereditary condition in which individuals receive mutant p53 alleles, resulting in the early onset of various cancers (Harris, supra); Frebourg et al., *PNAS* 89, 6413–6417 (1992); Malkin et al., *Science* 250, 1233 (1990)). These mutations are associated with instability in the rest of the genome, creating multiple genetic alterations, and eventually leading to cancer.

hMLH1 and hMSH2 are mismatch repair genes which are causal agents in hereditary nonpolyposis colorectal cancer in individuals with mutant hMLH1 or hMSH2 alleles (Fishel et al., supra, and Papadopoulos et al., supra). Hereditary nonpolyposis colorectal cancer is a common genetic disorders, affecting about 1 in 200 individuals (Lynch et al., *Gastroenterology* 104, 1535 (1993)). Detection of hMLH1 and hMSH2 mutations in the population allows diagnosis of nonpolyposis colorectal cancer prone individuals prior to the manifestation of disease. This allows for the implementation of special screening programs for cancer-prone individuals to ensure early detection of cancer, thereby enhancing survival rates of afflicted individuals. In addition, genetic counselors may use the information derived from HMLH1 and HMSH2 chips to improve family planning as described for cystic fibrosis chips. The detection of mutations in hMLH1 and hMSH2 individually or in combination with p53 can also be used by clinicians to assess cancer prognosis and treatment modality. Finally, the information can be used to target appropriate individuals for gene therapy.

The entire hMLH1 gene is less than 85 kbp in length, comprising 2268 coding nucleotides (Papadopoulos et al., supra). Sequences from the gene have been deposited with GenBank (accession number U07418). Mutations associated with hereditary nonpolyposis colorectal cancer include the deletion of exon 5 (codons 578–632), a 4 base pair deletion of codons 727 and 728 resulting in a shift in the reading frame of the gene, a 4 base pair insertion at codons 755 and 756 resulting in an extension of the COOH terminus, a 371 base pair deletion and frameshift mutation at position 347, and a transversion causing an alteration of codon 252 resulting in the insertion of a stop codon (id.).

hMSH2 is a human homologue of the bacterial MutS and *S. cerevisiae* MSH mismatch-repair genes. MSH2, like hMLH1 is associated with hereditary nonpolyposis cancer. Although only a few MSH2 gene samples from tumor tissue have been characterized, at least some tumor samples show a T to C transition mutation at position 2020 of the cDNA sequence, resulting in the loss of an intron-exon splice acceptor site.

In view of the role of mutations in p53, MSH2 and/or hMLH1 in hereditary predisposition to cancer, to neoplastic transformation events leading to cancer and to cancer prognosis, it is important to screen individuals to determine whether they possess mutant alleles, and to identify precisely which mutations the individuals possess. Because many mutations are point mutations, or extremely small insertions or deletions, which are generally undetectable by standard Southern analysis, accurate diagnosis requires a capacity to examine a gene nucleotide-by-nucleotide.

Mutations in the hMSH2, hMLH1 or p53 genes, irrespective of whether previously characterized, can be detected by any of the tiling strategies noted above. Reference sequences of interest include full-length genomic and cDNA sequences of each of these genes and subsequences thereof, such as exons and introns. For example, each nucleotide in the 20 kb p53 genomic sequence can be tiled using the basic strategy with an array of about 80,000 probes. As in the CFTR chip, some reference sequences are comparatively short sequences including the site of a known mutation and a few flanking nucleotides. However, in general, the types and locations of mutations show more variability between patients than is the case for the CFTR chip.

Some chips tile reference sequences that encompass mutational "hot spots." For instance, a variety of cellular and oncoviral proteins bind to specific regions of p53, including Mdm2, SV40 T antigen, E1b from adenovirus and E6 from human papilloma virus. These binding sites correlate to some extent with observed high frequency somatic mutation regions of p53 found in tumor cells from cancer patients (see Harris et al., supra). Hot spots include exons 2, 3, 5, 6, 7 and 8 and the intronic regions between exons 2 and 3, 3 and 4 and 4 and 5. Fragments of the hMLH1 gene of particular interest include those encoding codons 578–632, 727, 728, 347, 252. Some chips are tiled to read mutations in each of the hMSH2, hMLH1 and p53 genes, both wildtype and mutant versions.

Standard or asymmetric PCR can be used to generate the target DNA used in the tiling assays described above. In general, PCR is used to amplify hMSH2, hMLH1 or p53 sequences from a tissue of interest such as a tumor. Mixed PCR reactions can also be used to generate hMSH2, hMLH1 or p53 sequences simultaneously in a single reaction mixture. Any of the coding or noncoding sequences from the genes may be amplified for use in the tiling assays described above.

Table 8 below provides examples of primers which are useful in synthesizing specific regions of hMSH2, hMHLH1 and p53. Other primers can readily be devised from the known genomic and cDNA sequences of the genes. The primers described in Table 8 specific for p53 amplification have ends tailored to facilitate cloning into standard restriction enzyme cloning sites.

TABLE 8

Examples of PCR primers useful in amplifying regions of p53, hMHH1 and hMSH2.

| Region Amplified | Primer Sequence (SEQ. ID. Nos. 132–143) | Description |
|---|---|---|
| Exon 5 (p53) | TAA TAC GAC TCA CTA TAG GGA GA CCC TGG GCA ACC AGC CCT GTC GT | Exon 5 T7 Primer (5' T7 to p53 3'). |

TABLE 8-continued

Examples of PCR primers useful in amplifying regions of p53, hMHH1 and hMSH2.

| Region Amplified | Primer Sequence (SEQ. ID. Nos. 132–143) | Description |
|---|---|---|
| Exon 5 (p53) | ATG CAA TTA ACC CTC ACT AAA GGG AGA CAC TTG TGC CCT GAC TTT CAA C | Exon 5 T3 Primer (5' T3 to p53 3'). |
| Exon 6 (p53) | TAA TAC GAC TCA CTA TAG GGA GCC TCC TCC CAG AGA CCC | Exon 6 T7 Primer (5' T7 to p53 3'). |
| Exon 6 (p53) | ATG CAA TTA ACC CTC ACT AA GGG AGA TCC CCA GGC CTC TGA TTC CTC ACT G | Exon 6 T3 Primer (5' T3 to p53 3'). |
| Exon 7 (p53) | TAA TAC GAC TCA CTA TAG GGA CTG GGG CAC AGC CAG GCC AGT GTG CA | Exon 7 T7 Primer (5' T7 to p53 3'). |
| Exon 7 (p53) | ATG CAA TTA ACC CTC ACT AAA GGG AGA GTC TCC CCA AGG CGC ACT GGC CTC A | Exon 7 T3 Primer (5' T3 to p53 3'). |
| Exon 8 (p53) | TAA TAC GAC TCA CTA TAG GGA GGG CAT AAC TGC ACC CTT GGT CTC CTC C | Exon 8 T7 Primer (5' T7 to p53 3'). |
| Exon 8 (p53) | ATG CAA TTA ACC CTC ACT AAA GGG AGA GGA CCT GAT TTC CTT ACT GCC TCT TGC | Exon 8 T3 Primer (5' T3 to p53 3'). |
| hMSH2 | GAC ATG GCG GTG CAG CCG AAG GAG A | Primer for MSH2, 5' to 3'. If used with MSH2 primer below, a 3033 base pair amplicon will result |
| hMSH2 | CTA TGT CAA TTG CAA ACA GTG CTC AGT TAC AG | Primer for hMSH2 5' to 3'. |
| hMLH1 | CTT GGC TCT TCT GGC GCC AAA ATG TCG TTC | Primer for hMLH1, 5' to 3'. If used with hMLH1 primer below, a 2484 base pair amplicon will result. |
| hMLH1 | TAT GTT AAG ACA CAT CTA TTT ATT TAT AAT CAA TCC | Primer for hMLH1 5' to 3'. |

After PCR amplification of the target amplicon one strand of the amplicon can be isolated, i.e., using a biotinylated primer that allows capture of the undesired strand on streptavidin beads. Alternatively, asymmetric PCR can be used to generate a single-stranded target. Another approach involves the generation of single stranded RNA from the PCR product by incorporating a T7 or other RNA polymerase promoter in one of the primers. The single-stranded material can optionally be fragmented to generate smaller nucleic acids with less significant secondary structure than longer nucleic acids.

In one such method, fragmentation is combined with labeling. To illustrate, degenerate 8-mers or other degenerate short oligonucleotides are hybridized to the single-stranded target material. In the next step, a DNA polymerase is added with the four different dideoxynucleotides, each labeled with a different fluorophore. Fluorophore-labeled dideoxynucleotide are available from a variety of commercial suppliers. Hybridized 8-mers are extended by a labeled dideoxynucleotide. After an optional purification step, i.e., with a size exclusion column, the labeled 9-mers are hybridized to the chip. Other methods of target fragmentation can be employed. The single-stranded DNA can be fragmented by partial degradation with a DNAse or partial depurination with acid. Labeling can be accomplished in a separate step, i.e., fluorophore-labeled nucleotides are incorporated before the fragmentation step or a DNA binding fluorophore, such as ethidium homodimer, is attached to the target after fragmentation.

Exemplary Chips a. Exon VI Chip

To illustrate the value of the DNA chips of the present invention in such a method, a DNA chip was synthesized by the VLSIPS™ method to provide an array of overlapping probes which represent or tile across a 60 base region of exon 6 of the p53 gene. To demonstrate the ability to detect substitution mutations in the target, twelve different single substitution mutations (wild type and three different substitutions at each of three positions) were represented on the chip along with the wild type. Each of these mutations was represented by a series of twelve 12-mer oligonucleotide probes, which were complementary to the wild type target except at the one substituted base. Each of the twelve probes was complementary to a different region of the target and contained the mutated base at a different position, e.g., if the substitution was at base 32, the set of probes would be complementary—with the exception of base 32—to regions of the target 21–32, 22–33, and 32–43). This enabled investigation of the effect of the substitution position within the probe. The alignment of some of the probes with a 12-mer model target nucleic acid is shown in FIG. 27.

Figures 27, 28:
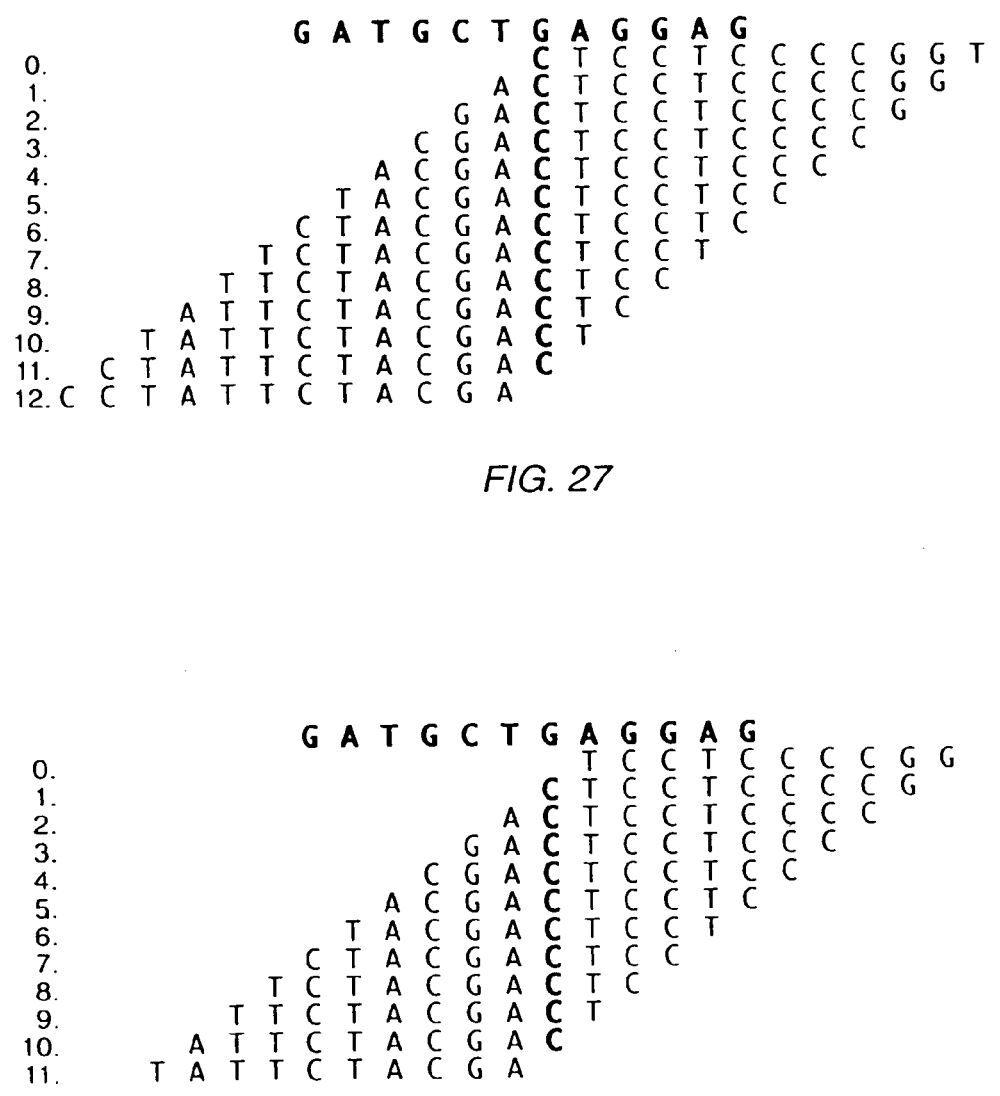

To demonstrate the effect of probe length, an additional series of ten 10-mer probes was included for each mutation (see FIG. 28). In the vicinity of the substituted positions, the wild-type sequence was represented by every possible overlapping 12-mer and 10-mer probe. To simplify comparisons, the probes corresponding to each varied position were arranged on the chip in the rectangular regions with the following structure: each row of cells represents one substitution, with the top row representing the wild type. Each column contains probes complementary to the same region of the target, with probes complementary to the 3'-end of the target on the left and probes complementary to the 5'-end of the target on the right. The difference between two adjacent columns is a single base shift in the positioning of the probes. Whenever possible, the series of 10-mer probes were placed in four rows immediately underneath and aligned with the 4 rows of 12-mer probes for the same mutation.

To provide model targets, 5' fluoresceinated 12-mers containing all possible substitutions in the first position of codon 192 were synthesized (see the starred position in the target in FIG. 27). Solutions containing 10 nM target DNA in 6×SSPE, 0.25% Triton X-100 were hybridized to the chip at room temperature for several hours. While target nucleic was hybridized to the chip, the fluorophores on the chip were excited by light from an argon laser, and the chip was scanned with an autofocusing confocal microscope. The emitted signals were processed by a PC to produce an image using image analysis software. By 1 to 3 hours, the signal had reached a plateau; to remove the hybridized target and allow hybridization to another target, the chip was stripped with 60% formamide, 2×SSPE at 17° C. for 5 minutes. The washing buffer and temperature can vary, but the buffer typically contains 2-to-3×SSPE, 10-to-60% formamide (one can use multiple washes, increasing the formamide concentration by 10% each wash, and scanning between washes to determine when the wash is complete), and optionally a small percentage of Triton X-100, and the temperature is typically in the range of 15-to-18° C.

Figure 31:
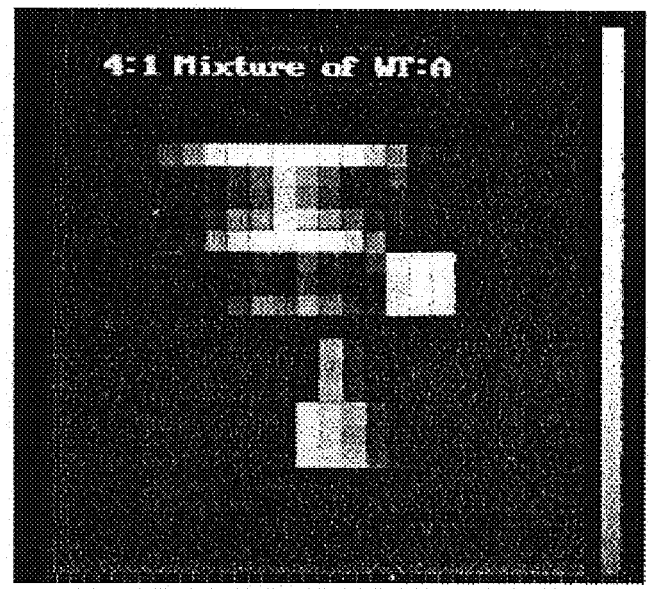
FIG. 31 shows the results of hybridizing mixed target populations of WT and mutant p53 genes to the p53 DNA chip.
Figure 32A:
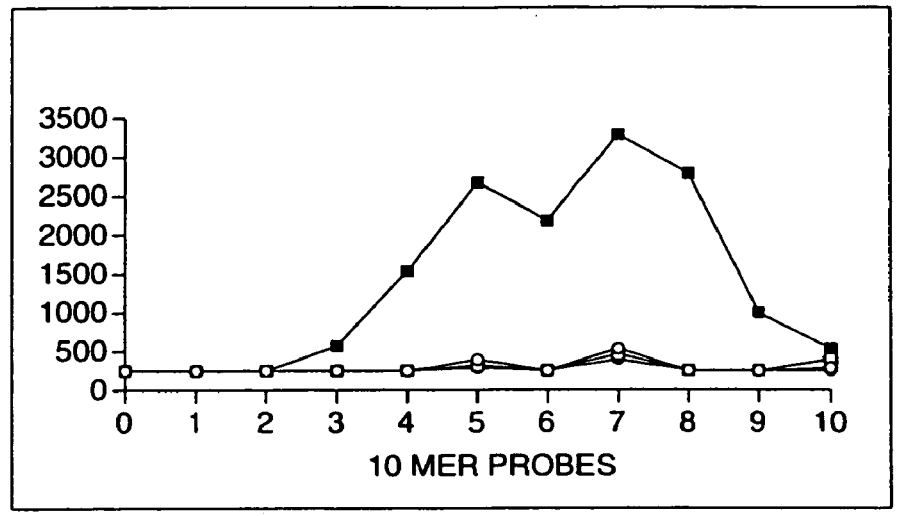
FIG. 32, in graphs 1–4, shows (see FIG. 30 as well) the hybridization efficiency of a 10-mer probe array as compared to a 12-mer probe array.
Figure 32B:
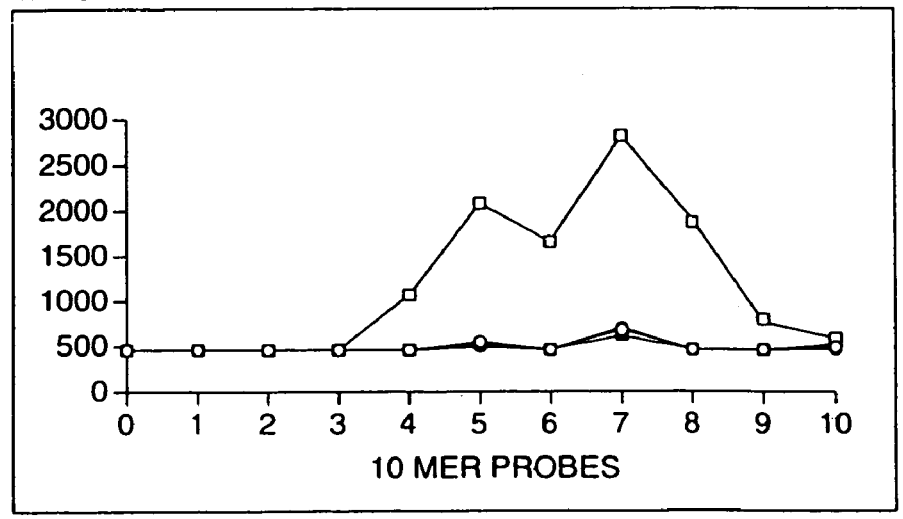
Figure 32C:
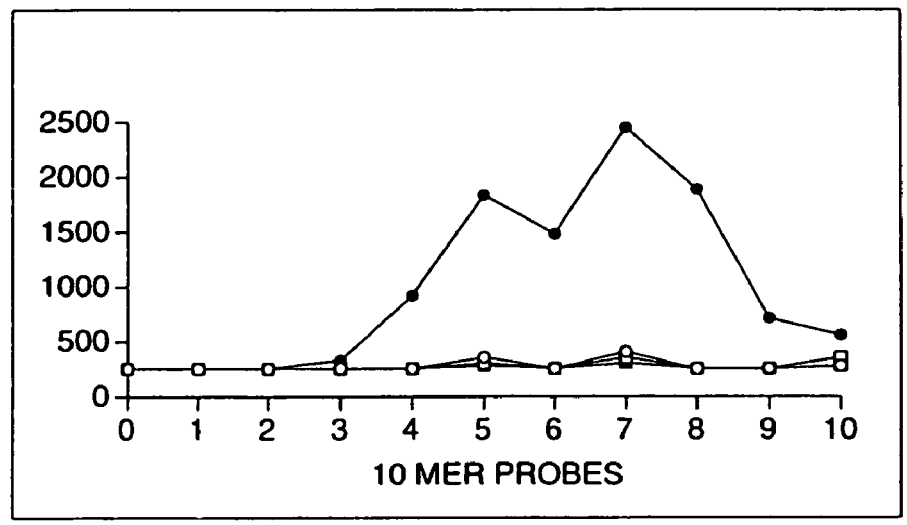
Figure 32D:
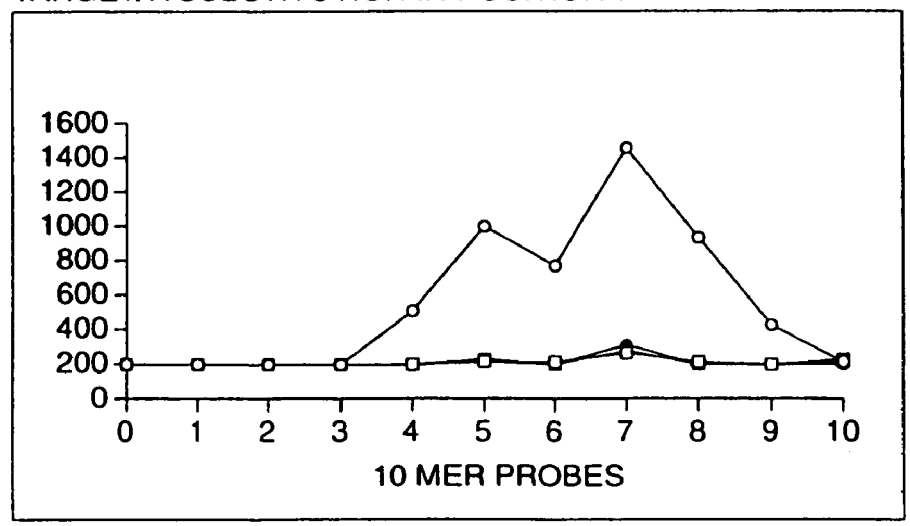

Very distinct patterns were observed after hybridization with targets with 1 base substitutions and visualization with a confocal microscope and software analysis, as shown in FIG. 29. In general, the probes which form perfect matches with the target retain the highest signal. For example, in the first image, the 12-mer probes that form perfect matches with the wild-type (WT) target are in the first row (top). The 12-mer probes with single base mismatches are located in the second, third, and fourth rows and have much lower signals. The data is also depicted graphically in FIG. 30. On each graph, the X ordinate is the position of the probe in its row on the chip, and the Y ordinate is the signal at that probe site after hybridization. When a target with a different one base substitution is hybridized the complementary set of probes has the highest signal (see pictures 2, 3, and 4 in FIG. 29 and graphs 2, 3, and 4 in FIG. 30). In each case, the probe set with no mismatches with the target has the highest signals. Within a 12-mer probe set, the signal was highest at position 6 or 7. The graphs show that the signal difference between 12-mer probes at the same X ordinate tended to be greatest at positions 5 and 8 when the target and the complementary probes formed 10 base pairs and 11 base pairs, respectively. Because tumors often have both WT and mutant p53 genes, mixed target populations were also hybridized to the chip, as shown in FIG. 31. When the hybridization solution consisted of a 1:1 mixture of WT 12-mer and a 12-mer with a substitution in position 7 of the target, the sets of probes that were perfectly matched to both targets showed higher signals than the other probe sets.

The hybridization efficiency of a 10-mer probe array as compared to a 12-mer probe array was also compared. The 10-mer and 12-mer probe arrays gave comparable signals (see graphs 1–4 in FIG. 30 and graphs 1–4 in FIG. 32). However, the 10-mer probe sets, which are in rows 5–8 (see images in FIG. 29), seemed to be better in this model system than the 12-mer probe sets at resolving one target from another, consistent with the expectation that one base mismatches are more destabilizing for 10-mers than 12-mers. Hybridization results within probe sets perfectly matched to target also followed the expectation that, the more matches the individual probe formed with the target, the higher the signal. However, duplexes with two 3' dangles (see FIG. 30, position 6 in graphs 1–4) have about as much signal as the probes which are matched along their entire length (see FIG. 30, position 7, in graphs 1–4).

This illustrative model system shows that 12-mer targets that differ by one base substitutions can be readily distinguished from one another by the novel probe array provided by the invention and that resolution of the different 12-mer targets was somewhat better with the 10-mer probe sets than with the 12-mer probe sets.

b. Exon V Chip

To analyze DNA from exon 5 of the p53 tumor suppressor gene, a set of overlapping 17-mer probes was synthesized on a chip. The probes for the WT allele were synthesized so as to tile across the entire exon with single base overlaps between probes. For each WT probe, a sets of 4 additional probes, one for each possible base substitution at position 7, were synthesized and placed in a column relative to the WT probe. Exon 5 DNA was amplified by PCR with primers flanking the exon. One of the primers was labeled with fluorescein; the other primer was labeled with biotin. After amplification, the biotinylated strand was removed by binding to streptavidin beads. The fluoresceinated strand was used in hybridization.

Figure 33:
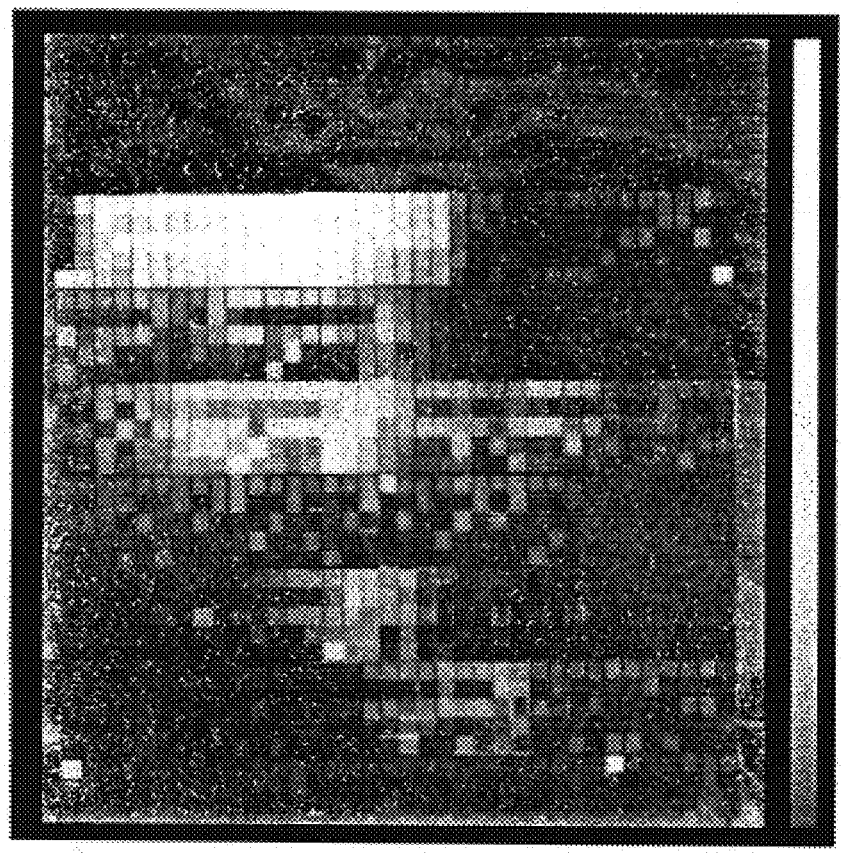
FIG. 33 shows an image of a p53 DNA chip hybridized to a target DNA.
Figure 34:
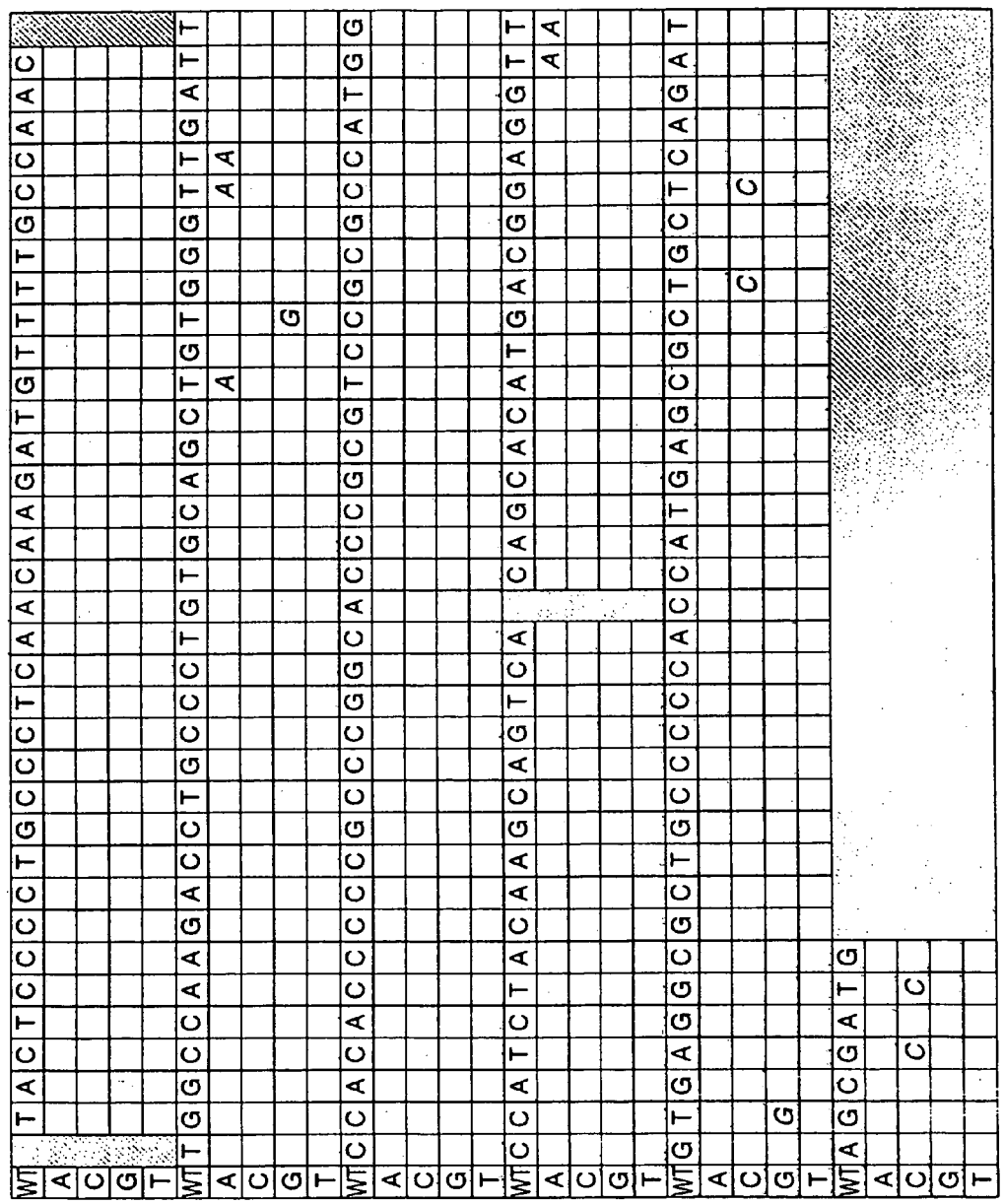
FIG. 34 illustrates how the actual sequence was read from the chip shown in FIG. 33. Gaps in the sequence of letters in the WT rows (SEQ. ID. No. 569) correspond to control probes or sites. Positions at which bases are miscalled are represented by letters in italic type in cells corresponding to probes in which the WT bases have been substituted by other bases.

About 1/3 of the amplified, single-stranded nucleic acid was hybridized overnight in 5×SSPE at 60° C. to the probe chip (under a cover slip). After washing with 6×SSPE, the chip was scanned using confocal microscopy. FIG. 33 shows an image of the p53 chip hybridized to the target DNA. Analysis of the intensity data showed that 93.5% of the 184 bases of exon 5 were called in agreement with the WT sequence (see Buchman et al., 1988, *Gene* 70: 245–252, incorporated herein by reference). The miscalled bases were from positions where probe signal intensities were tied (1.6%) and where non-WT probes had the highest signal intensity (4.9%). FIG. 34 illustrates how the actual sequence was read. Gaps in the sequence of letters in the WT rows correspond to control probes or sites. Positions at which bases are miscalled are represented by letters in italic type in cells corresponding to probes in which the WT bases have been substituted by other bases.

As the diagram indicates, the miscalled bases are from the low intensity areas of the image, which may be due to secondary structure in the target or probes preventing intermolecular hybridization. To diminish the effects due to secondary structure, one can employ shorter targets (i.e., by target fragmentation) or use more stringent hybridization conditions. In addition, the use of a set of probes synthesized by tiling across the other strand of a duplex target can also provide sequence information buried in secondary structure in the other strand. It should be appreciated, however, that the pattern of low intensity areas that forms as a result of secondary structure in the target itself provides a means to identify that a specific target sequence is present in a sample. Other factors that may contribute to lower signal intensities include differences in probe densities and hybridization stabilities.

These results demonstrate the advantages provided by the DNA chips of the invention to genetic analysis. As another example, heterozygous mutations are currently sequenced by an arduous process involving cloning and repurification of DNA. The cloning step is required, because the gel sequencing systems are poor at resolving even a 1:1 mixture of DNA. First, the target DNA is amplified by PCR with primers allowing easy ligation into a vector, which is taken up by transformation of *E. coli*, which in turn must be cultured, typically on plates overnight. After growth of the bacteria, DNA is purified in a procedure that typically takes about 2 hours; then, the sequencing reactions are performed, which takes at least another hour, and the samples are run on the gel for several hours, the duration depending on the length of the fragment to be sequenced. By contrast, the present invention provides direct analysis of the PCR amplified material after brief transcription and fragmentation steps, saving days of time and labor.

D. Mitochondrial Genome Chips

A human cell may have several hundred mitochondria, each with more than one copy of mtDNA. There is strand asymmetry in the base compositions, with one strand (Heavy) being relatively G rich, and the other strand (Light) being C rich. The L strand is 30.9% A, 31.2% C, 13.1% G, and 24.7% T. Human mtDNA is information-rich, encoding some 22 tRNAs, 12S and 16S rRNAs, and 13 polypeptides involved in oxidative phosphorylation. No introns have been detected. RNAs are processed by cleavage at tRNA sequences, and polyadenylated postranscriptionally. In some transcripts, polyadenylation also creates the stop codon, illustrating the parsimony of coding. In many individuals, mtDNA can be treated as haploid. However, some individuals are heteroplasmic (have more than one mtDNA sequence), and the degree of heteroplasmy can vary from tissue to tissue. Also, the rate of replication of mtDNAs can differ and together with random segregation during cell division, can lead to changes in heteroplasmy over time.

The human mitochondrial genome is 16,569 nucleotides long. The sequence of the L-strand is numbered arbitrarily from the MboI-5/7 boundary in the D-loop region. The complete sequence of the human mitochondrial genome has been published. See Anderson et al., *Nature* 290, 457–465 (1981). Mitochondrial DNA is maternally inherited, and has a mutation rate estimated to be tenfold higher than single copy nuclear DNA (Brown et al., *Proc. Natl. Acad. Sci. USA* 76, 1967–1971 (1979)). Human mtDNAs differ, on average, by about 70 base substitutions (Wallace, *Ann. Rev. Biochem.* 61, 1175–1212 (1992)). Over 80% of substitutions are transitions (i.e., pyrimidine-pyrimidine or purine-purine).

Analysis of mitochondrial DNA serves several purposes. Detection of mutations in the mitochondrial genome allows diagnosis of a number of diseases. The mitochondrial genome has been identified as the locus of several mutations associated with human diseases. Some of the mutations result in stop codons in structural genes. Such mutations have been mapped and associated with diseases, such as Leber's hereditary optic neuropathy, neurogenic muscular weakness, ataxia and retinitis pigmentosa. Other mutations (nucleotide substitutions) occur in tRNA coding sequences, and presumably cause conformational defects in transcribed tRNA molecules. Such mutations have also been mapped and associated with diseases such as Myoclonic Epilepsy and Ragged Red Fiber Disease. Another type of mutation commonly found is deletions and/or insertions. Some deletions span segments of several kb. Again, such mutations have been mapped and associated with diseases, for example, ocular myopathy and Person Syndrome. See Wallace, *Ann. Rev. Biochem.* 61-1175–1212 (1992) (incorporated by reference in its entirety for all purposes). Early detection of such diseases allows metabolic or genetic therapy to be administered before irretrievable damage has occurred. Id. Analysis of mitochondrial DNA is also important for forensic screening. Because the mitochondrial genome is a locus of high variability between individuals, sequencing a substantial length of mitochondrial DNA provides a fingerprint that is highly specific to an individual. Analysis of mitochondrial DNA is also important for evolutionary and epidemiological studies.

The reference sequence can be an entire mitochondrial genome or any fragment thereof. For forensic and epidemiological studies, the reference sequence is often all or part of the D-loop region in which variability between individuals is greatest (e.g., from 16024–16401 and 29–408). For detection of mutations, analysis of the entire genome is useful as a reference sequence, but shorter segments including the sites of known mutations, and about 1–20 flanking bases are also useful. Some chips have probes tiling paired reference sequences, representing wildtype and mutant versions of a sequence. Tiling a second reference sequence is particularly useful for detecting an insertion mutation occurring in 30–50% of ocular myopathy and Pearson syndrome patients, which consists of direct repeats of the sequence ACCTCCCTCACCA (SEQ. ID. No. 144). Some chips include reference sequences from more than one mitochondrial genome.

Mitochondrial reference sequences can be tiled using any of the strategies noted above. The block tiling strategy is particularly useful for analyzing short reference sequences or known mutations. Either the block strategy or the basic strategy is suitable for analyzing long reference sequences. In many of the tiling strategies, it is possible to use fewer probes compared with the number used in other chips without significant loss of sequence information. As noted above, most point mutations in mitochondrial DNA are transitions, so for each wildtype nucleotide in a reference sequence, one of the three possible nucleotide substitutions is much more likely than the other two. Accordingly, in the basic tiling strategy, for example, a reference sequence can be tiled using only two probe sets. One probe sets comprises a plurality of probes, each probe having a segment exactly complementary to the reference sequence. The second probe set comprises a corresponding probe for each probe in the first set. However, a probe from the second probe set differs from the corresponding probe from the first probe set in an interrogation position, in which the probe from the second probe set includes the transition of the nucleotide present in that position in the probe from the first probe set.

Target mitochondrial DNA can be amplified, labelled and fragmented prior to hybridization using the same procedures as described for other chips. Use of at least two labelled nucleotides is desirable to achieve uniform labelling. Some exemplary primers are described below and other primers can be designed from the known sequence of mitochondrial DNA. Because mitochondrial DNA is present in multiple copies per cell, it can also be hybridized directly to a chip without prior amplification.

Exemplary Chips

The invention provides a DNA chip for analyzing sequences contained in a 1.3 kb fragment of human mitochondrial DNA from the "D-loop" region, the most polymorphic region of human mitochondrial DNA. One such chip comprises a set of 269 overlapping oligonucleotide probes of varying length in the range of 9–14 nucleotides with varying overlaps arranged in ~600×600 micron features or synthesis sites in an array 1 cm×1 cm in size. The probes on the chip are shown in columnar form below. An illustrative mitochondrial DNA chip of the invention comprises the following probes (X, Y coordinates are shown, followed by the sequence; "DL3" represents the 3'-end of the probe, which is covalently attached to the chip surface.) (SEQ. ID. Nos. 145–157, 578, 579, 158–392, 580, and 394–406)

| | | | | | |
|---|---|---|---|---|---|
| | | | 6 | 2 | DL3GTTGGGGGCG |
| 0 | 0 | DL3AGTGGGGTATTT | 7 | 2 | DL3GGGGCGGGTA |
| 1 | 0 | DL3GGGTATTTAGTT | 8 | 2 | DL3GCGGGTAGGAT |
| 2 | 0 | DL3TTAGTTTATCCAA | 9 | 2 | DL3GGTAGGATGGGT |
| 3 | 0 | DL3ATCCAAACCAGG | 10 | 2 | DL3GGATGGGTCGTG |
| 4 | 0 | DL3ACCAGGATCGGA | 11 | 2 | DL3GGTCGTGTGTGT |
| 5 | 0 | DL3CGTGTGTGTGTGG | 12 | 2 | DL3GTGTGTGTGGCG |
| 6 | 0 | DL3CGTGTGTGTGTGGC | 13 | 2 | DL3TGTGGCGACGAT |
| 7 | 0 | DL3TCGTGTGTGTGTGG | 14 | 2 | DL3GACGATTGGGGT |
| 8 | 0 | DL3GTAGGATGGGTC | 15 | 2 | DL3ATTGGGGTATGG |
| 9 | 0 | DL3AGGATGGGTCGT | 16 | 2 | DL3GTATGGGGCTTG |
| 10 | 0 | DL3GATGGGTCGTGT | 0 | 3 | DL3GGATTGTGGTCG |
| 11 | 0 | DL3TGGCGACGATTG | 1 | 3 | DL3TGGTCGGATTGG |
| 12 | 0 | DL3GCGACGATTGGG | 2 | 3 | DL3GGATTGGTCTAAA |
| 13 | 0 | DL3TGGGGGGGA | 3 | 3 | DL3TCTAAAGTTTAAA |
| 14 | 0 | DL3GAGGGGGCG | 4 | 3 | DL3GTTTAAAATAGAA |
| 15 | 0 | DL3GGAGGGGGCGA | 5 | 3 | DL3ATAGAAAAACCG |
| 16 | 0 | DL3GAGGGGGCGA | 6 | 3 | DL3AGAAAAACCGC |
| 0 | 1 | DL3GGCTTGGTTGG | 7 | 3 | DL3AACCGCCATAC |
| 1 | 1 | DL3GGTTGGTTTGGG | 8 | 3 | DL3CCATACGTGAAAA |
| 2 | 1 | DL3TGGGGTTTCTAG | 9 | 3 | DL3ACGTGAAAATTGT |
| 3 | 1 | DL3GTTTCTAGTGGG | 10 | 3 | DL3AATTGTCAGTGGG |
| 4 | 1 | DL3AGTGGGGGGTGT | 11 | 3 | DL3TGTCAGTGGGGG |
| 5 | 1 | DL3GGGGTGTCAAAT | 12 | 3 | DL3TGGGGGGTTGA |
| 6 | 1 | DL3GTCAAATACATCG | 13 | 3 | DL3GGGTTGATTGTGT |
| 7 | 1 | DL3ACATCGAATGGAG | 14 | 3 | DL3TTGTGTAATAAAA |
| 8 | 1 | DL3CGAATGGAGGAG | 15 | 3 | DL3AATAAAAGGGGA |
| 9 | 1 | DL3GAGGAGTTTCGT | 16 | 3 | DL3TAAAAGGGGAGG |
| 10 | 1 | DL3TTTCGTTATGTGA | 0 | 4 | DL3GTTTTTTAAAGG |
| 11 | 1 | DL3ATGTGACTTTTAC | 1 | 4 | DL3TTTTAAAGGTGG |
| 12 | 1 | DL3GACTTTTACAAAT | 2 | 4 | DL3AGGTGGTTTGG |
| 13 | 1 | DL3AAATCTGCCCGA | 3 | 4 | DL3TTGGGGGGGAG |
| 14 | 1 | DL3AATCTGCCCGAG | 4 | 4 | DL3GGAGGGGGCG |
| 15 | 1 | DL3CCCGAGTGTAGT | 5 | 4 | DL3GGGGCGAAGAC |
| 16 | 1 | DL3AGTGTAGTGGGG | 6 | 4 | DL3GAAGACCGGATG |
| 0 | 2 | DL3GGGAGGGTGAG | 7 | 4 | DL3CCGGATGTCGTG |
| 1 | 2 | DL3GGTGAGGGTATG | 8 | 4 | DL3GTCGTGAATTTGT |
| 2 | 2 | DL3GGTATGATGATTAG | 9 | 4 | DL3CGTGAATTTGTGT |
| 3 | 2 | DL3GATTAGAGTAAGT | 10 | 4 | DL3TTGTGTAGAGACG |
| 4 | 2 | DL3TTAGAGTAAGTTA | 11 | 4 | DL3TAGAGACGGTTT |
| 5 | 2 | DL3AAGTTATGTTGGG | | | |

-continued

| | | |
|---|---|---|
| 12 | 4 | DL3ACGGTTTGGGG |
| 13 | 4 | DL3TGGGGTTTTTGT |
| 14 | 4 | DL3GGGTTTTTGTTT |
| 15 | 4 | DL3TTGTTTCTTGGG |
| 16 | 4 | DL3TCTTGGGATTGTG |
| 0 | 5 | DL3TGTATGAATGATTT |
| 1 | 5 | DL3TGATTTCACACAA |
| 2 | 5 | DL3ACACAATTAATTAA |
| 3 | 5 | DL3AATTAATTACGAA |
| 4 | 5 | DL3TACGAACATCCTG |
| 5 | 5 | DL3ACGAACATCCTGT |
| 6 | 5 | DL3TCCTGTATTATTA |
| 7 | 5 | DL3GTATTATTATTGTT |
| 8 | 5 | DL3ATTGTTAAACTTA |
| 9 | 5 | DL3AAACTTACAGACG |
| 10 | 5 | DL3ACAGACGTGTCG |
| 11 | 5 | DL3GTGTCGGTGAAA |
| 12 | 5 | DL3GTGAAAGGTGTGT |
| 13 | 5 | DL3GGTGTGTCTGTAG |
| 14 | 5 | DL3TGTGTCTGTAGTA |
| 15 | 5 | DL3GTAGTATTGTTTT |
| 16 | 5 | DL3AGTATTGTTTTTT |
| 0 | 6 | DL3CCTCGTGGGATA |
| 1 | 6 | DL3TGGGATACAGCG |
| 2 | 6 | DL3GATACAGCGTCAT |
| 3 | 6 | DL3GCGTCATAGACAG |
| 4 | 6 | DL3AGACAGAAACTAA |
| 5 | 6 | DL3CAGAAACTAAGGA |
| 6 | 6 | DL3TAAGGACGGAGT |
| 7 | 6 | DL3GACGGAGTAGGA |
| 8 | 6 | DL3GTAGGATAATAAA |
| 9 | 6 | DL3TAATAAATAGCG |
| 10 | 6 | DL3ATAGCGTAGGAT |
| 11 | 6 | DL3TAGCGTAGGATG |
| 12 | 6 | DL3AGGATGCAAGTT |
| 13 | 6 | DL3ATGCAAGTTATAA |
| 14 | 6 | DL3GTTATAATGTCCG |
| 15 | 6 | DL3ATGTCCGCTTGT |
| 16 | 6 | DL3TCCGCTTGTATG |
| 0 | 7 | DL3GTGAGTGCCCTC |

-continued

| | | |
|---|---|---|
| 1 | 7 | DL3TGCCCTCGAGAG |
| 2 | 7 | DL3CCTCGAGAGGTA |
| 3 | 7 | DL3AGAGGTACGTAA |
| 4 | 7 | DL3ACGTAAACCATA |
| 5 | 7 | DL3ACCATAAAAGCAG |
| 6 | 7 | DL3AAAGCAGACCC |
| 7 | 7 | DL3AGACCCCCCAT |
| 8 | 7 | DL3CCCCCATACGT |
| 9 | 7 | DL3CATACGTGCGCT |
| 10 | 7 | DL3GTGCGCTATCAG |
| 11 | 7 | DL3GCGCTATCAGTA |
| 12 | 7 | DL3TCAGTAACGCTC |
| 13 | 7 | DL3GTAACGCTCTGC |
| 14 | 7 | DL3CTCTGCGACCTC |
| 15 | 7 | DL3GACCTCGGCCT |
| 16 | 7 | DL3CGGCCTCGTG |
| 0 | 8 | DL3GATGAAGTCCCAG |
| 1 | 8 | DL3AGTCCCAGTATTT |
| 2 | 8 | DL3GTATTTCGGATTT |
| 3 | 8 | DL3TCGGATTTATCG |
| 4 | 8 | DL3GATTTATCGGGT |
| 5 | 8 | DL3ATCGGGTGTGCA |
| 6 | 8 | DL3TGTGCAAGGGGA |
| 7 | 8 | DL3CAAGGGGAATTT |
| 8 | 8 | DL3GAATTTATTCTGTA |
| 9 | 8 | DL3TCTGTAGTGCTAC |
| 10 | 8 | DL3GTAGTGCTACCT |
| 11 | 8 | DL3GCTACCTAGTAG |
| 12 | 8 | DL3CTAGTAGTCCAGA |
| 13 | 8 | DL3TCCAGATAGTGGG |
| 14 | 8 | DL3AGATAGTGGGATA |
| 15 | 8 | DL3GGGATAATTGGT |
| 16 | 8 | DL3TAATTGGTGAGTG |
| 0 | 9 | DL3TATAGGGCGTGT |
| 1 | 9 | DL3GGCGTGTTCTCA |
| 2 | 9 | DL3GTGTTCTCACGAT |
| 3 | 9 | DL3TCACGATGAGAGG |
| 4 | 9 | DL3ATGAGAGGAGCG |
| 5 | 9 | DL3AGGAGCGAGGC |
| 6 | 9 | DL3CGAGGCCCGG |

-continued

| | | |
|---|---|---|
| 7 | 9 | DL3GCCCGGGTATT |
| 8 | 9 | DL3CGGGTATTGTGA |
| 9 | 9 | DL3GTGAACCCCCAT |
| 10 | 9 | DL3CCCCATCGATTT |
| 11 | 9 | DL3ATCGATTTCACTT |
| 12 | 9 | DL3TTTCACTTGACAT |
| 13 | 9 | DL3TTGACATAGAGCT |
| 14 | 9 | DL3TAGAGCTGTAGAC |
| 15 | 9 | DL3GTAGACCAAGGA |
| 16 | 9 | DL3ACCAAGGATGAAG |
| 0 | 10 | DL3CGTGTAATGTCAG |
| 1 | 10 | DL3TGTCAGTTTAGGG |
| 2 | 10 | DL3TCAGTTTAGGGA |
| 3 | 10 | DL3TAGGGAAGAGCA |
| 4 | 10 | DL3AAGAGCAGGGGT |
| 5 | 10 | DL3CAGGGGTACCTA |
| 6 | 10 | DL3GGTACCTACTGG |
| 7 | 10 | DL3TACTGGGGGGA |
| 8 | 10 | DL3GGGGGAGTCTAT |
| 9 | 10 | DL3AGTCTATCCCCA |
| 10 | 10 | DL3ATCCCCAGGGA |
| 11 | 10 | DL3CAGGGAACTGGT |
| 12 | 10 | DL3ACTGGTGGTAGG |
| 13 | 10 | DL3CTGGTGGTAGGA |
| 14 | 10 | DL3GTAGGAGGCACA |
| 15 | 10 | DL3GGCACATTTAGT |
| 16 | 10 | DL3TTTAGTTATAGGG |
| 0 | 11 | DL3AGGTTTACGGTG |
| 1 | 11 | DL3TACGGTGGGA |
| 2 | 11 | DL3GTGGGGAGTGG |
| 3 | 11 | DL3GGGAGTGGGTGA |
| 4 | 11 | DL3GGGTGATCCTATG |
| 5 | 11 | DL3CCTATGGTTGTTT |
| 6 | 11 | DL3GGTTGTTTGGATG |
| 7 | 11 | DL3GTTTGGATGGGT |
| 8 | 11 | DL3ATGGGTGGGAAT |
| 9 | 11 | DL3GGGAATTGTCATG |
| 10 | 11 | DL3GTCATGTATCATGT |
| 11 | 11 | DL3TCATGTATTTCGG |
| 12 | 11 | DL3TATTTCGGTAAA |

-continued

| | | |
|---|---|---|
| 13 | 11 | DL3TTCGGTAAATGG |
| 14 | 11 | DL3GTAAATGGCATGT |
| 15 | 11 | DL3GCATGTAATCGTG |
| 16 | 11 | DL3GTAATCGTGTAAT |
| 5 | 12 | DL3GGGAGGGGTAC |
| 6 | 12 | DL3GGGTACGAATGT |
| 7 | 12 | DL3ACGAATGTTCGTT |
| 8 | 12 | DL3TGTTCGTTCATGT |
| 9 | 12 | DL3CGTTCATGTCGTT |
| 10 | 12 | DL3GTCGTTAGTTGG |
| 11 | 12 | DL3TAGTTGGGAGTT |
| 12 | 12 | DL3GGAGTTGATAGTG |
| 13 | 12 | DL3ATAGTGTGTAGTT |
| 14 | 12 | DL3GTGTAGTTGACGT |
| 15 | 12 | DL3TGACGTTGAGGT |
| 16 | 12 | DL3CGTTGAGGTTTA |
| 5 | 13 | DL3TATAACATGCCAT |
| 6 | 13 | DL3AACATGCCATGGT |
| 7 | 13 | DL3CCATGGTATTTAT |
| 8 | 13 | DL3ATTTATGAACTGG |
| 9 | 13 | DL3AACTGGTGGACAT |
| 10 | 13 | DL3TGGACATCATGTA |
| 11 | 13 | DL3CATGTATTTTTGG |
| 12 | 13 | DL3TTTTGGGTTAGG |
| 13 | 13 | DL3GGGTTAGGATGT |
| 14 | 13 | DL3GGATGTAGTTTTG |
| 15 | 13 | DL3TGTAGTTTTGGG |
| 16 | 13 | DL3TTTGGGGGAGG |
| 5 | 14 | DL3GGGTTCATAACTG |
| 6 | 14 | DL3ATAACTGAGTGGG |
| 7 | 14 | DL3AACTGAGTGGGT |
| 8 | 14 | DL3GTGGGTAGTTGT |
| 9 | 14 | DL3GTAGTTGTTGGC |
| 10 | 14 | DL3GTTGGCGATACA |
| 11 | 14 | DL3CGATACATAAAAG |
| 12 | 14 | DL3TAAAAGCATGTAA |
| 13 | 14 | DL3GCATGTAATGACG |
| 14 | 14 | DL3ATGACGGTCGGT |
| 15 | 14 | DL3GTCGGTGGTACT |
| 16 | 14 | DL3GGTACTTATAACA |

```
                    -continued
    5          15    DL3TCGATTCTAAGAT 6          15    DL3TAAGATTAAATTT 7          15    DL3AAATTTGAATAAG 8          15    DL3AATAAGAGACAAG 9          15    DL3AAGAGACAAGAAA 10          15    DL3AAGAAAGTACCC 11          15    DL3AAAGTACCCCTT 12          15    DL3CCCCTTCGTCTA 13          15    DL3CTTCGTCTAAAC 14          15    DL3CTAAACCCATGG 15          15    DL3AACCCATGGTGG 16          15    DL3TGGTGGGTTCAT 5          16    DL3TTGGAAAAAGGT 6          16    DL3AAAAGGTTCCTG 7          16    DL3GGTTCCTGTTTA 8          16    DL3CCTGTTTAGTCTC 9          16    DL3TTAGTCTCTTTTT 10          16    DL3CTTTTTCAGAAAT 11          16    DL3AGAAATTGAGGTG 12          16    DL3AAATTGAGGTGGT 13          16    DL3GGTGGTAATCGT 14          16    DL3TAATCGTGGGTT 15          16    DL3GTGGGTTTCGAT 16          16    DL3GGTTTCGATTCT
```

Figure 35:
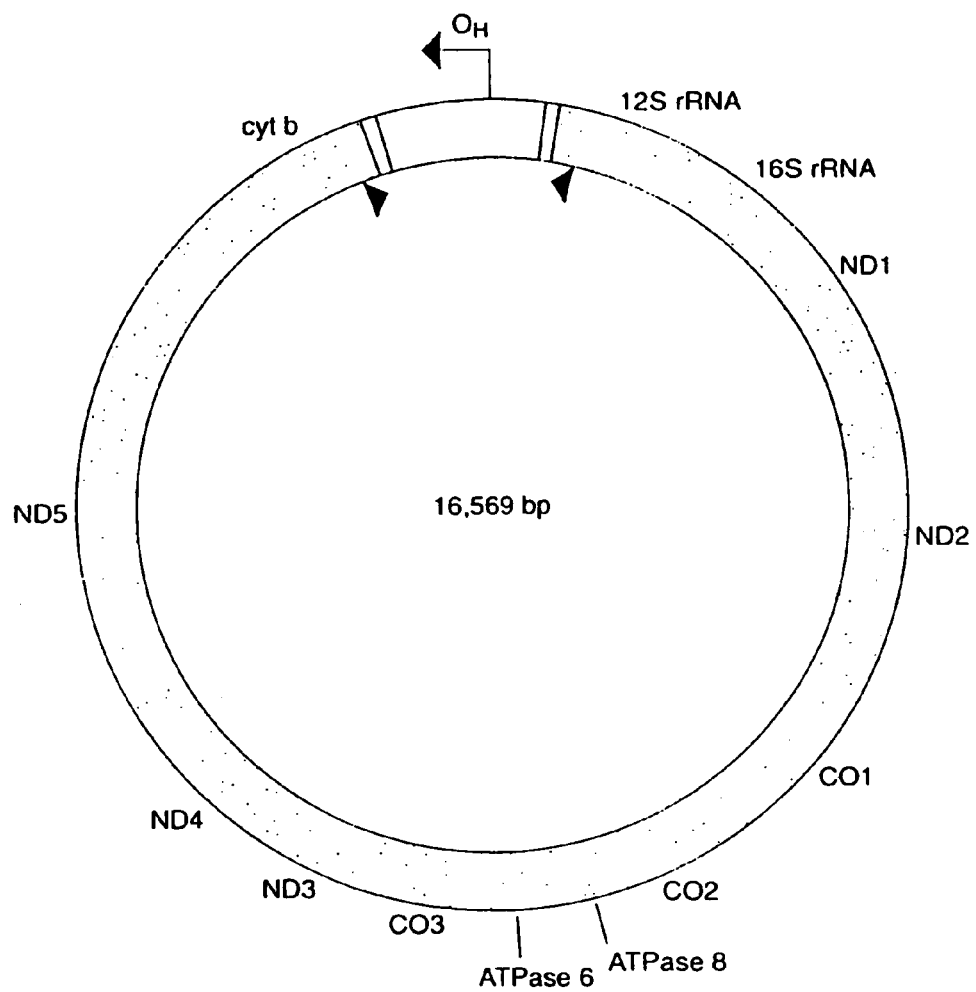
FIG. 35 shows the human mitochondrial genome; "$O_H$" is the H strand origin of replication, and arrows indicate the cloned unshaded sequence.

No probes were present in positions X, Y=0, 12 to X, Y=4, 12; X, Y=0, 13 to X, Y=4, 13; X, Y=0, 14 to X, Y=4, 14; X, Y=0, 15 to X, Y=4, 15; X, Y=0, 16 to X, Y=4, 16;

The length of each of the probes on the chip was variable to minimize differences in melting temperature and potential for cross-hybridization. Each position in the sequence was represented by at least one probe and most positions were represented by 2 or more probes. As noted above, the amount of overlap between the oligonucleotides varied from probe to probe. FIG. 35 shows the human mitochondrial genome; "$O_H$" is the H strand origin of replication, and arrows indicate the cloned unshaded sequence.

DNA was prepared from hair roots of six human donors (mt1 to mt6) and then amplified by PCR and cloned into M13; the resulting clones were sequenced using chain terminators to verify that the desired specific sequences were present. DNA from the sequenced M13 clones was amplified by PCR, transcribed in vitro, and labeled with fluorescein-UTP using T3 RNA polymerase. The 1.3 kb RNA transcripts were fragmented and hybridized to the chip. The results showed that each different individual had DNA that produced a unique hybridization fingerprint on the chip and that the differences in the observed patterns could be correlated with differences in the cloned genomic DNA sequence. The results also demonstrated that very long sequences of a target nucleic acid can be represented comprehensively as a specific set of overlapping oligonucleotides and that arrays of such probe sets can be usefully applied to genetic analysis.

Figure 36:
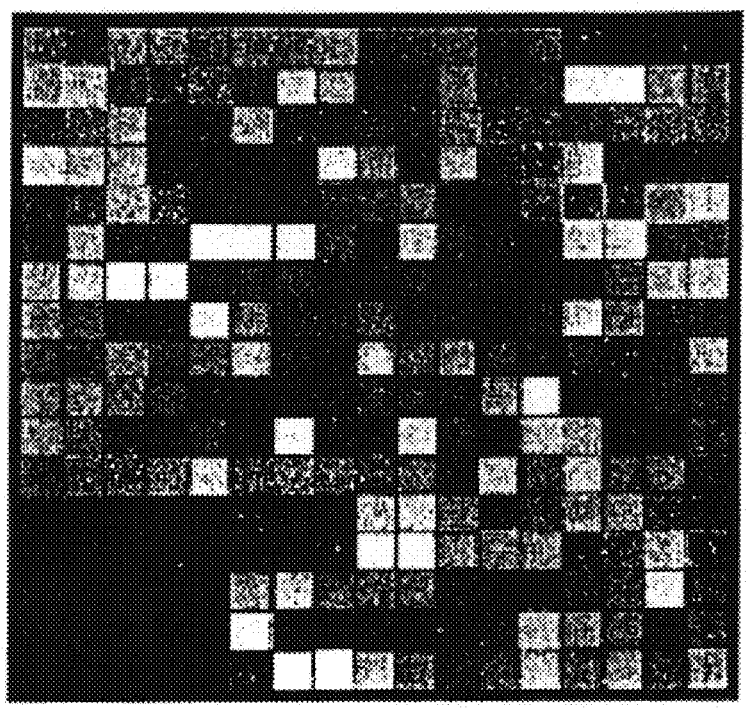
FIG. 36 shows the image observed from application of a sample of mitochondrial DNA derived nucleic acid (from the mt4 sample) on a DNA chip.
Figure 37:
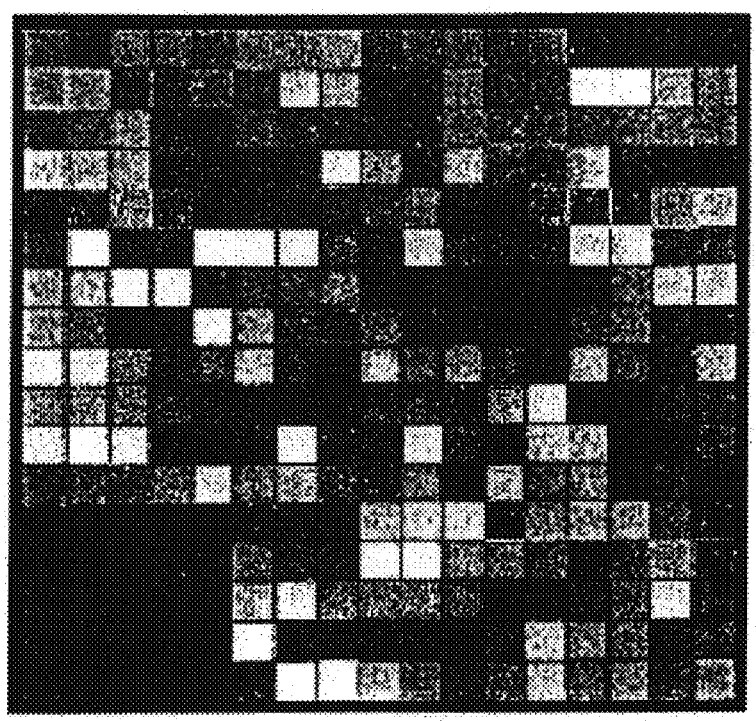
FIG. 37 is similar to FIG. 36 but shows the image observed from the mt5 sample.
Figure 38:
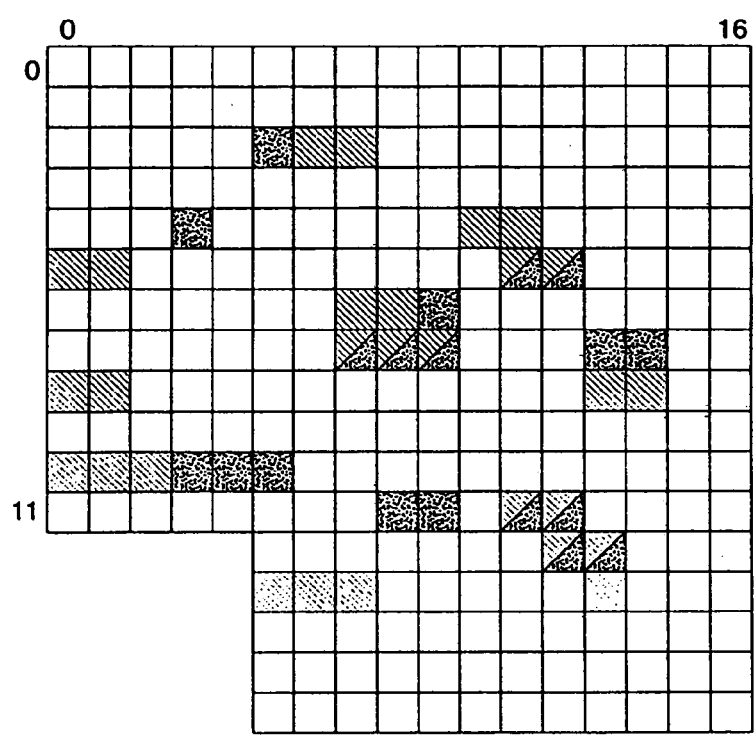
FIG. 38 shows the predicted difference image between the mt4 and mt5 samples on the DNA chip based on mismatches between the two samples and the reference sequence.
Figure 39:
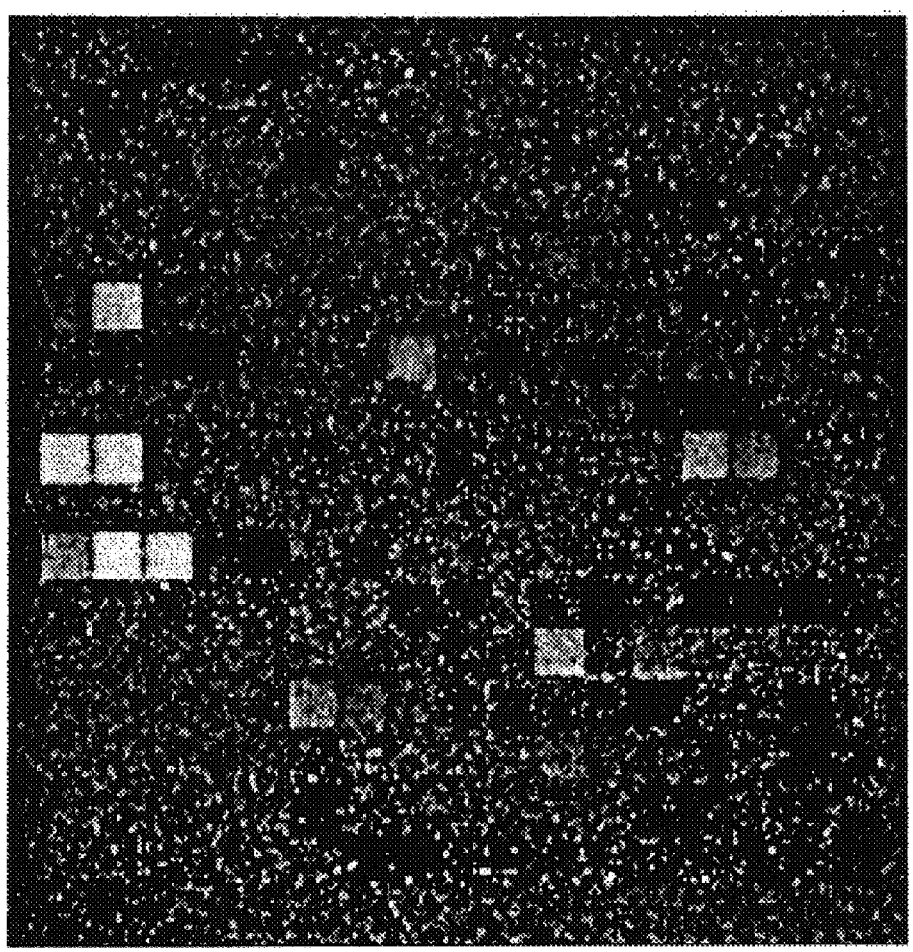
FIG. 39 shows the actual difference image observed for the mt4 and mt5 samples.

The sample nucleic acid was hybridized to the chip in a solution composed of 6×SSPE, 0.1% Triton-X 100 for 60 minutes at 15° C. The chip was then scanned by confocal scanning fluorescence microscopy. The individual features on the chip were 588×588 microns, but the lower left 5×5 square features in the array did not contain probes. To quantitate the data, pixel counts were measured within each synthesis site. Pixels represent 50×50 microns. The fluorescence intensity for each feature was scaled to a mean determined from 27 bright features. After scanning, the chip was stripped and rehybridized; all six samples were hybridized to the same chip. FIG. 36 shows the image observed from the mt4 sample on the DNA chip. FIG. 37 shows the image observed from the mt5 sample on the DNA chip. FIG. 38 shows the predicted difference image between the mt4 and mt5 samples on the DNA chip based on mismatches between the two samples and the reference sequence (see Anderson et al., supra). FIG. 39 shows the actual difference image observed.

Figure 40A:
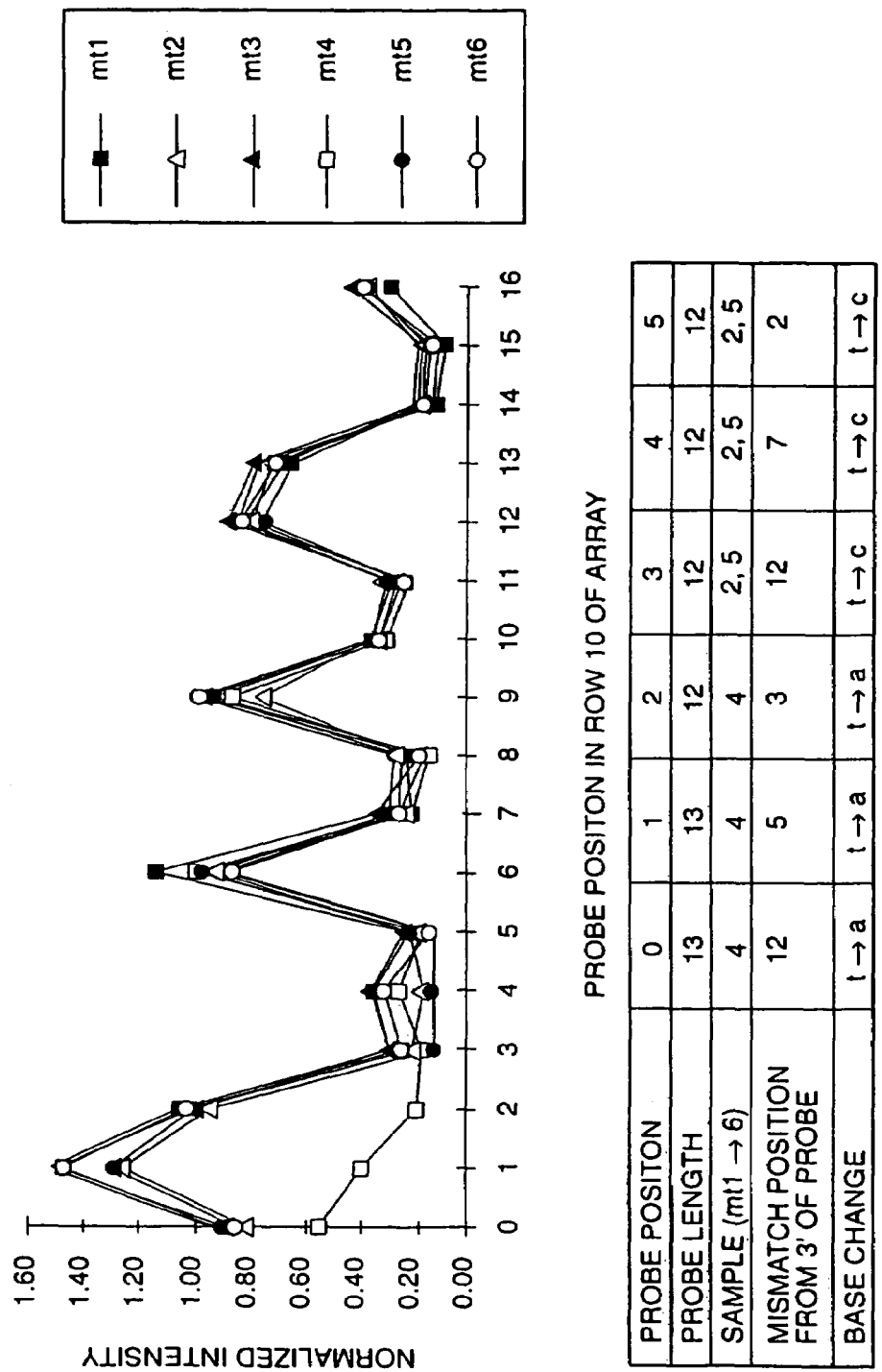
FIG. 40, in sheets 1 and 2, shows a plot of normalized intensities across rows 10 and 11 of the array and a tabulation of the mutations detected.
Figure 40B:
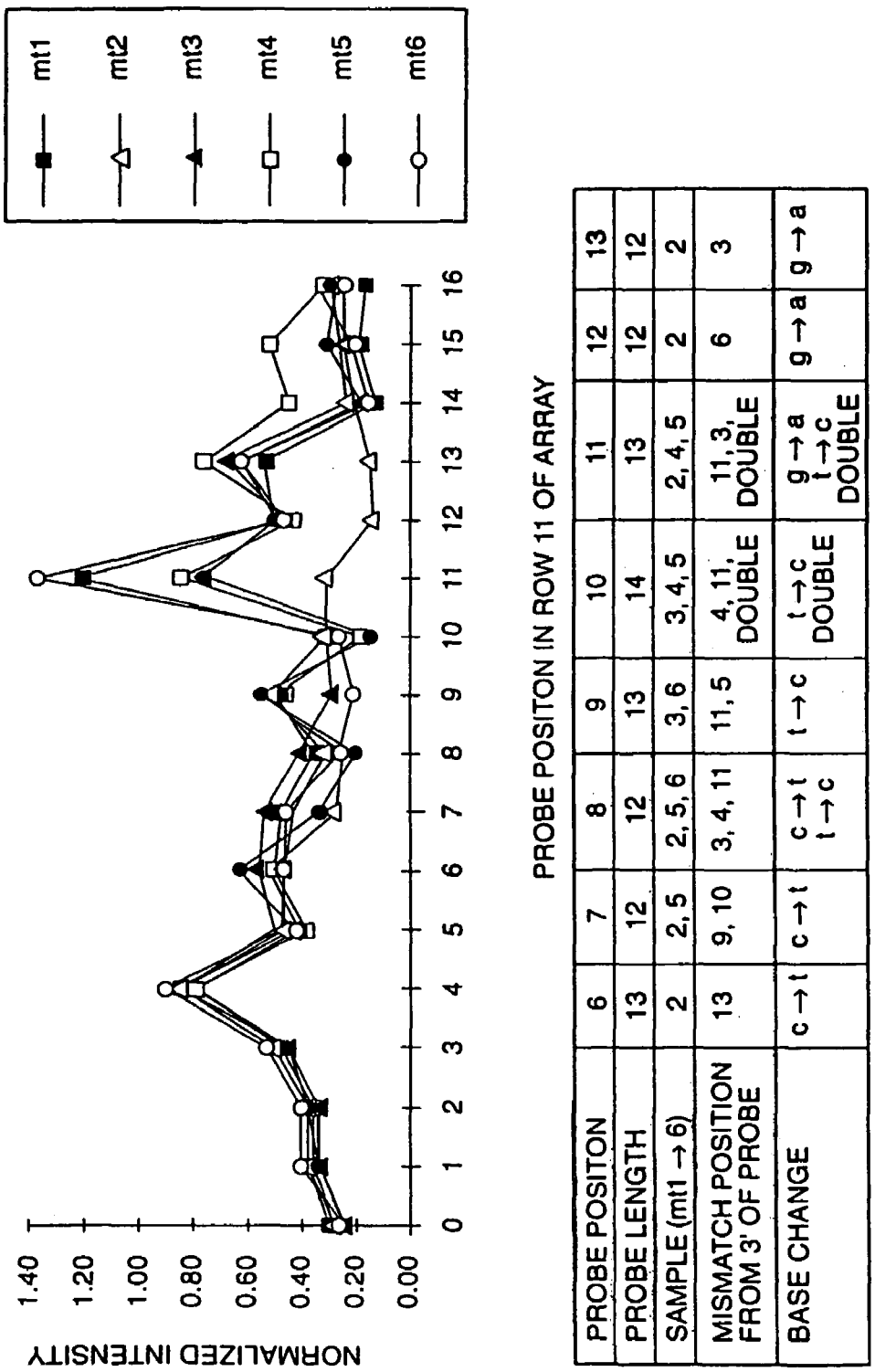

The results show that, in almost all cases, mismatched probe/target hybrids resulted in lower fluorescence intensity than perfectly matched hybrids. Nonetheless, some probes detected mutations (or specific sequences) better than others, and in several cases, the differences were within noise levels. Improvements can be realized by increasing the amount of overlap between probes and hence overall probe density and, for duplex DNA targets, using a second set of probes, either on the same or a separate chip, corresponding to the second strand of the target. FIG. 40, in sheets 1 and 2, shows a plot of normalized intensities across rows 10 and 11 of the array and a tabulation of the mutations detected.

Figure 41:
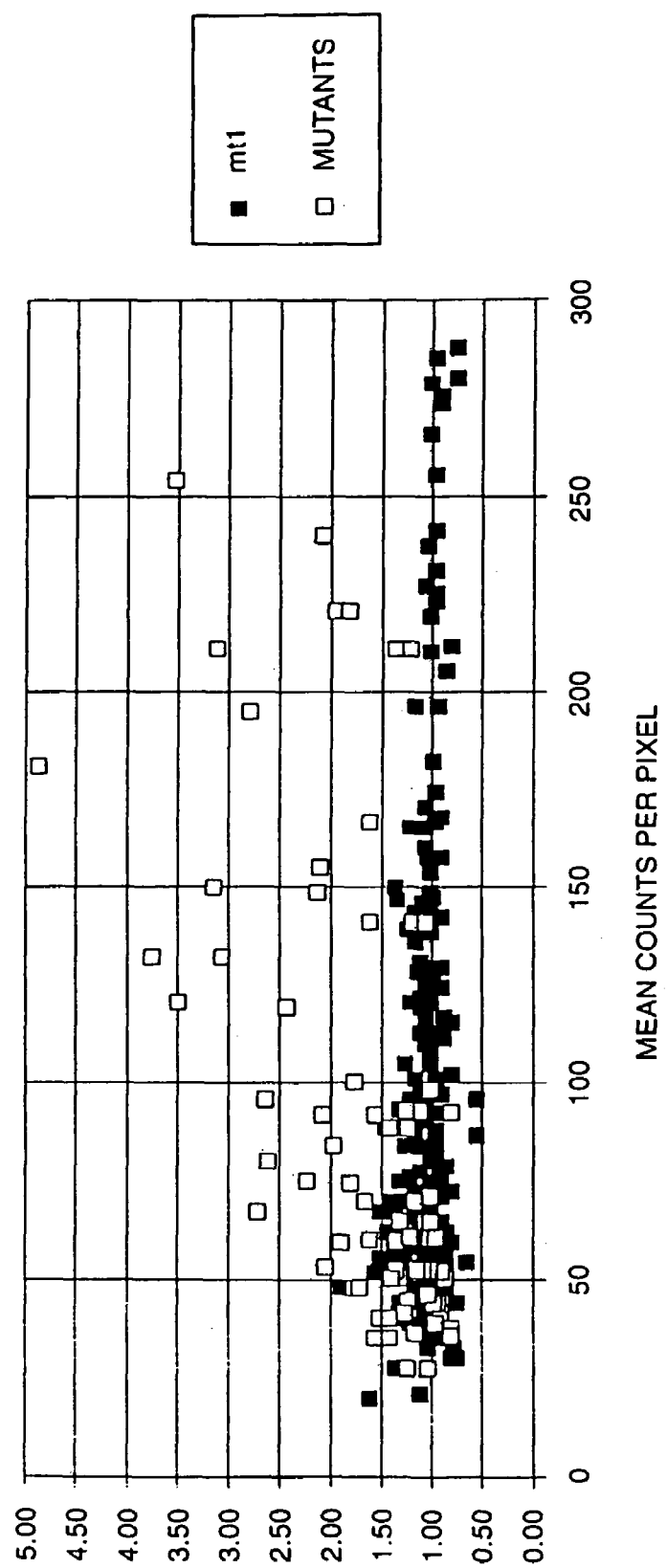
FIG. 41 shows the discrimination between wild-type and mutant hybrids obtained with the chip. A median of the six normalized hybridization scores for each probe was taken; the graph plots the ratio of the median score to the normalized hybridization score versus mean counts. A ratio of 1.6 and mean counts above 50 yield no false positives.
Figure 42:
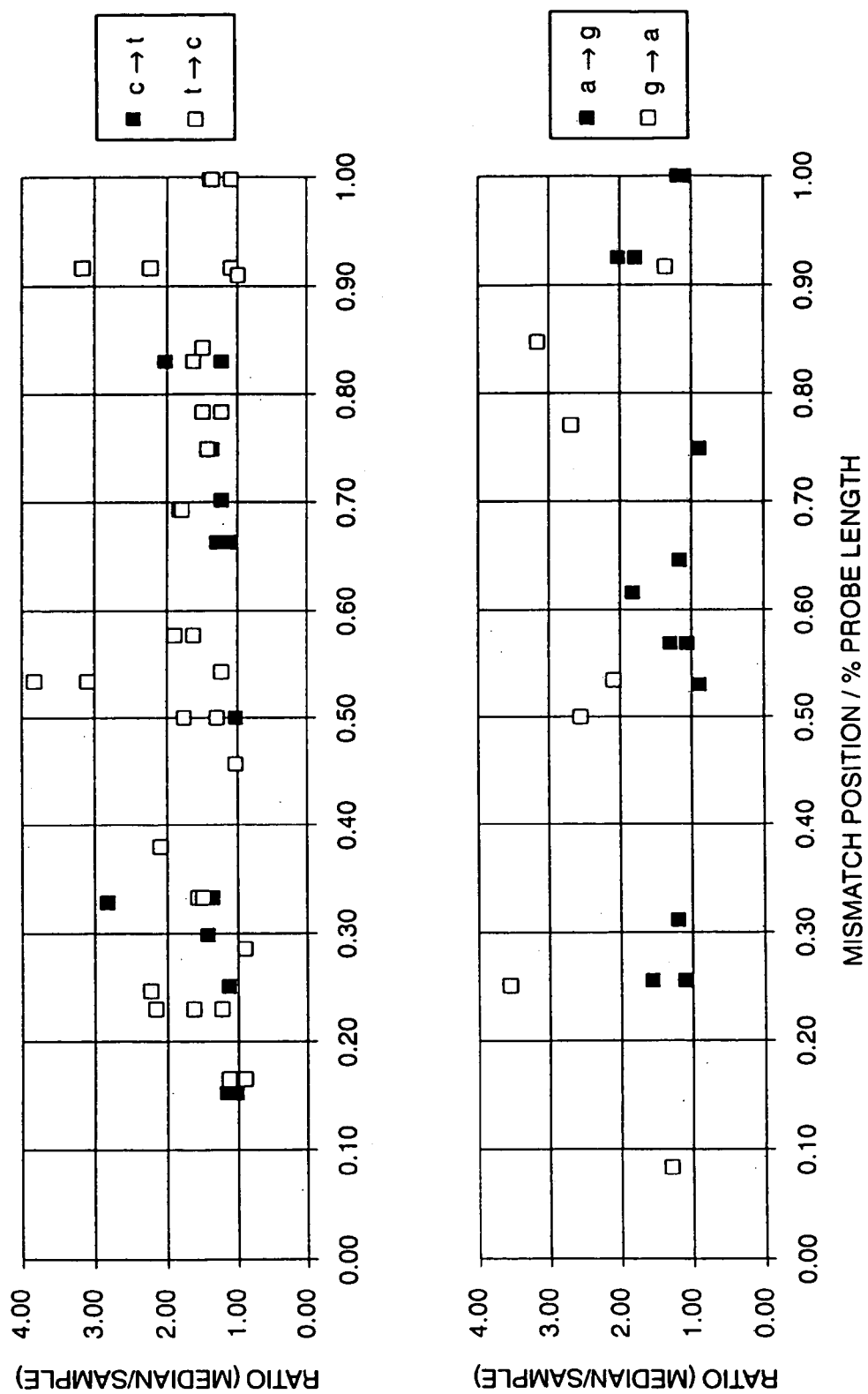
FIG. 42 illustrates how the identity of the base mismatch may influence the ability to discriminate mutant and wild-type sequences more than the position of the mismatch within an oligonucleotide probe. The mismatch position is expressed as % of probe length from the 3'-end. The base change is indicated on the graph.

FIG. 41 shows the discrimination between wild-type and mutant hybrids obtained with this chip. The median of the six normalized hybridization scores for each probe was taken. The graph plots the ratio of the median score to the normalized hybridization score versus mean counts. On this graph, a ratio of 1.6 and mean counts above 50 yield no false positives, and while it is clear that detection of some mutants can be improved, excellent discrimination is achieved, considering the small size of the array. FIG. 42 illustrates how the identity of the base mismatch may influence the ability to discriminate mutant and wild-type sequences more than the position of the mismatch within an oligonucleotide probe. The mismatch position is expressed as % of probe length from the 3'-end. The base change is indicated on the graph. These results show that the DNA chip increases the capacity of the standard reverse dot blot format by orders of magnitude, extending the power of that approach many fold and that the methods of the invention are more efficient and easier to automate than gel-based methods of nucleic acid sequence and mutation analysis.

To illustrate further these advantages, a second chip was prepared for analyzing a longer segment from human mitochondrial DNA (mtDNA). The chip "tiles" through 648 nucleotides of a reference sequence comprising human H strand mtDNA from positions 16280 to 356, and allows analysis of each nucleotide in the reference sequence. The probes in the array are 15 nucleotides in length, and each position in the target sequence is represented by a set of 4 probes (A, C, G, T substitutions), which differed from one another at position 7 from the 3'-end. The array consists of 13 blocks of 4×50 probes: each block scans through 50 nucleotides of contiguous mtDNA sequence. The blocks are separated by blank rows. The 4 corner columns contain control probes; there are a total of 2600 probes in a 1.28 cm×1.28 cm square area (feature), and each area is 256×197 microns.

Target RNA was prepared as above. The RNA was fragmented and hybridized to the oligonucleotide array in a solution composed of 6×SSPE, 0.1% Triton X-100 for 60 minutes at 18° C. Unhybridized material was washed away with buffer, and the chip was scanned at 25 micron pixel resolution.

Figure 43:
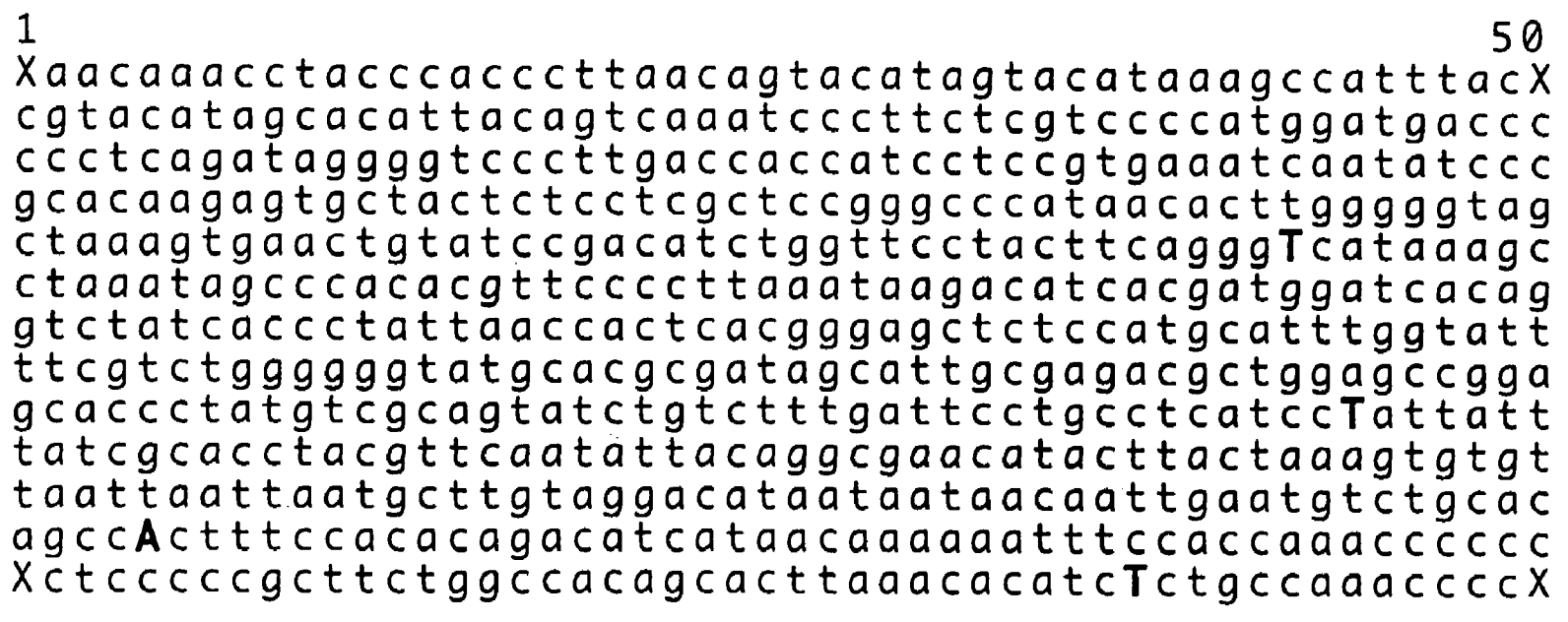
Figure 44:
FIG. 44 shows the fluorescence image produced by scanning the chip described in FIG. 43 when hybridized to a sample.

FIG. 43 provides a 5' to 3' sequence listing of one target corresponding to the probes on the chip. X is a control probe. Positions that differ in the target (i.e., are mismatched with the probe at the designated site) are in bold. FIG. 44 shows the fluorescence image produced by scanning the chip when hybridized to this sample. About 95% of the sequence could be read correctly from only one strand of the original duplex target nucleic acid. Although some probes did not provide excellent discrimination and some probes did not appear to hybridize to the target efficiently, excellent results were achieved. The target sequence differed from the probe set at six positions: 4 transitions and 2 insertions. All 4 transitions were detected, and specific probes could readily be incorporated into the array to detect insertions or deletions. FIG. 45 illustrates the detection of 4 transitions in the target sequence relative to the wild-type probes on the chip.

A further chip was constructed comprising probes tiling across the entire D-loop region (1.3 kb) of mt DNA sequences from two humans. The probes were tiled in rows of four using the basic tiling strategy. The probes were overlapping 15 mers having an interrogation position 7 nucleotides from the 3' end. The complete group of probes tiled on the reference sequence from the first individual, designated mt1, occupied the upper half of the chip. The lower half of the chip contained a similar arrangement based on a second clone, mt2. The probes were synthesized in a 1.28×1.28 cm area, which contained a matrix of 115×120 cells. The chip contained a total of 10,488 mtDNA probes.

Six samples of target DNA was extracted form hair roots from six individuals. The 1.3 kb region spanning positions 15935 to 667 of human mtDNA was PCR amplified, cloned in bacteriophage M13 and sequenced by conventional methods. The 1.3 kb region was reamplified from the phage clone using primers, L15935-T3 (SEQ. ID. No. 407), 5'CTCG-GAATTAACCCTCACTAAAGGAAACCTTTTTCC-AAGGA and H667-T7 (SEQ. ID. No. 408), 5'TAATAC-GACTCACTATAGGGAGAGGCTAGGACCAAACCT-ATT tagged with T3 and T7 RNA polymerase promoter sequences. Labelled RNA was generated by in vitro transcription using T3 RNA polymerase and fluoresceinated nucleotides, fragmented, and hybridized to the mtDNA control region resequencing chip at room temperature for 60 min, in 6×SSPE+0.05% triton X-100. Six washes were carried out at room temperature, using 6×SSPE+0.005% triton X-100, and the chip was read. Signal intensities varied considerably over the chip, but the large dynamic range of the detection system allowed accurate quantitation of intensities over several orders of magnitude. Even relatively low signal intensities yielded accurate results.

Five different clones (mt1–5) were hybridized, each to a separate chip. The reference sequence was also hybridized for comparative purposes. Mean counts per probe cell were determined, and used by automated basecalling software to read the sequence. The accuracy of sequence read from the chip is summarized as follows. Combining the data from the five targets analyzed, the chip read a total of 6310 nucleotides. Of these nucleotides in the target sequences, 55 were different from the reference sequence (as judged by conventional sequencing) (41 of these 55 nucleotides were both detected and read correctly from the chip). 6 of 55 nucleotides were detected as being ambiguous but their identity could not be read. 2 of 55 nucleotides were detected as mutations, but their identity was miscalled. 6 of 55 nucleotides were incorrectly called as wildtype. Of the 6255 nucleotides in the target sequence that were identical to the reference sequence, only 36 (0.57%) were miscalled or scored as ambiguous.

A further chip was constructed comprising probes tiling across a reference sequence comprising an entire mitochondrial genome. In this chip, a block tiling strategy was used. Each block was designed to analyze seven nucleotides from a target sequence. Each block consisted of four probe sets, the probe sets each having seven probes. A block was laid down on the chip in seven columns of four probes. The upper probe was the same in each column, this being a probe exactly complementary to a subsequence of the reference sequence. The three other probes in each column were identical to the upper probe except in an interrogation position, which was occupied by a different base in each of the four probes in the column. The interrogation position shifted by one position between successive columns. Thus, except for the seven interrogation positions, one in each of the columns of probes, all probes occupying a block were identical. The array comprised many such blocks, each tiled to successive subsequences of the mitochondrial DNA reference sequence. In all, the chip tiled 15,569 nucleotides of reference sequence with double tiling at 42 positions. 66,276 probes occupied an array of 304×315 cells, each cell having an area of 42×41 microns.

The chip was hybridized to the same target sequences as described for the D-loop region, except that hybridization was at 15° C. for 2 hr. The chip was scanned at 5 micron resolution to give an image with approximately 64 pixels per cell. For blocks of probes tiling across the D-loop region, a sequence-specific hybridization pattern was obtained. For other blocks, only background hybridization was observed.

These results illustrate that longer sequences can be read using the DNA chips and methods of the invention, as compared to conventional sequencing methods, where reading length is limited by the resolution of gel electrophoresis. Hybridization and signal detection require less than an hour and can be readily shortened by appropriate choice of buffers, temperatures, probes, and reagents.

III. Modes of Practicing the Invention

A. VLSIPS™ Technology

Figure 46:
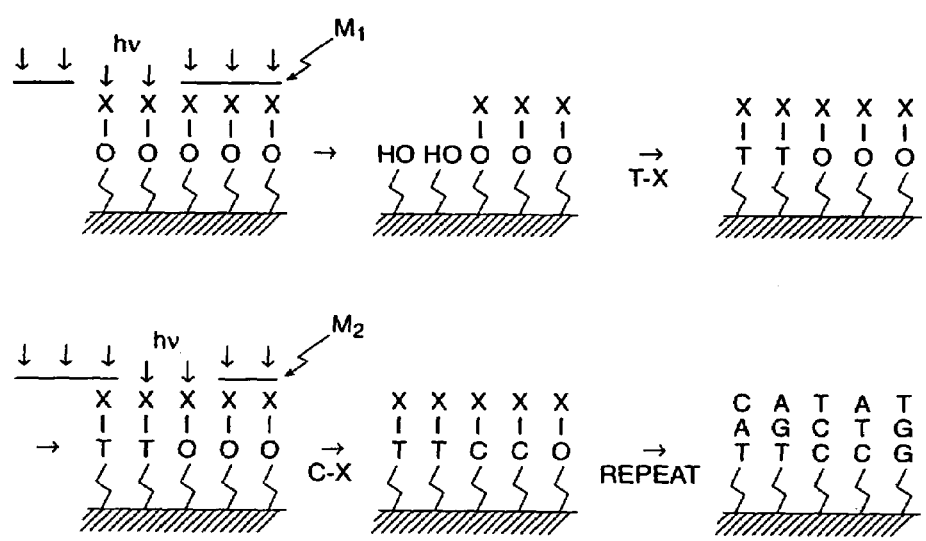
FIG. 46: VLSIPS™ technology applied to the light directed synthesis of oligonucleotides. Light (hv) is shone through a mask ($M_1$) to activate functional groups (—OH) on a surface by removal of a protecting group (X). Nucleoside building blocks protected with photoremovable protecting groups (T-X, C-X) are coupled to the activated areas. By repeating the irradiation and coupling steps, very complex arrays of oligonucleotides can be prepared.
Figure 47:
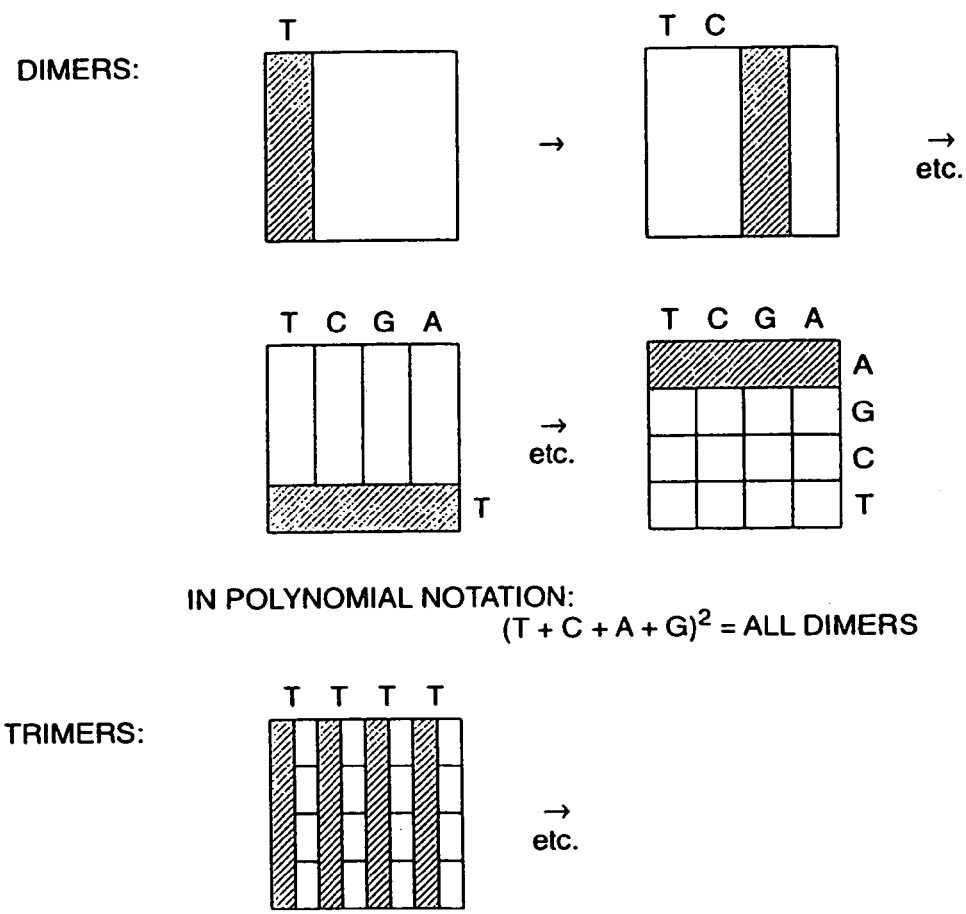
FIG. 47: Use of the VLSIPS™ process to prepare "nucleoside combinatorials" or oligonucleotides synthesized by coupling all four nucleosides to form dimers, trimers, and so forth.

As noted above, the VLSIPS™ technology is described in a number of patent publications and is preferred for making the oligonucleotide arrays of the invention. A brief description of how this technology can be used to make and screen DNA chips is provided in this Example and the accompanying Figures. In the VLSIPS™ method, light is shone through a mask to activate functional (for oligonucleotides, typically an —OH) groups protected with a photoremovable protecting group on a surface of a solid support. After light activation, a nucleoside building block, itself protected with a photoremovable protecting group (at the 5'-OH), is coupled to the activated areas of the support. The process can be repeated, using different masks or mask orientations and building blocks, to prepare very dense arrays of many different oligonucleotide probes. The process is illustrated in FIG. 46; FIG. 47 illustrates how the process can be used to prepare "nucleoside combinatorials" or oligonucleotides synthesized by coupling all four nucleosides to form dimers, trimers and so forth.

New methods for the combinatorial chemical synthesis of peptide, polycarbamate, and oligonucleotide arrays have recently been reported (see Fodor et al., 1991, Science 251: 767–773; Cho et al., 1993, Science 261: 1303–1305; and Southern et al., 1992, Genomics 13: 1008–10017, each of which is incorporated herein by reference). These arrays, or biological chips (see Fodor et al., 1993, Nature 364: 555–556, incorporated herein by reference), harbor specific chemical compounds at precise locations in a high-density, information rich format, and are a powerful tool for the study of biological recognition processes. A particularly exciting application of the array technology is in the field of DNA sequence analysis. The hybridization pattern of a DNA target to an array of shorter oligonucleotide probes is used to gain primary structure information of the DNA target. This format has important applications in sequencing by hybridization, DNA diagnostics and in elucidating the thermodynamic parameters affecting nucleic acid recognition.

Conventional DNA sequencing technology is a laborious procedure requiring electrophoretic size separation of labeled DNA fragments. An alternative approach, termed Sequencing By Hybridization (SBH), has been proposed (Lysov et al., 1988, Dokl. Akad. Nauk SSSR 303:1508–1511; Bains et al., 1988, J. Theor. Biol. 135:303–307; and Drmanac et al., 1989, Genomics 4:114–128, incorporated herein by reference and discussed in Description of Related Art, supra). This method uses a set of short oligonucleotide probes of defined sequence to search for complementary sequences on a longer target strand of DNA. The hybridization pattern is used to reconstruct the target DNA sequence. It is envisioned that hybridization analysis of large numbers of probes can be used to sequence long stretches of DNA. In immediate applications of this methodology, a small number of probes can be used to interrogate local DNA sequence. The strategy of SBH can be illustrated by the following example. A 12-mer target DNA sequence, AGCCTAGCTGAA, is mixed with a complete set of octanucleotide probes. If only perfect complementarity is considered, five of the 65,536 octamer probes-TCGGATCG, CGGATCGA, GGATCGAC, GATCGACT, and ATCGACTT will hybridize to the target. Alignment of the overlapping sequences from the hybridizing probes reconstructs the complement of the original 12-mer target:

TCGGATCG
CGGATCGA
GGATCGAC
GATCGACT
ATCGACTT
TCGGATCGACTT (SEQ. ID. No. 409)

Hybridization methodology can be carried out by attaching target DNA to a surface. The target is interrogated with a set of oligonucleotide probes, one at a time (see Strezoska et al., 1991, Proc. Natl. Acad. Sci. USA 88:10089–10093, and Drmanac et al., 1993, Science 260:1649–1652, each of which is incorporated herein by reference). This approach can be implemented with well established methods of immobilization and hybridization detection, but involves a large number of manipulations. For example, to probe a sequence utilizing a full set of octanucleotides, tens of thousands of hybridization reactions must be performed. Alternatively, SBH can be carried out by attaching probes to a surface in an array format where the identity of the probes at each site is known. The target DNA is then added to the array of probes. The hybridization pattern determined in a single experiment directly reveals the identity of all complementary probes.

As noted above, a preferred method of oligonucleotide probe array synthesis involves the use of light to direct the synthesis of oligonucleotide probes in high-density, miniaturized arrays. Photolabile 5'-protected N-acyl-deoxynucleoside phosphoramidites, surface linker chemistry, and versatile combinatorial synthesis strategies have been developed for this technology. Matrices of spatially-defined oligonucleotide probes have been generated, and the ability to use these arrays to identify complementary sequences has been demonstrated by hybridizing fluorescent labeled oligonucleotides to the DNA chips produced by the methods. The hybridization pattern demonstrates a high degree of base specificity and reveals the sequence of oligonucleotide targets.

The basic strategy for light-directed oligonucleotide synthesis (1) is outlined in FIG. 46. The surface of a solid support modified with photolabile protecting groups (X) is illuminated through a photolithographic mask, yielding reactive hydroxyl groups in the illuminated regions. A 3'-O-phosphoramidite activated deoxynucleoside (protected at the 5'-hydroxyl with a photolabile group) is then presented to the surface and coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of products is obtained.

Light directed chemical synthesis lends itself to highly efficient synthesis strategies which will generate a maximum number of compounds in a minimum number of chemical steps. For example, the complete set of $4^n$ polynucleotides (length n), or any subset of this set can be produced in only 4×n chemical steps. See FIG. 47. The patterns of illumination and the order of chemical reactants ultimately define the products and their locations. Because photolithography is used, the process can be miniaturized to generate high-density arrays of oligonucleotide probes. For an example of the nomenclature useful for describing such arrays, an array containing all possible octanucleotides of dA and dT is written as $(A+T)^8$. Expansion of this polynomial reveals the identity of all 256 octanucleotide probes from AAAAAAAA to TTTTTTTT. A DNA array composed of complete sets of dinucleotides is referred to as having a complexity of 2. The array given by (A+T+C+G)8 is the full 65,536 octanucleotide array of complexity four. Computer-aided methods of laying down predesigned arrays of probes using VLSIPS™ technology are described in commonly-assigned co-pending application U.S. Ser. No. 08/249,188, filed May 24, 1994 (incorporated by reference in its entirety for all purposes).

In a variation of the VLSIPS™ methods, multiple copies of an array of probes are synthesized simultaneously. The multiple copies are effectively stacked in a pile during the synthesis process in a manner such that each copy is accessible to irradiation. For example, synthesis can occur through the volume of a slab of polymer gel that is transparent to the source of radiation used to remove photoprotective groups. Suitable polymers are described in U.S. Ser. No. 08/431,196, filed Apr. 27, 1995 (incorporated by reference in its entirety for all purposes). For example, a polymer formed from a 90:10% w/w mixture of acylamide and N-2-aminoethylacrylamide is suitable.

After synthesis, the gel is sliced into thin layers (e.g., with a microtome). Each layer is attached to a glass substrate to constitute a separate chip. Alternatively, a pile can be formed from layers of gel separated by layers of a transparent substance that can be mechanically or chemically removed after synthesis has occurred. Using these methods, up to about 10, 100 or 1000 identical arrays can be synthesized simultaneously.

To carry out hybridization of DNA targets to the probe arrays, the arrays are mounted in a thermostatically controlled hybridization chamber. Fluorescein labeled DNA targets are injected into the chamber and hybridization is allowed to proceed for 5 min to 24 hr. The surface of the matrix is scanned in an epifluorescence microscope (Zeiss Axioscop 20) equipped with photon counting electronics using 50–100 μW of 488 nm excitation from an Argon ion laser (Spectra Physics Model 2020). Measurements may be made with the target solution in contact with the probe matrix or after washing. Photon counts are stored and image files are presented after conversion to an eight bit image format. See FIG. 51.

When hybridizing a DNA target to an oligonucleotide array, N=Lt−(Lp−1) complementary hybrids are expected, where N is the number of hybrids, Lt is the length of the DNA target, and Lp is the length of the oligonucleotide probes on the array. For example, for an 11-mer target hybridized to an octanucleotide array, N=4. Hybridizations with mismatches at positions that are 2 to 3 residues from either end of the probes will generate detectable signals. Modifying the above expression for N, one arrives at a relationship estimating the number of detectable hybridizations (Nd) for a DNA target of length Lt and an array of complexity C. Assuming an average of 5 positions giving signals above background:

Nd=(1+5(C−1))[Lt−(Lp−1)].

Arrays of oligonucleotides can be efficiently generated by light-directed synthesis and can be used to determine the identity of DNA target sequences. Because combinatorial strategies are used, the number of compounds increases exponentially while the number of chemical coupling cycles increases only linearly. For example, synthesizing the complete set of $4^8$ (65,536) octanucleotides will add only four hours to the synthesis for the 16 additional cycles. Furthermore, combinatorial synthesis strategies can be implemented to generate arrays of any desired composition. For example, because the entire set of dodecamers ($4^{12}$) can be produced in 48 photolysis and coupling cycles (b$^n$ compounds requires b×n cycles), any subset of the dodecamers (including any subset of shorter oligonucleotides) can be constructed with the correct lithographic mask design in 48 or fewer chemical coupling steps. In addition, the number of compounds in an array is limited only by the density of synthesis sites and the overall array size. Recent experiments have demonstrated hybridization to probes synthesized in 25 μm sites. At this resolution, the entire set of 65,536 octanucleotides can be placed in an array measuring 0.64 cm square, and the set of 1,048,576 dodecanucleotides requires only a 2.56 cm array.

Genome sequencing projects will ultimately be limited by DNA sequencing technologies. Current sequencing methodologies are highly reliant on complex procedures and require substantial manual effort. Sequencing by hybridization has the potential for transforming many of the manual efforts into more efficient and automated formats. Light-directed synthesis is an efficient means for large scale production of miniaturized arrays for SBH. The oligonucleotide arrays are not limited to primary sequencing applications. Because single base changes cause multiple changes in the hybridization pattern, the oligonucleotide arrays provide a powerful means to check the accuracy of previously elucidated DNA sequence, or to scan for changes within a sequence. In the case of octanucleotides, a single base change in the target DNA results in the loss of eight complements, and generates eight new complements. Matching of hybridization patterns may be useful in resolving sequencing ambiguities from standard gel techniques, or for rapidly detecting DNA mutational events. The potentially very high information content of light-directed oligonucleotide arrays will change genetic diagnostic testing. Sequence comparisons of hundreds to thousands of different genes will be assayed simultaneously instead of the current one, or few at a time format. Custom arrays can also be constructed to contain genetic markers for the rapid identification of a wide variety of pathogenic organisms.

Oligonucleotide arrays can also be applied to study the sequence specificity of RNA or protein-DNA interactions. Experiments can be designed to elucidate specificity rules of non Watson-Crick oligonucleotide structures or to investigate the use of novel synthetic nucleoside analogs for antisense or triple helix applications. Suitably protected RNA monomers may be employed for RNA synthesis. The oligonucleotide arrays should find broad application deducing the thermodynamic and kinetic rules governing formation and stability of oligonucleotide complexes.

Figure 48:
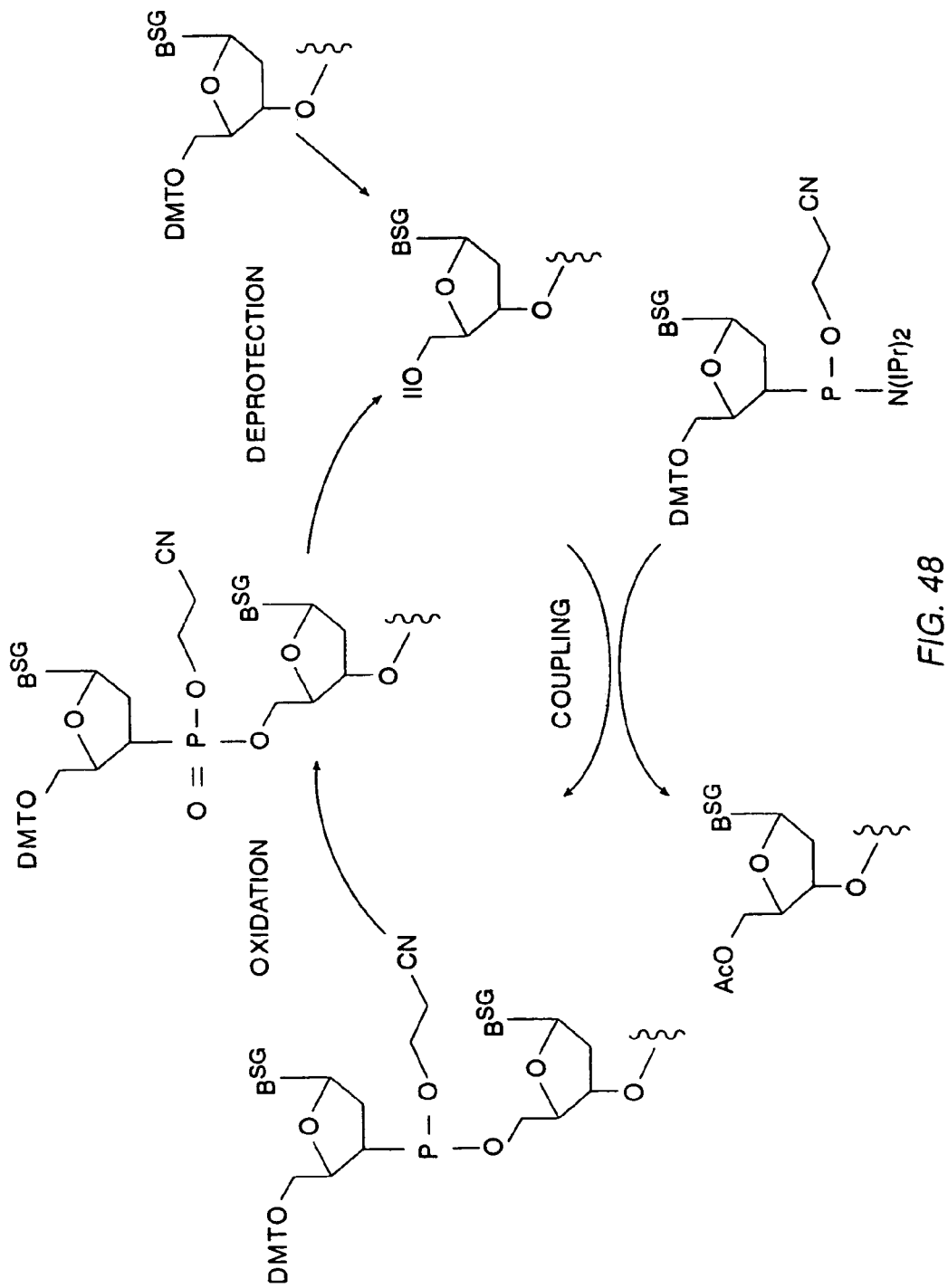
FIG. 48: Deprotection, coupling, and oxidation steps of a solid phase DNA synthesis method.
Figure 49:
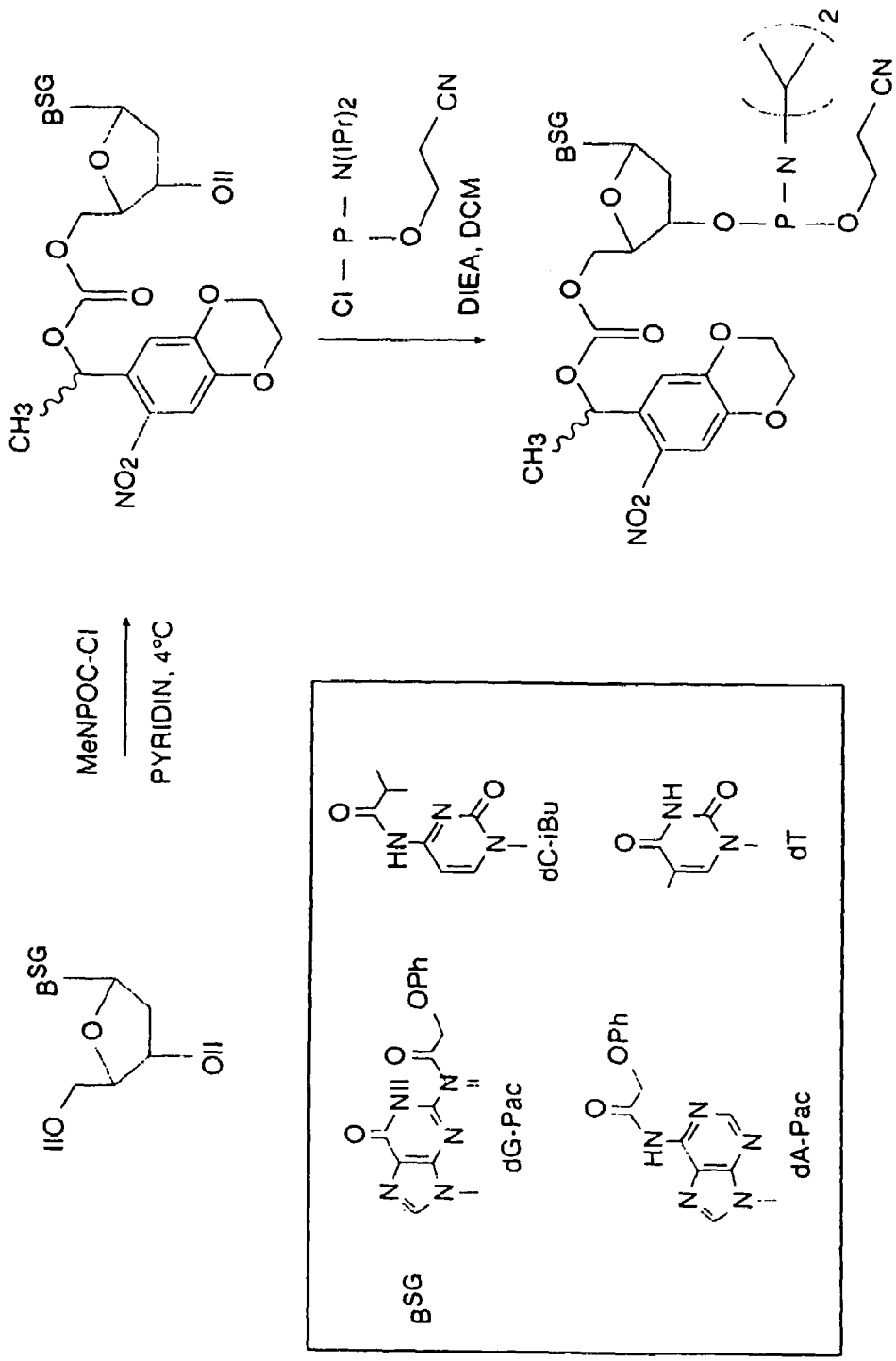
FIG. 49: An illustrative synthesis route for the nucleoside building blocks used in the VLSIPS™ method.
Figure 50:
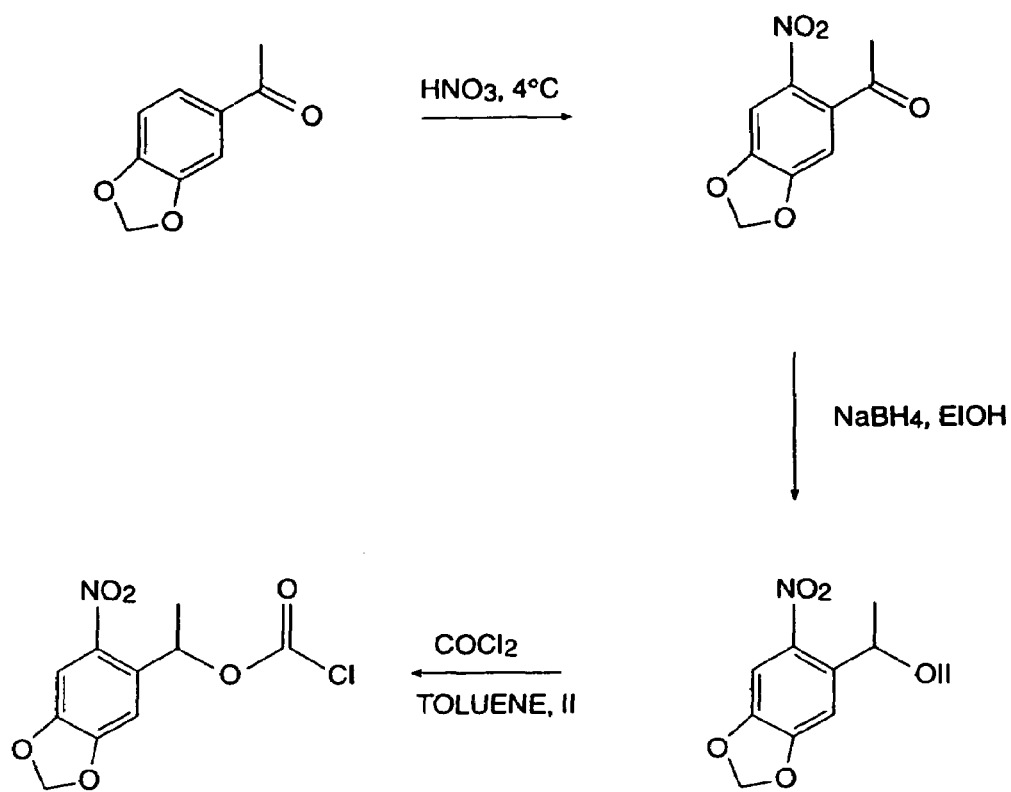
FIG. 50: A preferred photoremovable protecting group, MeNPOC, and preparation of the group in active form.

Other than the use of photoremovable protecting groups, the nucleoside coupling chemistry is very similar to that used routinely today for oligonucleotide synthesis. FIG. 48 shows the deprotection, coupling, and oxidation steps of a solid phase DNA synthesis method. FIG. 49 shows an illustrative synthesis route for the nucleoside building blocks used in the method. FIG. 50 shows a preferred photoremovable protecting group, MeNPOC, and how to prepare the group in active form. The procedures described below show how to prepare these reagents. The nucleoside building blocks are 5'-MeNPOC-THYMIDINE-3'-OCEP; 5'-MeNPOC-N$^4$-t-BUTYL PHENOXYACETYL-DEOXYCYTIDINE-3'-OCEP; 5'-MeNPOC-N$^4$-t-BUTYL PHENOXYACETYL-DEOXYGUANOSINE-3'-OCEP; and 5'-MeNPOC-N$^4$-t-BUTYL PHENOXYACETYL-DEOXYADENOSINE-3'-OCEP.

1. Preparation of 4,5-methylenedioxy-2-nitroacetophenone

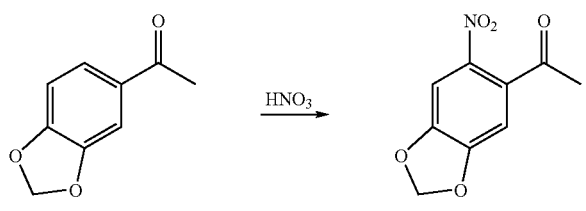

A solution of 50 g (0.305 mole) 3,4-methylenedioxyacetophenone (Aldrich) in 200 mL glacial acetic acid was added dropwise over 30 minutes to 700 mL of cold (2–4° C.) 70% HNO$_3$ with stirring (NOTE: the reaction will overheat without external cooling from an ice bath, which can be dangerous and lead to side products). At temperatures below 0° C., however, the reaction can be sluggish. A temperature of 3–5° C. seems to be optimal). The mixture was left stirring for another 60 minutes at 3–5° C., and then allowed to approach ambient temperature. Analysis by TLC (25% EtOAc in hexane) indicated complete conversion of the starting material within 1–2 hr. When the reaction was complete, the mixture was poured into ~3 liters of crushed ice, and the resulting yellow solid was filtered off, washed with water and then suction-dried. Yield 53 g (84%), used without further purification.

2. Preparation of 1-(4,5-Methylenedioxy-2-nitrophenyl) ethanol

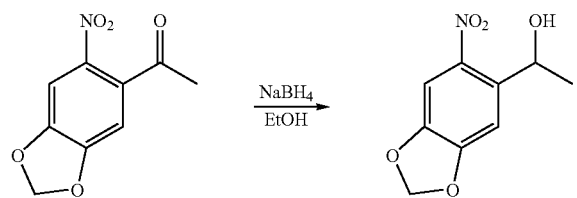

Sodium borohydride (log; 0.27 mol) was added slowly to a cold, stirring suspension of 53 g (0.25 mol) of 4,5-methylenedioxy-2-nitroacetophenone in 400 mL methanol. The temperature was kept below 10° C. by slow addition of the NaBH$_4$ and external cooling with an ice bath. Stirring was continued at ambient temperature for another two hours, at which time TLC (CH$_2$Cl$_2$) indicated complete conversion of the ketone. The mixture was poured into one liter of ice-water and the resulting suspension was neutralized with ammonium chloride and then extracted three times with 400 mL CH$_2$Cl$_2$ or EtOAc (the product can be collected by filtration and washed at this point, but it is somewhat soluble in water and this results in a yield of only ~60%). The combined organic extracts were washed with brine, then dried with MgSO$_4$ and evaporated. The crude product was purified from the main byproduct by dissolving it in a minimum volume of CH$_2$Cl$_2$ or THF(~175 ml) and then precipitating it by slowly adding hexane (1000 ml) while stirring (yield 51 g; 80% overall). It can also be recrystallized (e.g., toluene-hexane), but this reduces the yield.

3. Preparation of 1-(4,5-methylenedioxy-2-nitrophenyl) ethyl chloroformate (MeNPOC-Cl)

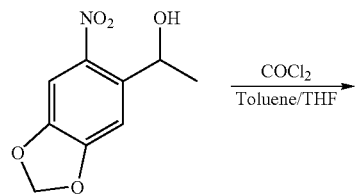

-continued

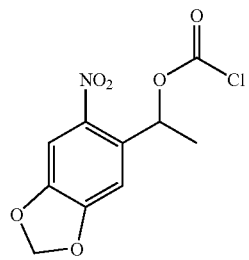

Phosgene (500 mL of 20% w/v in toluene from Fluka: 965 mmole; 4 eq.) was added slowly to a cold, stirring solution of 50 g (237 mmole; 1 eq.) of 1-(4,5-methylenedioxy-2-nitrophenyl) ethanol in 400 mL dry THF. The solution was stirred overnight at ambient temperature at which point TLC (20% Et$_2$O/hexane) indicated >95% conversion. The mixture was evaporated (an oil-less pump with downstream aqueous NaOH trap is recommended to remove the excess phosgene) to afford a viscous brown oil. Purification was effected by flash chromatography on a short (9×13 cm) column of silica gel eluted with 20% Et$_2$O/hexane. Typically 55 g (85%) of the solid yellow MeNPOC-Cl is obtained by this procedure. The crude material has also been recrystallized in 2–3 crops from 1:1 ether/hexane. On this scale, 100 ml is used for the first crop, with a few percent THF added to aid dissolution, and then cooling overnight at –20° C. (this procedure has not been optimized). The product should be stored desiccated at –20° C.

4. Synthesis of 5'-Menpoc-2'-deoxynucleoside-3'-(N,N-diisopropyl 2-cyanoethyl phosphoramidites (a.) 5'-MeNPOC-Nucleosides

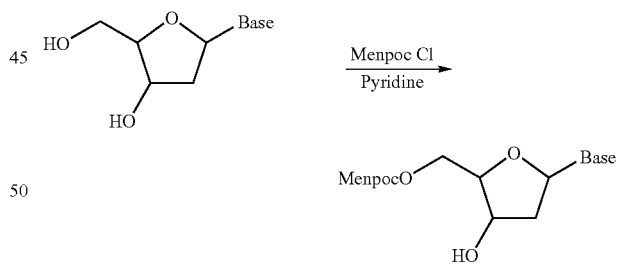

Base=THYMIDINE (T); N-4-ISOBUTYRYL 2'-DEOXYCYTIDINE (ibu-dC)

N-2-PHENOXYACETYL 2'DEOXYGUANOSINE (PAC-dG); and

N-6-PHENOXYACETYL 2'DEOXYADENOSINE (PAC-dA)

All four of the 5'-MeNPOC nucleosides were prepared from the base-protected 2'-deoxynucleosides by the following procedure. The protected 2'-deoxynucleoside (90 mmole) was dried by co-evaporating twice with 250 mL anhydrous pyridine. The nucleoside was then dissolved in 300 mL anhydrous pyridine (or 1:1 pyridine/DMF, for the dG$^{PAC}$ nucleoside) under argon and cooled to ~2° C. in an ice bath. A solution of 24.6 g (90 mmole) MeNPOC-Cl in 100 mL dry THF was then added with stirring over 30 minutes. The ice bath was removed, and the solution allowed to stir overnight at room temperature (TLC: 5–10% MeOH in CH$_2$Cl$_2$; two diastereomers) After evaporating the solvents under vacuum, the crude material was taken up in 250 mL ethyl acetate and extracted with saturated aqueous NaHCO$_3$ and brine. The organic phase was then dried over Na$_2$SO$_4$, filtered and evaporated to obtain a yellow foam. The crude products were finally purified by flash chromatography (9×30 cm silica gel column eluted with a stepped gradient of 2%–6% MeOH in CH$_2$Cl$_2$). Yields of the purified diastereomeric mixtures are in the range of 65–75%.

(b.) 5'-Menpoc-2'-deoxynucleoside-3'-(N,N-diisopropyl 2-cyanoethyl phosphoramidites)

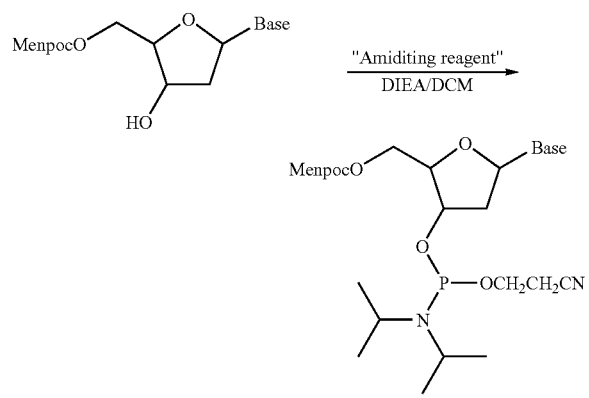

The four deoxynucleosides were phosphitylated using either 2-cyanoethyl-N,N-diisopropyl chlorophosphoramidite, or 2-cyanoethyl-N,N,N',N'-tetraisopropylphosphorodiamidite. The following is a typical procedure. Add 16.6 g (17.4 ml; 55 mmole) of 2-cyanoethyl-N,N,N',N'-tetraisopropylphosphoro-diamidite to a solution of 50 mmole 5'-MeNPOC-nucleoside and 4.3 g (25 mmole) diisopropylammonium tetrazolide in 250 mL dry CH$_2$Cl$_2$ under argon at ambient temperature. Continue stirring for 4–16 hours (reaction monitored by TLC: 45:45:10 hexane/CH$_2$Cl$_2$/Et$_3$N). Wash the organic phase with saturated aqueous NaHCO$_3$ and brine, then dry over Na$_2$SO$_4$, and evaporate to dryness. Purify the crude amidite by flash chromatography (9×25 cm silica gel column eluted with hexane/CH$_2$Cl$_2$/TEA-45:45:10 for A, C, T; or 0:90:10 for G). The yield of purified amidite is about 90%.

B. Preparation of Labeled DNA/Hybridization to Array

1. PCR

PCR amplification reactions are typically conducted in a mixture composed of, per reaction: 1 µl genomic DNA; 10 µl each primer (10 µmol/µl stocks); 10 µl 10×PCR buffer (100 mM Tris.Cl pH8.5, 500 mM KCl, 15 mM MgCl$_2$); 10 µl 2 mM dNTPs (made from 100 mM dNTP stocks); 2.5 U Taq polymerase (Perkin Elmer AmpliTaq™, 5 U/µl); and H$_2$O to 100 µl. The cycling conditions are usually 40 cycles (94° C. 45 sec, 55° C. 30 sec, 72° C. 60 sec) but may need to be varied considerably from sample type to sample type. These conditions are for 0.2 mL thin wall tubes in a Perkin Elmer 9600 thermocycler. See Perkin Elmer 1992/93 catalogue for 9600 cycle time information. Target, primer length and sequence composition, among other factors, may also affect parameters.

For products in the 200 to 1000 bp size range, check 2 µl of the reaction on a 1.5% 0.5×TBE agarose gel using an appropriate size standard (phiX174 cut with HaeIII is convenient). The PCR reaction should yield several picomoles of product. It is helpful to include a negative control (i.e., 1 µl TE instead of genomic DNA) to check for possible contamination. To avoid contamination, keep PCR products from previous experiments away from later reactions, using filter tips as appropriate. Using a set of working solutions and storing master solutions separately is helpful, so long as one does not contaminate the master stock solutions.

For simple amplifications of short fragments from genomic DNA it is, in general, unnecessary to optimize Mg$^{2+}$ concentrations. A good procedure is the following: make a master mix minus enzyme; dispense the genomic DNA samples to individual tubes or reaction wells; add enzyme to the master mix; and mix and dispense the master solution to each well, using a new filter tip each time.

2. Purification

Removal of unincorporated nucleotides and primers from PCR samples can be accomplished using the Promega Magic PCR Preps DNA purification kit. One can purify the whole sample, following the instructions supplied with the kit (proceed from section IIIB, 'Sample preparation for direct purification from PCR reactions'). After elution of the PCR product in 50 µl of TE or H$_2$O, one centrifuges the eluate for 20 sec at 12,000 rpm in a microfuge and carefully transfers 45 µl to a new microfuge tube, avoiding any visible pellet. Resin is sometimes carried over during the elution step. This transfer prevents accidental contamination of the linear amplification reaction with 'Magic PCR' resin. Other methods, e.g., size exclusion chromatography, may also be used.

3. Linear Amplification

In a 0.2 mL thin-wall PCR tube mix: 4 µl purified PCR product; 2 µl primer (10 µmol/µl); 4 µl 10×PCR buffer; 4 µl dNTPs (2 mM dA, dC, dG, 0.1 mM dT); 4 µl 0.1 mM dUTP; 1 µl 1 mM fluorescein dUTP (Amersham RPN 2121); 1 U Taq polymerase (Perkin Elmer, 5 U/µl); and add H$_2$O to 40 µl. Conduct 40 cycles (92° C. 30 sec, 55° C. 30 sec, 72° C. 90 sec) of PCR. These conditions have been used to amplify a 300 nucleotide mitochondrial DNA fragment but are applicable to other fragments. Even in the absence of a visible product band on an agarose gel, there should still be enough product to give an easily detectable hybridization signal. If one is not treating the DNA with uracil DNA glycosylase (see Section 4), dUTP can be omitted from the reaction.

4. Fragmentation

Purify the linear amplification product using the Promega Magic PCR Preps DNA purification kit, as per Section 2 above. In a 0.2 mL thin-wall PCR tube mix: 40 µl purified labeled DNA; 4 µl 10×PCR buffer; and 0.5 µl uracil DNA glycosylase (BRL 1 U/µl). Incubate the mixture 15 min at 37° C., then 10 min at 97° C.; store at −20° C. until ready to use.

5. Hybridization, Scanning & Stripping

A blank scan of the slide in hybridization buffer only is helpful to check that the slide is ready for use. The buffer is removed from the flow cell and replaced with 1 ml of (fragmented) DNA in hybridization buffer and mixed well.

Optionally, standard hybridization buffer can be supplemented with tetramethylammonium chloride (TMACL) or betaine (N,N,N-trimethylglycine; $(CH_3)_3$ $N+CH_2COO^-$) to improve discrimination between perfectly matched targets and single-base mismatches. Betaine is zwitterionic at neutral pH and alters the composition-dependent stability of nucleic acids without altering their polyelectrolyte behavior. Betaine is preferably used at a concentration between 1 and 10 M and, optimally, at about 5 M. For example, 5 M betaine in 2×SSPE is suitable. Inclusion of betaine at this concentration lowers the average hybridization signal about four fold, but increases the discrimination between matched and mismatched probes.

Figure 51:
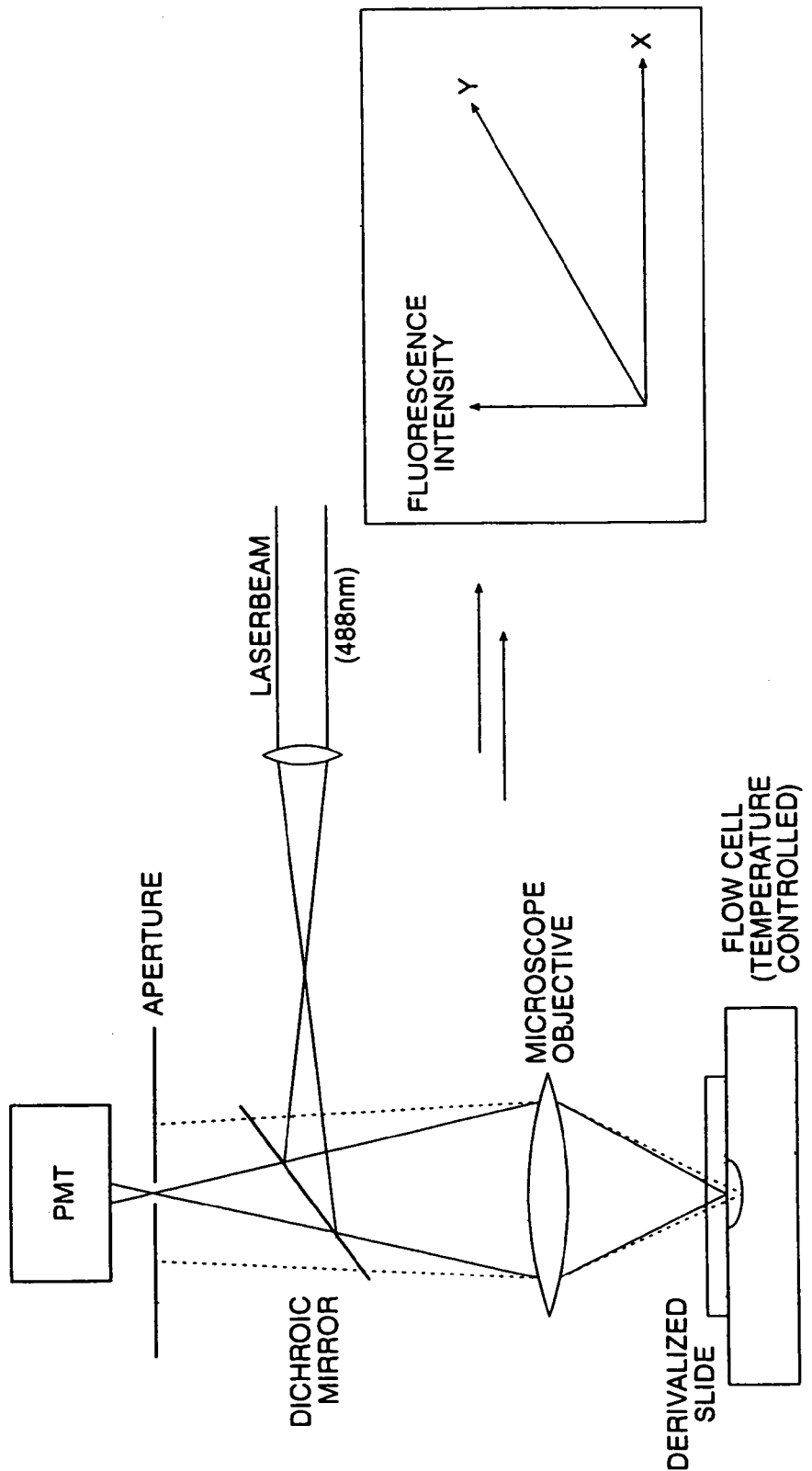
FIG. 51: Detection system for scanning a DNA chip.

The scan is performed in the presence of the labeled target. FIG. 51 illustrates an illustrative detection system for scanning a DNA chip. A series of scans at 30 min intervals using a hybridization temperature of 25° C. yields a very clear signal, usually in at least 30 min to two hours, but it may be desirable to hybridize longer, i.e., overnight. Using a laser power of 50 µW and 50 µm pixels, one should obtain maximum counts in the range of hundreds to low thousands/pixel for a new slide. When finished, the slide can be stripped using 50% formamide. rinsing well in deionized $H_2O$, blowing dry, and storing at room temperature.

C. Preparation of Labeled RNA/Hybridization to Array

1. Tagged Primers

The primers used to amplify the target nucleic acid should have promoter sequences if one desires to produce RNA from the amplified nucleic acid. Suitable promoter sequences are shown below and include:

(1) the T3 promoter sequence (SEQ. ID. Nos. 410–411):
5'-CGGAATTAACCCTCACTAAAGG
5'-AATTAACCCTCACTAAAGGGAG;

(2) the T7 promoter sequence (SEQ. ID. No. 412):
5' TAATACGACTCACTATAGGGAG;

and (3) the SP6 promoter sequence (SEQ. ID. No. 413):
5' ATTTAGGTGACACTATAGAA.

The desired promoter sequence is added to the 5' end of the PCR primer. It is convenient to add a different promoter to each primer of a PCR primer pair so that either strand may be transcribed from a single PCR product.

Synthesize PCR primers so as to leave the DMT group on. DMT-on purification is unnecessary for PCR but appears to be important for transcription. Add 25 µl 0.5M NaOH to collection vial prior to collection of oligonucleotide to keep the DMT group on. Deprotect using standard chemistry—55° C. overnight is convenient.

HPLC purification is accomplished by drying down the oligonucleotides, resuspending in 1 mL 0.1 M TEAA (dilute 2.0 M stock in deionized water, filter through 0.2 micron filter) and filter through 0.2 micron filter. Load 0.5 mL on reverse phase HPLC (column can be a Hamilton PRP-1 semi-prep, #79426). The gradient is 0->50% $CH_3CN$ over 25 min (program 0.2 µmol.prep. 0–50, 25 min). Pool the desired fractions, dry down, resuspend in 200 µl 80% HAc. 30 min RT. Add 200 µl EtOH; dry down. Resuspend in 200 µl $H_2O$, plus 20 µl NaAc pH5.5, 600 µl EtOH. Leave 10 min on ice; centrifuge 12,000 rpm for 10 min in microfuge. Pour off supernatant. Rinse pellet with 1 mL EtOH, dry, resuspend in 200 µl $H_2O$. Dry, resuspend in 200 µl TE. Measure A260, prepare a 10 µmol/µl solution in TE (10 mM Tris.Cl pH 8.0, 0.1 mM EDTA). Following HPLC purification of a 42 mer, a yield in the vicinity of 15 nmol from a 0.2 µmol scale synthesis is typical.

2. Genomic DNA Preparation

Add 500 µl (10 mM Tris.Cl pH8.0, 10 mM EDTA, 100 mM NaCl, 2% (w/v) SDS, 40 mM DTT, filter sterilized) to the sample. Add 1.25 µl 20 mg/ml proteinase K (Boehringer) Incubate at 55° C. for 2 hours, vortexing once or twice. Perform 2×0.5 mL 1:1 phenol:$CHCl_3$ extractions. After each extraction, centrifuge 12,000 rpm 5 min in a microfuge and recover 0.4 mL supernatant. Add 35 µl NaAc pH5.2 plus 1 mL EtOH. Place sample on ice 45 min; then centrifuge 12,000 rpm 30 min, rinse, air dry 30 min, and resuspend in 100 µl TE.

3. PCR

PCR is performed in a mixture containing, per reaction: 1 µl genomic DNA; 4 µl each primer (10 µmol/µl stocks); 4 µl 10×PCR buffer (100 mM Tris.Cl pH8.5, 500 mM KCl, 15 mM $MgCl_2$); 4 µl 2 mM dNTPs (made from 100 mM dNTP stocks); 1 U Taq polymerase (Perkin Elmer, 5 U/µl); $H_2O$ to 40 µl. About 40 cycles (94° C. 30 sec, 55° C. 30 sec, 72° C. 30 sec) are performed, but cycling conditions may need to be varied. These conditions are for 0.2 mL thin wall tubes in Perkin Elmer 9600. For products in the 200 to 1000 bp size range, check 2 µl of the reaction on a 1.5% 0.5×TBE agarose gel using an appropriate size standard. For larger or smaller volumes (20–100 µl), one can use the same amount of genomic DNA but adjust the other ingredients accordingly.

4. In Vitro Transcription

Mix: 3 µl PCR product; 4 µl 5× buffer; 2 µl DTT; 2.4 µl 10 mM rNTPs (100 mM solutions from Pharmacia); 0.48 µl 10 mM fluorescein-UTP (Fluorescein-12-UTP, 10 mM solution, from Boehringer Mannheim); 0.5 µl RNA polymerase (Promega T3 or T7 RNA polymerase); and add $H_2O$ to 20 µl. Incubate at 37° C. for 3 h. Check 2 µl of the reaction on a 1.5% 0.5×TBE agarose gel using a size standard. 5× buffer is 200 mM Tris pH 7.5, 30 mM $MgCl_2$, 10 mM spermidine, 50 mM NaCl, and 100 mM DTT (supplied with enzyme). The PCR product needs no purification and can be added directly to the transcription mixture. A 20 µl reaction is suggested for an initial test experiment and hybridization; a 100 µl reaction is considered "preparative" scale (the reaction can be scaled up to obtain more target).

The amount of PCR product to add is variable; typically a PCR reaction will yield several picomoles of DNA. If the PCR reaction does not produce that much target, then one should increase the amount of DNA added to the transcription reaction (as well as optimize the PCR). The ratio of fluorescein-UTP to UTP suggested above is 1:5, but ratios from 1:3 to 1:10—all work well. One can also label with biotin-UTP and detect with streptavidin-FITC to obtain similar results as with fluorescein-UTP detection.

For nondenaturing agarose gel electrophoresis of RNA, note that the RNA band will normally migrate somewhat faster than the DNA template band, although sometimes the two bands will comigrate. The temperature of the gel can effect the migration of the RNA band. The RNA produced from in vitro transcription is quite stable and can be stored for months (at least) at −20° C. without any evidence of degradation. It can be stored in unsterilized 6×SSPE 0.1% triton X-100 at −20° C. for days (at least) and reused twice (at least) for hybridization, without taking any special precautions in preparation or during use. RNase contamination should of course be avoided. When extracting RNA from cells, it is preferable to work very rapidly and to use strongly denaturing conditions. Avoid using glassware previously contaminated with RNases. Use of new disposable plasticware (not necessarily sterilized) is preferred, as new plastic tubes, tips, etc., are essentially RNase free. Treatment with DEPC or autoclaving is typically not necessary.

5. Fragmentation

Heat transcription mixture at 94 degrees for forty min. The extent of fragmentation is controlled by varying $Mg^{2+}$ concentration (30 mM is typical), temperature, and duration of heating.

6. Hybridization, Scanning, & Stripping

A blank scan of the slide in hybridization buffer only is helpful to check that the slide is ready for use. The buffer is removed from the flow cell and replaced with 1 mL of (hydrolysed) RNA in hybridization buffer and mixed well. Incubate for 15–30 min at 18° C. Remove the hybridization solution, which can be saved for subsequent experiments. Rinse the flow cell 4–5 times with fresh changes of 6×SSPE 0.1% Triton X-100, equilibrated to 18° C. The rinses can be performed rapidly, but it is important to empty the flow cell before each new rinse and to mix the liquid in the cell thoroughly. A series of scans at 30 min intervals using a hybridization temperature of 25° C. yields a very clear signal, usually in at least 30 min to two hours, but it may be desirable to hybridize longer, i.e., overnight. Using a laser power of 50 µW and 50 µm pixels, one should obtain maximum counts in the range of hundreds to low thousands/pixel for a new slide. When finished, the slide can be stripped using warm water.

These conditions are illustrative and assume a probe length of ~15 nucleotides. The stripping conditions suggested are fairly severe, but some signal may remain on the slide if the washing is not stringent. Nevertheless, the counts remaining after the wash should be very low in comparison to the signal in presence of target RNA. In some cases, much gentler stripping conditions are effective. The lower the hybridization temperature and the longer the duration of hybridization, the more difficult it is to strip the slide. Longer targets may be more difficult to strip than shorter targets.

7. Amplification of Signal

A variety of methods can be used to enhance detection of labelled targets bound to a probe on the array. In one embodiment, the protein MutS (from *E. coli*) or equivalent proteins such as yeast MSH1, MSH2, and MSH3; mouse Rep-3, and *Streptococcus* Hex-A, is used in conjunction with target hybridization to detect probe-target complex that contain mismatched base pairs. The protein, labeled directly or indirectly, can be added to the chip during or after hybridization of target nucleic acid, and differentially binds to homo- and heteroduplex nucleic acid. A wide variety of dyes and other labels can be used for similar purposes. For instance, the dye YOYO-1 is known to bind preferentially to nucleic acids containing sequences comprising runs of 3 or more G residues.

8. Detection of Repeat Sequences

In some circumstances, i.e., target nucleic acids with repeated sequences or with high G/C content, very long probes are sometimes required for optimal detection. In one embodiment for detecting specific sequences in a target nucleic acid with a DNA chip, repeat sequences are detected as follows. The chip comprises probes of length sufficient to extend into the repeat region varying distances from each end. The sample, prior to hybridization, is treated with a labelled oligonucleotide that is complementary to a repeat region but shorter than the full length of the repeat. The target nucleic is labelled with a second, distinct label. After hybridization, the chip is scanned for probes that have bound both the labelled target and the labelled oligonucleotide probe; the presence of such bound probes shows that at least two repeat sequences are present.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

TABLE 6

| Mutation | Exon | Exon size | Pop Freq | Location | Sequence Around Mutation Site | PRIMERS | Amp Sz. | SEQ ID NO. |
|---|---|---|---|---|---|---|---|---|
| 297-3 C>T | 2 | 109 | Manchester | Sub C>T + 3 Exon 3 | CTTTTTATTC TTTTG(C>T)AGAG AATGGGATAG A | 787/788 | 297 | 414 |
| R75Q | 3 | 109 | Manchester | Substitute G>A at 60 | TAATGCCCTT CGGC(G>A)ATGTT TTTTGTGGA | 787/788 | 297 | 415 |
| 300 del A | 3 | 109 | Manchester | Delete A at 4 | ATTCTTTTGC AGAGAaTGGG ATAGAGAGCT GGCT | 787/788 | 297 | 416 |
| E60X | 3 | 109 | Manchester | Substitute G>T at 14 | GAATGGGATA GA (G>T) AGCTGGC TTCAAAGA | 787/788 | 297 | 417 |
| L88S | 3 | 109 | Manchester | Substitute T>C at 99 | CTATGGAATC TTTT(T>C) ATATT TAGGGGTAAG | 787/788 | 297 | 418 |
| G86E | 3 | 109 | 0.70% | Substitute G>A at 90 | TTATGTTCTA TG(G>A)AATCTTT TTATATTTAG | 787/788 | 297 | 419 |
| R117H | 4 | 216 | 0.80% | Substitute G>A at 77 | AACAAGGAGG AAC(G>A)CTCTAT CGCGATTTAT | 851/769 | 381 | 420 |
| R117C | 4 | 216 | rare | Substitute C>T at 76 | AACAAGGAGG AA(C>t)GCTCTAT CGCGATTTAT | 851/769 | 381 | 421 |
| Y122X | 4 | 216 | 0.30% | Substitute T>A at 93 | TATCGCGATT TA(T>A)CTAGGCA TAGGCTTATG | 851/769 | 381 | 422 |
| I148T | 4 | 216 | 0.30% | Substitute T>C at 170 | GGCCTTCATC ACA(T>C)TGGAAT GCAGATGAGA | 851/769 | 381 | 423 |
| 621+1G>T | 4 | 216 | 1.30% | Sub G>T after last base | GATTTATAAG AAG(G>T)TAATAC TTCCTTGCAC | 851/769 | 381 | 424 |
| 711+1G>T | 5 | 90 | 0.90% | Sub G>T after last base | CAAATTTGAT GAA(G>t)TATGTA CCTATTGATT | 887/888 | 289 | 425 |
| L206W | 6a | 164 | Fr Can (10%) | Substitute T>G at 38 | TGGATCGCTC CTT(T>G)GCAAGT GGCACTCCTC | 934/935 | 331 | 426 |
| 1138 ins G | 7 | 247 | Manchester | Insert G at 137 | AATCATCCTC CGGAAAgATA TTCACCACCA TCT | 789/790 | 404 | 427 |

TABLE 6-continued

| Mutation | Exon | Exon size | Pop Freq | Location | Sequence Around Mutation Site | PRIMERS | Amp Sz. | SEQ ID NO. |
|---|---|---|---|---|---|---|---|---|
| 1154 ins TC | 7 | 247 | Manchester | Insert TC at 153 | TATTCACCAC CATCTCtcAT TCTGCATTGT T | 789/790 | 404 | 428 |
| 1161 del C | 7 | 247 | Manchester | Delete C at 160 | CCACCATCTC ATTCTGcATT CTTCTGCGCA TGG | 789/790 | 404 | 429 |
| R334W | 7 | 247 | 0.40% | Substitute C>T at 131 | AAGGAATCAT CCTC(C>T)GGAAA ATATTCATTA | 789/790 | 404 | 430 |
| R347H | 7 | 247 | 0.10% | Substitute G>A at 171 | CTGCATTGTT CTGC(G>A)CATGG CGGTCACTCG | 789/790 | 404 | 431 |
| R347L | 7 | 247 | rare | Substitute G>T at 171 | CTGCATTGTT CTGC(G>T)CATGG CGGTCACTCG | 789/790 | 404 | 432 |
| R347P | 7 | 247 | 0.50% | Substitute G>C at 171 | CTGCATTGTT CTGC(G>c)CATGG CGGTCACTCG | 789/790 | 404 | 433 |
| 1078 del T | 7 | 247 | 1.10% | Delete T at 77 | CTTCTTCTCA GGGTTCTTGT GGTGTTTTTA TC | 789/790 | 404 | 434 |
| 1248 + 1 G>A | 7 | 247 | Manchester | Sub G>A1 after Exon 7 | AAACAAAATA CAG(G>A)TAATGT ACCATAATG | 789/790 | 404 | 435 |
| A455E | 9 | 183 | 0.40% | Substitute C>A at 155 | AGGACAGTTG TTGG(c>a)GGTTG CTGGATCCA | 891/892 | 386 | 436 |
| G480C | 10 | 192 | rare | Substitute G>T at 46 | GGAGCCTTGA CAG(G>T)GTAAAA TTAAGCACA | 760/850 | 304 | 437 |
| O493X | 10 | 192 | 0.30% | Substitute C>T at 85 | TCATTCTGTT CT(C>T)AGTTTTC CTGGATTAT | 760/850 | 304 | 438 |
| DI1507 | 10 | 192 | 0.50% | Delete 126, 127, 128 | ATTAAAGAAA ATATcatCTT TGGTGTTTCC TATG | 760/850 | 304 | 439 |
| F508C | 10 | 192 | rare | Substitute T>G at 131 | TAAAGAAAAT ATCATCT(T>g)TG GTGTTTCCTA | 760/850 | 304 | 440 |
| DF508 | 10 | 192 | 67.20% | Delete 129, 130, 131 | ATTAAAGAAA ATATCATcTG GTGTTTCCTA TG | 760/850 | 304 | 441 |
| V520F | 10 | 192 | 0.20% | Substitute G>T at 166 | TAGATACAGA AGC(G>T)TCATCA AAGCATGCC | 760/850 | 304 | 442 |
| 1717-1G>A | 10 | 95 | 1.10% | Sub G>A at +1 Ex11 | TATTTTTGGT AATA(G>a)GACAT CTCCAAGTTT | 762/763 | 233 | 443 |
| G542X | 11 | 95 | 3.40% | Substitute G>T at 40 | ACAATATAGT TCTT(G>T)GAGAA GGTGGAAT | 762/762 | 233 | 444 |
| S549N | 11 | 95 | rare | Substitute G>A at 62 | AGGTGGAATC ACACTGA(G>A)TG GAGGTCAACG | 762/763 | 233 | 445 |
| S549I | 11 | 95 | rare | Substitute G>T at 62 | AGGTGGAATCA CACTGA(G>T)TGG AGGTCAACG | 762/763 | 233 | 446 |
| S549R (A>C) | 11 | 95 | rare | Substitute A>C at 61 | AGGTGGAATC ACACTG(A>c)GTG GAGGTCAACG | 762/763 | 233 | 447 |
| S549R (T>G) | 11 | 95 | 0.30% | Substitute T>G at 63 | AGGTGGAATC ACACTGAG(T>G)G GAGGTCAACG | 762/763 | 233 | 448 |
| G551D | 11 | 95 | 2.40% | Substitute G>A at 88 | ATCACACTGA GTGGAG(G>A)TCA ACGAGCAAGA | 762/763 | 233 | 449 |
| G551S | 11 | 95 | rare | Substitute G>A at 67 | ATCACACTGA GTGGA(G>A)GTCA ACGAGCAAGA | 762/763 | 233 | 450 |
| O552X | 11 | 95 | rare | Substitute C>T at 70 | ACACTGAGTG GAGGT(C>T)AACG AGCAAGAATT | 762/763 | 233 | 451 |
| R522Q | 11 | 95 | rare | Substitute G>A at 74 | TGAGTGGAGG TCAAC(G>A)AGCA AGAATTTCT | 762/763 | 233 | 452 |
| R563X | 11 | 95 | 1.30% | Substitute C>T at 73 | TGAGTGGAGG TCAA(C>t)GAGCA AGAATTTCTT T | 762/763 | 233 | 453 |
| A559T | 11 | 95 | rare | Substitute G>A at 91 | GCAAGAATTT CTTTA(G>A)CAAG GTGAATAAC | 762/763 | 233 | 454 |
| R560T | 11 | 95 | 0.40% | Substitute G>C at 95 | ATTTCTTTAG CAA(G>C)GTGAAT AACTAA | 762/763 | 233 | 455 |
| R560K | 11 | 95 | rare | Substitute G>A at 95 | GAATTTCTTT AGCAA(G>A)GTGA ATAACTAA | 762/763 | 233 | 456 |
| 1898 + 1G>A | 12 | 95 | 0.90% | Sub G>A after last Ex12 | GAAATATTTG AAAG(G>A)TATGT TCTTTGAAT | 931/932 | 299 | 457 |
| D648V | 13 | 724 | Nst Am (63%) | Substitute A>T at 177 | AACTCATGGG ATGTG(A>T)TTCT TTCGACCAAT | 955/884 | 360 | 458 |
| 2184 del A | 13 | 724 | 0.70% | Delete A at 286 | GACGAAACAA AAAAaCAATC TTTTAAACAG AC | 955/884 | 360 | 459 |
| 2184 ins A | 13 | 724 | rare | Insert A after 286 | GACAGAAACA AAAAAAaCAA TCTTTTAAAG CGAC | 955/884 | 360 | 460 |
| 2789+5G>A | 14b | 38 | 1.10% | Sub G>A 5 one after last | CTCCTTGGAA AGTGA(G>A)TATT CCATGTCCTA | 885/886 | 374 | 461 |
| 3272-26A>G | 17a | 228 | rare | Sub A>G 26 before 17b | TTTATGTTAT TTGCA(A>G)TGTT TTCTATGGAA A | 782/901 | 414 | 462 |
| 3272-93T>C | 17a | 228 | rare | Sub T>C 93 before 17b | ATTTGTGATA TGATTA(T>C)TCT AATTTAGTCT TT | 782/901 | 414 | 463 |
| R1066C | 17b | 228 | rare | Substitute C>T at 57 | AGGACTATGG ACACTT(C>T)GTG CCTTCGGACG GC | 782/901 | 414 | 464 |

TABLE 6-continued

| Mutation | Exon | Exon size | Pop Freq | Location | Sequence Around Mutation Site | PRIMERS | Amp Sz. | SEQ ID NO. |
|---|---|---|---|---|---|---|---|---|
| L1077P | 17b | 228 | rare | Substitute T>C at 91 | TTACTTTGAA ACTC(T>C)GTTCC ACAAAGCTC | 782/901 | 414 | 465 |
| Y1092X | 17b | 228 | 0.50% | Substitute C>A at 137 | CCAACTGGTT CTTGTA(C>A)CTG TCAACACTGC G | 782/901 | 414 | 466 |
| M1101K | 17b | 228 | Mut (65%) | Substitute T>A at 163 | TGCGCTGGTT CCAAA(T>A)GAGA ATAGAAATGA T | 782/901 | 414 | 467 |
| R1152X | 19 | 249 | 0.90% | Substitute C>T at 16 | ATGCGATCTG TGAGC(C>T)GAGT CTTTAAGTTC | 784/785 | 356 | 468 |
| 3659 del C | 19 | 249 | 0.80% | Delete C at 59 | AAGGTAAACC TACCAAGTCA ACCAAACCAT ACA | 784/785 | 356 | 469 |
| 3849 + 4 A>G | 19 | 249 | 1.00% | Sub A>G 4 after last base | TCCTGGCCAG AGGGTG(A>G)GAT TTGAACACT | 784/785 | 356 | 470 |
| 3849 10kb | 19 | 10kb | 1.40% | Sub C>T EcoR1 Fragment | ATAAAATGG(C>T)GAGTAAGACA | 792/791 | 450 | 471 |
| W1282R | 20 | 156 | rare | Substitute T>C at 127 | AATAACTTTG CAACAG(T>C)GGA GGAAAGCCTT T | 764/786 | 351 | 472 |
| W1282X | 20 | 156 | 2.10% | Substitute G>A at 129 | AATAACTTTG CAACAGTG(G>A)A GGAAAGCCTT T | 764/786 | 351 | 473 |
| 3905 ins T | 20 | 156 | 2.10% | Insert T at 58 | CTTTGTTATC AGCTTTTTTG AGACTACTGA ACAC | 764/786 | 351 | 474 |
| 4005 + 1 G>A | 20 | 156 | Manchester | Sub G>A after Exon 20 | AGTGATACCA CAG(G>A)TGAGCA AAAGGACTT | 764/786 | 351 | 475 |
| N1303K | 21 | 90 | 1.80% | Substitute C>G at 36 | CATTTAGAAA AAA(C>G)TTGGAT CCCTATGAAC | 756/793 | 396 | 476 |
| N1303H | 21 | 90 | rare | Substitute A>C at 34 | CATTTAGAAA A(A>C)ACTTGGAT CCCTATGAAC | | | 477 |

What is claimed is:

1. An array of nucleic acid probes immobilized on a solid support, the array comprising at least two sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
   wherein the probes in the first probe set collectively have at least three interrogation positions respectively corresponding to each of three contiguous nucleotides in the reference sequence;
   provided that the array does not consist of a complete set of probes of a given length, wherein a complete set is all permutations of nucleotides A, C, G and T/U; and wherein the reference sequence is at least 50 bases, and the first probe set comprises overlapping probes spanning the reference sequence.

2. The array of claim 1, wherein the reference sequence is from an hMLH1 gene.

3. The array of claim 1, wherein the reference sequence is from an MSH2 gene.

4. An array of nucleic acid probes immobilized on a solid support, the array comprising at least first, second and third probe groups, each group comprising a first and second sets of probes as defined by claim 1;
   wherein each probe in the first probe set from the first group is exactly complementary to a subsequence of a first reference sequence and each probe in the first probe set from the second group is exactly complementary to a subsequence from a second reference sequence; and each probe in the first probe set from the third group is exactly complementary to as subsequence of a third reference sequence;
   wherein the first, second and third reference sequences are from a p53 gene, an hMLH1 gene, and an MSH2 gene, respectively.

5. An array of nucleic acid probes immobilized on a solid support, the array comprising at least four sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) second, third and fourth probe sets, each set comprising a probe for each interrogation position in the first probe set, each probe in the second, third and fourth probe sets being identical to a sequence comprising a corresponding probe from the first probe set or a subsequence of at least six nucleotides thereof that includes the interrogation position, except that the interrogation position is occupied by a different nucleotide in each of the four corresponding probes from the four probe sets;
   provided the array does not consist of a complete set of probes of a given length, wherein a complete set is all permutations of nucleotides A, C, G and T/U; and wherein the reference sequence is at least 50 bases, and the first probe set comprises overlapping probes spanning the reference sequence.

6. The array of claim 5, wherein the first probe set has at least three interrogation positions respectively corresponding to each of three contiguous nucleotides in a reference sequence.

7. The array of claim 5, wherein the first probe set has at least 50 interrogation positions respectively corresponding to each of 50 contiguous nucleotides in a reference sequence.

8. The array of claim 5, wherein the probes are linked to the support via a spacer.

9. The array of claim 5, wherein the segment in each probe of the first probe set that is exactly complementary to the subsequence of the reference sequence is 9–21 nucleotides.

10. The array of claim 5, wherein each probe of the first probe set consists of the segment that is exactly complementary to the subsequence of the reference sequence.

11. The array of claim 5, wherein the probes in the second, third and fourth probe sets are identical to the corresponding probe from the first probe set except that the at least one interrogation position is occupied by a different nucleotide in each of the four corresponding probes from the four probe sets.

12. An array of nucleic acid probes immobilized on a solid support, the array comprising at least four sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) second, third and fourth probe sets, each set comprising a probe for each interrogation position in the first probe set, each probe in the second, third and fourth probe sets being identical to a sequence comprising a corresponding probe from the first probe set or a subsequence of at least six nucleotides thereof that includes the interrogation position, except that the interrogation position is occupied by a different nucleotide in each of the four corresponding probes from the four probe sets;
   (3) a fifth probe set comprising a probe for each interrogation position in the first probe set, each probe in the fifth probe set being identical to a sequence comprising a corresponding probe from the first probe set or a subsequence of at least six nucleotides thereof that includes the interrogation position, except that the interrogation position is deleted in the corresponding probe from the fifth probe set
   provided the array does not consist of a complete set of probes of a given length, wherein a complete set is all permutations of nucleotides A, C, G and T/U.

13. An array of nucleic acid probes immobilized on a solid support, the array comprising at least four sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) second, third and fourth probe sets, each set comprising a probe for each interrogation position in the first probe set, each probe in the second, third and fourth probe sets being identical to a sequence comprising a corresponding probe from the first probe set or a subsequence of at least six nucleotides thereof that includes the interrogation position, except that the interrogation position is occupied by a different nucleotide in each of the four corresponding probes from the four probe sets;
   (3) a fifth probe set comprising a probe for each interrogation position in the first probe set, each probe in the fifth probe set being identical to a sequence comprising the corresponding probe from the first probe set or a subsequence of at least six nucleotides thereof that includes the interrogation position, except that an additional nucleotide is inserted adjacent to the one interrogation position in the corresponding probe from the first probe set.

14. An array of nucleic acid probes immobilized on a solid support, the array comprising at least four sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) second, third and fourth probe sets, each set comprising a probe for each interrogation position in the first probe set, each probe in the second, third and fourth probe sets being identical to a sequence comprising a corresponding probe from the first probe set or a subsequence of at least six nucleotides thereof that includes the interrogation position, except that the interrogation position is occupied by a different nucleotide in each of the four corresponding probes from the four probe sets;
   provided the array does not consist of a complete set of probes of a given length, wherein a complete set is all permutations of nucleotides A, C, G and T/U;
   wherein the array has between 100 and 100,000 probes.

15. An array of nucleic acid probes immobilized on a solid support, the array comprising at least one pair of first and second probe groups, each group comprising at least two sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
   wherein the probes in the first probe set collectively have at least three interrogation positions respectively corresponding to each of three contiguous nucleotides in the reference sequence;
   provided that the array does not consist of a complete set of probes of a given length, wherein a complete set is all permutations of nucleotides A, C, G and T/U;
   wherein each probe in the first probe set from the first group is exactly complementary to a subsequence of a first reference sequence and each probe in the first probe set from the second group is exactly complementary to a subsequence from a second reference sequence and the second reference sequence is a mutated form of the first reference sequence.

16. The array of claim 15, wherein each group further comprises third and fourth probe sets, each comprising a corresponding probe for each probe in the first probe set, the probes in the second, third and fourth probe sets being identical to a sequence comprising the corresponding probe from the first probe set or a subsequence of at least six nucleotides thereof that includes the interrogation position, except that the interrogation position is occupied by a different nucleotide in each of the four corresponding probes from the four probe sets.

17. The array of claim 16 that comprises at least forty pairs of first and second probe groups, wherein the probes in the first probe sets from the first groups of the forty pairs are exactly complementary to subsequences from forty respective first reference sequences.

18. An array of probes immobilized to a solid support comprising two blocks of probes, each block as defined by claim 17, a first block comprising a wildtype probe comprising a segment exactly complementary to a subsequence of a first reference sequence and a second block comprising a wildtype probe comprising a segment exactly complementary to a subsequence of a second reference sequence.

19. The array of claim 18, comprising at least 10–100 blocks of probes, each comprising a wildtype probe comprising a segment exactly complementary to a subsequence of at least 10–100 respective reference sequences.

20. A method of comparing a target nucleic acid with a reference sequence comprising a predetermined sequence of nucleotides, the method comprising:
hybridizing the target sequence to the array of claim 15;
determining which probes in the first group, relative to one another, hybridize to the target sequence, the relative specific binding of the probes indicating whether the target sequence is the same or different from the first reference sequence;
determining which probes in the second group, relative to one another, hybridize to the target sequence, the relative specific binding of the probes indicating whether the target sequence is the same or different from the second reference sequence.

21. The method of claim 20, wherein the hybridizing step comprising hybridizing the target sequence and a second target sequence to the array, and the relative specific binding of the probes from the first group indicates that the target is identical to the first reference sequence, and the relative specific binding of the probes from the second group indicates that the second target sequence is identical to the second reference sequence.

22. The method of claim 21, wherein the first and second target sequences are heterozygous alleles.

23. A block of nucleic acid probes immobilized on a solid support, the array comprising:
a wildtype probe comprising a segment of at least six nucleotides exactly complementary to a subsequence of a reference sequence, the segment having a plurality of interrogation positions respectively corresponding to a plurality of nucleotides in the reference sequence,
for each interrogation position, three mutant probes, each identical to a sequence comprising the wildtype probe or a subsequence of at least six nucleotides thereof including the plurality of interrogation positions, except in the interrogation position, which is occupied by a different nucleotide in each of the three mutant probes and the wildtype probe;
provided the array does not consist of a complete set of probes of a given length, wherein a complete set is all permutations of nucleotides A, C, G and T/U;
wherein the reference sequence is from a gene having a variant form associated with development of cancer, a pathogenic microorganism, a biotransformation gene, or a gene associated with a hereditary disorder.

24. The array of claim 23, wherein the segment of the wildtype probe comprises 3–20 interrogation positions corresponding to 3–20 respective nucleotides in the reference sequence.

25. An array of nucleic acid probes immobilized on a solid support, the array comprising at least four probes:
a first probe comprising first and second segments, each of at least three nucleotides and each exactly complementary to first and second subsequences of a reference sequence, the segments including at least one interrogation position corresponding to a nucleotide in the reference sequence, wherein either (1) the first and second subsequences are noncontiguous, or (2) the first and second subsequences are contiguous and the first and second segments are inverted relative to the complement of the first and second subsequences in the reference sequence;
second, third and fourth probes, identical to a sequence comprising the first probe or a subsequence thereof comprising at least three nucleotides from each of the first and second segments, except in an interrogation position, which differs in each of the probes;
provided the array does not consist of a complete set of probes of a given length, wherein a complete set is all permutations of nucleotides A, C, G and T/U.

26. The array of any one of claims, 1, 5, 15, 23 and 25, wherein the reference sequence is from a gene having a variant form associated with development of cancer.

27. An array of nucleic acid probes immobilized on a solid support, the array comprising at least two sets of probes,
(1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
(2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
wherein the probes in the first probe set collectively have at least three interrogation positions respectively corresponding to each of three contiguous nucleotides in the reference sequence;
provided that the array does not consist of a complete set of probes of a given length, wherein a complete set is all permutations of nucleotides A, C, G and T/U;
wherein the reference sequence is from a p53 gene.

28. The array of claim 27, wherein the first probe set has at least 60 interrogation positions corresponding to at least 60 contiguous nucleotides from exon 6 of the p53 gene.

29. An array of nucleic acid probes immobilized on a solid support, the array comprising at least a set of four probes, each of the probes comprising a segment of at least 7 nucleotides that is exactly complementary to a subsequence from a reference sequence, except that the segment may or may not be exactly complementary at two interrogation positions, wherein:
the first interrogation position is occupied by a different nucleotide in each of the four probes,
the second interrogation position is occupied by a different nucleotide in each of the four probes, in first and second probes, the segment is exactly complementary to the subsequence, except at not more than one of the interrogation positions, and in third and fourth probes, the segment is exactly complementary to the subsequence, except at both of the interrogation positions, provided the array does not consist of a complete set of probes of a given length, wherein a complete set is all permutations of nucleotides A, C, G and T/U.

30. A method of comparing a target nucleic acid with a reference sequence comprising a predetermined sequence of nucleotides, the method comprising:
(a) hybridizing a sample comprising the target nucleic acid to an array of nucleic acid probes immobilized on a solid support, the array comprising a set of probes comprising:

a first probe comprising a segment of at least 7 nucleotides exactly complementary to a subsequence of a reference sequence except at one or two positions, the segment including an interrogation position not at the one or two positions;

second, third and fourth mutant probes, each identical to a sequence comprising the wildtype probe or a subsequence thereof including the interrogation position and the one or two positions, except in the interrogation position, which is occupied by a different nucleotide in each of the four probes;

provided the array does not consist of a complete set of probes of a given length, wherein a complete set is all permutations of nucleotides A, C, G and T/U.

31. A method of comparing a target nucleic acid with a reference sequence comprising a predetermined sequence of nucleotides, the method comprising:
(a) hybridizing a sample comprising the target nucleic acid to an array of nucleic acid probes immobilized on a solid support, the array comprising:
  (1) a first probe set comprising a plurality of probes, each probe comprising a segment of at least six nucleotides exactly complementary to a subsequence of the reference sequence, the segment including at least one interrogation position complementary to a corresponding nucleotide in the reference sequence;
  (2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
wherein, the probes in the first probe set have at least three interrogation positions respectively corresponding to each of at least three nucleotides in the reference sequence, and wherein the reference sequence is at least 50 bases, and the first probe set comprises overlapping probes spanning the reference sequence and
(b) determining which probes, relative to one another, in the first and second probe sets specifically bind to the target nucleic acid, the relative specific binding of corresponding probes in the first and second probe sets indicating whether a nucleotide in the target sequence is the same or different from the corresponding nucleotide in the reference sequence.

32. The method of claim 31, wherein the array further comprises third and fourth probe sets, each set comprising a probe for each interrogation position in the first probe set, each probe in the second, third and fourth probe sets being identical to a sequence comprising a corresponding probe from the first probe set or a subsequence of at least six nucleotides thereof that includes the interrogation position, except that the interrogation position is occupied by a different nucleotide in each of the four corresponding probes from the four probe sets;

and the determining step comprises determining which probes, relative to one another, in the first, second, third and fourth probe sets specifically bind to the target nucleic acid, the relative specific binding of corresponding probes in the first, second, third and fourth probe sets indicating whether a nucleotide in the target sequence is the same or different from the corresponding nucleotide in the reference sequence.

33. The method of claim 32, wherein the determining comprises:
(1) comparing the relative specific binding of four corresponding probes from the first, second, third and fourth probe sets;
(2) assigning a nucleotide in the target sequence as the complement of the interrogation position of the probe having the greatest specific binding;
(3) repeating (1) and (2) by comparing the relative specific binding of a further four corresponding probes from the first, second, third and fourth probe sets until each nucleotide of interest in the target sequence has been assigned.

34. A method of comparing a target nucleic acid with a reference sequence comprising a predetermined sequence of nucleotides, the method comprising:
(a) hybridizing a sample comprising the target nucleic acid to an array of nucleic acid probes immobilized on a solid support, the array comprising:
  (1) a first probe set comprising a plurality of probes, each probe comprising a segment of at least six nucleotides exactly complementary to a subsequence of the reference sequence, the segment including at least one interrogation position complementary to a corresponding nucleotide in the reference sequence;
  (2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
wherein, the probes in the first probe set have at least three interrogation positions respectively corresponding to each of at least three nucleotides in the reference sequence, and:
(b) comparing the relative specific binding of two corresponding probes from the first and second probe sets;
(c) assigning a nucleotide in the target sequence as the complement of the interrogation position of the probe having the greater specific binding;
(d) repeating (1) and (2) by comparing the relative specific binding of a further two corresponding probes from the first and second probe sets until each nucleotide of interest in the target sequence has been assigned.

35. A method of comparing a target nucleic acid with a reference sequence comprising a predetermined sequence of nucleotides, the method comprising:
(a) hybridizing the target nucleic acid to an array of probes immobilized on a solid support, the array comprising:
a wildtype probe comprising a segment of at least six nucleotides exactly complementary to a subsequence of a reference sequence, the segment having a plurality of interrogation positions respectively corresponding to a plurality of nucleotides in the reference sequence, wherein the reference sequence is from a gene having a variant form associated with development of cancer;
for each interrogation position, three mutant probes, each identical to a sequence comprising the wildtype probe or a subsequence of at least six nucleotides thereof including the plurality of interrogation positions, except in the interrogation position, which is occupied by a different nucleotide in each of the three mutant probes and the wildtype probe;
(b) for each interrogation position,
(1) comparing the relative specific binding of the three mutant probes and the wildtype probe;
(2) assigning a nucleotide in the target sequence as the complement of the interrogation position of the probe having the greatest specific binding.

36. The method of claim 35, wherein the target sequence has an undetermined substitution relative to the reference sequence, and the method assigns a nucleotide to the substitution.

37. The method of claim 36, wherein:
the hybridizing step comprises hybridizing the target nucleic acid and a second target nucleic acid and the determining step comprises determining which probes, relative to one another, in the array bind specifically to the target nucleic acid or the second target nucleic acid, the relative specific binding of the probes indicating whether the target sequence is the same or different from the reference sequence and whether the second target sequence is the same or different from the reference sequence.

38. The method of claim 37, wherein the target sequence has a label and the second target sequence has a second label different from the label.

39. The method of claim 38, wherein undetermined first and second proportions of the first and second target sequences are hybridized to the array and the specific binding indicates the proportions.

40. A method of comparing a target nucleic acid with a reference sequence comprising a predetermined sequence of nucleotides, the method comprising:
(a) hybridizing the reference sequence to an array of nucleic acid probes immobilized on a solid support, the array comprising;
(1) a first probe set comprising a plurality of probes, each probe comprising a segment of at least six nucleotides exactly complementary to a subsequence of the reference sequence except in an interrogation position;
(2) a second probe set comprising a corresponding probe for each probe in the first probe set, the corresponding probe in the second probe set being identical to a sequence comprising the corresponding probe from the first probe set or a subsequence of at least six nucleotides thereof that includes the interrogation position, except that the one interrogation position is occupied by a different nucleotide in each of the two corresponding probes from the first and second probe sets and
wherein the reference sequence is at least 50 bases, and the first probe set comprises overlapping probes spanning the reference sequence; and
(b) determining which probes in the first and second probe sets, relative to one another, in the array bind specifically to the reference sequence;
(c) hybridizing a target sequence to the array;
(d) determining which probes, relative to one another, in the array bind specifically to the target sequence;
wherein the probes in the first probe set collectively have at least three interrogation positions respectively corresponding to each of three contiguous nucleotides in the reference sequence, wherein the relative specific binding of the probes to the reference and the target sequence indicates whether the reference sequence is the same or different from the target sequence.

41. The method of any one of claims 31–40, wherein the reference sequence is from a gene having a variant form associated with development of cancer.

42. An array of nucleic acid probes immobilized on a solid support, the array comprising at least two sets of probes,
(1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
(2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
wherein the probes in the first probe set collectively have at least three interrogation positions respectively corresponding to each of three contiguous nucleotides in the reference sequence;
provided that the array does not consist of a complete set of probes of a given length, wherein a complete set is all permutations of nucleotides A, C, G and T/U and wherein the reference sequence is at least 50 bases, and the first probe set comprises overlapping probes spanning the reference sequence;
wherein the reference sequence is from a gene from an HIV virus.

43. An array of nucleic acid probes immobilized on a solid support, the array comprising at least two sets of probes,
(1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
(2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;

wherein the probes in the first probe set collectively have at least three interrogation positions respectively corresponding to each of three contiguous nucleotides in the reference sequence;

provided that the array does not consist of a complete set of probes of a given length, wherein a complete set is all permutations of nucleotides A, C, G and T/U and wherein the reference sequence is at least 50 bases, and the first probe set comprises overlapping probes spanning the reference sequence, wherein the reference sequence is from a CFTR gene.

44. An array of nucleic acid probes immobilized on a solid support, the array comprising at least two sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
   wherein the probes in the first probe set collectively have at least three interrogation positions respectively corresponding to each of three contiguous nucleotides in the reference sequence;
   provided that the array does not consist of a complete set of probes of a given length, wherein a complete set is all permutations of nucleotides A, C, G and T/U and wherein the reference sequence is at least 50 bases, and the first probe set comprises overlapping probes spanning the reference sequence,
   wherein the reference sequence is from a mitochondrial genome.

45. An array of nucleic acid probes immobilized on a solid support, the array comprising at least two sets of probes,
   (1) a first probe set comprising a plurality of probes, each probe comprising a segment of at least six nucleotides exactly complementary to a subsequence of a reference sequence, the segment including at least one interrogation position complementary to a corresponding nucleotide in the reference sequence,
   (2) a second probe set comprising a probe for each interrogation position in the first probe set, each probe in the second probe set being identical to a sequence comprising a corresponding probe from the first probe set or a subsequence of at least six nucleotides thereof that includes the interrogation position, except that the interrogation position is occupied by a different nucleotide in each of the two corresponding probes from the first and second probe sets;
   wherein the probes in the first probe set collectively have at least three interrogation positions respectively corresponding to each of three contiguous nucleotides in the reference sequence;
   provided that the array does not consist of a complete set of probes of a given length, wherein a complete set is all permutations of nucleotides A, C, G and T/U, the reference sequence is at least 50 bases, and the first probe set comprises overlapping probes spanning the reference sequence, and
   wherein the reference sequence is from a biotransformation gene.

46. An array of any one of claims 42–45, wherein the reference sequence is at least 50 bases, and the first probe set comprises overlapping probes spanning the reference sequence.

47. A method of comparing a target sequence with a reference sequence, the method comprising:
   identifying variants of a reference sequence differing from the reference sequence in at least one nucleotide;
   assigning each variant a designation,
   providing an array of pools of probes, each pool occupying a separate cell of the array, wherein each pool comprises a plurality of different probes, the different probes comprising different segments exactly complementary to respective different variant sequences assigned a particular designation,
   contacting the array with a target sequence comprising a variant of the reference sequence;
   determining the relative hybridization intensities of the pools in the array to the target sequence;
   determining the target sequence from the relative hybridization intensities of the pools.

* * * * *

SEQUENCE LISTING (1) GENERAL INFORMATION:

(iii) NUMBER OF SEQUENCES: 585

(2) INFORMATION FOR SEQ ID NO: 1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO: 1:

TAACCACTCA CGGGAGCA                                      18

(2) INFORMATION FOR SEQ ID NO: 2:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO: 2:

ATTGGMGAGT GCCC                                          14

(2) INFORMATION FOR SEQ ID NO: 3:

(i) SEQUENCE CHARACTERISTICS:
      (A) LENGTH: 14 base pairs
      (B) TYPE: nucleic acid

```
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 3:

ATTGGAGAGT GCCC                                                          14

(2) INFORMATION FOR SEQ ID NO: 4:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 4:

ATTGGCGAGT GCCC                                                          14

(2) INFORMATION FOR SEQ ID NO: 5:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 5:

ATTGGKGAGT GCCC                                                          14

(2) INFORMATION FOR SEQ ID NO: 6:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 6:

ATTGGGGAGT GCCC                                                          14

(2) INFORMATION FOR SEQ ID NO: 7:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 7:

ATTGGTGAGT GCCC                                                          14

(2) INFORMATION FOR SEQ ID NO: 8:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)
```

(xi) SEQUENCE DESCRIPTION: SEQ ID NO: 8:

ATTGGRGAGT GCCC                                                         14

(2) INFORMATION FOR SEQ ID NO: 9:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 9:

TAACCCCTCA CGGGAGCA                                                     18

(2) INFORMATION FOR SEQ ID NO: 10:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 10:

TAACCGCTCA CGGGAGCA                                                     18

(2) INFORMATION FOR SEQ ID NO: 11:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 11:

TAACCTCTCA CGGGAGCA                                                     18

(2) INFORMATION FOR SEQ ID NO: 12:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 12:

ATTAACCACT CACGGGAGCT CT                                                22

(2) INFORMATION FOR SEQ ID NO: 13:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: DNA (oligonucleotide)

(xi) SEQUENCE DESCRIPTION: SEQ ID NO: 13:

TGGTGNKYGC CCT                                                          13

(2) INFORMATION FOR SEQ ID NO: 14:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 14:

TGGTGAGCGC CCT                                        13

(2) INFORMATION FOR SEQ ID NO: 15:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 15:

TGGTGCGCGC CCT                                        13

(2) INFORMATION FOR SEQ ID NO: 16:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 16:

TGGTGGGCGC CCT                                        13

(2) INFORMATION FOR SEQ ID NO: 17:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 17:

TGGTGTGCGC CCT                                        13

(2) INFORMATION FOR SEQ ID NO: 18:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 18:

TGGTGATCGC CCT                                        13

(2) INFORMATION FOR SEQ ID NO: 19:

-continued

```
    (i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 19:

TGGTGCTCGC CCT                                                          13

(2) INFORMATION FOR SEQ ID NO: 20:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 20:

TGGTGGTCGC CCT                                                          13

(2) INFORMATION FOR SEQ ID NO: 21:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 21:

TGGTGTTCGC CCT                                                          13

(2) INFORMATION FOR SEQ ID NO: 22:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 22:

TGGTGAGTGC CCT                                                          13

(2) INFORMATION FOR SEQ ID NO: 23:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 23:

TGGTGCGTGC CCT                                                          13

(2) INFORMATION FOR SEQ ID NO: 24:

(i) SEQUENCE CHARACTERISTICS:
        (A) LENGTH: 13 base pairs
        (B) TYPE: nucleic acid
        (C) STRANDEDNESS: single
```

(D) TOPOLOGY: linear (ii) MOLECULE TYPE: DNA (oligonucleotide)

(xi) SEQUENCE DESCRIPTION: SEQ ID NO: 24:

TGGTGCGCGC CCT                                                          13

(2) INFORMATION FOR SEQ ID NO: 25:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 25:

TGGTGTGTGC CCT                                                          13

(2) INFORMATION FOR SEQ ID NO: 26:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 26:

TGGTGATTGC CCT                                                          13

(2) INFORMATION FOR SEQ ID NO: 27:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 27:

TGGTGCTTGC CCT                                                          13

(2) INFORMATION FOR SEQ ID NO: 28:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 28:

TGGTGGTTGC CCT                                                          13

(2) INFORMATION FOR SEQ ID NO: 29:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 29:

TGGTGTTTGC CCT                                                                              13

(2) INFORMATION FOR SEQ ID NO: 30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 30:

ATTAACCACT CCCGGGAGCT CT                                                                    22

(2) INFORMATION FOR SEQ ID NO: 31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 31:

ATTAACCACT CGCGGGAGCT CT                                                                    22

(2) INFORMATION FOR SEQ ID NO: 32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 32:

ATTAACCACT CTCGGGAGCT CT                                                                    22

(2) INFORMATION FOR SEQ ID NO: 33:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 33:

TAATTNKYGA GTG                                                                              13

(2) INFORMATION FOR SEQ ID NO: 34:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 34:

AATTGNKRAG TGC                                                                              13

(2) INFORMATION FOR SEQ ID NO: 35:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 35:

ATTGGNKRGT GCC                                      13

(2) INFORMATION FOR SEQ ID NO: 36:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 36:

TTGGTNMRTG CCC                                      13

(2) INFORMATION FOR SEQ ID NO: 37:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 37:

GGTGANKRCC CTC                                      13

(2) INFORMATION FOR SEQ ID NO: 38:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 38:

GTGAGNKYCC TCG                                      13

(2) INFORMATION FOR SEQ ID NO: 39:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 39:

TGAGTNMYCT CGA                                      13

(2) INFORMATION FOR SEQ ID NO: 40:

(i) SEQUENCE CHARACTERISTICS:

(A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 40:

GAGTGNMYTC GAG                                                              13

(2) INFORMATION FOR SEQ ID NO: 41:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 41:

AGTGCNMYCG AGA                                                              13

(2) INFORMATION FOR SEQ ID NO: 42:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 42:

ATTNKYGAGT GCC                                                              13

(2) INFORMATION FOR SEQ ID NO: 43:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 43:

ATTGNKRAGT GCC                                                              13

(2) INFORMATION FOR SEQ ID NO: 44:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 44:

ATTGGNKRGT GCC                                                              13

(2) INFORMATION FOR SEQ ID NO: 45:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 45:

ATTRGTNMGT GCC                                                              13

(2) INFORMATION FOR SEQ ID NO: 46:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 46:

ATTKRTGNGT GCC                                                              13

(2) INFORMATION FOR SEQ ID NO: 47:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 47:

TAAGCACTCA CGGGAGCA                                                         18

(2) INFORMATION FOR SEQ ID NO: 48:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 48:

TAATCACTCA CGGGAGCA                                                         18

(2) INFORMATION FOR SEQ ID NO: 49:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 49:

TAAACACTCA CGGGAGCA                                                         18

(2) INFORMATION FOR SEQ ID NO: 50:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 50:

TAACGACTCA CGGGAGCA                                              18

(2) INFORMATION FOR SEQ ID NO: 51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 51:

TAACTACTCA CGGGAGCA                                              18

(2) INFORMATION FOR SEQ ID NO: 52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 52:

TAACAACTCA CGGGAGCA                                              18

(2) INFORMATION FOR SEQ ID NO: 53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 53:

TAACCAGTCA CGGGAGCA                                              18

(2) INFORMATION FOR SEQ ID NO: 54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 54:

TAACCATTCA CGGGAGCA                                              18

(2) INFORMATION FOR SEQ ID NO: 55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 55:

TAACCAATCA CGGGAGCA                                              18

(2) INFORMATION FOR SEQ ID NO: 56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 56:

TAACCACACA CGGGAGCA                                            18

(2) INFORMATION FOR SEQ ID NO: 57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 57:

TAACCACCCA CGGGAGCA                                            18

(2) INFORMATION FOR SEQ ID NO: 58:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 58:

TAACCACGCA CGGGAGCA                                            18

(2) INFORMATION FOR SEQ ID NO: 59:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 59:

CACGGGAGCA                                                            10

(2) INFORMATION FOR SEQ ID NO: 60:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 60:

ATTGNTNAGT GCCC                                                  14

(2) INFORMATION FOR SEQ ID NO: 61:

(i) SEQUENCE CHARACTERISTICS:
        (A) LENGTH: 14 base pairs (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 61:

ATTGNANAGT GCCC                                                         14

(2) INFORMATION FOR SEQ ID NO: 62:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 62:

ATTGRYRHGT GCCC                                                         14

(2) INFORMATION FOR SEQ ID NO: 63:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 63:

ATTGKWKVGT GCCC                                                         14

(2) INFORMATION FOR SEQ ID NO: 64:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 64:

ATTGDHSMGT GCCC                                                         14

(2) INFORMATION FOR SEQ ID NO: 65:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 65:

TGGCTACGAG GAATCATCTG TTA                                               23

(2) INFORMATION FOR SEQ ID NO: 66:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 66:

GCTCCCCGAT                                                                    10

(2) INFORMATION FOR SEQ ID NO: 67:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 67:

GCACCCCGAT                                                                    10

(2) INFORMATION FOR SEQ ID NO: 68:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 68:

GCCCCCCGAT                                                                    10

(2) INFORMATION FOR SEQ ID NO: 69:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 69:

GCGCCCCGAT                                                                    10

(2) INFORMATION FOR SEQ ID NO: 70:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 70:

AGTACCAGAT CTCTAA                                                             16

(2) INFORMATION FOR SEQ ID NO: 71:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 71:

-continued

CATGGNCAGA GA                                                           12

(2) INFORMATION FOR SEQ ID NO: 72:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 72:

GTAGAATTCT GTTGACTCAG ATTGG                                             25

(2) INFORMATION FOR SEQ ID NO: 73:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 73:

AAATCCATAC AATACTCCAG TATTTGC                                           27

(2) INFORMATION FOR SEQ ID NO: 74:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 74:

GATAAGCTTG GGCCTTATCT ATTCCAT                                           27

(2) INFORMATION FOR SEQ ID NO: 75:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 75:

ACCCATCCAA AGGAATGGAG GTTCTTTC                                          28

(2) INFORMATION FOR SEQ ID NO: 76:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 76:

AATTAACCCT CACTAAAGGG AGAGGAAGAA TCTGTTGACT CAGATTGGT                   49

(2) INFORMATION FOR SEQ ID NO: 77:

(i) SEQUENCE CHARACTERISTICS:
    (A) LENGTH: 56 base pairs
    (B) TYPE: nucleic acid
    (C) STRANDEDNESS: single
    (D) TOPOLOGY: linear (ii) MOLECULE TYPE: DNA (primer)

(xi) SEQUENCE DESCRIPTION: SEQ ID NO: 77:

AATTTAATAC GACTCACTAT AGGGATTTCC CCACTAACTT CTGTATGTCA TTGACA        56

(2) INFORMATION FOR SEQ ID NO: 78:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 78:

AATTAACCCT CACTAAAGGG AGAAGTATAC TGCATTACCA TACCTAGTA        49

(2) INFORMATION FOR SEQ ID NO: 79:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 79:

TAATACGACT CACTATAGGG AGATCGACGC AGGACTCGGC TTGCTGAA        48

(2) INFORMATION FOR SEQ ID NO: 80:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 80:

AATTAACCCT CACTAAAGGG AGACCTTGTA AGTCATTGGT CTTAAAGGTA        50

(2) INFORMATION FOR SEQ ID NO: 81:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 81:

TCTCCTTGGA TATACTTGTG TGAATCAA        28

(2) INFORMATION FOR SEQ ID NO: 82:

(i) SEQUENCE CHARACTERISTICS:
        (A) LENGTH: 26 base pairs
        (B) TYPE: nucleic acid

```
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 82:

TCACCAGATT TCGTAGTCTT TTCATA                                            26

(2) INFORMATION FOR SEQ ID NO: 83:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 83:

GTCTTGTGTT GAAATTCTCA GGGTAT                                            26

(2) INFORMATION FOR SEQ ID NO: 84:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 84:

CTTGTACCAG CTCACTACCT AAT                                               23

(2) INFORMATION FOR SEQ ID NO: 85:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 85:

ACCTGAGAAG ATAGTAAGCT AGATGAA                                           27

(2) INFORMATION FOR SEQ ID NO: 86:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 86:

AACTCCGCCT TTCCAGTTGT AT                                                22

(2) INFORMATION FOR SEQ ID NO: 87:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)
```

(xi) SEQUENCE DESCRIPTION: SEQ ID NO: 87:

TTAGTTTCTA GGGGTGGAAG ATACA                                         25

(2) INFORMATION FOR SEQ ID NO: 88:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 88:

TTAATGACAC TGAAGATCAC TGTTCTAT                                      28

(2) INFORMATION FOR SEQ ID NO: 89:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 89:

GCACATTTTT GCAAAGTTCA TTAGA                                         25

(2) INFORMATION FOR SEQ ID NO: 90:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 90:

TCATGGGCCA TGTGCTTTTC AA                                            22

(2) INFORMATION FOR SEQ ID NO: 91:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 91:

ACCTTCCAGC ACTACAAACT AGAA                                          24

(2) INFORMATION FOR SEQ ID NO: 92:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 92:

CAAGTGAATC CTGAGCGTGA TTT                                           23

(2) INFORMATION FOR SEQ ID NO: 93:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 93:

GGTAGTGTGA AGGGTTCATA TGCATA                                        26

(2) INFORMATION FOR SEQ ID NO: 94:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 94:

GATTACATTA GAAGGAAGAT GTGCCTTT                                    28

(2) INFORMATION FOR SEQ ID NO: 95:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 95:

ACATGAATGA CATTTACAGC AAATGCTT                                    28

(2) INFORMATION FOR SEQ ID NO: 96:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 96:

GTGACCATAT TGTAATGCAT GTAGTGA                                     27

(2) INFORMATION FOR SEQ ID NO: 97:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 97:

ATGGTGAACA TATTTCTCAA GAGGTAA                                     27

(2) INFORMATION FOR SEQ ID NO: 98:

```
       (i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 98:

TGTCTCTGTA AACTGATGGC TAACA                                              25

(2) INFORMATION FOR SEQ ID NO: 99:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 99:

TCGTATAGAG TTGATTGGAT TGAGAA                                             26

(2) INFORMATION FOR SEQ ID NO: 100:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 100:

CCATTAACTT AATGTGGTCT CATCACAA                                           28

(2) INFORMATION FOR SEQ ID NO: 101:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 101:

CTACCATAAT GCTTGGGAGA AATGAA                                             26

(2) INFORMATION FOR SEQ ID NO: 102:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 102:

TCAAAGAATG GCACCAGTGT GAAA                                               24

(2) INFORMATION FOR SEQ ID NO: 103:

(i) SEQUENCE CHARACTERISTICS:
            (A) LENGTH: 26 base pairs
            (B) TYPE: nucleic acid
            (C) STRANDEDNESS: single
```

(D) TOPOLOGY: linear (ii) MOLECULE TYPE: DNA (oligonucleotide)

(xi) SEQUENCE DESCRIPTION: SEQ ID NO: 103:

TGCTTAGCTA AAGTTAATGA GTTCAT                                            26

(2) INFORMATION FOR SEQ ID NO: 104:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 104:

AATTGTGAAA TTGTCTGCCA TTCTTAA                                           27

(2) INFORMATION FOR SEQ ID NO: 105:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 105:

GATTCACTTA CTGAACACAG TCTAACAA                                          28

(2) INFORMATION FOR SEQ ID NO: 106:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 106:

AGGCTTCTCA GTGATCTGTT G                                                 21

(2) INFORMATION FOR SEQ ID NO: 107:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 107:

GAATCATTCA GTGGGTATAA GCA                                               23

(2) INFORMATION FOR SEQ ID NO: 108:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

-continued (xi) SEQUENCE DESCRIPTION: SEQ ID NO: 108:

GCCATGGTAC CTATATGTCA CAGAA                                                  25

(2) INFORMATION FOR SEQ ID NO: 109:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 109:

TGCAGAGTAA TATGAATTTC TTGAGTACA                                              29

(2) INFORMATION FOR SEQ ID NO: 110:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 110:

GGGACTCCAA ATATTGCTGT AGTAT                                                  25

(2) INFORMATION FOR SEQ ID NO: 111:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 111:

GTACCTGTTG CTCCAGGTAT GTT                                                    23

(2) INFORMATION FOR SEQ ID NO: 112:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 112:

TTTATANTAG AAACC                                                             15

(2) INFORMATION FOR SEQ ID NO: 113:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 113:

TTATAGNAGA AACCA                                                             15

-continued (2) INFORMATION FOR SEQ ID NO: 114:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 114:

TATAGTNGAA CCAC                                    14

(2) INFORMATION FOR SEQ ID NO: 115:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 115:

ATAGTANAAA CCACA                                  15

(2) INFORMATION FOR SEQ ID NO: 116:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 116:

TAGTAGNAAC CACAA                                  15

(2) INFORMATION FOR SEQ ID NO: 117:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 117:

AGTAGANACC ACAAA                                  15

(2) INFORMATION FOR SEQ ID NO: 118:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 118:

GTAGAANCCA CAAAG                                  15

(2) INFORMATION FOR SEQ ID NO: 119:

(i) SEQUENCE CHARACTERISTICS:

(A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 119:

TAGAAANCAC AAAGG                                                    15

(2) INFORMATION FOR SEQ ID NO: 120:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 120:

AGAAACNACA AAGGA                                                    15

(2) INFORMATION FOR SEQ ID NO: 121:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 121:

CATTAAAGAA AATATCATCT TTGGTGTTTC CTATGATGA                          39

(2) INFORMATION FOR SEQ ID NO: 122:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 122:

CATTAAAGAA AATATCATTG GTGTTTCCTA TGATGA                             36

(2) INFORMATION FOR SEQ ID NO: 123:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 123:

AACACCAATG ATGAT                                                    15

(2) INFORMATION FOR SEQ ID NO: 124:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 124:

CCTTCAGAGG GTAAAATTAA G                                                        21

(2) INFORMATION FOR SEQ ID NO: 125:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 125:

CCTTCAGAGT GTAAAATTAA G                                                        21

(2) INFORMATION FOR SEQ ID NO: 126:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 126:

TAATACGACT CACTATAGGG AGATGACCTA ATAATGATGG GTTT                                44

(2) INFORMATION FOR SEQ ID NO: 127:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 127:

TAATACGACT CACTATAGGG AGTAGTGTGA AGGGTTCATA TGC                                 43

(2) INFORMATION FOR SEQ ID NO: 128:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 128:

CTCGGAATTA ACCCTCACTA AAGGTAGTGT GAAGGGTTCA TATGC                               45

(2) INFORMATION FOR SEQ ID NO: 129:

(i) SEQUENCE CHARACTERISTICS:
            (A) LENGTH: 43 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 129:

```
TAATACGACT CACTATAGGG AGAGCATACT AAAAGTGACT CTC                    43

(2) INFORMATION FOR SEQ ID NO: 130:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 130:

TAATACGACT CACTATAGGG AGACATGAAT GACATTTACA GCAA                   44

(2) INFORMATION FOR SEQ ID NO: 131:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 131:

CGGAATTAAC CCTCACTAAA GGACATGAAT GACATTTACA GCAA                   44

(2) INFORMATION FOR SEQ ID NO: 132:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 132:

TAATACGACT CACTATAGGG AGACCCTGGG CAACCAGCCC TGTCGT                 46

(2) INFORMATION FOR SEQ ID NO: 133:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 133:

ATGCAATTAA CCCTCACTAA AGGGAGACAC TTGTGCCCTG ACTTTCAAC              49

(2) INFORMATION FOR SEQ ID NO: 134:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 134:

TAATACGACT CACTATAGGG AGCCTCCTCC CAGAGACCC                         39
```

(2) INFORMATION FOR SEQ ID NO: 135:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 135:

ATGCAATTAA CCCTCACTAA GGGAGATCCC CAGGCCTCTG ATTCCTCACT G        51

(2) INFORMATION FOR SEQ ID NO: 136:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 136:

TAATACGACT CACTATAGGG ACTGGGGCAC AGCCAGGCCA GTGTGCA        47

(2) INFORMATION FOR SEQ ID NO: 137:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 137:

ATGCAATTAA CCCTCACTAA AGGGAGAGTC TCCCCAAGGC GCACTGGCCT CA        52

(2) INFORMATION FOR SEQ ID NO: 138:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 138:

TAATACGACT CACTATAGGG AGGGCATAAC TGCACCCTTG GTCTCCTCC        49

(2) INFORMATION FOR SEQ ID NO: 139:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 139:

ATGCAATTAA CCCTCACTAA AGGGAGAGGA CCTGATTTCC TTACTGCCTC TTGC        54

(2) INFORMATION FOR SEQ ID NO: 140:

(i) SEQUENCE CHARACTERISTICS:
        (A) LENGTH: 25 base pairs (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 140:

GACATGGCGG TGCAGCCGAA GGAGA                                            25

(2) INFORMATION FOR SEQ ID NO: 141:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 141:

CTATGTCAAT TGCAAACAGT GCTCAGTTAC AG                                    32

(2) INFORMATION FOR SEQ ID NO: 142:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 142:

CTTGGCTCTT CTGGCGCCAA AATGTCGTTC                                       30

(2) INFORMATION FOR SEQ ID NO: 143:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (primer)

(xi) SEQUENCE DESCRIPTION: SEQ ID NO: 143:

TATGTTAAGA CACATCTATT TATTTATAAT CAATCC                                36

(2) INFORMATION FOR SEQ ID NO: 144:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 144:

ACCTCCCTCA CCA                                                         13

(2) INFORMATION FOR SEQ ID NO: 145:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 145:

TTTATGGGGT GA                                                                    12

(2) INFORMATION FOR SEQ ID NO: 146:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 146:

TTGATTTATG GG                                                                    12

(2) INFORMATION FOR SEQ ID NO: 147:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 147:

AACCTATTTG ATT                                                                   13

(2) INFORMATION FOR SEQ ID NO: 148:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 148:

GGACCAAACC TA                                                                    12

(2) INFORMATION FOR SEQ ID NO: 149:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 149:

AGGCTAGGAC CA                                                                    12

(2) INFORMATION FOR SEQ ID NO: 150:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 150:

```
GGTGTGTGTG TGC                                                          13

(2) INFORMATION FOR SEQ ID NO: 151:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 151:

CGGTGTGTGT GTGC                                                         14

(2) INFORMATION FOR SEQ ID NO: 152:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 152:

GGTGTGTGTG TGCT                                                         14

(2) INFORMATION FOR SEQ ID NO: 153:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 153:

CTGGGTAGGA TG                                                           12

(2) INFORMATION FOR SEQ ID NO: 154:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 154:

TGCTGGGTAG GA                                                           12

(2) INFORMATION FOR SEQ ID NO: 155:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 155:

TGTGCTGGGT AG                                                           12

(2) INFORMATION FOR SEQ ID NO: 156:
```

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 156:

GTTAGCAGCG GT                                                              12

(2) INFORMATION FOR SEQ ID NO: 157:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 157:

GGGTTAGCAG CG                                                              12

(2) INFORMATION FOR SEQ ID NO: 158:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 158:

AGCGGGGGAG G                                                               11

(2) INFORMATION FOR SEQ ID NO: 159:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 159:

AGCGGGGGAG                                                                 10

(2) INFORMATION FOR SEQ ID NO: 160:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 160:

GGTTGGTTCG G                                                               11

(2) INFORMATION FOR SEQ ID NO: 161:

(i) SEQUENCE CHARACTERISTICS:
            (A) LENGTH: 12 base pairs
            (B) TYPE: nucleic acid

```
        (C) STRANDEDNESS: single
        (D) TOPOLOGY: linear (ii) MOLECULE TYPE: DNA (probe)

(xi) SEQUENCE DESCRIPTION: SEQ ID NO: 161:

GGGTTTGGTT GG                                                          12

(2) INFORMATION FOR SEQ ID NO: 162:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 162:

GATCTTTGGG GT                                                          12

(2) INFORMATION FOR SEQ ID NO: 163:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 163:

GGGTGATCTT TG                                                          12

(2) INFORMATION FOR SEQ ID NO: 164:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 164:

TGTGGGGGGT GA                                                          12

(2) INFORMATION FOR SEQ ID NO: 165:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 165:

TAAACTGTGG GG                                                          12

(2) INFORMATION FOR SEQ ID NO: 166:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)
```

(xi) SEQUENCE DESCRIPTION: SEQ ID NO: 166:

GCTACATAAA CTG                                                          13

(2) INFORMATION FOR SEQ ID NO: 167:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 167:

GAGGTAAGCT ACA                                                          13

(2) INFORMATION FOR SEQ ID NO: 168:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 168:

GAGGAGGTAA GC                                                           12

(2) INFORMATION FOR SEQ ID NO: 169:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 169:

TGCTTTGAGG AG                                                           12

(2) INFORMATION FOR SEQ ID NO: 170:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 170:

AGTGTATTGC TTT                                                          13

(2) INFORMATION FOR SEQ ID NO: 171:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 171:

CATTTTCAGT GTA                                                          13

(2) INFORMATION FOR SEQ ID NO: 172:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 172:

TAAACATTTT CAG                                                  13

(2) INFORMATION FOR SEQ ID NO: 173:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 173:

AGCCCGTCTA AA                                                   12

(2) INFORMATION FOR SEQ ID NO: 174:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 174:

GAGCCCGTCT AA                                                   12

(2) INFORMATION FOR SEQ ID NO: 175:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 175:

TGATGTGAGC CC                                                   12

(2) INFORMATION FOR SEQ ID NO: 176:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 176:

GGGGTGATGT GA                                                   12

(2) INFORMATION FOR SEQ ID NO: 177:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 177:

GAGTGGGAGG G                                                                11

(2) INFORMATION FOR SEQ ID NO: 178:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 178:

GTATGGGAGT GG                                                               12

(2) INFORMATION FOR SEQ ID NO: 179:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 179:

GATTAGTAGT ATGG                                                             14

(2) INFORMATION FOR SEQ ID NO: 180:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 180:

TGAATGAGAT TAG                                                              13

(2) INFORMATION FOR SEQ ID NO: 181:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 181:

ATTGAATGAG ATT                                                              13

(2) INFORMATION FOR SEQ ID NO: 182:

(i) SEQUENCE CHARACTERISTICS:
        (A) LENGTH: 13 base pairs
        (B) TYPE: nucleic acid
        (C) STRANDEDNESS: single

```
        (D) TOPOLOGY: linear (ii) MOLECULE TYPE: DNA (probe)

(xi) SEQUENCE DESCRIPTION: SEQ ID NO: 182:

GGGTTGTATT GAA                                                              13

(2) INFORMATION FOR SEQ ID NO: 183:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 183:

GCGGGGGTTG                                                                  10

(2) INFORMATION FOR SEQ ID NO: 184:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 184:

ATGGGCGGGG                                                                  10

(2) INFORMATION FOR SEQ ID NO: 185:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 185:

TAGGATGGGC G                                                                11

(2) INFORMATION FOR SEQ ID NO: 186:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 186:

TGGGTAGGAT GG                                                               12

(2) INFORMATION FOR SEQ ID NO: 187:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)
```

```
        (xi) SEQUENCE DESCRIPTION: SEQ ID NO: 187:

GTGCTGGGTA GG                                                              12

(2) INFORMATION FOR SEQ ID NO: 188:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 188:

TGTGTGTGCT GG                                                              12

(2) INFORMATION FOR SEQ ID NO: 189:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 189:

GCGGTGTGTG TG                                                              12

(2) INFORMATION FOR SEQ ID NO: 190:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 190:

TAGCAGCGGT GT                                                              12

(2) INFORMATION FOR SEQ ID NO: 191:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 191:

TGGGGTTAGC AG                                                              12

(2) INFORMATION FOR SEQ ID NO: 192:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 192:

GGTATGGGGT TA                                                              12
```

(2) INFORMATION FOR SEQ ID NO: 193:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 193:

GTTCGGGGTA TG                                                           12

(2) INFORMATION FOR SEQ ID NO: 194:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 194:

GCTGGTGTTA GG                                                           12

(2) INFORMATION FOR SEQ ID NO: 195:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 195:

GGTTAGGCTG GT                                                           12

(2) INFORMATION FOR SEQ ID NO: 196:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 196:

AAATCTGGTT AGG                                                          13

(2) INFORMATION FOR SEQ ID NO: 197:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 197:

AAATTTGAAA TCT                                                          13

(2) INFORMATION FOR SEQ ID NO: 198:

(i) SEQUENCE CHARACTERISTICS:

```
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 198:

AAGATAAAAT TTG                                                      13

(2) INFORMATION FOR SEQ ID NO: 199:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 199:

GCCAAAAAGA TA                                                       12

(2) INFORMATION FOR SEQ ID NO: 200:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 200:

CGCCAAAAAG A                                                        11

(2) INFORMATION FOR SEQ ID NO: 201:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 201:

CATACCGCCA A                                                        11

(2) INFORMATION FOR SEQ ID NO: 202:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 202:

AAAAGTGCAT ACC                                                      13

(2) INFORMATION FOR SEQ ID NO: 203:

(i) SEQUENCE CHARACTERISTICS:
        (A) LENGTH: 13 base pairs
        (B) TYPE: nucleic acid
        (C) STRANDEDNESS: single
        (D) TOPOLOGY: linear
```

```
        (ii) MOLECULE TYPE: DNA (probe)

(xi) SEQUENCE DESCRIPTION: SEQ ID NO: 203:

TGTTAAAAGT GCA                                                    13

(2) INFORMATION FOR SEQ ID NO: 204:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 204:

GGGTGACTGT TAA                                                    13

(2) INFORMATION FOR SEQ ID NO: 205:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 205:

GGGGGTGACT GT                                                     12

(2) INFORMATION FOR SEQ ID NO: 206:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 206:

AGTTGGGGGG T                                                      11

(2) INFORMATION FOR SEQ ID NO: 207:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 207:

TGTGTTAGTT GGG                                                    13

(2) INFORMATION FOR SEQ ID NO: 208:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 208:
```

```
AAAATAATGT GTT                                                          13

(2) INFORMATION FOR SEQ ID NO: 209:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 209:

AGGGGAAAAT AA                                                           12

(2) INFORMATION FOR SEQ ID NO: 210:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 210:

GGAGGGGAAA AT                                                           12

(2) INFORMATION FOR SEQ ID NO: 211:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 211:

GGAAATTTTT TG                                                           12

(2) INFORMATION FOR SEQ ID NO: 212:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 212:

GGTGGAAATT TT                                                           12

(2) INFORMATION FOR SEQ ID NO: 213:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 213:

GGTTTGGTGG A                                                            11
```

(2) INFORMATION FOR SEQ ID NO: 214:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 214:

GAGGGGGGGT T                                        11

(2) INFORMATION FOR SEQ ID NO: 215:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 215:

GCGGGGGAGG                                         10

(2) INFORMATION FOR SEQ ID NO: 216:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 216:

CAGAAGCGGG G                                        11

(2) INFORMATION FOR SEQ ID NO: 217:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 217:

GTAGGCCAGA AG                                      12

(2) INFORMATION FOR SEQ ID NO: 218:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 218:

GTGCTGTAGG CC                                      12

(2) INFORMATION FOR SEQ ID NO: 219:

(i) SEQUENCE CHARACTERISTICS:
        (A) LENGTH: 13 base pairs

```
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 219:

TGTTTAAGTG CTG                                                13

(2) INFORMATION FOR SEQ ID NO: 220:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 220:

TGTGTTTAAG TGC                                                13

(2) INFORMATION FOR SEQ ID NO: 221:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 221:

GCAGAGATGT GTT                                                13

(2) INFORMATION FOR SEQ ID NO: 222:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 222:

TTTGGCAGAG AT                                                 12

(2) INFORMATION FOR SEQ ID NO: 223:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 223:

GGGGTTTGGC A                                                  11

(2) INFORMATION FOR SEQ ID NO: 224:

(i) SEQUENCE CHARACTERISTICS:
        (A) LENGTH: 12 base pairs
        (B) TYPE: nucleic acid
        (C) STRANDEDNESS: single
        (D) TOPOLOGY: linear
```

-continued (ii) MOLECULE TYPE: DNA (probe)

(xi) SEQUENCE DESCRIPTION: SEQ ID NO: 224:

TGTTTTTGGG GT                                                    12

(2) INFORMATION FOR SEQ ID NO: 225:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 225:

TTTGTTTTTG GG                                                    12

(2) INFORMATION FOR SEQ ID NO: 226:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 226:

GGGTTCTTTG TT                                                    12

(2) INFORMATION FOR SEQ ID NO: 227:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 227:

GTGTTAGGGT TCT                                                   13

(2) INFORMATION FOR SEQ ID NO: 228:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 228:

TTTAGTAAGT ATGT                                                  14

(2) INFORMATION FOR SEQ ID NO: 229:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 229:

```
AACACACTTT AGT                                                    13
```

(2) INFORMATION FOR SEQ ID NO: 230:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 230:

```
AATTAATTAA CACA                                                   14
```

(2) INFORMATION FOR SEQ ID NO: 231:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 231:

```
AAGCATTAAT TAA                                                    13
```

(2) INFORMATION FOR SEQ ID NO: 232:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 232:

```
GTCCTACAAG CAT                                                    13
```

(2) INFORMATION FOR SEQ ID NO: 233:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 233:

```
TGTCCTACAA GCA                                                    13
```

(2) INFORMATION FOR SEQ ID NO: 234:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 234:

```
ATTATTATGT CCT                                                    13
```

(2) INFORMATION FOR SEQ ID NO: 235:

```
     (i) SEQUENCE CHARACTERISTICS:
         (A) LENGTH: 14 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 235:

TTGTTATTAT TATG                                                         14

(2) INFORMATION FOR SEQ ID NO: 236:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 236:

ATTCAAATTG TTA                                                          13

(2) INFORMATION FOR SEQ ID NO: 237:

(i) SEQUENCE CHARACTERISTICS:
         (A) LENGTH: 13 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 237:

GCAGACATTC AAA                                                          13

(2) INFORMATION FOR SEQ ID NO: 238:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 238:

GCTGTGCAGA CA                                                           12

(2) INFORMATION FOR SEQ ID NO: 239:

(i) SEQUENCE CHARACTERISTICS:
         (A) LENGTH: 12 base pairs
         (B) TYPE: nucleic acid
         (C) STRANDEDNESS: single
         (D) TOPOLOGY: linear (ii) MOLECULE TYPE: DNA (probe)

(xi) SEQUENCE DESCRIPTION: SEQ ID NO: 239:

AAAGTGGCTG TG                                                           12

(2) INFORMATION FOR SEQ ID NO: 240:

(i) SEQUENCE CHARACTERISTICS:
         (A) LENGTH: 13 base pairs
         (B) TYPE: nucleic acid
```

-continued

```
        (C) STRANDEDNESS: single
        (D) TOPOLOGY: linear (ii) MOLECULE TYPE: DNA (probe)

(xi) SEQUENCE DESCRIPTION: SEQ ID NO: 240:

TGTGTGGAAA GTG                                                    13

(2) INFORMATION FOR SEQ ID NO: 241:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 241:

GATGTCTGTG TGG                                                    13

(2) INFORMATION FOR SEQ ID NO: 242:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 242:

ATGATGTCTG TGT                                                    13

(2) INFORMATION FOR SEQ ID NO: 243:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 243:

TTTTGTTATG ATG                                                    13

(2) INFORMATION FOR SEQ ID NO: 244:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 244:

TTTTTTGTTA TGA                                                    13

(2) INFORMATION FOR SEQ ID NO: 245:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)
```

(xi) SEQUENCE DESCRIPTION: SEQ ID NO: 245:

ATAGGGTGCT CC                                                    12

(2) INFORMATION FOR SEQ ID NO: 246:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 246:

GCGACATAGG GT                                                    12

(2) INFORMATION FOR SEQ ID NO: 247:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 247:

TACTGCGACA TAG                                                   13

(2) INFORMATION FOR SEQ ID NO: 248:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 248:

GACAGATACT GCG                                                   13

(2) INFORMATION FOR SEQ ID NO: 249:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 249:

AATCAAAGAC AGA                                                   13

(2) INFORMATION FOR SEQ ID NO: 250:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 250:

AGGAATCAAA GAC                                                   13

(2) INFORMATION FOR SEQ ID NO: 251:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 251:

TGAGGCAGGA AT                                                          12

(2) INFORMATION FOR SEQ ID NO: 252:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 252:

AGGATGAGGC AG                                                          12

(2) INFORMATION FOR SEQ ID NO: 253:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 253:

AAATAATAGG ATG                                                       13

(2) INFORMATION FOR SEQ ID NO: 254:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 254:

GCGATAAATA AT                                                          12

(2) INFORMATION FOR SEQ ID NO: 255:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 255:

TAGGATGCGA TA                                                          12

(2) INFORMATION FOR SEQ ID NO: 256:

```
    (i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 256:

GTAGGATGCG AT                                                           12

(2) INFORMATION FOR SEQ ID NO: 257:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 257:

TTGAACGTAG GA                                                           12

(2) INFORMATION FOR SEQ ID NO: 258:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 258:

AATATTGAAC GTA                                                          13

(2) INFORMATION FOR SEQ ID NO: 259:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 259:

GCCTGTAATA TTG                                                          13

(2) INFORMATION FOR SEQ ID NO: 260:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 260:

TGTTCGCCTG TA                                                           12

(2) INFORMATION FOR SEQ ID NO: 261:

(i) SEQUENCE CHARACTERISTICS:
        (A) LENGTH: 12 base pairs
        (B) TYPE: nucleic acid
        (C) STRANDEDNESS: single
```

-continued (D) TOPOLOGY: linear (ii) MOLECULE TYPE: DNA (probe)

(xi) SEQUENCE DESCRIPTION: SEQ ID NO: 261:

GTATGTTCGC CT                                                                12

(2) INFORMATION FOR SEQ ID NO: 262:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 262:

CTCCCGTGAG TG                                                                12

(2) INFORMATION FOR SEQ ID NO: 263:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 263:

GAGAGCTCCC GT                                                                12

(2) INFORMATION FOR SEQ ID NO: 264:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 264:

ATGGAGAGCT CC                                                                12

(2) INFORMATION FOR SEQ ID NO: 265:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 265:

AATGCATGGA GA                                                                12

(2) INFORMATION FOR SEQ ID NO: 266:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

-continued

```
    (xi) SEQUENCE DESCRIPTION: SEQ ID NO: 266:

ATACCAAATG CA                                                    12

(2) INFORMATION FOR SEQ ID NO: 267:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 267:

GACGAAAATA CCA                                                   13

(2) INFORMATION FOR SEQ ID NO: 268:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 268:

CCCAGACGAA A                                                     11

(2) INFORMATION FOR SEQ ID NO: 269:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 269:

TACCCCCCAG A                                                     11

(2) INFORMATION FOR SEQ ID NO: 270:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 270:

TGCATACCCCC                                                      11

(2) INFORMATION FOR SEQ ID NO: 271:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 271:

TCGCGTGCAT AC                                                    12
```

(2) INFORMATION FOR SEQ ID NO: 272:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 272:

GACTATCGCG TG                                                          12

(2) INFORMATION FOR SEQ ID NO: 273:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 273:

ATGACTATCG CG                                                          12

(2) INFORMATION FOR SEQ ID NO: 274:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 274:

CTCGCAATGA CT                                                          12

(2) INFORMATION FOR SEQ ID NO: 275:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 275:

CGTCTCGCAA TG                                                          12

(2) INFORMATION FOR SEQ ID NO: 276:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 276:

CTCCAGCGTC TC                                                          12

(2) INFORMATION FOR SEQ ID NO: 277:

(i) SEQUENCE CHARACTERISTICS:

```
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 277:

TCCGGCTCCA G                                                          11

(2) INFORMATION FOR SEQ ID NO: 278:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 278:

GTGCTCCGGC T                                                          11

(2) INFORMATION FOR SEQ ID NO: 279:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 279:

GACCCTGAAG TAG                                                        13

(2) INFORMATION FOR SEQ ID NO: 280:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 280:

TTTATGACCC TGA                                                        13

(2) INFORMATION FOR SEQ ID NO: 281:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 281:

TTTAGGCTTT ATG                                                        13

(2) INFORMATION FOR SEQ ID NO: 282:

(i) SEQUENCE CHARACTERISTICS:
        (A) LENGTH: 12 base pairs
        (B) TYPE: nucleic acid
        (C) STRANDEDNESS: single
        (D) TOPOLOGY: linear
```

(ii) MOLECULE TYPE: DNA (probe)

(xi) SEQUENCE DESCRIPTION: SEQ ID NO: 282:

GCTATTTAGG CT                                                                   12

(2) INFORMATION FOR SEQ ID NO: 283:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 283:

TGGGCTATTT AG                                                                   12

(2) INFORMATION FOR SEQ ID NO: 284:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 284:

ACGTGTGGGC TA                                                                   12

(2) INFORMATION FOR SEQ ID NO: 285:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 285:

AGGGGAACGT GT                                                                   12

(2) INFORMATION FOR SEQ ID NO: 286:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 286:

TTTAAGGGGA AC                                                                   12

(2) INFORMATION FOR SEQ ID NO: 287:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 287:

```
ATGTCTTATT TAAG                                                    14
```

(2) INFORMATION FOR SEQ ID NO: 288:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 288:

```
CATCGTGATG TCT                                                     13
```

(2) INFORMATION FOR SEQ ID NO: 289:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 289:

```
TCCATCGTGA TG                                                      12
```

(2) INFORMATION FOR SEQ ID NO: 290:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 290:

```
GATGATCCAT CG                                                      12
```

(2) INFORMATION FOR SEQ ID NO: 291:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 291:

```
AGACCTGATG ATC                                                     13
```

(2) INFORMATION FOR SEQ ID NO: 292:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 292:

```
GGGTGATAGA CCT                                                     13
```

(2) INFORMATION FOR SEQ ID NO: 293:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 293:

ATAGGGTGAT AGA                                                          13

(2) INFORMATION FOR SEQ ID NO: 294:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 294:

TGGTTAATAG GG                                                           12

(2) INFORMATION FOR SEQ ID NO: 295:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 295:

GTGAGTGGTT AAT                                                          13

(2) INFORMATION FOR SEQ ID NO: 296:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 296:

TGTGCGGGAT AT                                                           12

(2) INFORMATION FOR SEQ ID NO: 297:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 297:

ACTCTTGTGC GG                                                           12

(2) INFORMATION FOR SEQ ID NO: 298:

(i) SEQUENCE CHARACTERISTICS:
        (A) LENGTH: 13 base pairs

```
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 298:

TAGCACTCTT GTG                                                              13

(2) INFORMATION FOR SEQ ID NO: 299:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 299:

GGAGAGTAGC ACT                                                              13

(2) INFORMATION FOR SEQ ID NO: 300:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 300:

GCGAGGAGAG TA                                                               12

(2) INFORMATION FOR SEQ ID NO: 301:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 301:

CGGAGCGAGG A                                                                11

(2) INFORMATION FOR SEQ ID NO: 302:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 302:

GGCCCGGAGC                                                                  10

(2) INFORMATION FOR SEQ ID NO: 303:

(i) SEQUENCE CHARACTERISTICS:
        (A) LENGTH: 11 base pairs
        (B) TYPE: nucleic acid
        (C) STRANDEDNESS: single
        (D) TOPOLOGY: linear
```

-continued (ii) MOLECULE TYPE: DNA (probe)

(xi) SEQUENCE DESCRIPTION: SEQ ID NO: 303:

TTATGGGCCC G                                                                                                           11

(2) INFORMATION FOR SEQ ID NO: 304:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 304:

AGTGTTATGG GC                                                                                            12

(2) INFORMATION FOR SEQ ID NO: 305:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 305:

TACCCCCAAG TG                                                                                            12

(2) INFORMATION FOR SEQ ID NO: 306:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 306:

TTTAGCTACC CC                                                                                            12

(2) INFORMATION FOR SEQ ID NO: 307:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 307:

TTCACTTTAG CTA                                                                                       13

(2) INFORMATION FOR SEQ ID NO: 308:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 308:

```
TACAGTTCAC TTT                                                      13
```

(2) INFORMATION FOR SEQ ID NO: 309:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 309:

```
TCGAGATACA GTT                                                      13
```

(2) INFORMATION FOR SEQ ID NO: 310:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 310:

```
CAGATGTCGA GAT                                                      13
```

(2) INFORMATION FOR SEQ ID NO: 311:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 311:

```
AGGAACCAGA TG                                                       12
```

(2) INFORMATION FOR SEQ ID NO: 312:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 312:

```
GAAGTAGGAA CCA                                                      13
```

(2) INFORMATION FOR SEQ ID NO: 313:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 313:

```
GACTGTAATG TGC                                                      13
```

(2) INFORMATION FOR SEQ ID NO: 314:

```
    (i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 314:

GGGATTTGAC TGT                                                              13

(2) INFORMATION FOR SEQ ID NO: 315:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 315:

AGGGATTTGA CT                                                               12

(2) INFORMATION FOR SEQ ID NO: 316:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 316:

ACGAGAAGGG AT                                                               12

(2) INFORMATION FOR SEQ ID NO: 317:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 317:

TGGGGACGAG AA                                                               12

(2) INFORMATION FOR SEQ ID NO: 318:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 318:

ATCCATGGGG AC                                                               12

(2) INFORMATION FOR SEQ ID NO: 319:

(i) SEQUENCE CHARACTERISTICS:
        (A) LENGTH: 12 base pairs
        (B) TYPE: nucleic acid
```

```
        (C) STRANDEDNESS: single
        (D) TOPOLOGY: linear (ii) MOLECULE TYPE: DNA (probe)

(xi) SEQUENCE DESCRIPTION: SEQ ID NO: 319:

GGTCATCCAT GG                                                        12

(2) INFORMATION FOR SEQ ID NO: 320:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 320:

AGGGGGGTCA T                                                         11

(2) INFORMATION FOR SEQ ID NO: 321:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 321:

TATCTGAGGG GG                                                        12

(2) INFORMATION FOR SEQ ID NO: 322:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 322:

ACCCCTATCT GA                                                        12

(2) INFORMATION FOR SEQ ID NO: 323:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 323:

AGGGACCCCT A                                                         11

(2) INFORMATION FOR SEQ ID NO: 324:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)
```

(xi) SEQUENCE DESCRIPTION: SEQ ID NO: 324:

TGGTCAAGGG AC                                                    12

(2) INFORMATION FOR SEQ ID NO: 325:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 325:

GGATGGTGGT CA                                                    12

(2) INFORMATION FOR SEQ ID NO: 326:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 326:

AGGATGGTGG TC                                                    12

(2) INFORMATION FOR SEQ ID NO: 327:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 327:

ACACGGAGGA TG                                                    12

(2) INFORMATION FOR SEQ ID NO: 328:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 328:

TGATTTACAC GG                                                    12

(2) INFORMATION FOR SEQ ID NO: 329:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 329:

GGGATATTGA TTT                                                   13

(2) INFORMATION FOR SEQ ID NO: 330:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 330:

GTGGCATTTG GA                                            12

(2) INFORMATION FOR SEQ ID NO: 331:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 331:

AGGGGTGGCA T                                             11

(2) INFORMATION FOR SEQ ID NO: 332:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 332:

GGTGAGGGGT G                                             11

(2) INFORMATION FOR SEQ ID NO: 333:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 333:

AGTGGGTGAG GG                                          12

(2) INFORMATION FOR SEQ ID NO: 334:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 334:

GTATCCTAGT GGG                                       13

(2) INFORMATION FOR SEQ ID NO: 335:

-continued (i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 335:

TTTGTTGGTA TCC                                                                13

(2) INFORMATION FOR SEQ ID NO: 336:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 336:

GTAGGTTTGT TGG                                                                13

(2) INFORMATION FOR SEQ ID NO: 337:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 337:

TGGGTAGGTT TG                                                                 12

(2) INFORMATION FOR SEQ ID NO: 338:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 338:

TAAGGGTGGG TA                                                                 12

(2) INFORMATION FOR SEQ ID NO: 339:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 339:

GTACTGTTAA GGG                                                                13

(2) INFORMATION FOR SEQ ID NO: 340:

(i) SEQUENCE CHARACTERISTICS:
        (A) LENGTH: 14 base pairs
        (B) TYPE: nucleic acid
        (C) STRANDEDNESS: single -continued (D) TOPOLOGY: linear (ii) MOLECULE TYPE: DNA (probe)

(xi) SEQUENCE DESCRIPTION: SEQ ID NO: 340:

TGTACTATGT ACTG                                                          14

(2) INFORMATION FOR SEQ ID NO: 341:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 341:

GGCTTTATGT ACT                                                           13

(2) INFORMATION FOR SEQ ID NO: 342:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 342:

AAATGGCTTT AT                                                            12

(2) INFORMATION FOR SEQ ID NO: 343:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 343:

GGTAAATGGC TT                                                            12

(2) INFORMATION FOR SEQ ID NO: 344:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 344:

TGTACGGTAA ATG                                                           13

(2) INFORMATION FOR SEQ ID NO: 345:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 345:

GTGCTAATGT ACG                                                          13

(2) INFORMATION FOR SEQ ID NO: 346:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 346:

TAATGTGCTA ATG                                                          13

(2) INFORMATION FOR SEQ ID NO: 347:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 347:

CATGGGGAGG G                                                            11

(2) INFORMATION FOR SEQ ID NO: 348:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 348:

TGTAAGCATG GG                                                           12

(2) INFORMATION FOR SEQ ID NO: 349:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 349:

TTGCTTGTAA GCA                                                          13

(2) INFORMATION FOR SEQ ID NO: 350:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 350:

TGTACTTGCT TGT                                                          13

-continued (2) INFORMATION FOR SEQ ID NO: 351:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 351:

```
TTGCTGTACT TGC                                                13
```

(2) INFORMATION FOR SEQ ID NO: 352:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 352:

```
GGTTGATTGC TG                                                 12
```

(2) INFORMATION FOR SEQ ID NO: 353:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 353:

```
TTGAGGGTTG AT                                                 12
```

(2) INFORMATION FOR SEQ ID NO: 354:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 354:

```
GTGATAGTTG AGG                                                13
```

(2) INFORMATION FOR SEQ ID NO: 355:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 355:

```
TTGATGTGTG ATA                                                13
```

(2) INFORMATION FOR SEQ ID NO: 356:

(i) SEQUENCE CHARACTERISTICS:

```
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 356:

TGCAGTTGAT GTG                                                          13

(2) INFORMATION FOR SEQ ID NO: 357:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 357:

TGGAGTTGCA GT                                                           12

(2) INFORMATION FOR SEQ ID NO: 358:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 358:

ATTTGGAGTT GC                                                           12

(2) INFORMATION FOR SEQ ID NO: 359:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 359:

TACCGTACAA TAT                                                          13

(2) INFORMATION FOR SEQ ID NO: 360:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 360:

TGGTACCGTA CAA                                                          13

(2) INFORMATION FOR SEQ ID NO: 361:

(i) SEQUENCE CHARACTERISTICS:
        (A) LENGTH: 13 base pairs
        (B) TYPE: nucleic acid
        (C) STRANDEDNESS: single
        (D) TOPOLOGY: linear
```

-continued

```
    (ii) MOLECULE TYPE: DNA (probe)

(xi) SEQUENCE DESCRIPTION: SEQ ID NO: 361:

TATTTATGGT ACC                                                          13

(2) INFORMATION FOR SEQ ID NO: 362:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 362:

GGTCAAGTAT TTA                                                          13

(2) INFORMATION FOR SEQ ID NO: 363:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 363:

TACAGGTGGT CAA                                                          13

(2) INFORMATION FOR SEQ ID NO: 364:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 364:

ATGTACTACA GGT                                                          13

(2) INFORMATION FOR SEQ ID NO: 365:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 365:

GGTTTTTATG TAC                                                          13

(2) INFORMATION FOR SEQ ID NO: 366:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 366:
```

```
GGATTGGGTT TT                                                            12

(2) INFORMATION FOR SEQ ID NO: 367:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 367:

TGTAGGATTG GG                                                            12

(2) INFORMATION FOR SEQ ID NO: 368:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 368:

GTTTTGATGT AGG                                                           13

(2) INFORMATION FOR SEQ ID NO: 369:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 369:

GGGTTTTGAT GT                                                            12

(2) INFORMATION FOR SEQ ID NO: 370:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 370:

GGAGGGGGTT T                                                             11

(2) INFORMATION FOR SEQ ID NO: 371:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 371:

GTCAATACTT GGG                                                           13
```

(2) INFORMATION FOR SEQ ID NO: 372:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 372:

```
GGGTGAGTCA ATA                                              13
```

(2) INFORMATION FOR SEQ ID NO: 373:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 373:

```
TGGGTGAGTC AA                                               12
```

(2) INFORMATION FOR SEQ ID NO: 374:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 374:

```
TGTTGATGGG TG                                               12
```

(2) INFORMATION FOR SEQ ID NO: 375:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 375:

```
CGGTTGTTGA TG                                               12
```

(2) INFORMATION FOR SEQ ID NO: 376:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 376:

```
ACATAGCGGT TG                                               12
```

(2) INFORMATION FOR SEQ ID NO: 377:

(i) SEQUENCE CHARACTERISTICS:
        (A) LENGTH: 13 base pairs

```
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 377:

GAAAATACAT AGC                                                          13

(2) INFORMATION FOR SEQ ID NO: 378:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 378:

AATGTACGAA AAT                                                          13

(2) INFORMATION FOR SEQ ID NO: 379:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 379:

GCAGTAATGT ACG                                                          13

(2) INFORMATION FOR SEQ ID NO: 380:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 380:

TGGCTGGCAG TA                                                           12

(2) INFORMATION FOR SEQ ID NO: 381:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 381:

TCATGGTGGC TG                                                           12

(2) INFORMATION FOR SEQ ID NO: 382:

(i) SEQUENCE CHARACTERISTICS:
        (A) LENGTH: 13 base pairs
        (B) TYPE: nucleic acid
        (C) STRANDEDNESS: single
        (D) TOPOLOGY: linear
```

```
        (ii) MOLECULE TYPE: DNA (probe)

(xi) SEQUENCE DESCRIPTION: SEQ ID NO: 382:

ACAATATTCA TGG                                                          13

(2) INFORMATION FOR SEQ ID NO: 383:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 383:

TAGAATCTTA GCT                                                          13

(2) INFORMATION FOR SEQ ID NO: 384:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 384:

TTTAAATTAG AAT                                                          13

(2) INFORMATION FOR SEQ ID NO: 385:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 385:

GAATAAGTTT AAA                                                          13

(2) INFORMATION FOR SEQ ID NO: 386:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 386:

GAACAGAGAA TAA                                                          13

(2) INFORMATION FOR SEQ ID NO: 387:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 387:
```

```
AAAGAACAGA GAA                                                          13

(2) INFORMATION FOR SEQ ID NO: 388:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 388:

CCCATGAAAG AA                                                           12

(2) INFORMATION FOR SEQ ID NO: 389:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 389:

TTCCCCATGA AA                                                           12

(2) INFORMATION FOR SEQ ID NO: 390:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 390:

ATCTGCTTCC CC                                                           12

(2) INFORMATION FOR SEQ ID NO: 391:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 391:

CAAATCTGCT TC                                                           12

(2) INFORMATION FOR SEQ ID NO: 392:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 392:

GGTACCCAAA TC                                                           12

(2) INFORMATION FOR SEQ ID NO: 393:
```

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 393:

ATTGMWMBGT GCCC                                                              14

(2) INFORMATION FOR SEQ ID NO: 394:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 394:

TACTTGGGTG GT                                                                12

(2) INFORMATION FOR SEQ ID NO: 395:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 395:

TGGAAAAAGG TT                                                                12

(2) INFORMATION FOR SEQ ID NO: 396:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 396:

GTCCTTGGAA AA                                                                12

(2) INFORMATION FOR SEQ ID NO: 397:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 397:

ATTTGTCCTT GG                                                                12

(2) INFORMATION FOR SEQ ID NO: 398:

(i) SEQUENCE CHARACTERISTICS:
            (A) LENGTH: 13 base pairs
            (B) TYPE: nucleic acid

```
        (C) STRANDEDNESS: single
        (D) TOPOLOGY: linear (ii) MOLECULE TYPE: DNA (probe)

(xi) SEQUENCE DESCRIPTION: SEQ ID NO: 398:

CTCTGATTTG TCC                                                          13

(2) INFORMATION FOR SEQ ID NO: 399:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 399:

TTTTTCTCTG ATT                                                          13

(2) INFORMATION FOR SEQ ID NO: 400:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 400:

TAAAGACTTT TTC                                                          13

(2) INFORMATION FOR SEQ ID NO: 401:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 401:

GTGGAGTTAA AGA                                                          13

(2) INFORMATION FOR SEQ ID NO: 402:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 402:

TGGTGGAGTT AAA                                                          13

(2) INFORMATION FOR SEQ ID NO: 403:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)
```

(xi) SEQUENCE DESCRIPTION: SEQ ID NO: 403:

TGCTAATGGT GG                                                                    12

(2) INFORMATION FOR SEQ ID NO: 404:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 404:

TTGGGTGCTA AT                                                                    12

(2) INFORMATION FOR SEQ ID NO: 405:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 405:

TAGCTTTGGG TG                                                                    12

(2) INFORMATION FOR SEQ ID NO: 406:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 406:

TCTTAGCTTT GG                                                                    12

(2) INFORMATION FOR SEQ ID NO: 407:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 407:

CTCGGAATTA ACCCTCACTA AAGGAAACCT TTTTCCAAGG A                                    41

(2) INFORMATION FOR SEQ ID NO: 408:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO: 408:

TAATACGACT CACTATAGGG AGAGGCTAGG ACCAAACCTA TT                                   42

(2) INFORMATION FOR SEQ ID NO: 409:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 409:

TCGGATCGAC TT                                                          12

(2) INFORMATION FOR SEQ ID NO: 410:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 410:

CGGAATTAAC CCTCACTAAA GG                                  22

(2) INFORMATION FOR SEQ ID NO: 411:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 411:

AATTAACCCT CACTAAAGGG AG                                  22

(2) INFORMATION FOR SEQ ID NO: 412:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 412:

TAATACGACT CACTATAGGG AG                                  22

(2) INFORMATION FOR SEQ ID NO: 413:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 413:

ATTTAGGTGA CACTATAGAA                                    20

(2) INFORMATION FOR SEQ ID NO: 414:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (oligonucleotide)

(xi) SEQUENCE DESCRIPTION: SEQ ID NO: 414:

CTTTTTATTC TTTTGYAGAG AATGGGATAG A                          31

(2) INFORMATION FOR SEQ ID NO: 415:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 415:

TAATGCCCTT CGGCRATGTT TTTTCTGGA                              29

(2) INFORMATION FOR SEQ ID NO: 416:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 416:

ATTCTTTTGC AGAGATGGGA TAGAGAGCTG GCT                         33

(2) INFORMATION FOR SEQ ID NO: 417:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 417:

GAATGGGATA GAKAGCTGGC TTCAAAGA                               28

(2) INFORMATION FOR SEQ ID NO: 418:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 418:

CTATGGAATC TTTTYATATT TAGGGGTAAG                             30

(2) INFORMATION FOR SEQ ID NO: 419:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: DNA (oligonucleotide)

(xi) SEQUENCE DESCRIPTION: SEQ ID NO: 419:

TTATGTTCTA TGRAATCTTT TTATATTTAG                              30

(2) INFORMATION FOR SEQ ID NO: 420:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 420:

AACAAGGAGG AACRCTCTAT CGCGATTTAT                              30

(2) INFORMATION FOR SEQ ID NO: 421:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 421:

AACAAGGAGG AAYGCTCTAT CGCGATTTAT                              30

(2) INFORMATION FOR SEQ ID NO: 422:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 422:

TATCGCGATT TAWCTAGGCA TAGGCTTATG                              30

(2) INFORMATION FOR SEQ ID NO: 423:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 423:

GGCCTTCATC ACAYTGGAAT GCAGATGAGA                              30

(2) INFORMATION FOR SEQ ID NO: 424:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 424:

GATTTATAAG AAGKTAATAC TTCCTTGCAC                                    30

(2) INFORMATION FOR SEQ ID NO: 425:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 425:

CAAATTTGAT GAAKTATGTA CCTATTGATT                                    30

(2) INFORMATION FOR SEQ ID NO: 426:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 426:

TGGATCGCTC CTTKGCAAGT GGCACTCCTC                                    30

(2) INFORMATION FOR SEQ ID NO: 427:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 427:

AATCATCCTC CGGAAAGATA TTCACCACCA TCT                                33

(2) INFORMATION FOR SEQ ID NO: 428:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 428:

TATTCACCAC CATCTCTCAT TCTGCATTGT T                                  31

(2) INFORMATION FOR SEQ ID NO: 429:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 429:

CCACCATCTC ATTCTGCATT TTCTGCGCAT GG                                 32

(2) INFORMATION FOR SEQ ID NO: 430:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 430:

AAGGAATCAT CCTCYGGAAA ATATTCATTA                                    30

(2) INFORMATION FOR SEQ ID NO: 431:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 431:

CTGCATTGTT CTGCRCATGG CGGTCACTCG                                    30

(2) INFORMATION FOR SEQ ID NO: 432:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 432:

CTGCATTGTT CTGCKCATGG CGGTCACTCG                                    30

(2) INFORMATION FOR SEQ ID NO: 433:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 433:

CTGCATTGTT CTGCSCATGG CGGTCACTCG                                    30

(2) INFORMATION FOR SEQ ID NO: 434:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 434:

CTTCTTCTCA GGGTTCTTGT GGTGTTTTTA TC                                 32

(2) INFORMATION FOR SEQ ID NO: 435:

(i) SEQUENCE CHARACTERISTICS:

```
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 435:

AAACAAAATA CAGRTAATGT ACCATAATG                                     29

(2) INFORMATION FOR SEQ ID NO: 436:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 436:

AGGACAGTTG TTGGMGGTTG CTGGATCCA                                     29

(2) INFORMATION FOR SEQ ID NO: 437:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 437:

GGAGCCTTCA GAGKGTAAAA TTAAGCACA                                     29

(2) INFORMATION FOR SEQ ID NO: 438:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 438:

TCATTCTGTT CTYAGTTTTC CTGGATTAT                                     29

(2) INFORMATION FOR SEQ ID NO: 439:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 439:

ATTAAAGAAA ATATCTTTGG TGTTTCCTAT G                                  31

(2) INFORMATION FOR SEQ ID NO: 440:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(ii) MOLECULE TYPE: DNA (oligonucleotide)

(xi) SEQUENCE DESCRIPTION: SEQ ID NO: 440:

TAAAGAAAAT ATCATCTKTG GTGTTTCCTA                                       30

(2) INFORMATION FOR SEQ ID NO: 441:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 441:

ATTAAAGAAA ATATCATTGG TGTTTCCTAT G                                     31

(2) INFORMATION FOR SEQ ID NO: 442:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 442:

TAGATACAGA AGCKTCATCA AAGCATGCC                                        29

(2) INFORMATION FOR SEQ ID NO: 443:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 443:

TATTTTTGGT AATARGACAT CTCCAAGTTT                                       30

(2) INFORMATION FOR SEQ ID NO: 444:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 444:

ACAATATAGT TCTTKGAGAA GGTGGAAT                                         28

(2) INFORMATION FOR SEQ ID NO: 445:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 445:

AGGTGGAATC ACACTGARTG GAGGTCAACG                                      30

(2) INFORMATION FOR SEQ ID NO: 446:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 446:

AGGTGGAATC ACACTGAKTG GAGGTCAACG                                      30

(2) INFORMATION FOR SEQ ID NO: 447:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 447:

AGGTGGAATC ACACTGMGTG GAGGTCAACG                                      30

(2) INFORMATION FOR SEQ ID NO: 448:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 448:

AGGTGGAATC ACACTGAGKG GAGGTCAACG                                      30

(2) INFORMATION FOR SEQ ID NO: 449:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 449:

ATCACACTGA GTGGAGRTCA ACGAGCAAGA                                      30

(2) INFORMATION FOR SEQ ID NO: 450:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 450:

ATCACACTGA GTGGARGTCA ACGAGCAAGA                                      30

(2) INFORMATION FOR SEQ ID NO: 451:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 451:

ACACTGAGTG GAGGTYAACG AGCAAGAATT                               30

(2) INFORMATION FOR SEQ ID NO: 452:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 452:

TGAGTGGAGG TCAACRAGCA AGAATTTCT                                29

(2) INFORMATION FOR SEQ ID NO: 453:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 453:

TGAGTGGAGG TCAAYGAGCA AGAATTTCTT T                              31

(2) INFORMATION FOR SEQ ID NO: 454:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 454:

GCAAGAATTT CTTTARCAAG GTGAATAAC                                29

(2) INFORMATION FOR SEQ ID NO: 455:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 455:

AATTTCTTTA GCAASGTGAA TAACTAA                                    27

(2) INFORMATION FOR SEQ ID NO: 456:

(i) SEQUENCE CHARACTERISTICS:
        (A) LENGTH: 28 base pairs

```
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 456:

GAATTTCTTT AGCAARGTGA ATAACTAA                                    28

(2) INFORMATION FOR SEQ ID NO: 457:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 457:

GAAATATTTG AAAGRTATGT TCTTTGAAT                                   29

(2) INFORMATION FOR SEQ ID NO: 458:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 458:

AACTCATGGG ATGTGWTTCT TTCGACCAAT                                  30

(2) INFORMATION FOR SEQ ID NO: 459:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 459:

GACAGAAACA AAAAACAATC TTTTAAACAG AC                               32

(2) INFORMATION FOR SEQ ID NO: 460:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 460:

GACAGAAACA AAAAAACAA TCTTTTAAAC AGAC                              34

(2) INFORMATION FOR SEQ ID NO: 461:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(ii) MOLECULE TYPE: DNA (oligonucleotide)

(xi) SEQUENCE DESCRIPTION: SEQ ID NO: 461:

CTCCTTGGAA AGTGARTATT CCATGTCCTA        30

(2) INFORMATION FOR SEQ ID NO: 462:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 462:

TTTATGTTAT TTGCARTGTT TTCTATGGAA A       31

(2) INFORMATION FOR SEQ ID NO: 463:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 463:

ATTTGTGATA TGATTAYTCT AATTTAGTCT TT      32

(2) INFORMATION FOR SEQ ID NO: 464:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 464:

AGGACTATGG ACACTTYGTG CCTTCGGACG GC      32

(2) INFORMATION FOR SEQ ID NO: 465:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 465:

TTACTTTGAA ACTCYGTTCC ACAAAGCTC          29

(2) INFORMATION FOR SEQ ID NO: 466:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 466:

```
CCAACTGGTT CTTGTAMCTG TCAACACTGC G                              31

(2) INFORMATION FOR SEQ ID NO: 467:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 467:

TGCGCTGGTT CCAAAWGAGA ATAGAAATGA T                              31

(2) INFORMATION FOR SEQ ID NO: 468:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 468:

ATGCGATCTG TGAGCYGAGT CTTTAAGTTC                                30

(2) INFORMATION FOR SEQ ID NO: 469:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 469:

AAGGTAAACC TACAAGTCAA CCAAACCATA CA                             32

(2) INFORMATION FOR SEQ ID NO: 470:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 470:

TCCTGGCCAG AGGGTGRGAT TTGAACACT                                 29

(2) INFORMATION FOR SEQ ID NO: 471:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 471:

ATAAAATGGY GAGTAAGACA                                           20

(2) INFORMATION FOR SEQ ID NO: 472:
```

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 472:

AATAACTTTG CAACAGYGGA GGAAAGCCTT T                                       31

(2) INFORMATION FOR SEQ ID NO: 473:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 473:

AATAACTTTG CAACAGTGRA GGAAAGCCTT T                                       31

(2) INFORMATION FOR SEQ ID NO: 474:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 474:

CTTTGTTATC AGCTTTTTTG AGACTACTGA ACAC                                    34

(2) INFORMATION FOR SEQ ID NO: 475:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 475:

AGTGATACCA CAGRTGAGCA AAAGGACTT                                          29

(2) INFORMATION FOR SEQ ID NO: 476:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 476:

CATTTAGAAA AAASTTGGAT CCCTATGAAC                                         30

(2) INFORMATION FOR SEQ ID NO: 477:

(i) SEQUENCE CHARACTERISTICS:
        (A) LENGTH: 30 base pairs
        (B) TYPE: nucleic acid

```
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 477:

CATTTAGAAA AMACTTGGAT CCCTATGAAC                                    30

(2) INFORMATION FOR SEQ ID NO: 478:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 478:

ACTGTTAGCT AATTGG                                                    16

(2) INFORMATION FOR SEQ ID NO: 479:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 479:

GGGCAATCGA GGGGGG                                                    16

(2) INFORMATION FOR SEQ ID NO: 480:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (oligonucleotide)

(xi) SEQUENCE DESCRIPTION: SEQ ID NO: 480:

AAAGAAAAAA GACAGTACTA AATGGA                                         26

(2) INFORMATION FOR SEQ ID NO: 481:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 481:

TACTGTATTT TTT                                                       13

(2) INFORMATION FOR SEQ ID NO: 482:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)
```

```
       (xi) SEQUENCE DESCRIPTION: SEQ ID NO: 482:

TACTGTCTTT TTT                                                         13

(2) INFORMATION FOR SEQ ID NO: 483:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 483:

TACTGTGTTT TTT                                                         13

(2) INFORMATION FOR SEQ ID NO: 484:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 484:

TACTGTTTTT TTT                                                         13

(2) INFORMATION FOR SEQ ID NO: 485:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 485:

GTACTGACTT TTT                                                         13

(2) INFORMATION FOR SEQ ID NO: 486:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 486:

GTACTGCCTT TTT                                                         13

(2) INFORMATION FOR SEQ ID NO: 487:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (probe)

(xi) SEQUENCE DESCRIPTION: SEQ ID NO: 487:

GTACTGGCTT TTT                                                         13
```

(2) INFORMATION FOR SEQ ID NO: 488:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 488:

GTACTGTCTT TTT                                                     13

(2) INFORMATION FOR SEQ ID NO: 489:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 489:

AGTACTAGCT TTT                                                     13

(2) INFORMATION FOR SEQ ID NO: 490:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 490:

AGTACTCGCT TTT                                                     13

(2) INFORMATION FOR SEQ ID NO: 491:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 491:

AGTACTGGCT TTT                                                     13

(2) INFORMATION FOR SEQ ID NO: 492:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 492:

AGTACTTGCT TTT                                                     13

(2) INFORMATION FOR SEQ ID NO: 493:

```
    (i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 493:

GGGNCCCTTAA                                                              11

(2) INFORMATION FOR SEQ ID NO: 494:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 494:

TAAAGTAAGA CATAAC                                                        16

(2) INFORMATION FOR SEQ ID NO: 495:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 495:

GGCTGACGTC AGCAAT                                                        16

(2) INFORMATION FOR SEQ ID NO: 496:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 496:

TTGCTGACAT CAGCC                                                         15

(2) INFORMATION FOR SEQ ID NO: 497:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 497:

TTGCTGACCT CAGCC                                                         15

(2) INFORMATION FOR SEQ ID NO: 498:

(i) SEQUENCE CHARACTERISTICS:
        (A) LENGTH: 15 base pairs
        (B) TYPE: nucleic acid
        (C) STRANDEDNESS: single
```

(D) TOPOLOGY: linear (ii) MOLECULE TYPE: DNA (probe)

(xi) SEQUENCE DESCRIPTION: SEQ ID NO: 498:

TTGCTGACGT CAGCC                                                    15

(2) INFORMATION FOR SEQ ID NO: 499:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 499:

TTGCTGACTT CAGCC                                                    15

(2) INFORMATION FOR SEQ ID NO: 500:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 500:

ATTCCCGGGA TC                                                       12

(2) INFORMATION FOR SEQ ID NO: 501:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 501:

GGAAGAAATC TGTTGACTCA GATTGGTTGT ACTTTAAATT TCCCCATTAG TCCTATTGAA      60

ACTGTACCAG TAAAATTAAA GCCAGGAATG GATGGCCCAA AAGTTAAGCA ATGGCCATTG     120

ACAGAAGAAA AAATAAAAGC ATTAGTAGAG ATATGTACAG AAATGGAAAA GGAAGGGAAA     180

ATTTCAAAAA TTGGGCCTGA AAATCCATAC AATACTCCAG TATTTGCTAT AAAGAAAAAA     240

GACAGTACTA AATGGAGAAA ACTAGTAGAT TTCAGAGAAC TTAATAAAAG AACTCAAGAC     300

TTCTGGGAAG TTCAGTTAGG AATACCACAC CCCGCAGGGT TAAAAAAGAA AAAATCAGTA     360

ACAGTATTGG ATGTGGGTGA TGCATACTTT TCAGTTCCCT TAGATAAAGA CTTTAGAAAG     420

TATACTGCAT TTACCATACC TAGTATAAAC AATGAGACAC CAGGGATTAG ATATCAGTAC     480

AATGTGCTGC CACAGGGATG GAAAGGATCA CCAGCAATAT TCCAAAGTAG CATGACAAAA     540

ATCTTAGAGC CTTTTAGAAA ACAGAATCCA GACATAGTTA TCTATCAATA CATGGATGAT     600

TTGTATGTAG GATCTGACTT AGAAATAGGG CAGCATAGAA CAAAAATAGA GGAACTGAGA     660

CAGCATCTGT TGAGGTGGGG ATTTACCACA CCAGACAAAA AACATCAGAA AGAACCTCCA     720

TTCCTTTGGA TGGGTTATGA ACTCCATCCT GATAAATGGA CAGTACAGCC TATAATGCTG     780

CCAGAAAAAG ACAGCTGGAC TGTCAATGAC ATACAGAAGT TAGTGGGAAA A             831

(2) INFORMATION FOR SEQ ID NO: 502:

(i) SEQUENCE CHARACTERISTICS:
       (A) LENGTH: 831 base pairs
       (B) TYPE: nucleic acid
       (C) STRANDEDNESS: single
       (D) TOPOLOGY: linear (ii) MOLECULE TYPE: DNA (oligonucleotide)

(xi) SEQUENCE DESCRIPTION: SEQ ID NO: 502:

```
GGRAGAAATN NNNNNTCTCA GATTGGTTGT NNNNBCNNNN NNNNNNNNNN NNNNNTNNNN      60

ACTGNNNCAG NNNNNNAAAA GCCAGGGAGG GATGGCCNNN NAGTTAAGCA ANNNNCNTTG     120

ACAGAAGAAA ANATAAAAGC ATTAGTAGAG ATATGTASAG AAAGGGAAAA GGAAGGGAAA     180

ANNNNNNNAA TTGGGCCTGA AANTCNNGNN NNNACNNNNN NNNNNNNNNT AANNGAAAAA     240

GACAGTANTA AATGGAGAAA ACTAGNAGAT TTCAGAGAAC NNNNNNRAAG AACTCANNNN     300

TTCTGGGAAG TTCAGTTAGG AATACCACAC NCNNNNGGGT TAAAGAGNRA AAAATCAGTA     360

ACAGTATTGG ATGTGGGTGA TGCNNNNNNN NNNNNNNNCN NNGATAAANN NNNTNNNNAG     420

TATACNNNAT TNACNNTACC NNNTNNNNAC AATGAGACAC CAGGGATTAG NNNTCAGTAC     480

AATGTGCTGC CACAGGGATG GAAGGGATCA CCAGCAATNN NNNNAAAGTAG CATGACARNN     540

NNCTTAGAGN CTTNNNNAAA ACAGAATCCA GACATANNNN NNNNNNNNNA CAGGGATGAT     600

TNNTATGTAG GATCTGACNT AGAAATAGGG CAGCATAGAA GAAAATAGA GGAACTGAGA     660

CAGCANCTGT TGAGGTGGGG ATTTACCACA CCAGACAAAA NACATCAGAA AGAACCNNNN     720

NNNNNNNGGA TGGGTTATGA NNTCNNNNNN NNNNAATGGA CAGTACAGNN NNNNNTGCTG     780

CCAGRARARG ACAGCTNNAC TGTNNNNGAC ATACAGAAGT TAGTGGGGRA A             831
```

(2) INFORMATION FOR SEQ ID NO: 503:

(i) SEQUENCE CHARACTERISTICS:
       (A) LENGTH: 831 base pairs
       (B) TYPE: nucleic acid
       (C) STRANDEDNESS: single
       (D) TOPOLOGY: linear (ii) MOLECULE TYPE: DNA (oligonucleotide)

(xi) SEQUENCE DESCRIPTION: SEQ ID NO: 503:

```
GGRAGAAATN NNNNNNCTCA GATTGGTTGT ACNNNNNNNN NNNNNNTNNN NNCTATTGAA      60

ACTGTNCCAG TAAAATAAAA GCCAGGRAGG GAWGGCCCAA AAGTTAAGCA AWNNCNATTG     120

ACAGAAGAAA AAATAAAAGC ATTAGTAGAG ATATGTACAG AAAGGGAAAR GGAAGGGAAA     180

AGNNNNNAAA TTGGGCCTGA AAATCCAGAN ANTACTNNNG TATTNNCTAT AAAGRAAAAA     240

GACAGTACTA AATGGAGAAA ACTAGTAGAT TTCAGAGAAC TTANNAAAAG AACTCAANAC     300

TTCTGGGAAG TTCAGTTAGG AATACCACAC CCCNCNGGGT TAAAGAGGAA AAAATCAGTA     360

ACAGTATTGG ATGTGGGTGA TGCANNNNNN NNNNNCCCT TAGATAAAGA CTTTAGNAAG     420

TATACTGCAT TTACCATACC NNGTATAAAC AATGAGACAC CAGGGATTAG ATATCAGTAC     480

AATGTGCTGC CACAGGGATG GAARGGATCA CCAGCAATAT TCCAAAGTAG CATGACAAAA     540

ATCTTAGAGC CTTTTAGAAA ACAGAATCCA GACATAGTNN NNNNNNNATA CAKGGATGAT     600

TTGTATGTAG GATCTGACTT AGAAATAGGG CAGCATAGAA GAAAATAGA GGAACTGAGA     660

CAGCATCTGT TGAGGTGGGG ATTTACCACA CCAGACAAAA AACATCAGAA AGAACCTCNN     720

NNNNNNTGGA TGGGTTATGA ACTCCANNNN NNNAAATGGA CAGTACAGCC NNNNATGCTV     780
```

CCAGAAAAAG ACAGCTGNAC TGTCNNNNAC ATACAGAAGT TAGTGGGGAG A        831

(2) INFORMATION FOR SEQ ID NO: 504:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 504:

GGRAGGAATC TGTTNNCTCA GATTGGTTGT ACTNNNNNNN NNNCCATTNN TCCTATTGAA        60
ACTGTACCAG KAAAATAAAA GCCAGGAAGG GATGGCCCAA AAGTTAAGCA ATGRCBMWTG        120
ACAGAAGAAA AATAAAAGC ATTAGTAGAG ATATGTACAG AAAGGGAAAR GGAAGGGAAA        180
AKTNNNAAAA TTGGGCCTGA AAATCCAGAC AATACTCNNG TATTTGCTAT AAAGAAAAAA        240
GACAGTACTA AATGGAGAAA ACTAGTAGAT TTCAGAGAAC TTAATAAAAG AACTCAAGAC        300
TTCTGGGAAG TTCAGTTAGG AATACCACAC CCCNNAGGGT TAAARAGGAA AAAATCAGTA        360
ACAGTATTGG ATGTGGGTGA TGCATNNNTT CSNNNTCCCT TAGATAAAGA CTTTAGAAAG        420
TATACTGCAT TTACCATACC TAGTATAAAC AATGAGACAC CAGGGATTAG ATATCAGTAC        480
AATGTGCTGC CACAGGGATG GAAAGGATCA CCAGCAATAT TCCAAAGTAG CATGACAAAA        540
ATCTTAGAGC CTTTTAGAAA ACAGAATCCA GACATAGTTA TNTNTCAATA CATGGATGAT        600
TTGTATGTAG GATCTGACTT AGAAATAGGG CAGCATAGAA CAAAAATAGA GGAACTGAGA        660
CAGCATCTGT TGAGGTGGGG ATTTACCACA CCAGACAAAA AACATCAGAA AGAACCTCCN        720
NNNNNNTGGA TGGGTTATGA ACTCCATNNN NNTAAATGGA CAGTACAGCC TNNNATGCTA        780
CCAGAARAAG ACAGCTGGAC TGTCAANGAC ATACAGAAGT TAGTGGGGRG A        831

(2) INFORMATION FOR SEQ ID NO: 505:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 505:

GGAAGAAATC TGTTGACTCA GATTGGTTGT ACTTTAAANN NNCCCATTAG TCCTATTGAA        60
ACTGTACCAG TAAAATWAAA GCCAGGAAKG GATGGCCCAA AAGTTAAGCA ATGRMVGATG        120
ACAGAAGAAA AATAAAAGC ATTAGTAGAG ATATGTACAG AAADGGAAAR GGAAGGGAAA        180
AKTTCAAAAA TTGGGCCTGA AAATCCAKAC AATACTCCAG TATTTGCTAT AAAGAAAAAA        240
GACAGTACTA AATGGAGAAA ACTAGTAGAT TTCAGAGAAC TTAATAAAAG AACTCAAGAC        300
TTCTGGGAAG TTCAGTTAGG AATACCACAC CCCGCNGGGT TAAARAAGAA AAAATCAGTA        360
ACAGTATTGG ATGTGGGTGA TGCATACNNN NNNNNTCCCT TAGATAAAGA CTTTAGAAAG        420
TATACTGCAT TTACCATACC TAGTATAAAC AATGAGACAC CAGGGATTAG ATATCAGTAC        480
AATGTGCTGC CACAGGGATG GAAAGGATCA CCAGCAATAT TCCAAAGTAG CATGACAAAA        540
ATCTTAGAGC CTTTTAGAAA ACAGAATCCA GACATAGTTA TCTATCAATA CATGGATGAT        600
TTGTATGTAG GATCTGACTT AGAAATAGGG CAGCATAGAA CAAAAATAGA GGAACTGAGA        660

```
CAGCATCTGT TGAGGTGGGG ATTTACCACA CCAGACAAAA AACATCAGAA AGAACCTCCN      720

NNNNNTTGGA TGGGTTATGA ACTCCATCNN NATAAATGGA CAGTACAGCC TANNATGCTG      780

CCAGAAAAAG ACAGCTGGAC TGTCAATGAC ATACAGAAGT TAGTGGGGGG A               831

(2) INFORMATION FOR SEQ ID NO: 506:

(i) SEQUENCE CHARACTERISTICS:
        (A) LENGTH: 831 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 506:

NGAAGAAANC TNNNNNCTCA GATTGNNNNC NNNNNNNNNN NNNNNNNNNN CNNNNNNNNG       60

NCTGNNNCAG TANNATAAAA GCCAGGAAGG GATGGCCCAA ANNNNNNNGN NNNNNNNTTG      120

ACAGAAGAAA AAATAAAAGC ATTAGGGGRG NNNNNGNSAG RGGGGGAAAA GGAAGGGAAA      180

AGNNNNNNAA TTGGGCCTGA AAATCNNGAC NANACNNNNN TNNNNNNCNN NNGGGGRAAG      240

AACNNNNNTA GAKGGRGAGA ATNNNNNNAT TTCAGAGAAC TNNNNNGGNN NACTCAAGNC      300

TTCDGGGAAG TTNNANGNGG AATACCNNNN NNNNNNGGGT TAAAGGGGRA AAAATCAGTA      360

ANNNNNCNGG AGGTGGGTGA TGCNNNNNNN NNNNNNNNCN NNNNDGRNNN NNNNNNNNNN      420

NNNNNNNNAT TNACNNTACC NNNTNNNAAC AATGAGACAC CAGGGATTAG ATATCAGTAC      480

AATNNNNNNN NACAGGGATG GAAGGGATCA CCAGCAATNN NNNAAAGTAG CATGACAAAA      540

NNCTTAGAGC CTTNNANNGG NGNANNGCCA GACATAGNNN NNNNNNNNTA CATGGATGAT      600

TTNTATGTAG GATCTGACTT AGAAATAGGG CAGCATAGAA GAAAAATAGA GGAGCTGAGG      660

GAANNNNNGT TGAGGTGGGG RCCNNNNAGA CCAGAACGNG NACATCAGAA AGAACCTCNN      720

NNNNNNNGGA TGGGTTATGA NCTCCNTNNN NNTAAATGGA CAGTACAGCN NNNNNNNCTG      780

CCAGRARARG ACAGCTGGAC TGTCNNNGAC ATACAGAAGT TAGKGGGGAA A               831

(2) INFORMATION FOR SEQ ID NO: 507:

(i) SEQUENCE CHARACTERISTICS:
        (A) LENGTH: 830 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 507:

GGRAGAAATC TGTTGACTCA GATTGGTTNC NNNNNNNNNN NNNNNNNNNN CNNNNNNNAG       60

ACTGTNCCAG TAAAATAAAA GCCAGGAAGG GATGGCCCAA ANNNNNNAGN NNNNNNATTG      120

ACAGAAGAAA AAATAAAAGC ATTAGTAGRR ANNGGACAGR GRGGGAAARG GAAGGGAAAA      180

GTNNNNAAAT TGGGCCTGAA AATCCAGACA ATACTNNNGT NNNNNNCNNN ARGGARAAGA      240

ACANNNCTAG ATGGAGAAAA TTANNNGATT TCAGAGAACT TNNNNNGAGA ACTCAAGACT      300

TCTGGGAAGT TCNATGAGGA ATACCANNTC MNNNNGGGTT AAAGAGGAAA AAATCAGTAA      360

CNNTNCTGGA KGTGGGTGAT GCANNNNNNN NNNNTCCCTN NNATGANNNN NNNNNNNNNN      420

NNNNNNCATT TACCATACCT NGTATAAACA ATGAGACACC AGGGATTAGA TATCAGTACA      480

ATGNNNNTCC ACAGGGATGG AAGGGATCAC CAGCAATATT CCAAAGTAGC ATGACAAAAA      540

TCTTAGAGCC TTTTANNGGV VAAAAGCCAG ACATAGTTNN NTANNNATAC ATGGATGATT      600
```

```
TGTATGTAGG ATCTGACTTA GAAATAGGGC AGCATAGAAG AAAAATAGAG GAGCTGAGRS    660

AMCNNNTGTT GAGGTGGGGA CCNNNGNSAC CAGAMCVAAA ACATCAGAAA GAACCTCCNN    720

NNNNNTGGAT GGGTTATGAA CTCCATCCTG NTAAATGGAC AGTACAGCCN NNNGNGCTGC    780

CAGAAAAAGA VAGCTGGACT GTCANTGACA KACAGAAGTT AGKGGGGAAA              830
```

(2) INFORMATION FOR SEQ ID NO: 508:

(i) SEQUENCE CHARACTERISTICS:
        (A) LENGTH: 827 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 508:

```
GGAAGAAATC TGTTGACTCA GATTGGTTSC ACNNNNNNNN NNNNNNNNNN CNNNNNNNAG     60

ACTGTACCAG KAAAATAAAA GCCAGGAAGG GAWGGCCCAA AAGNNNAASN NNNANTAWTG    120

ACAGAAGRAA AAATAAAAGC ATTAGTAGAA AATGGGACAG RGRGGGAAAR GGAAGGGAAA    180

GTTNNAAAAT TGGGCCTGAA AATCCAGACA ATACTCNNGT NNNNNNCNNG AGGGAAAAGA    240

ACAGHACTAG ATGGAGAAAA TTAGNAGATT TCAGAGAACT TAATAAGAGA ACTCAAGACT    300

TCTGGGAAGT TCAATKAGGA ATACCACATC CNCNGGGTTA AARARGAAAA AATCAGTAAC    360

AGTACTGGAK GTGGGTGATG CADNTNNNNN NNTTCCCTTA GATGAANNNN NCNNNNNAGA    420

TANNGCATTT ACCATACCTA GTATAAACAA TGAGACACCA GGGATTAGAT ATCAGTACAA    480

TGTNNTTMCA CAGRGATGGA ARGGATCACC AGCAATATTC CAAAGTAGCA TGACAAAAAT    540

CTTAGAGCCT TTTAGARRAC AAAAKCCAGA CATAGTTATC TATCAATACA TGGATGATTT    600

GTATGTAGGA TCTGACTTAG AAATAGGGSA GCATAGAASA AAAATAGAGG AGCTGAGRCA    660

ACANCTGTTG AGGTGGGGCV VGGACACCAG AMCMAAAACA TCAGAAAGAA CCTCCNNNNN    720

NTTGGATGGG TTATGAACTC CATNCNGATA AATGGACAGT ACAGCCTNNN GNGCTGCCAG    780

AARAAGACAG CTGGACTGTC AANGACATAC AGAAGTTAGT GGGGAAA                 827
```

(2) INFORMATION FOR SEQ ID NO: 509:

(i) SEQUENCE CHARACTERISTICS:
        (A) LENGTH: 825 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 509:

```
GGAAGAAATC TGTTGACTCA GATTGGTTSC MCTNNNNNNN NNNNNNNNNN CNNNNTTGAG     60

ACTGTACCAG TAAAAWAAAA GCCAGGAAKG GAWGGCCCAA AAGTNAAASN NNNAMMRDTG    120

ACAGAAGAAA AAATAAAAGC ATTAGTAGAA AATKGGACAG RGRGGGAAAR GGAAGGGRAA    180

ADTCAAAAAT TGGGCCTGAA AATCCAKACA ATACTCCANT ATNTGCCMGG ARGGAAAARA    240

ACAGYACTAG ATGGAGAAAA TTAGTAGATT TCAGAGAACT TAATAAGAGA ACTCAAGACT    300

TCTGGGAAGT TCAATTAGGA ATACCACATC CGCNGGGTTA AARAGAAAA AATCAGTAAC     360

AGTACTGGAT GTGGGTGATG CADATNNNNN NNTTCCCTTA GATGAAGANW NCNNNNNAKA    420

TACTGCATTT ACCATACCTA GTATAAACAA TGAGACACCA GGGATTAGAT ATCAGTACAA    480
```

```
TGTGCTTHCA CAGGGATGGA RGGATCACCA GCAATATTCC AAAGTAGCAT GACAAAAATC    540

TTAGAGCCTT TTAGAAAACA AAAKCCAGAC ATAGTTATCT ATCAATACAT GGATGATTTG    600

TATGTAGGAT CTGACTTAGA AATAGGGSAG CATAGAACAA AAATAGAGGA GCTGAGACAA    660

CATCTGTTGA GGTGGGGCCT GACACCAGAM CMAAAACATC AGAAGAACC  TCCATNNNTT    720

TGGATGGGTT ATGAACTCCA TCNNNATAAA TGGACAGTAC AGCCTANNGT GCTGCCAGAA    780

AAAGACAGCT GGACTGTCAA TGACATACAG AAGTTAGKGG GGAAA                   825
```

(2) INFORMATION FOR SEQ ID NO: 510:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 510:

```
AAAGAAAAAA GACAGTACTA AATGGAGAAA AAT                                 33
```

(2) INFORMATION FOR SEQ ID NO: 511:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 511:

```
TACTGTTTTT TT                                                        12
```

(2) INFORMATION FOR SEQ ID NO: 512:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 512:

```
GTACTGTTTT TTTC                                                      14
```

(2) INFORMATION FOR SEQ ID NO: 513:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 513:

```
AGTACTGTTT TTTTCT                                                    16
```

(2) INFORMATION FOR SEQ ID NO: 514:

(i) SEQUENCE CHARACTERISTICS:
        (A) LENGTH: 18 base pairs
        (B) TYPE: nucleic acid
        (C) STRANDEDNESS: single (D) TOPOLOGY: linear (ii) MOLECULE TYPE: DNA (probe)

(xi) SEQUENCE DESCRIPTION: SEQ ID NO: 514:

TAGTACTGTT TTTTTCTT                                                         18

(2) INFORMATION FOR SEQ ID NO: 515:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 515:

AAAGAAAAAA AACAGTACTA AATGGAGAAA AAT                                        33

(2) INFORMATION FOR SEQ ID NO: 516:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 516:

TCGAGATAAT CTATGTCCTC GTCTACTATG TCATAATCTT CTTTACTTAA ACGGTCCTTT           60

TACCTTTGGT TTTTACTATC CCCCTTAACC TCCAAAATAG TTTCATTCTG TCATGCTAGT          120

CTATGGACAT CTTTAGACAC CTGTATTTCG ATATCCATGT                                160

(2) INFORMATION FOR SEQ ID NO: 517:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 517:

NNGAGATANN NTATGTCCTC GTCYACTATG TNANNNNNNN NNNNRRNAAA CGGTCCTNNN           60

NNNNNNNNNN NNNNNNNNWN CNNCSTAACC TCCAAAATAN NNNNNNTCTN NNNNANNNNT          120

CTANNNGNAG NNNNAGANAR NCCNNNNNNN NNATNCATGT                                160

(2) INFORMATION FOR SEQ ID NO: 518:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 518:

TCGAGATAAT CTATGTCCTC GTCTACTATG TCATAATNNN NNNNACTTAA ACGGTCCTTT           60

TACCTTTGGT TTTTACTATC CCCCTTAACC TCCAAAATAG TTTCATTCTG NCATANNAGT          120

CTATGNGNNG NNNTAGACAG NCNNNNNTCG ATATCCATGT                                160

(2) INFORMATION FOR SEQ ID NO: 519:

(i) SEQUENCE CHARACTERISTICS:
       (A) LENGTH: 160 base pairs
       (B) TYPE: nucleic acid
       (C) STRANDEDNESS: single
       (D) TOPOLOGY: linear (ii) MOLECULE TYPE: DNA (oligonucleotide)

(xi) SEQUENCE DESCRIPTION: SEQ ID NO: 519:

TCGAGATAAT CTATGTCCTC GTCTACTATG TCATAATCTT CTTTACTTAA ACGGTCCTTT      60

TACCTTTGGT TTTTACTATC CNNCTTAACC TCCAAAATAG TTTCATTCTG TCATACTAGT     120

CTATGGGTAG CTTTAGACAN CCGTATTTCG ATATCCATGT                          160

(2) INFORMATION FOR SEQ ID NO: 520:

(i) SEQUENCE CHARACTERISTICS:
       (A) LENGTH: 160 base pairs
       (B) TYPE: nucleic acid
       (C) STRANDEDNESS: single
       (D) TOPOLOGY: linear (ii) MOLECULE TYPE: DNA (oligonucleotide)

(xi) SEQUENCE DESCRIPTION: SEQ ID NO: 520:

TCGAGATAAT CTATGTCCTC GTCTACTATG TCATAATCTT CTTTACTTAA ACGGTCCTTT      60

TACCTTTGGT TTTTACTATC CCNCTTAACC TCCAAAATAG TTTCATTCTG TCATACTAGT     120

CTATGGGTAG CTTTAGACAC CGGTATTTCG ATATCCATGT                          160

(2) INFORMATION FOR SEQ ID NO: 521:

(i) SEQUENCE CHARACTERISTICS:
       (A) LENGTH: 160 base pairs
       (B) TYPE: nucleic acid
       (C) STRANDEDNESS: single
       (D) TOPOLOGY: linear (ii) MOLECULE TYPE: DNA (oligonucleotide)

(xi) SEQUENCE DESCRIPTION: SEQ ID NO: 521:

NCGGGATANT NTATGTCCTC GTCNACTATG TCANNNNNCN NNCNNNNCAA ACGGTCCNCC      60

NNNNNCNNNN NNCNNCNANN AAWCNCAACC TCCAAAATAN NNNNNNTCTN NNNNANNNCN     120

CTNNNNNNAG NGNNAGACAC CTGTATNNNN NTATNCAYGT                          160

(2) INFORMATION FOR SEQ ID NO: 522:

(i) SEQUENCE CHARACTERISTICS:
       (A) LENGTH: 160 base pairs
       (B) TYPE: nucleic acid
       (C) STRANDEDNESS: single
       (D) TOPOLOGY: linear (ii) MOLECULE TYPE: DNA (oligonucleotide)

(xi) SEQUENCE DESCRIPTION: SEQ ID NO: 522:

TCGNGATAAT CTATGTCCTC GTCTACTATG TCATAATCCN NNCNNCTCAA ACGGTCCTYC      60

CNNNNYTGGT NYTTACTATC CCCCTTAACC TCCAAAATAG TTTCATTCTG NCATACNNST     120

CTANNNNNAG NGTTAGACAC CTGTATTTCG ATATCCATGT                          160

(2) INFORMATION FOR SEQ ID NO: 523:

```
    (i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 523:

TCGAGATAAT CTATGTCCTC GTCTACTATG TCATAATCCN NNCTACTCAA ACGGTCCTTC     60

TACCTTTGGT TTTTACTATC CNCCTTAACC TCCAAAATAG TTTCATTCTG TCATACTAGT    120

CTATGAGTAG CTTTAGACAC CTGTATTTCG ATATCCATGT                         160

(2) INFORMATION FOR SEQ ID NO: 524:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 524:

TCGAGATAAT CTATGTCCTC GTCTACTATG TCATAATCTT CTTTACYCAA ACGGTCCTNC     60

TACCTTTGGT TTTTACTATC CCNCTTAACC TCCAAAATAG TTTCATTCTG TCATACTAGT    120

CTATGAGTAC CTTTAGACAC CTGTATTTCG ATATCCATGT                         160

(2) INFORMATION FOR SEQ ID NO: 525:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 525:

AGGTCAACGA GCAA                                                      14

(2) INFORMATION FOR SEQ ID NO: 526:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 526:

AGGTCAATGA GCAA                                                      14

(2) INFORMATION FOR SEQ ID NO: 527:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 527:
```

```
GTAATTTCTT TTATAGTAGA AACCACAAAG GATAC                                    35

(2) INFORMATION FOR SEQ ID NO: 528:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 528:

CATTAAAGAA AATATCATCT TTGGTGTTTC CTATG                                    35

(2) INFORMATION FOR SEQ ID NO: 529:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 529:

CATTAAAGAA AATATCATTG GTGTTTCCTA TG                                       32

(2) INFORMATION FOR SEQ ID NO: 530:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 530:

CATTAAAGAA AATATCAT                                                       18

(2) INFORMATION FOR SEQ ID NO: 531:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 531:

TATTAAAGAA AATATCATCT TTGGTGTTTC CTATC                                    35

(2) INFORMATION FOR SEQ ID NO: 532:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 532:

CCTTAAAGAA AATATCATCT TTGGTGTTTC CTAAA                                    35

(2) INFORMATION FOR SEQ ID NO: 533:
```

```
    (i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (oligonucletide)

(xi) SEQUENCE DESCRIPTION: SEQ ID NO: 533:

CTTTAAAGAA AATAAAAAAA TTGGTGTTTC CTAAA                                    35

(2) INFORMATION FOR SEQ ID NO: 534:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 534:

GGAAGTCTCC CATTTTAATT                                                    20

(2) INFORMATION FOR SEQ ID NO: 535:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 535:

CCTTCAGAGG GTAAAATTAA                                                    20

(2) INFORMATION FOR SEQ ID NO: 536:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 536:

CCTTCAGAGK GTAAAATTAA                                                    20

(2) INFORMATION FOR SEQ ID NO: 537:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 537:

CCTTCAGAGT GTAAAATTAA                                                    20

(2) INFORMATION FOR SEQ ID NO: 538:

(i) SEQUENCE CHARACTERISTICS:
        (A) LENGTH: 19 base pairs
        (B) TYPE: nucleic acid
```

```
          (C) STRANDEDNESS: single
          (D) TOPOLOGY: linear (ii) MOLECULE TYPE: DNA (probe)

(xi) SEQUENCE DESCRIPTION: SEQ ID NO: 538:

CCTTCAGAGG GTAAAATCA                                           19

(2) INFORMATION FOR SEQ ID NO: 539:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (probe)

(xi) SEQUENCE DESCRIPTION: SEQ ID NO: 539:

GATTCAGAGT GTAAAATAC                                           19

(2) INFORMATION FOR SEQ ID NO: 540:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: DNA (probe)

(xi) SEQUENCE DESCRIPTION: SEQ ID NO: 540:

AAAAAAGAGT GTAAAATGA                                           19

(2) INFORMATION FOR SEQ ID NO: 541:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (probe)

(xi) SEQUENCE DESCRIPTION: SEQ ID NO: 541:

GTAATTTCTT TTATAGTAGA AACCACAAAG GATAC                         35

(2) INFORMATION FOR SEQ ID NO: 542:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: DNA (oligonucleotide)

(xi) SEQUENCE DESCRIPTION: SEQ ID NO: 542:

CATTAAAGAA AATAACATCA TTGGTGTTTC CTATG                         35

(2) INFORMATION FOR SEQ ID NO: 543:

(i) SEQUENCE CHARACTERISTICS:
          (A) LENGTH: 12 base pairs
          (B) TYPE: nucleic acid
          (C) STRANDEDNESS: single
          (D) TOPOLOGY: linear (ii) MOLECULE TYPE: DNA (probe)
```

(xi) SEQUENCE DESCRIPTION: SEQ ID NO: 543:

GATGCTGAGG AG                                                                 12

(2) INFORMATION FOR SEQ ID NO: 544:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 544:

CTCCTCCCCG GT                                                                 12

(2) INFORMATION FOR SEQ ID NO: 545:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 545:

ACTCCTCCCC GG                                                                 12

(2) INFORMATION FOR SEQ ID NO: 546:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 546:

GACTCCTCCC CG                                                                 12

(2) INFORMATION FOR SEQ ID NO: 547:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 547:

CGACTCCTCC CC                                                                 12

(2) INFORMATION FOR SEQ ID NO: 548:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 548:

ACGACTCCTC CC                                                                 12

```
(2) INFORMATION FOR SEQ ID NO: 549:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 549:

TACGACTCCT CC                                                         12

(2) INFORMATION FOR SEQ ID NO: 550:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 550:

CTACGACTCC TC                                                         12

(2) INFORMATION FOR SEQ ID NO: 551:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 551:

TCTACGACTC CT                                                         12

(2) INFORMATION FOR SEQ ID NO: 552:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 552:

TTCTACGACT CC                                                         12

(2) INFORMATION FOR SEQ ID NO: 553:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 553:

ATTCTACGAC TC                                                         12

(2) INFORMATION FOR SEQ ID NO: 554:
```

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 554:

TATTCTACGA CT                                                                12

(2) INFORMATION FOR SEQ ID NO: 555:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 555:

CTATTCTACG AC                                                                12

(2) INFORMATION FOR SEQ ID NO: 556:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 556:

CCTATTCTAC GA                                                                12

(2) INFORMATION FOR SEQ ID NO: 557:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 557:

TCCTCCCCGG                                                                   10

(2) INFORMATION FOR SEQ ID NO: 558:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 558:

CTCCTCCCCG                                                                   10

(2) INFORMATION FOR SEQ ID NO: 559:

(i) SEQUENCE CHARACTERISTICS:
        (A) LENGTH: 10 base pairs
        (B) TYPE: nucleic acid
        (C) STRANDEDNESS: single -continued (D) TOPOLOGY: linear (ii) MOLECULE TYPE: DNA (probe)

(xi) SEQUENCE DESCRIPTION: SEQ ID NO: 559:

ACTCCTCCCC                                                              10

(2) INFORMATION FOR SEQ ID NO: 560:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 560:

GACTCCTCCC                                                              10

(2) INFORMATION FOR SEQ ID NO: 561:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 561:

CGACTCCTCC                                                              10

(2) INFORMATION FOR SEQ ID NO: 562:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 562:

ACGACTCCTC                                                              10

(2) INFORMATION FOR SEQ ID NO: 563:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 563:

TACGACTCCT                                                              10

(2) INFORMATION FOR SEQ ID NO: 564:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (probe)

```
       (xi) SEQUENCE DESCRIPTION: SEQ ID NO: 564:

CTACGACTCC                                                                    10

(2) INFORMATION FOR SEQ ID NO: 565:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 565:

TCTACGACTC                                                                    10

(2) INFORMATION FOR SEQ ID NO: 566:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 566:

TTCTACGACT                                                                    10

(2) INFORMATION FOR SEQ ID NO: 567:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 567:

ATTCTACGAC                                                                    10

(2) INFORMATION FOR SEQ ID NO: 568:

(i) SEQUENCE CHARACTERISTICS:
           (A) LENGTH: 10 base pairs
           (B) TYPE: nucleic acid
           (C) STRANDEDNESS: single
           (D) TOPOLOGY: linear (ii) MOLECULE TYPE: DNA (probe)

(xi) SEQUENCE DESCRIPTION: SEQ ID NO: 568:

TATTCTACGA                                                                    10

(2) INFORMATION FOR SEQ ID NO: 569:

(i) SEQUENCE CHARACTERISTICS:
           (A) LENGTH: 184 base pairs
           (B) TYPE: nucleic acid
           (C) STRANDEDNESS: single
           (D) TOPOLOGY: linear (ii) MOLECULE TYPE: DNA (oligonucleotide)

(xi) SEQUENCE DESCRIPTION: SEQ ID NO: 569:

TACTCCCCTG CCCTCAACAA GATGTTTTGC CAACTGGCCA AGACCTGCCC TGTGCAGCWG             60
```

```
KGGGWWGATT CCACACCCCC GCCCGGCACC CGCGTCCGCG CCATGGCCAT CTACAAGCAG        120

TCACAGCACA TGACGGAGGW WGKGAGGCGC TGCCCCCACC ATGAGCGCYG CYCAGATAGC        180

SAYG                                                                    184
```

(2) INFORMATION FOR SEQ ID NO: 570:

(i) SEQUENCE CHARACTERISTICS:
        (A) LENGTH: 646 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 570:

```
AACAAACCTA CCCACCCTTA ACAGTACATA GTACATAAAG CCATTTACCG TACATAGCAC         60

ATTACAGTCA AATCCCTTCT CGTCCCCATG GATGACCCCC CTCAGATAGG GGTCCCTTGA        120

CCACCATCCT CCGTGAAATC AATATCCCGC ACAAGAGTGC TACTCTCCTC GCTCCGGGCC        180

CATAACACTT GGGGGTAGCT AAAGTGAACT GTATCCGACA TCTGGTTCCT ACTTCAGGGT        240

CATAAAGCCT AAATAGCCCA CACGTTCCCC TTAAATAAGA CATCACGATG GATCACAGGT        300

CTATCACCCT ATTAACCACT CACGGGAGCT CTCCATGCAT TTGGTATTTT CGTCTGGGGG        360

GTATGCACGC GATAGCATTG CGAGACGCTG GAGCCGGAGC ACCCTATGTC GCAGTATCTG        420

TCTTTGATTC CTGCCTCATC CTATTATTTA TCGCACCTAC GTTCAATATT ACAGGCGAAC        480

ATACTTACTA AAGTGTGTTA ATTAATTAAT GCTTGTAGGA CATAATAATA ACAATTGAAT        540

GTCTGCACAG CCACTTTCCA CACAGACATC ATAACAAAAA ATTTCCACCA AACCCCCCCT        600

CCCCCGCTTC TGGCCACAGC TCTTAAACAC ATCTCTGCCA AACCCC                      646
```

(2) INFORMATION FOR SEQ ID NO: 571:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 571:

```
TGGTGGGTGC CCT                                                           13
```

(2) INFORMATION FOR SEQ ID NO: 572:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 572:

```
ATTGGNNAGT GCCC                                                          14
```

(2) INFORMATION FOR SEQ ID NO: 573:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 573:

ATTGYRYDGT GCCC                                                          14

(2) INFORMATION FOR SEQ ID NO: 574:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 574:

ATTGMWMBGT GCCC                                                          14

(2) INFORMATION FOR SEQ ID NO: 575:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 575:

ATTGGNNAGT GCCC                                                          14

(2) INFORMATION FOR SEQ ID NO: 576:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 576:

TAACATTCAC GGGAGCA                                                       17

(2) INFORMATION FOR SEQ ID NO: 577:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 577:

CCATTCCAAG ATCCCTGATA TTTTGAA                                            27

(2) INFORMATION FOR SEQ ID NO: 578:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 578:

```
AGGGGGGGT                                                              9

(2) INFORMATION FOR SEQ ID NO: 579:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 579:

GCGGGGGGAG                                                            10

(2) INFORMATION FOR SEQ ID NO: 580:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 580:

GGTGGTACCC AA                                                         12

(2) INFORMATION FOR SEQ ID NO: 581:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 581:

AAAGAAAAAA GACATACTAA ATGGA                                           25

(2) INFORMATION FOR SEQ ID NO: 582:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 582:

AGTACTAGTT TTT                                                        13

(2) INFORMATION FOR SEQ ID NO: 583:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 583:

AGTACTCGTT TTT                                                        13
```

```
(2) INFORMATION FOR SEQ ID NO: 584:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 584:

AGTACTGGTT TTT                                                          13

(2) INFORMATION FOR SEQ ID NO: 585:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (probe)

(xi) SEQUENCE DESCRIPTION: SEQ ID NO: 585:

AGTACTTGTT TTT                                                          13
```